(12) United States Patent
Bergmann et al.

(10) Patent No.: US 9,119,822 B2
(45) Date of Patent: Sep. 1, 2015

(54) USE OF PDE7 INHIBITORS FOR THE TREATMENT OF MOVEMENT DISORDERS

(71) Applicant: Omeros Corporation, Seattle, WA (US)

(72) Inventors: John E. Bergmann, Albany, CA (US); Neil S. Cutshall, Snohomish, WA (US); Gregory A. Demopulos, Mercer Island, WA (US); Vincent A. Florio, Seattle, WA (US); George A. Gaitanaris, Seattle, WA (US); Patrick Gray, Seattle, WA (US); John Hohmann, Seattle, WA (US); Rene Onrust, Mercer Island, WA (US); Hongkui Zeng, Seattle, WA (US)

(73) Assignee: Omeros Corporation, Seattle, WA (US)

(*) Notice: Subject to any disclaimer, the term of this patent is extended or adjusted under 35 U.S.C. 154(b) by 0 days.

(21) Appl. No.: 14/106,206

(22) Filed: Dec. 13, 2013

(65) Prior Publication Data
US 2014/0179717 A1    Jun. 26, 2014

Related U.S. Application Data

(63) Continuation of application No. 12/435,347, filed on May 4, 2009, now Pat. No. 8,637,528, which is a continuation-in-part of application No. 12/057,368, filed on Mar. 27, 2008, now abandoned.

(60) Provisional application No. 60/920,496, filed on Mar. 27, 2007.

(51) Int. Cl.
*A61K 31/198* (2006.01)
*A61K 31/00* (2006.01)
(Continued)

(52) U.S. Cl.
CPC .............. *A61K 31/198* (2013.01); *A61K 31/00* (2013.01); *A61K 31/137* (2013.01);
(Continued)

(58) Field of Classification Search
CPC ..................................................... A61K 31/198
See application file for complete search history.

(56) References Cited

U.S. PATENT DOCUMENTS 6,146,876 A    11/2000 Robison
6,531,498 B1    3/2003 Eggenweiler
(Continued)

FOREIGN PATENT DOCUMENTS

CN    1976938 A    6/2007
DE    199 50 647 A1    4/2001
(Continued)

OTHER PUBLICATIONS

Siuciak, J.A., et al., "Inhibition of the Striatum-Enriched Phosphodiesterase PDE10A: A Novel Approach to the Treatment of Psychosis," *Neuropharmacology* 51:386-396 (2006).
(Continued)

*Primary Examiner* — Paul Zarek
(74) *Attorney, Agent, or Firm* — Tineka J. Quinton; Marcia S. Kelbon

(57) ABSTRACT

A method of treating a movement abnormality associated with the pathology of a neurological movement disorder, such as Parkinson's disease or Restless Leg(s) Syndrome by administering a therapeutically effective amount of a PDE7 inhibitory agent. An aspect of the invention provides for the administration of a PDE& inhibitory agent in conjunction with a dopamine agonist or precursor, such as levodopa. In another aspect of the invention, the PDE7 inhibitory agent may be selective for PDE7 relative to other molecular targets (i) known to be involved with the pathology of Parkinson's disease or (ii) at which other drug(s) that are therapeutically effective to treat Parkinson's disease act.

37 Claims, 23 Drawing Sheets

(51) Int. Cl.
  *A61K 31/137* (2006.01)
  *A61K 31/195* (2006.01)
  *A61K 31/425* (2006.01)
  *A61K 31/433* (2006.01)
  *A61K 31/519* (2006.01)
  *A61K 31/527* (2006.01)
  *A61K 45/06* (2006.01)
  *C07D 471/04* (2006.01)

(52) U.S. Cl.
  CPC ............ *A61K 31/195* (2013.01); *A61K 31/425* (2013.01); *A61K 31/433* (2013.01); *A61K 31/519* (2013.01); *A61K 31/527* (2013.01); *A61K 45/06* (2013.01); *C07D 471/04* (2013.01)

(56) References Cited

U.S. PATENT DOCUMENTS

| | | |
|---|---|---|
| 6,613,778 B1 | 9/2003 | Eggenweiler |
| 6,617,357 B2 | 9/2003 | Aubart |
| 6,734,003 B2 | 5/2004 | Loughney |
| 6,737,436 B1 | 5/2004 | Eggenweiler |
| 6,753,340 B2 | 6/2004 | Vergne |
| 6,818,651 B2 | 11/2004 | Weinbrenner |
| 6,838,559 B2 | 1/2005 | Vaccaro |
| 6,849,638 B2 | 2/2005 | Stolle |
| 6,852,720 B2 | 2/2005 | Vergne |
| 6,884,800 B1 | 4/2005 | Eggenweiler |
| 6,903,109 B2 | 6/2005 | Heintzelman |
| 6,936,609 B2 | 8/2005 | Ergüden |
| 6,958,328 B2 | 10/2005 | Heintzelman |
| 7,022,849 B2 | 4/2006 | Pitts |
| 7,087,614 B2 | 8/2006 | Guo |
| 7,091,024 B2 | 8/2006 | Fidock |
| 7,122,565 B2 | 10/2006 | Vergne |
| 7,186,710 B2 | 3/2007 | Sterk |
| 7,214,676 B2 | 5/2007 | Bernardelli |
| 7,217,527 B2 | 5/2007 | Corbin |
| 7,268,128 B2 | 9/2007 | Inoue |
| 7,378,428 B2 | 5/2008 | Ohhata |
| 7,491,742 B2 | 2/2009 | Eggenweiler |
| 7,498,334 B2 | 3/2009 | Eggenweiler |
| 7,507,742 B2 | 3/2009 | Rawson |
| 2002/0156064 A1 | 10/2002 | Aubart |
| 2002/0198198 A1 | 12/2002 | Bernardelli |
| 2003/0045557 A1 | 3/2003 | Vergne |
| 2003/0069169 A1 | 4/2003 | Macor |
| 2003/0092721 A1 | 5/2003 | Pitts |
| 2003/0092908 A1 | 5/2003 | Pitts |
| 2003/0100571 A1 | 5/2003 | Vaccaro |
| 2003/0104974 A1 | 6/2003 | Pitts |
| 2003/0119829 A1 | 6/2003 | Stolle |
| 2003/0162802 A1 | 8/2003 | Guo |
| 2003/0186988 A1 | 10/2003 | Vergne |
| 2003/0191167 A1 | 10/2003 | Vergne |
| 2003/0195140 A1 | 10/2003 | Ackman |
| 2003/0211040 A1 | 11/2003 | Greengard |
| 2004/0044212 A1 | 3/2004 | Weinbrenner |
| 2004/0082061 A1 | 4/2004 | Astromoff |
| 2004/0082578 A1 | 4/2004 | Heintzelman |
| 2004/0106631 A1 | 6/2004 | Bernardelli |
| 2004/0127707 A1 | 7/2004 | Sterk |
| 2004/0137508 A1 | 7/2004 | Fidock |
| 2004/0138279 A1 | 7/2004 | Eggenweiler |
| 2004/0162294 A1 | 8/2004 | Lebel |
| 2004/0214843 A1 | 10/2004 | Bernardelli |
| 2004/0249148 A1 | 12/2004 | Erguden |
| 2005/0059686 A1 | 3/2005 | Eggenweiler |
| 2005/0130971 A1 | 6/2005 | Stephenson |
| 2005/0148604 A1 | 7/2005 | Inoue |
| 2005/0222138 A1 | 10/2005 | Ohhata |
| 2005/0250739 A1 | 11/2005 | Christian |
| 2006/0116516 A1 | 6/2006 | Pitts |
| 2006/0128707 A1 | 6/2006 | Inoue |
| 2006/0128728 A1 | 6/2006 | Inoue |
| 2006/0154949 A1 | 7/2006 | Heintzelman |
| 2006/0229306 A1 | 10/2006 | Terricabras Belart |
| 2006/0286622 A1 | 12/2006 | Soulard |
| 2007/0049558 A1 | 3/2007 | Bernardelli |
| 2007/0129388 A1 | 6/2007 | Rawson |
| 2007/0208029 A1 | 9/2007 | Barlow |
| 2007/0270419 A1 | 11/2007 | Inoue |
| 2008/0260643 A1 | 10/2008 | Bergmann |
| 2009/0131413 A1 | 5/2009 | Inoue |
| 2010/0113486 A1 | 5/2010 | Bergmann |

FOREIGN PATENT DOCUMENTS

| | | |
|---|---|---|
| EP | 1 193 261 A1 | 4/2002 |
| EP | 1 195 435 A1 | 4/2002 |
| EP | 1 348 433 A1 | 10/2003 |
| EP | 1 348 701 A1 | 10/2003 |
| EP | 1 386 967 A2 | 2/2004 |
| EP | 1 400 244 A1 | 3/2004 |
| EP | 1 454 897 A1 | 9/2004 |
| EP | 1 775 298 A1 | 4/2007 |
| JP | 2005-520801 A | 7/2005 |
| WO | WO 00/23091 A2 | 4/2000 |
| WO | WO 00/68203 A1 | 11/2000 |
| WO | WO 00/68230 A1 | 11/2000 |
| WO | WO 01/29049 A1 | 4/2001 |
| WO | WO 01/32175 A1 | 5/2001 |
| WO | WO 01/32618 A1 | 5/2001 |
| WO | WO 01/34601 A2 | 5/2001 |
| WO | WO 01/36425 A2 | 5/2001 |
| WO | WO 01/62904 A1 | 8/2001 |
| WO | WO 01/74786 A1 | 10/2001 |
| WO | WO 01/98274 A2 | 12/2001 |
| WO | WO 02/26954 A2 | 4/2002 |
| WO | WO 02/28847 A1 | 4/2002 |
| WO | WO 02/40449 A1 | 5/2002 |
| WO | WO 02/40450 A1 | 5/2002 |
| WO | WO 02/074754 A1 | 9/2002 |
| WO | WO 02/076953 A1 | 10/2002 |
| WO | WO 02/085906 A2 | 10/2002 |
| WO | WO 02/087513 A2 | 11/2002 |
| WO | WO 02/087519 A2 | 11/2002 |
| WO | WO 02/088079 A2 | 11/2002 |
| WO | WO 02/088080 A2 | 11/2002 |
| WO | WO 02/088138 A1 | 11/2002 |
| WO | WO 02/102313 A2 | 12/2002 |
| WO | WO 02/102314 A2 | 12/2002 |
| WO | WO 02/102315 A2 | 12/2002 |
| WO | WO 03/053975 A1 | 7/2003 |
| WO | WO 03/055882 A1 | 7/2003 |
| WO | WO 03/057149 A2 | 7/2003 |
| WO | WO 03/064389 A1 | 8/2003 |
| WO | WO 03/082277 A1 | 10/2003 |
| WO | WO 03/082839 A1 | 10/2003 |
| WO | WO 03/088963 A1 | 10/2003 |
| WO | WO 03/093499 A2 | 11/2003 |
| WO | WO 2004/026818 A1 | 4/2004 |
| WO | WO 2004/044235 A1 | 5/2004 |
| WO | WO 2004/065391 A1 | 8/2004 |
| WO | WO 2004/111053 A1 | 12/2004 |
| WO | WO 2004/111054 A1 | 12/2004 |
| WO | WO 2005/018563 A2 | 3/2005 |
| WO | WO 2006/004040 A1 | 1/2006 |
| WO | WO 2006/092691 A1 | 9/2006 |
| WO | WO 2006/092692 A1 | 9/2006 |
| WO | WO 2007/038551 A2 | 9/2006 |
| WO | WO 2007/063391 A2 | 6/2007 |
| WO | WO 2007/072163 A2 | 6/2007 |
| WO | WO 2008/113881 A1 | 9/2008 |
| WO | WO 2008/119057 A2 | 10/2008 |
| WO | WO 2008/127291 A2 | 10/2008 |
| WO | WO 2008/130619 A2 | 10/2008 |
| WO | WO 2008/142550 A2 | 11/2008 |

(56) References Cited

FOREIGN PATENT DOCUMENTS

WO   WO 2009/017625 A1   2/2009
WO   WO 2010/129036 A1   11/2010

OTHER PUBLICATIONS

Giembycz, M.A. et al., "Phosphodiesterase 7A: A New Therapeutic Target for Alleviating Chronic Inflammation?" *Current Pharmaceutical Design* 12:3207-3220 (2006).

Vergne, F., et al.., "PDE7 Inhibitors: Chemistry and Potential Therapeutic Utilities," *Annual Reports in Medicinal Chemistry* 40:227-241 (2005).

Pérez-Torres, S., et al., "Alterations on Phosphodiesterase Type 7 and 8 Isozyme mRNA Expression in Alzheimer's Disease Brains Examined by in situ Hybridization," *Experimental Neurology* 182(2):322-334 (2003).

Sasaki, T., et al., "Transcriptional Activation of Phosphodiesterase 7B1 by Dopamine D1 Receptor Stimulation Through the Cyclic AMP/Cyclic AMP-Dependent Protein in Kinase/Cyclic AMP-Response Element Binding Protein Pathway in Primary Striatal Neurons," *Journal of Neurochemistry* 89:474-483 (2004).

Sasaki, T., et al., "Identification of Human PDE7B, a cAMP-Specific Phosphodiesterase," *Biochemical and Biophysical Research Communications* 271(3):575-583 (2000).

Sasaki, T., et al., "Novel alternative splice varaiants of rat phosphodiesterase 7B showing unique tissue-specific expression and phosphorylation," *Biochem J* 361:211-220 (2002).

Nakata, A., et al., "Potential role of phosphodiesterase 7 in human T cell function: comparative effects of two phosphodiesterase inhibitors," *Clin Exp Immunol* 128:460-466 (2002).

Mally, J., et al., "Potential of Adenosine A2A Receptor Antagonists in the Treatment of of Movement Disorders," *CNS Drugs* 10(5): 311-320 (1998).

Mally, J., et al., "The Effect of Theophylline on Parkinsonian Symptoms," *J. Pharm. Pharmacol.* 46:515-517 (1994).

Shiozaki, S., et al., "Actions of Adenosine A2A Receptor Antagonis KW-6002 on Drug-Induced Catalepsy and Hypokinesia Caused by Reserpine or MPTP," *Psychopharmacology* 147:90-95 (1999).

Girault, J.-A., et al., "The Neurology of Dopamine Signaling," *Arch Neurol* 61:641-644 (2004).

Miró, X., et al., "Differential Distribution of cAMP-Specific Phosphodiesterase 7A mRNA in Rat Brain and Peripheral Organs," *Synapse* 40:201-214 (2001).

Reyes-Irisarri, E., et al., "Neuronal Expression of cAMP-Specific Phosphodiesterase 7B mRNA in the Rat Brain," *Neuroscience* 132:1173-1185 (2005).

Rascol, O., et al., "Induction by Dopamine D1 Receptor Agonist ABT-431 of Dyskinesia Similar to Levodopa in Patients With Parkinson Disease," *Arch Neurol* 58:249-254 (2001).

Giembycz, M.A., et al., "Phosphodiesterase 7 (PDE7) as a Therapeutic Target," *Drugs of the Future* 31(3):207-229 (2006).

Tillerson, J.L., et al., "Detection of Behavioral Impairments Correlated to Neurochemical Deficits in Mice Treated With Moderate Doses of 1-Methyl-4-phenyl-1,2,3,6-tetrahydropyridine," *Experimental Neurology* 178:80-90 (2002).

Langlois, M., et al., "New Perspectives on Dystonia," *Can. J. Neurol. Sci.* 30(Suppl 1): S34-S44 (2003).

Tillerson, J.L., et al., "Grid Performance Test to Measure Behavioral Impairment in the MPTP-Treated-Mouse Model of Parkinsonism," *Journal of Neuroscience Methods* 123(2):189-200 (2003).

Vergne, F., et al., "Discovery of Thiadiazoles as a Novel Structural Class of Potent and Selective PDE7 Inhibitors. Part 1: Design, Synthesis and Structure-Activity Relationship Studies," *Bioorganic & Medicinal Chemistry Letters* 14(18):4607-4613 (2004).

Vergne, F., et al., "Discovery of Thiadiazoles as a Novel Structural Class of Potent and Selective PDE7 Inhibitors. Part 2: Metabolism-Directed Optimization Studies Towards Orally Bioavailable Derivatives," *Biooragnic & Medicinal Chemistty Letters* 14:4615-4621 (2004).

Giorelli, M., et al., "Dopamine fails to regulate activation of peripheral blood lymphocytes from multiple sclerosis patients: Effects pf IFN-β," *J Interferon & Cytokine Res* 25:395-406 (2005).

Omeros Corporation, Omeros Anounces Expansion of Potential Indications for PDE7 Inhibitors, *Press Release* (2011).

Lorthiois, E., et al., "Spiroquinazolinones as Novel, Potent, and Selective PDE7 Inhibitors. Part 1," *Bioorganic & Medical Chemistry Letters* 14:4623-4626 (2004).

Smith, S.J., et al., "Discovery of BRL 50481 [3-(N,N-dimethylsulfonamido)-4-methyl-nitrobenzene], a Selective Inhibitor of Phosphodiesterase 7: In Vitro Studies in Human Monocytes, Lung Macrophages, and CD8+ T-Lymphcoytes," *Molecular Pharmacology* 66(6):1679-1689 (2004).

Malik, R., et al., "Cloning, Stable Expression of Human Phosphodiesterase 7A and Development of an Assay for Screening of PDE7 Selective Inhibitors," *Appl Microbiol Biotechnol* 77:1167-1173 (2008).

Yamamoto, S., et al., "Amelioration of Collagen-Induced Arthritis in Mice by a Novel Phosphodiesterase 7 and 4 Dual Inhibitor, YM-393059," *European Journal of Pharmacology* 559:219-226 (2007).

Han, P., et al., "PDE7A1, a cAMP-Specific Phosphodiesterase, Inhibits cAMP-Dependent Protein Kinase by a Direct Interaction with C," *Journal of Biological Chemistry* 281(22):15050-15057 (2006).

Kang, N.S., et al., "Docking and 3-D QSAR Studies of Dual PDE4-PDE7 Inhibitors," *Molecular Simulation* 33(14):1109-1117 (2007).

Pitts, W.J. et al., "Identification of Purine Inhibitors of Phosphodiesterase 7 (PDE7)," *Bioorganic & Medicinal Chemistry Letters* 14:2955-2958 (2004).

Kempson, J., et al., "Fused and Pyrimidine Based Inhibitors of Phosphodiesterase 7 (PDE7): Synthesis and Initial Structure—Activity Relationships," *Bioorganic & Medicinal Chemistry Letters* 15:1829-1833 (2005).

Yamamoto, S., et al., "Pharmacological Profile of a Novel Phosphodiesterase 7A and -4 Dual Inhibitor, YM-393059, on Acute and Chronic Inflammation Models," *European Journal of Pharmacology* 550:166-172 (2006).

Barlocco, D., "Guanine Analogues as Phosphodiesterase 7 (PDE7) Inhibitors," *Drug Discovery Today* 6(16):859 (2001).

Martinez, A. et al., "Benzyl Derivatives of 2,1,3-Benzo- and Benzothieno[3,2-α]thiadiazine 2,2-Dioxides: First Phosphodiesterase 7 Inhibitors," *J. Med. Chem* 43:683-689 (2000).

Castro, A. et al., CODES, a Novel Procedure for Ligand-Based Virtual Screening: PDE7 Inhibitors as an Application Example, *European Journal of Medicinal Chemistry* 43:1349-1359 (2008).

Wang, H., et al., "Multiple Elements Jointly Determine Inhibitor Selectivity of Cyclic Nucleotide Phosphodiesterases 4 and 7," *Journal of Biological Chemistry* 280(35):30949-30955 (2005).

Ke, H., et al., "Crystal structures of Phosphodiesterases and Implications on Substrate Specificity and Inhibitor Selectivity," *Current Topics in Medicinal Chemistry* 7(4):391-403 (2007).

Gilbert, D.L., "Tourette's Syndrome Improvement With Pergolide in a Randomized, Double-Blind, Crossover Trial," *Neurology* 54(6):1310-1315 (2000).

Bloom, T.J., et al., "Identification and Tissue-Specific Expression of PDE7 Phosphodiesterase Splice Variants," *PNAS (Proceedings of the National Academy of Sciences of the United States of America)* 93(24):14188-14192 (1996).

Baier, P.C., et al., "Assessement of Spontaneously Occurring Periodic Limb Movements in Sleep in the Rat," *Journal of the Neurological Sciences* 198:71-77 (2002).

Banks, W.A., et al., "Delivery Across the Blood-Brain Barrier of Antisense Directed Against Amyloid β: Reversal of Learning and Memory Deficits in Mice Overexpressing Amyloid Precursor Protein," *Journal of Pharmacology and Experimental Therapeutics* 297(3):1113-1121 (2001).

Barnes, M.J., et al., "Synthesis and Structure—Activity Relationships of Guanine Analogues as Phosphodiesterase 7 (PDE7) Inhibitors," *Bioorganic & Medicinal Chemistry Letters* 11:1081-1083 (2001).

(56) References Cited

OTHER PUBLICATIONS

Bernardelli, P., et al., Spiroquinazolinones as Novel, Potent, and Selective PDE7 Inhibitor. Part 2: Optimization of 5,8-Distributed Derivatives, *Bioorganic & Medicinal Chemistry Letters* 14:4627-4631 (2004).

Castro, A. et al., "CoMFA of Benzyl Derivatives of 2, 1, 3-Benzo and Benzothieno[3,2-α]thiadiazine 2,2-Dioxides: Clues for the Design of Phosphodiesterase 7 Inhibitors," *European Journal of Medicinal Chemistry* 36:333-338 (2001).

Castro, A. et al,, "Cyclic Nucleotide Phosphodiesterases and Their Role in Immunomodulatory Responses: Advances in the Development of Specific Phosphodiesterase Inhibitors," *Medicinal Research Reviews* 25(2):229-244 (2005).

Hetman, J.M., et al., "Cloning and Characterization of PDE7B, a cAMP-Specific Phosphodiesterase," *PNAS* (*Proceedings of the National Academy of Sciences of the United States of America*) 97(1):472-476 (2000).

Manconi, M., et al., "On the Pathway of an Animal Model for Restless Legs Syndrome . . . ," *Neurol Sci* 28:S53-S60 (2007).

Ondo, W.G., et al., "Clinical Correlates of 6-Hydroxydopamine Injections Into A11 Dopaminerigic Neurons in Rats: A Possible Model for Restless Leg Syndrome?" *Movement Disorders* 15(1):154-154 (2000).

Qu, S., et al., "Locomotion Is Increased in A11-Lesioned Mice With Iron Deprivation: A Possible Animal Model for Restless Legs Syndrome," *J Neuropathol Exp Neurol* 66(5):383-388 (2007).

Rotella, D.P., "Phosphodiesterase Enzymes—Target Overview," *Drug Discovery* 2007 22-23 (2007).

Stefanova, N., et al., "Animal Models of Multiple System Atrophy," *Trends in Neurosciences* 28(9):501-506 (2005).

Yamamoto, S., et al., "The Effects of a Novel Phosphodiesterase 7A and -4 Dual Inhibitor, YM-393059, on a T-Cell-Related Cytokine Production in vitro and in vivo," *European Journal of Pharmacology* 541:106-114 (2006).

Yang, G., et al., "Phosphodiesterase 7A-Deficient Mice Have Functional T Cells," *Journal of Immunology* 171:6414-6420 (2003).

"Gene and Product Information: PDE7A Phosphodiesterase 7A," © 2007 Sigma-Aldrich Co., http://www.sigmaaldrich.com/catalog.search/SIRNASearchGeneDetail/5150 [retrieved Feb. 27, 2008], 2 pages.

Menniti, F.S., et al., "Phosphodiesterases in the CNS: targets for drug development," *Nature Reviews: Drug Discovery* 5(8):660-670 (2006).

Bonelli, R.M., et al., "Pharmacological Management of Huntington's Disease: An Evidence-Based Review," *Current Pharmaceutical Design* 12(21):2701-2720 (2006).

Caudle, W.M., et al., "Use-Dependent Behavioral and Neurochemical Asymmetry in MPTP Mice," *Neuroscience Letters* 418(3):213-216 (2007).

Crocker, I.C., et al., "Therapeutic Potential of Phosphodiesterase 4 Inhibitors in Allergic Diseases," *Drugs of Today* 35(7):519-535 (2009).

Kish, S.J., et al., "Uneven Pattern of Dopamine Loss in the Striatum of Patients With Idiopathic Parkinson's Disease: Pathophysiologic and Clinical Implications," *New England Journal of Medicine* 318(14):876-880 (1988).

Lundblad, M., et al., "Pharmacological Validation of a Mouse Model of L-DOPA-Induced Dyskinesia," *Experimental Neurology* 194(1):66-75 (2005).

Manconi, M., et al., "First Night Efficacy of Pramipexole in Restless Legs Syndrome and Periodic Leg Movements," *Sleep Medicine* 8(5):491-497 (2007).

Poewe, W., et al., "Akathisia, Restless Legs and Periodic Limb Movements in Sleep in Parkinson's Disease," *Neurology* 63(Suppl 3):S12-S16 (2004).

Siuciak, J.A., et al., "Behavioral and Neurochemical Characterization of Mice Deficient in the Phosphodiesterase-1B (PDE1B) Enzyme," *Neuropharmacology* 53(1): 113-124 (2007).

Trenkwalder, C., et al., "Efficacy of Pergolide in Treatment of Restless Legs Syndrome: The PEARLS Study," *Neurology* 62(8):1391-1397 (2004).

Turjanski, N., et al., "Striatal Dopaminergic Function in Restless Legs Syndrome: 18F-dopa and 11C-raclopride PET Studies," *Neurology* 52(5):932-937 (1999).

Bankiewicz, K.S., et al., "Hemiparkinsonism in Monkeys After Unilateral Internal Carotid Artery Infusion of 1-methyl-4-phenyl-1,2,3,6-tetrahydropyridine (MPTP)," *Life Sceinces* 39(1):7-16 (1986).

Hening, W., et al., "The Treatment of Restless Legs Syndrome and Periodic Limb Movement Disorder," *Sleep* 22(7):970-999 (1999).

Jakowec, M.W., et al., "1-Methyl-4Phenyl-1,2,3,6-Tetrahydropyridine-Lesioned Model of Parkinson's Disease, With Emphasis on Mice and Nonhuman Primates," *Comparative Medicine* 54(5):497-513 (2004).

Jeon, B.S., "Dopa-Responsive Dystonia: A Syndrome of Selective Nigrostriatal Dopaminergic Deficiency," *J Korean Med Sci* 12(4):269-279 (1997).

Reuter, I., et al., "Late Onset Levodopa Responsive Huntington's Disease With Minimal Chorea Masquerading as Parkinson Plus Syndrome," *J Neurol Neurosurg Psychiatry* 68(2):238-241 (2000).

Burns, R.S., et al., "A Primate Model of Parkinsonism: Selective Destruction of Dopaminergic Neurons in the pars compacta of the substantia nigra by N-methyl-4-phenyl-1,2,3,6-tetrahydropyridine," *PNAS* (*Proceedings of the National Academy of Sciences of the United States of America*) 80(14):4546-4550 (1983).

Colosimo, C., et al., "Management of Multiple System Atrophy: State of the Art," *J Neural Transm* 112(12):1695-1704 (2005).

Forno, L.S., "Neuropathology of Parkinson's Disease," *Journal of Neuropathology and Experimental Neurology* 55(3):259-272 (1996).

Vonsattel, J.-P., et al., "Neuropathological Classification of Hungtington's Disease," *Journal of Neuropathology and Experimental Neurology* 44(6):559-577 (1985).

Bonelli, R.M., et al., "Pramipexole Ameliorates Neurologic and Psychiatric Symptoms in a Westphal Variant of Huntington's Disease," *Clinical Neuropharmacology* 25(1):58-60 (2002).

Polo, O., et al., "Entacapone Prolongs the Reduction of PLM by Levodopa/Carbidopa in Restless Legs Syndrome," *Clinical Neuropharmacology* 30(6):335-344 (2007).

van De Watermeemd, H., et al., "Property-Based Design: Optimization of Drug Absorption and Pharmacokinetics," *Journal of Medicinal Chemistry* 44(9):1313-1333 (2001).

Stedman's Medical Dictionary, $27^{th}$ ed., Lippincott, Elliams & Wilkins, Baltirmore (2000).

Standaert DG and Young AB, Chapter 22 Treatment of Central Nervous System Degenerative Disorders, "Goodman & Gilman's The Pharmacological Basis of Thrapeutics, $10^{th}$ ed." Hardman JG, Limbird LE, and Gilman AG, Eds., McGraw-Hill, 2001, 549-568, (pp. 549 and 555 provided).

Smeyne, R.J. and Jackson-Lewis, V., "The MPTP Model of Parkinson's Disease," *Brain Res. Mol. Brain Res* 134(1):57-66 (2005).

Hardman, J.G., et al., Chapter 22 Treatment of Central Nervous System Degenerative Disorders, "Goodman & Gilman's The Pharmacological Basis of Thrapeutics, $10^{th}$ ed." Hardman JG, Limbird, LE, and Gilman AG, Eds., McGraw-Hill, 2001, 549-568, (p. 556 provided).

USE OF PDE7 INHIBITORS FOR THE TREATMENT OF MOVEMENT DISORDERS

CROSS-REFERENCES TO RELATED APPLICATIONS

This application is a continuation of U.S. application Ser. No. 12/435,347, filed May 4, 2009, which is a continuation-in-part of U.S. application Ser. No. 12/057,368, filed Mar. 27, 2008, which claims the benefit of Application No. 60/920,496, filed Mar. 27, 2007, the disclosures of which are incorporated herein by reference in their entirety.

STATEMENT REGARDING SEQUENCE LISTING

The sequence listing associated with this application is provided in text format in lieu of a paper copy and is hereby incorporated by reference into the specification. The name of the text file containing the sequence listing is NE_1_0103_US2_SequenceListingasFiled.txt. The text file is 35 KB; was created on Dec. 9, 2013; and is being submitted via EFS-Web with the filing of the specification.

FIELD OF THE INVENTION

The present invention relates to methods of treating a movement abnormality associated with the pathology of a movement disorder comprising administering to a patient in need thereof an amount of a PDE7 inhibitory agent effective to inhibit the enzymatic activity of PDE7.

BACKGROUND

Parkinson's disease ("PD") is a progressive disorder that affects a small group of neurons (called the substantia nigra) in the midbrain. PD is associated with the depletion of dopamine, which is important for maintaining movement control through interaction with cells in the corpus striatum. Approximately one out of every 1,000 people contract the illness and about 1% of the population over the age of 65 suffers from PD. The common symptoms of PD include tremor at rest, stiffness (or rigidity) of muscles, slowness of movement (bradykinesia) and loss of balance (postural dysfunction).

Parkinson's disease is one of three distinct conditions that can be categorized together as Parkinsonism. Parkinson's disease, or paralysis agitans, is the most common form of Parkinsonism, afflicting approximately 75% of the cases and is of unknown origin or cause. A second type of Parkinsonism is caused by drugs and toxins, including carbon monoxide, manganese and a chemical compound known as MPTP (methylphenyltetrahydropyridine). A third form of Parkinsonism, referred to as Vascular Parkinsonism, may be caused by multiple small strokes that damage the dopamine-producing brain cells.

Many treatments have been tried since James Parkinson named and described the condition in 1817. Most treatments are symptomatic therapies, such as using pharmacologic therapy (e.g., levodopa, dopamine receptor agonists, MAO-B inhibitors, COMT inhibitors) or deep brain stimulation therapy, to alleviate the symptoms of the disease. Recently, neuroprotective therapies have been the subject of intense research and development efforts.

The therapeutic combination of levodopa (L-dopa), a dopamine precursor, and a dopa decarboxylase inhibitor (carbidopa), is considered to be one of the most effective treatments for symptoms of Parkinson's disease (*The Medical Letter* 35:31-34, 1993). However, certain limitations of the combination become apparent within two to five years of initiating the combination therapy. As the disease progresses, the benefit from each dose becomes shorter (the "wearing off effect") and some patients fluctuate unpredictably between mobility and immobility (the "on-off effect"). "On" periods are usually associated with high plasma levodopa concentrations and often include abnormal involuntary movements (i.e., dyskinesias). "Off" periods have been correlated with low plasma levodopa concentrations and bradykinetic episodes. Therefore, a need exists for additional effective treatments for Parkinson's disease.

The salient pathologic feature of Parkinson's disease is the degeneration of dopaminergic neurons in the substantia nigra pars compacta (SNc) that project to the striatum. Forno L. S., *J. Neuropathol Exp Neurol* 55:259-272, 1996. It is thought that the relatively selective dopamine depletion in the striatum and other basal ganglia results in increased and disordered discharge and synchronization in motor areas of the basal ganglia-thalamocorticol motor loops. Wichmann and Delong, *Neuropsychopharmacology: The Fifth Generation of Progress*, Chapter 122, "Neurocircuitry of Parkinson's Disease," 2002. In addition to Parkinson's disease, abnormal function of the basal ganglia has also been implicated in a variety of neurological disorders with movement abnormalities. Such neurological disorders include restless leg(s) syndrome (Hening, W., et al., *Sleep* 22:970-999, 1999) and Huntington's disease (Vonsattel, J. P., et al., *J. Neuropathol. Exp. Neurol.* 44:559-577, 1985). The study of the consequences of the pathophysiologic changes in the basal ganglia that result from the loss of dopaminergic transmission in the basal ganglia has been facilitated by the discovery that primates and rodents treated with MPTP develop behavioral and anatomic changes that closely mimic the features of Parkinson's disease in humans. See, e.g., Bankiewicz, K. S., et al., *Life Sci.* 39:7-16, 1986, Burns, R. S., et al., *PNAS* 80:4546-4550, 1983.

Cyclic nucleotide phosphodiesterases (PDEs) represent a family of enzymes that hydrolyze the ubiquitous intracellular second messengers, adenosine 3',5'-monophosphate (cAMP) and guanosine 3',5'-monophosphate (cGMP), to their corresponding inactive 5'-monophosphate metabolites. At least 11 distinct classes of PDE isozymes (PDE1-11) are believed to exist, each possessing unique physical and kinetic characteristics and representing unique gene families. Within each distinct class of PDE, there may be up to four distinct subtypes. (Crocker, I., et al., *Drugs Today* 35(7):519-535, 1999; Fawcett, L., et al., *PNAS* 97(7):3702-3703, 2000; and Yuasa, K., et al., *J. Biol. Chem.* 275(40):31496-31479, 2000).

Virtually all of the phosphodiesterases are expressed in the central nervous system ("CNS"), making this gene family a particularly attractive source of new targets for the treatment of psychiatric and neurodegenerative disorders. However, all neurons express multiple phosphodiesterases, which differ in cyclic nucleotide specificity, affinity, regulatory control, and subcellular compartmentalization, making linking the target for a specific disease with the treatment of the disease difficult. Therefore, there is a need to identify a target from the family of phosphodiesterases with the treatment of a specific CNS disease, such as Parkinson's disease and other neurological disorders with movement abnormalities.

Despite the advances in the research and treatment of Parkinson's disease, a need exists for new treatments for this disease and other neurological disorders with movement abnormalities. The present invention seeks to fulfill this need and provides further related advantages.

SUMMARY

In accordance with the foregoing, in one aspect, the invention provides a method of treating a movement abnormality associated with the pathology of a neurological movement disorder. The method according to this aspect of the invention comprises administering to a patient in need thereof an amount of a PDE7 inhibitory agent effective to inhibit the enzymatic activity of PDE7, wherein such inhibition of PDE7 enzymatic activity is the principal therapeutic mode of action of the PDE7 inhibitor in the treatment of the movement abnormality.

In accordance with the foregoing, in one aspect, the invention provides a method of treating a movement abnormality associated with the pathology of a neurological disorder. The method according to this aspect of the invention comprises administering to a patient in need thereof an amount of a PDE7 inhibitory agent effective to inhibit the enzymatic activity of PDE7, wherein such inhibition of PDE7 enzymatic activity is the principal therapeutic mode of action of the PDE7 inhibitor in the treatment of the movement abnormality.

In another aspect, the invention provides a method for identifying an agent that inhibits PDE7 activity useful for treating a movement abnormality associated with the pathology of a neurological movement disorder in a mammalian subject in need thereof. The method of this aspect of the invention comprises (a) determining the $IC_{50}$ for inhibiting PDE7A and/or PDE7B activity of each of a plurality of agents; (b) selecting agent(s) from the plurality of agents having an $IC_{50}$ for inhibition of PDE7A and/or PDE7B activity of less than about 1 µM; (c) determining the $IC_{50}$ for inhibiting PDE4 activity of the agent(s) having an $IC_{50}$ for inhibiting PDE7 activity of less than about 1 µM; (d) identifying agent(s) useful for treating a movement disorder by selecting compounds having an $IC_{50}$ for inhibiting PDE4 activity greater than 10 times the lesser of the $IC_{50}$ for inhibiting PDE7A activity and the $IC_{50}$ for inhibiting PDE7B activity; and (e) evaluating the activity of the identified compound(s) in a neurological movement disorder model assay, wherein an agent that has an $IC_{50}$ for PDE7A and/or PDE7B activity inhibition of less than about 1 µM, and an $IC_{50}$ for inhibiting PDE4 activity greater than 10 times the lesser of the $IC_{50}$ for inhibiting PDE7A activity and the $IC_{50}$ for inhibiting PDE7B activity, and is determined to be effective to treat at least one movement abnormality in a model assay, is indicative of a PDE7 inhibitory agent useful for treating a movement abnormality associated with the pathology of a neurological movement disorder in a mammalian subject.

In another aspect, the invention provides a method of treating a movement abnormality associated with the pathology of a neurological movement disorder. The method according to this aspect of the invention comprises administering to a patient in need thereof a therapeutically effective amount of a chemical compound that is a PDE7 inhibitor, the chemical compound characterized in that: (i) the chemical compound has an $IC_{50}$ for inhibiting PDE7A and/or PDE7B activity of less than about 1 µM; and (ii) the chemical compound has an $IC_{50}$ for inhibiting PDE 3 greater than 10 times the lesser of the $IC_{50}$ for inhibiting PDE7A activity and the $IC_{50}$ for inhibiting PDE7B activity.

The methods of the various aspects of the invention are useful to treat a movement abnormality associated with a neurological disorder. The methods of the various aspects of the invention are also useful to treat a neurological movement disorder. The methods of the various aspects of the invention are further useful to treat a movement abnormality associated with a neurological movement disorder.

In some embodiments of the various aspects of the invention, the methods are useful to treat a neurological movement disorder, a movement abnormality associated with a neurological disorder, and/or a movement abnormality associated with a neurological movement disorder, that is treatable with a dopamine receptor agonist or a precursor of a dopamine receptor agonist. In some embodiments, the methods are useful to treat a neurological movement disorder selected from the group of Parkinson's disease, Post-Encephalitic Parkinsonism, Dopamine-Responsive Dystonia, Shy-Drager Syndrome, Periodic Limb Movement Disorder (PLMD), Periodic Limb Movements in Sleep (PLMS), Tourette's Syndrome, and Restless Leg(s) Syndrome (RLS).

In some embodiments of the various aspects of the invention, the methods are useful to treat a movement abnormality associated with the pathology of a neurological movement disorder and/or the pathology of a neurological disorder. In some embodiments of the various aspects of the invention, the methods are useful to treat a movement abnormality associated with the pathology of a neurological movement disorder that is treatable with a dopamine receptor agonist or a precursor of a dopamine receptor agonist. In some embodiments, the methods are useful to treat a movement abnormality associated with the pathology of a neurological movement disorder selected from the group of Parkinson's disease, Post-Encephalitic Parkinsonism, Dopamine-Responsive Dystonia, Shy-Drager Syndrome, Periodic Limb Movement Disorder (PLMD), Periodic Limb Movements in Sleep (PLMS), Tourette's Syndrome, and Restless Leg(s) Syndrome (RLS).

DESCRIPTION OF THE DRAWINGS

The foregoing aspects and many of the attendant advantages of this invention will become more readily appreciated as the same become better understood by reference to the following detailed description, when taken in conjunction with the accompanying drawing. In certain of these figures, statistical significance is indicated by a marking in which "*" refers to a p value of less than 0.05, "" refers to a p value of less than 0.01, and "*" refers to a p value of less than 0.005. In the figures.

DETAILED DESCRIPTION

Figure 1:
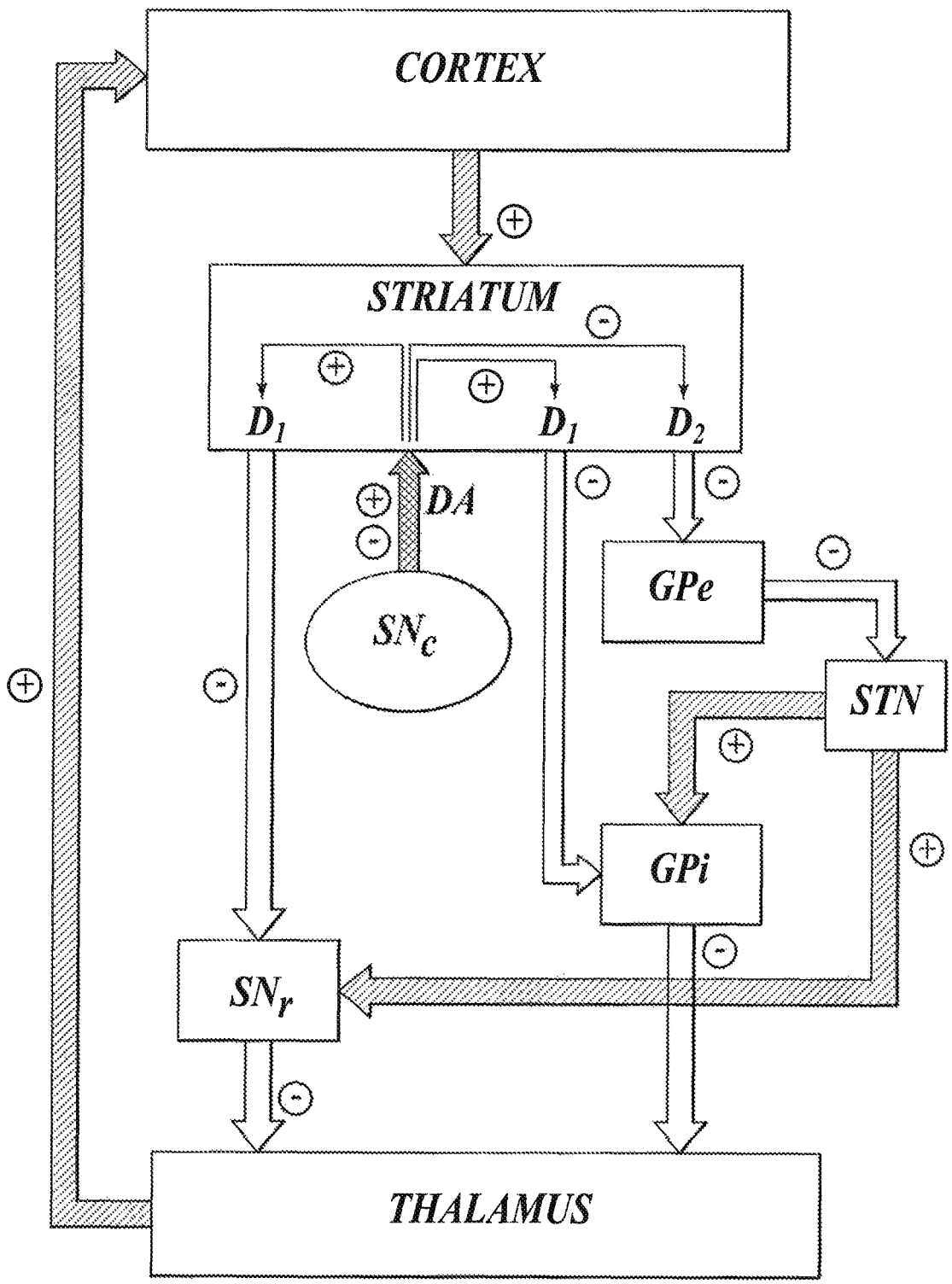
FIG. 1 is a flowchart illustrating the neurotransmission pathway in the basal ganglia in a mid-brain of a healthy mammalian subject, with excitatory pathways labeled "+" with hatched arrows, and with inhibitory pathways labeled "−" with open arrows.

The present invention is based upon the surprising discovery by the present inventors that selective inhibitors of the type 7 cyclic nucleotide phosphodiesterase (PDE7) cause a striking improvement in motor function in the mouse 1-methyl, 4-phenyl, 1,2,3,6-tetrahydropyridine (MPTP) model of Parkinson's disease (PD). Through the use of the MPTP animal model, the present inventors have shown that administration of selective PDE7 inhibitory agents in MPTP-lesioned mice is effective to restore stride length in these animals in a manner comparable to treatment with L-dopa, but at a surprisingly low dosage as compared to the dosage of L-dopa required to achieve an equivalent level of response. Furthermore, the inventors have demonstrated that the combination of suboptimal doses of L-dopa and a selective PDE7 inhibitor, when administered together, provide a greater than additive (i.e., synergistic) effect, again restoring stride length in MPTP-lesioned mice to normal values.

I. Definitions

Unless specifically defined herein, all terms used herein have the same meaning as would be understood by those of ordinary skill in the art of the present invention. The following definitions are provided in order to provide clarity with respect to the terms as they are used in the specification and claims to describe the present invention.

As used herein, the term "neurological movement disorder" refers to a movement disorder characterized by a deficiency or defect in dopamine signaling that is clinically manifested by one or more movement abnormalities associated with the pathology of the movement disorder, such as abnormal involuntary movements, tremor at rest, alterations in muscle tone, difficulty in the initiation of movement (bradykinesia) and/or disturbances in postural stability.

As used herein, the term "Parkinson's Disease" refers to a clinical syndrome marked by four cardinal signs: (1) tremor at rest; (2) rigidity, (3) bradykinesia, and (4) deficiency of postural reflexes.

As used herein, the term "Post-Encephalitic Parkinsonism" refers to Parkinsonism occurring after and presumably as a result of encephalitis.

As used herein, the term "Parkinsonism" refers to any of a group of neurological disorders similar to Parkinson's disease, marked by the four cardinal signs of Parkinson's disease: tremor at rest, muscular rigidity, bradykinesia and deficiency in postural reflexes.

As used herein, the term "bradykinesia" or "akinesia" refers to a paucity of automatic or spontaneous movement.

As used herein, the term "hyperkinesia" or "dyskinesia" refers to excessive or abnormal involuntary movement.

As used herein, the term "tremor" refers to relatively rhythmic oscillatory movements, which can, for example, result from alternating contractions of opposing muscle groups (e.g., Parkinson's tremor).

As used herein, the term "dystonia" refers to involuntary movements with sustained contractions at the end of the movement.

As used herein, the term "Dopamine-responsive Dystonia" refers to a neurological movement disorder in which sustained muscle contractions cause twisting and repetitive movements or abnormal postures, and which can be alleviated by agents that increase dopamine levels or enhance signaling through dopaminergic pathways. Such a disorder may be associated with Parkinson's disease, juvenile parkinsonism, progressive supranuclear palsy, cortical basal ganglionic degeneration, certain types of multiple system atrophy, or DYT3 X-linked recessive dystonia-parkinsonism.

As used herein, the term "Periodic Limb Movement in Sleep" (PLMS) refers to a condition in which the patient's legs move or twitch involuntarily during sleep. If these movements result in sleep disturbance, this syndrome is referred to as Periodic Limb Movement Disorder (PLMD).

As used herein, the term "Restless Leg(s) Syndrome" (RLS) refers to a neurological disorder of uncertain pathophysiology that is characterized by aching, burning, crawling, or creeping sensations of the legs that occur especially at night, usually when lying down (as before sleep) and cause a compelling urge to move the legs and that is often accompanied by difficulty in falling or staying asleep and by involuntary twitching of the legs during sleep.

As used herein, the term "Shy-Drager Syndrome" refers to a degenerative neurological disorder characterized by orthostatic hypotension, autonomic dysfunction, bladder dysfunction, and Parkinson's-like deficits in movement.

As used herein, the term "dopaminergic agent" refers to an agent which functions to enhance or replicate the effects mediated by dopamine in the central nervous system, including dopamine (if a clinically effective method of delivery should be developed), dopamine precursors, such as L-dopa, dopamine cofactors, inhibitors of enzymes that metabolize dopamine, other dopamine receptor agonists and precursor compounds that are metabolically converted to a dopamine receptor agonist, as well as dopamine reuptake inhibitors.

As used herein, the term "dopamine receptor agonist" refers to any molecule that causes the activation of one or more of the subtypes of the dopamine receptor protein family.

As used herein, the term "molecular target(s) known to be involved with the pathology of Parkinson's disease" includes catechol-O-methyltransferase (COMT), monamine oxidase B (MAO-B), dopamine transporters (DAT), tyrosine hydroxylase, dopamine receptors, adenosine $A_{2A}$ receptors, and gabapentin receptors.

As used herein, the term "molecular target(s) known to be associated with the dopamine signaling pathway" includes catechol-O-methyltransferase (COMT), monamine oxidase B (MAO-B), dopamine transporters (DAT), tyrosine hydroxylase, dopa decarboxylase, dopamine receptors, N-methyl D-aspartate (NMDA) receptors, muscarinic acetylcholine receptors, gamma amino butyric acid (GABA) receptors, adenylyl cyclase, protein kinase A (PKA), dopamine and cyclic AMP-regulated phosphoprotein of molecular weight 32,000 (DARPP32), and protein phosphatase-1.

As used herein, the term "treatment" includes symptomatic therapy to lessen, alleviate, or mask the symptoms of the disease or disorder, as well as therapy for preventing, lowering, stopping, or reversing the progression of severity of the condition or symptoms being treated. As such, the term "treatment" includes both medical therapeutic treatment of an established condition or symptoms and/or prophylactic administration, as appropriate.

As used herein, the term "treating a movement abnormality associated with the pathology of a neurological movement disorder" refers to reversing, alleviating, ameliorating, or inhibiting one or more movement abnormalities associated with the neurological movement disorder.

As used herein, the term "treating a neurological movement disorder" includes: (1) treating a movement abnormality associated with the pathology of a neurological movement disorder; and/or (2) treating a neurological movement disorder As used herein, the term "treating a neurological disorder" includes: (1) treating a movement abnormality associated with the pathology of a neurological disorder; and/or (2) treating a neurological disorder As used herein, the term "treating" also encompasses, depending on the condition of the subject in need thereof, preventing the neurological movement disorder or preventing the movement abnormality associated with the pathology of the neurological movement disorder or preventing the neurological disorder or preventing the movement abnormality associated with the pathology of the neurological disorder, including onset of the movement abnormality or of any symptoms associated therewith, as well as reducing the severity of the movement abnormality, or preventing a recurrence of a movement abnormality.

As used herein the term "PDE7" is used generically to refer to all translation products coded by transcripts of either or both of these two genes (PDE7A and/or PDE7B).

As used herein, the term "PDE7 inhibitory agent" refers to an agent, such as a chemical compound, a peptide, or a nucleic acid molecule, that directly or indirectly inhibits or blocks the phosphodiesterase activity of PDE7A, PDE7B, or PDE7A and PDE7B. In some cases, the agent may bind or interact directly with PDE7 protein. An agent that binds to PDE7 may act to inhibit or block the PDE7 activation by any suitable means, such as by inhibiting the binding of cAMP or substrate ligand with PDE7. In other cases, the PDE7 inhibitory agent may inhibit PDE7 activity indirectly, such as by decreasing expression of the PDE7 protein. In some cases, the PDE7 inhibitory agent may inhibit PDE7 activity by altering the cellular distribution of PDE7, for example, by interfering with the association between PDE7 and an intracellular anchoring protein.

As used herein, the term "mammalian subject" includes all mammals, including without limitation humans, non-human primates, dogs, cats, horses, sheep, goats, cows, rabbits, pigs, and rodents.

II. The Use of PDE7 Inhibitory Agents to Treat a Movement Abnormality Associated with the Pathology of a Neurological Movement Disorder The dopaminergic system is strongly implicated in the regulation of locomotor activity and movement in general. See, e.g., Tran, A. H., et al., *PNAS* 102:2117-2122, 2005; Tran, A. H., et al., *PNAS* 99:8986-8991, 2002. For example, evidence shows that a dopaminergic dysfunction plays a critical role in Parkinson's disease, Parkinsonism, Restless Leg(s) Syndrome ("RLS"), Periodic Limb Movement Disorder (PLMD), Periodic Limb Movement in Sleep ("PLMS"), and other movement disorders. In Parkinson's disease there is a deficiency of dopamine in the striatum, which results from a loss of pigmented neurons in the substantia nigra and locus ceruleus with corresponding loss of their dopamine and norepinephrine neurotransmitters. In postencephalitic Parkinsonism, the midbrain is affected, with loss of substantia nigra neurons. Wyngaarden and Smith, *Cecil Textbook of Medicine*, 17th Ed. "Neurological and Behavioral Disease Section 5: The Extrapyramidal Disorders: Parkinsonism," 1985.

It is thought that the relatively selective dopamine depletion in the striatum and other basal ganglia results in increased and disordered discharge and synchronization in motor areas of the basal ganglia-thalamocorticol motor loops. Wichmann and Delong, *Neuropsychopharmacology: The Fifth Generation of Progress*, Chapter 122, "Neurocircuitry of Parkinson's Disease," 2002.

The basal ganglia serves as a major input to the pyramidal tract motor system. The basal ganglia comprise five paired nuclei including: the caudate nucleus, putamen, pallidum, subthalamic nucleus, and substantia nigra. The subthalamic nucleus is in the diencephalon. The substantia nigra is located in the midbrain. The caudate nucleus, putamen, and pallidum lie within the cerebral hemispheres and are collectively referred to as the corpus striatum. The caudate and putamen are considered collectively as the striatum, which serves as the main site of neural input into the basal ganglia. The striatum receives afferents from all parts of the cerebral cortex and from the nucleus centrum medianum of the thalamus. The major output of the striatum is to the pallidum and the zona reticulata portion of the substania nigra. The dorsal part of the substantia nigra sends efferents to the striatum (the dopaminergic nigrostriatal pathway), and the ventral part of the substantia nigra receives fibers from the striatum.

FIG. 1 illustrates the neurotransmission pathway in the basal ganglia in the mid-brain of a healthy mammalian subject with excitatory pathways labeled "+" with hatched arrows, and with inhibitory pathways labeled "−" with open arrows. As shown in FIG. 1, neural pathways connect the output pathways of the basal ganglia, a group of functionally related subcortical nuclei that include the external portion of the globulus pallidus ("GPe"), the internal portion of the globulus pallidus ("GPi"), the substantia nigra pars compacta ("SNc"), and the substantia nigra pars reticulata ("SNr") to the striatum. FIG. 1 also illustrates the pathways connecting the subthalamic nucleus ("STN") to the GPe, the GPi and the SNr. As shown in FIG. 1, in a healthy subject, Dopamine ("DA") from dopamine producing cells in the SNc sends an excitatory signal to the dopamine D1 receptors ("D1"), which, once activated, send an inhibitory signal to the SNr and an inhibitory signal to the GPi. As further shown in FIG. 1, DA from dopamine producing cells in the SNc also sends an inhibitory signal to the dopamine D2 receptors ("D2"), which inhibits the D2 receptors from sending an inhibitory signal to the GPe.

The prominent pathologic feature of Parkinson's disease ("PD") is the degeneration of dopaminergic neurons in the substantia nigra pars compacta (SNc) that project to the striatum. Formo, L. S., *J. Neuropathol Exp Neurol* 55:259-272, 1996. In the early stages of Parkinson's disease, it has been determined that dopamine depletion is greatest in the sensorimotor territory of the striatum, consistent with the early manifestation of motor dysfunction. Kish, S. J., et al., *N. Engl. J. Med.* 318:876-880, 1988.

In PD and Parkinsonism diseases, dopamine producing cells in the SNc are lost, leading to a deficit in dopaminergic signaling to the striatum. Because DA usually activates the inhibitory striatal output to the SNr via D1 receptors in a healthy subject (as shown in FIG. 1), this pathway is attenuated in PD. Conversely, because DA inhibits the inhibitory striatal output to the GPe via D2 receptors in a healthy subject (as shown in FIG. 1), this pathway is augmented in PD. Therefore, a deficit in dopaminergic signaling to the striatum in PD has the net effect of causing net inhibition of the excitatory pathway from the thalamus to the cortex.

Cyclic adenosine monophosphate (cAMP) is a second messenger that mediates the biological response of cells to a wide range of extracellular stimuli. When the appropriate agonist binds to a specific cell surface receptor, adenylyl cyclase is activated to convert adenosine triphosphate (ATP) to cAMP. It is theorized that the agonist induced actions of cAMP within the cell are predominately mediated by the action of cAMP-dependent protein kinases. The intracellular actions of cAMP are terminated by either transporting the nucleotide outside of the cell, or by enzymatic cleavage by cyclic nucleotide phosphodiesterases (PDEs), which hydrolyze the 3'-phosphodiester bond to form 5'-adenosine monophosphate (5'-AMP), which is an inactive metabolite. Therefore, the intracellular enzyme family of PDEs regulates the level of cAMP in cells.

Figure 2A:
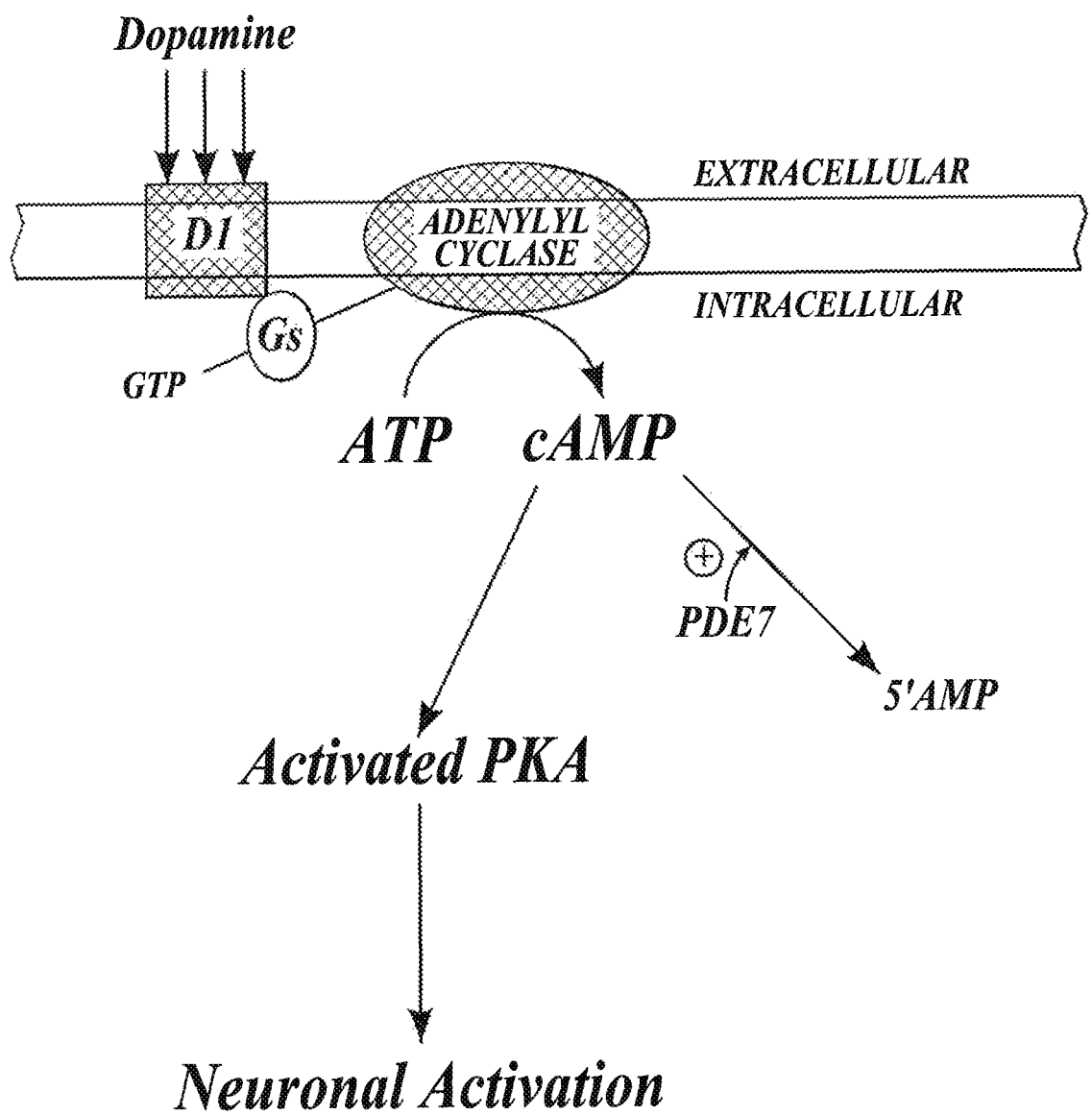
FIG. 2A illustrates a proposed model of the dopamine receptor activated pathway in a healthy subject, illustrating the new discovery that the dopamine receptor activated intracellular signaling pathway is downregulated or antagonized by PDE7, which hydrolyzes cAMP to its 5' monophosphate (5'AMP)

FIG. 2A illustrates a proposed model of the dopamine receptor activated pathway in a healthy subject. As shown in FIG. 2A, in healthy subjects Dopamine (DA) (depicted as three arrows) that is produced by the dopaminergic neurons in the substantia nigra pars compacta (SNc), binds to and activates the Dopamine D1 receptor which leads to adenylyl cyclase activation and increased cAMP levels. cAMP activates protein kinase A ("PKA"), which modulates phosphorylation of downstream elements in intracellular signaling pathways, leading to neuronal activation. As shown in FIG. 2A, it is theorized that the dopamine receptor activated intracellular signaling pathway is downregulated or antagonized by PDE7, which hydrolyzes cAMP to its 5' monophosphate (5'AMP).

Figure 2B:
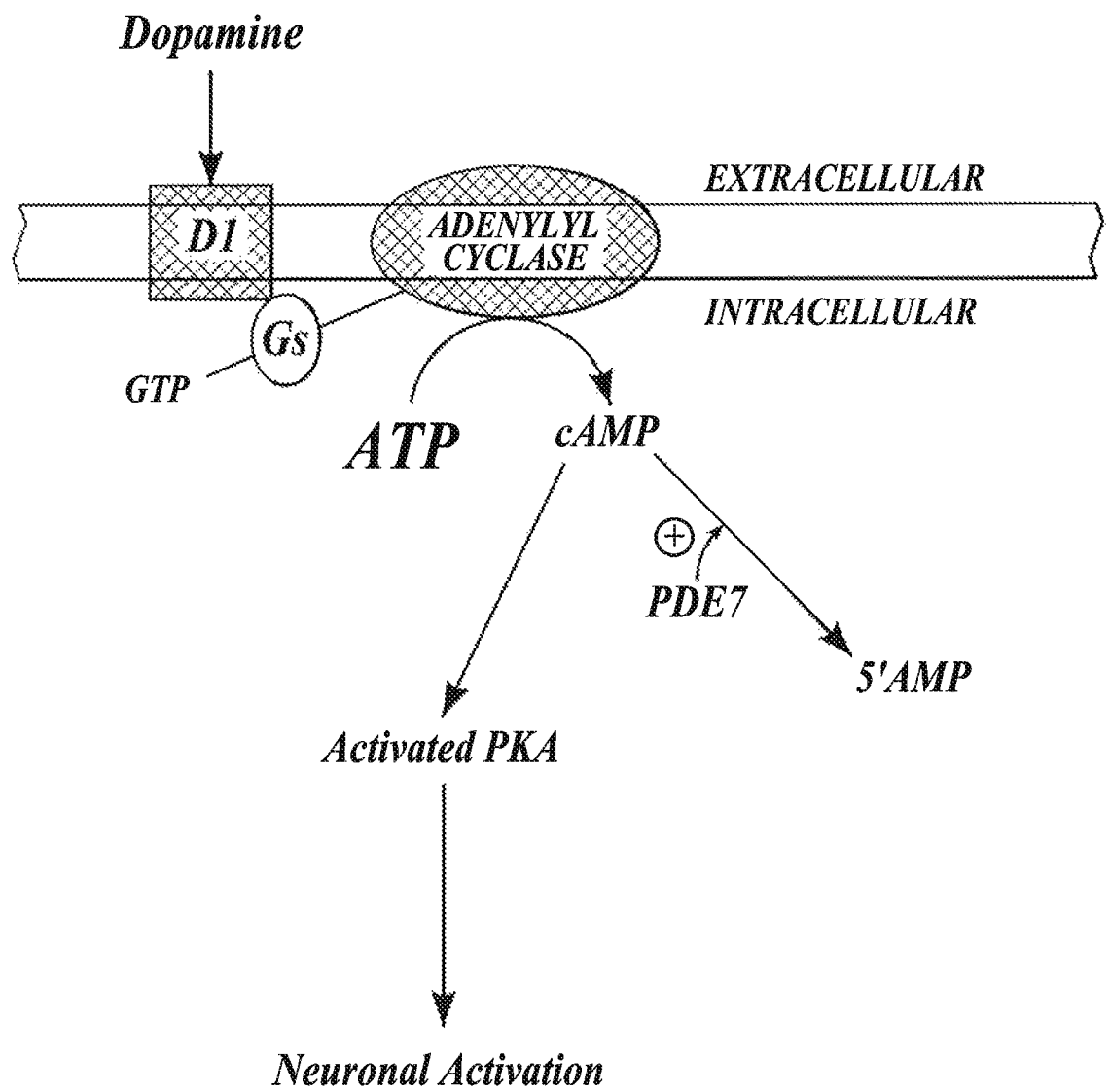
FIG. 2B illustrates a model proposed by the present inventors of the dopamine receptor activated pathway in an untreated subject with Parkinson's disease (PD), showing that the reduced amount of dopamine receptor activated intracellular signaling pathway is further downregulated or antagonized by PDE7, which hydrolyzes cAMP to its 5' monophosphate (5'AMP), leading to low levels of activated PKA and reduced neuronal activation as compared to a healthy subject.

FIG. 2B illustrates a proposed model of the dopamine receptor activated pathway in an untreated subject with Parkinson's disease (PD). As shown in FIG. 2B, in the PD subject a reduced amount of dopamine (DA) (depicted as one arrow as compared to three arrows in the healthy subject) is available for binding to the dopamine receptor (D1) because, as described with reference to FIG. 1, dopamine producing cells in the SNc are lost, leading to a deficit in dopaminergic signaling to the striatum. The reduced level of DA binds to and activates Dopamine D1 receptor to a lesser degree in the PD subject, which leads to minimal adenylyl cyclase activation and an attenuated increase in cAMP levels. As a result, the degree of activation of protein kinase A ("PKA") is less, which in turn leads to less phosphorylation of downstream elements in intracellular signaling pathways, and a lower degree of neuronal activation. As shown in FIG. 2B, it is theorized that the reduced amount of dopamine receptor activated intracellular signaling pathway is further downregulated or antagonized by PDE7, which hydrolyzes cAMP to its 5' monophosphate (5'AMP), leading to low levels of activated PKA and reduced neuronal activation as compared to a healthy subject.

Figure 2C:
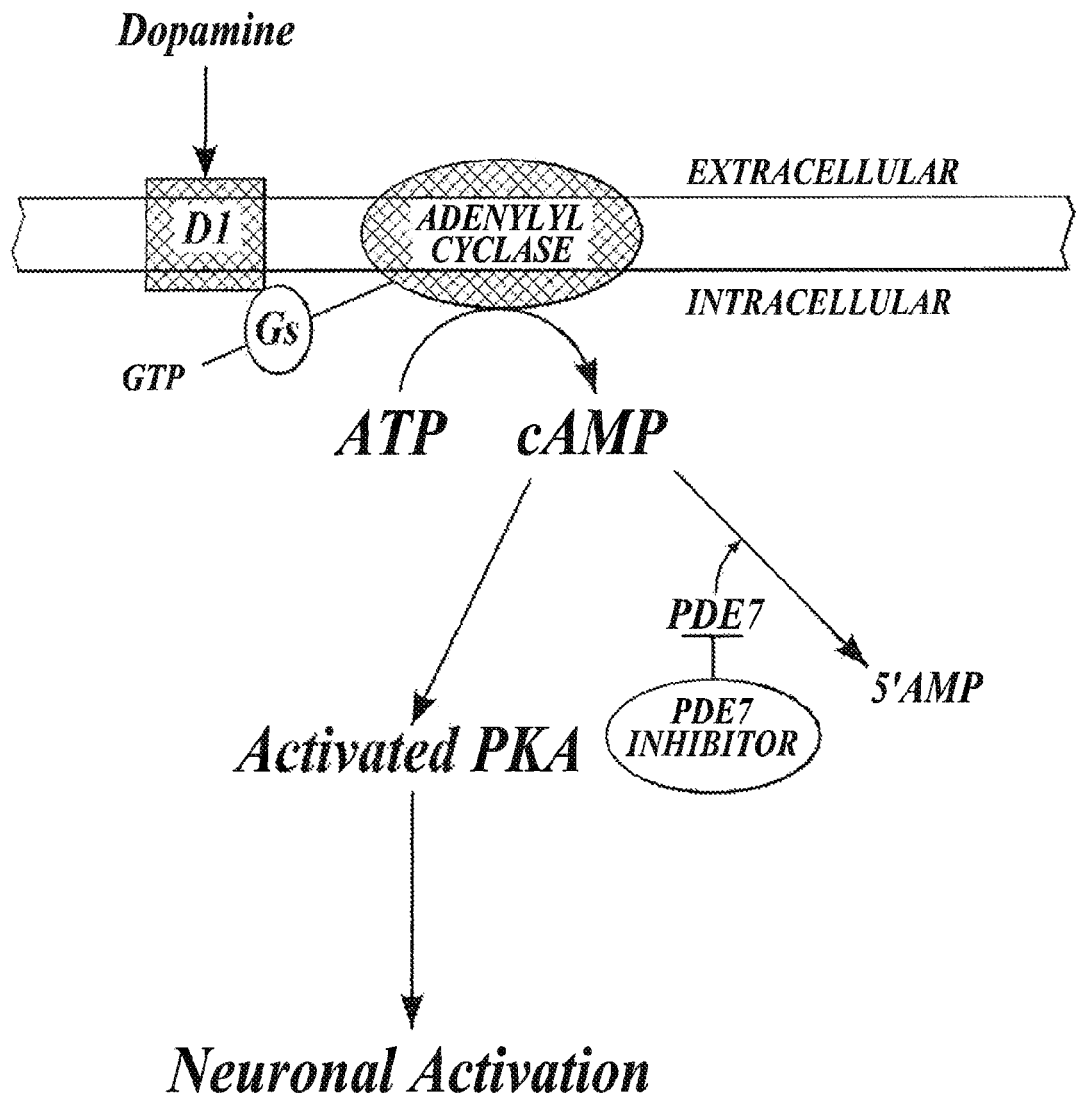
FIG. 2C illustrates a model proposed by the present inventors of the dopamine receptor activated pathway in a subject with Parkinson's disease (PD) treated with a PDE7 inhibitory agent, showing that the presence of a PDE7 inhibitory agent that is effective to inhibit PDE7 enzymatic activity blocks the hydrolysis of cAMP, effectively increasing the intracellular cAMP levels, activating protein kinase A ("PKA"), which modulates phosphorylation of downstream elements in intracellular signaling pathways, leading to an increase in neuronal activation in accordance with various embodiments of the methods of the invention.

FIG. 2C illustrates a proposed model of the dopamine receptor activated pathway in a subject with Parkinson's disease (PD) treated with a PDE7 inhibitory agent. As shown in FIG. 2C, in the PD subject a reduced amount of dopamine (DA) (depicted as one arrow as compared to three arrows in the healthy subject) is available for binding to the dopamine receptor (D1) because, as described with reference to FIG. 1, dopamine producing cells in the SNc are lost, leading to a deficit in dopaminergic signaling to the striatum. The reduced level of DA binds to and activates Dopamine D1 receptor to a lesser degree in the PD subject, which leads to minimal adenylyl cyclase activation and an attenuated increase in cAMP levels. However, as further shown in FIG. 2C, the presence of a PDE7 inhibitory agent that is effective to inhibit PDE7 enzymatic activity blocks the hydrolysis of cAMP, thereby increasing the intracellular cAMP levels, allowing a more normal degree of activation of protein kinase A ("PKA"), which modulates phosphorylation of downstream elements in intracellular signaling pathways, leading to an increase in neuronal activation.

In support of the dopamine signaling model shown in FIGS. 2A-2C, the present inventors have discovered that administration of a PDE7 inhibitory agent that inhibits the enzymatic activity of PDE7 results in improvement of a movement abnormality associated with the pathology of a movement disorder, such as Parkinson's disease. The data presented herein demonstrate that PDE7 inhibitors are effective to restore limb movement, as measured by paw stride length, in an MPTP-treated mouse, and that synergistic effects are observed when PDE7 inhibitors are combined with L-dopa in the MPTP mouse model. Based on the surprising discovery made by the present inventors, it is believed that PDE7 has a role in post-synaptic dopamine signaling in the brain, specifically in areas known to be associated with locomotion.

In addition to Parkinson's disease, abnormal function of the basal ganglia has also been implicated in a variety of neurological disorders with movement abnormalities. Such neurological disorders include restless leg(s) syndrome (Hening, W., et al., *Sleep* 22:970-999, 1999). Therefore, based on the studies described herein, it is believed that a PDE7 inhibitory agent will have a therapeutic effect on such neurological movement disorders.

Therefore, while not wishing to be bound by theory, it is believed that PDE7 inhibitory agents may be useful to treat neurological disorders characterized by abnormal function of the basal ganglia, such as a deficiency in dopamine receptor signaling, for example, Parkinson's disease, Post-encephalitic Parkinsonism, Drug-induced Parkinsonism, Dopamine-Responsive Dystonia, Shy-Drager Syndrome, Periodic Limb Movement Disorder (PLMD), Periodic Limb Movements in Sleep (PLMS), and Restless Leg(s) Syndrome (RLS) by inhibiting PDE7 activity, and thereby preventing degradation of cAMP in the basal ganglia. It is therefore believed that PDE7 inhibitory agents may be useful to treat these and other neurological movement disorders and neurological disorders characterized by movement abnormalities that are currently treated with L-dopa, other dopamine agonists or precursors or other dopaminergic agents.

In some aspects of the invention, PDE7 inhibitors are used to treat a movement abnormality associated with the pathology of a neurological disorder, whether or not such disorder is associated with dopamine signaling defect of deficiency, wherein such inhibition of PDE7 enzymatic activity is the principal therapeutic mode of action of the PDE7 inhibitor in the treatment of the movement abnormality.

In some embodiments, the invention provides methods of treating a movement abnormality associated with the pathology of a neurological movement disorder comprising administering to a patient in need thereof an amount of a PDE7 inhibitory agent effective to inhibit the enzymatic activity of PDE7, wherein such inhibition of PDE7 enzymatic activity is the principal therapeutic mode of action of the PDE7 inhibitor in the treatment of the movement abnormality. In some embodiments, the invention provides methods of ameliorating the symptoms of a movement disorder, including but not limited to a dopamine receptor intracellular signaling pathway disorder, comprising administering a PDE7 inhibitory agent that inhibits the enzymatic activity of PDE7. In some embodiments, the neurological movement disorder is treatable with a dopamine receptor agonist or a precursor of a dopamine receptor agonist.

Parkinson's Disease

Parkinsonism is a clinical syndrome consisting of four cardinal signs: (1) tremor at rest; (2) rigidity, (3) bradykinesia, and (4) deficiency of postural reflexes. Bradykinesia accounts for the majority of Parkinsonian symptoms and signs. Parkinsonism can be categorized into the following etiologic groups: the primary disorder referred to as Parkinson's disease, secondary, acquired Parkinsonism (due to exposure to drugs or toxins, previous strokes, or encephalitis), and "Parkinsonism-plus" syndrome (impaired ocular movements, orthostatic hypotension, cerebellar ataxia or dementia in a Parkinsonian patient).

Lesions of the substantia nigra with resulting loss of dopamine in the striatum result in the bradykinetic syndrome of Parkinsonism. In Parkinson's disease, there is a loss of pigmented neurons in the substantia nigra and locus ceruleus with subsequent loss of their dopamine and norepinephrine neurotransmitters.

Animal models of PD rely heavily on the fortuitous discovery that systemically administered MPTP (1-methyl-4-phenyl-1,2,3,6-tetrahydropyridine) causes specific neuronal cell death in the substantia nigra of humans, monkeys, and rodents (Jakowec, M. W., et al., *Comp. Med.* 54(5):497-513, 2004). The pattern of cell death is reminiscent of that seen in PD patients at the time of autopsy. Commonly used animal models for Parkinson's disease include a monkey MPTP model, a rat 6-OHDA model, and a mouse MPTP model. As described in Examples 5-7 herein, the MPTP lesioned mouse model of PD can be used to evaluate the efficacy of PDE7 inhibitory agents useful in the method of the invention to reduce or diminish the alterations induced by MPTP on their stride length, grid step length, and grid foot faults (Tillerson, J. L., et al., *Exp. Neurol.* 178(1):80-90, 2002).

As demonstrated in Examples 5-7, PDE7 inhibitory agents are effective to restore limb movement in an MPTP-treated mouse. Although current approaches to treating Parkinson's disease generally involve treatment with dopamine receptor agonists, the methods of the present invention are directed to inhibition of PDE7 phosphodiesterase activity in a subject with diminished dopamine signaling in order to increase cAMP levels, thereby leading to increased PKA activity. It is theorized that inhibitors of PDE7 may have advantages over current PD drugs or reduce the required levels of such drugs. For example, chronic use of L-dopa, the most common PD drug, causes severe dyskinesia (Bezard, E., et al., *Nat. Rev. Neurosci.* 2(8):577-88, 2001). Any PD drug alternative to L-dopa may avoid this serious side effect.

As further demonstrated in Examples 5-7, the combination of PDE7 inhibitory agent(s) and L-dopa, a dopamine receptor agonist, provides a synergistic effect, leading to even greater improvement in limb movement in an MPTP-treated mouse. A drug used in conjunction with L-dopa that allows for the lowering of the dose of L-dopa, such as a PDE7 inhibitory agent, may delay the onset of dyskinesia. Furthermore, because the increased levels of dopamine resulting from L-dopa therapy may increase oxidative damage to substantia nigra pars compacta neurons, an agent such as a PDE7 inhibitor that allows for the lowering of the dose of L-dopa may delay the progression of the disease. Accordingly, the PDE7 inhibitor(s) of the present invention may be administered in conjunction with L-dopa, other dopamine receptor agonist(s), dopamine receptor agonist precursor(s) or other dopaminergic agent(s), given in a combination dosage form, given concurrently (i.e., at the same time), or given sequentially (e.g., in rotation).

Restless Leg(s) Syndrome (RLS)

Restless leg(s) syndrome (RLS) is a common neurologic condition that also involves dopamine systems. RLS is a sensory-motor disorder for which the major mandatory criteria for diagnosis are: (1) an urge to move the legs, usually associated by an uncomfortable sensation in the limbs, (2) a worsening of symptoms during rest or inactivity periods, (3) an improvement of symptoms by movement; and (4) an appearance or worsening of symptoms during evening or night. Allen, R. P., et al., *Sleep Med* 4:101-119, 2003. Supportive criteria, which are common but not essential for RLS diagnosis, include the presence of periodic limb movements in sleep (PLMS), which are involuntary movements of the lower limbs during sleep, often occurring in sequences of at least 4, with an inter-movement interval of 5-90 seconds. (Baier, et al., *J. Neurological Sciences* 198:71-77, 2002). Other supportive criteria for diagnosis of RLS are responsiveness to low doses of dopaminergic treatments. Allen, R. P., et al., supra. RLS and PLMS are highly represented in patients affected by Parkinson's disease and other forms of Parkinsonism. Poewe, W., et al., *Neurology* 63:S12-S16, 2004.

It has been determined that the pathogenic mechanism of RLS is characterized by a neurological dysfunction of the dopaminergic system. The dopaminergic system has been implicated in RLS by functional imaging studies (Turjanski, N., et al., *Neurology* 52:932-37, 1999), and by the strong efficacy of dopamine-agonist treatment for human RLS and PLMS (Montplaisier, J., et al., *Neurology* 52:938-43, 1999; Trenkwalder, C., et al., *Neurology* 62:1391-97, 2004; and Walters, A. S., et al., *Mov. Disord.* 19:1414-23, 2004). For example, clinical studies with the following drugs used to treat Parkinson's disease have also shown efficacy for RLS: (1) DA agonists: Sinemet™ (L-dopa, carbidopa), Stalevo™ (L-dopa, carbidopa, entacapone), Permax™ (pergolide), Parlodel™ (bromocriptine); (2) D2, D3, D4 agonists: Mirapex™ (pramipexole), Requip™ (ropinirole); (3) mACh antagonists: Cogentin™ (benztropine), Artane™ (trihexyphenidyl); (4) MAO inhibitors: Eldepryl™ (selegiline), and (5) COMT inhibitor Tasmar™ (tolcapone). See e.g., Hentz J. G. et al., Mov Disord. 15(2): 324-7 (2000); Walters A. S. et al., Ann Neurol 24(3):455-8 (1988); Trenkwalder C. et al., Neurology 62(8): 1391-7 (2004); Polo O. et al., Clin Neuropharmacol 31(1):61 (2007); Kohnen R. Sleep 22(8):1073-81 (1999); and Shapiro C. Mov Disord 17(2): 398-401 (2002).

The MPTP mouse model described herein is widely known as a model of Parkinson's disease, but it can also represent disorders that are characterized by dopamine insufficiency or those that respond to dopamine receptor agonists (e.g., restless leg(s) syndrome). Therefore, the response observed in the MPTP-treated animals, as demonstrated in Examples 5-7 supra, can be reasonably considered to be transferable to Restless Leg(s) Syndrome, and other movement disorders characterized by dopamine insufficiency, such as Dopamine-Responsive Dystonia, Shy-Drager Syndrome, Periodic Limb Movements in Sleep (PLMS), and Tourette's syndrome.

Periodic Limb Movement Disorder (PLMD)/Periodic Limb Movements in Sleep (PLMS)

Periodic Limb Movement Disorder (PLMD) is a syndrome characterized by sleep disturbance secondary to periodic limb movement during sleep (PLMS). While commonly associated with RLS (Manconi M. et al., *Sleep Med.* 8(5):491-7 (2007); Haba-Rubio J. et al., *Neurophysiol Clin.* 33(4):180-4 (2003)), PLMD can also be observed in the setting of spinal cord injury (De Mello M. T. et al., *Spinal Cord.* 42(4):218-21 (2004)), narcolepsy (Hornyak M. et al., *Sleep Med. Rev.* 10(3):169-77 (2006)), other sleep disorders (Horyak, 2006 supra, Saletu M. et al., *Hum Psychopharmacol.* 16(2):177-187 (2001)), or uremia (Walker S. L., et al., *Sleep* 19(3):214-8 (1996)).

PLMD can occur in the absence of an identifiable primary pathology (Vetrugno R. et al., Neurol Sci. 28 Suppl 1:S9-S14 (2007), Horyak, 2006 supra). In all these settings, an underlying dysfunction in dopamine signaling is indicated by the clinical improvement observed with L-dopa (Wolkove N. et al., *CMAJ.* 176(10):1449-54 (2007), De Mello M. T. et al. 2004, supra) or dopaminergic agonists (Manconi M. et al., *Sleep Med.* 8(5):491-7 (2007); Haba-Rubio J. et al., *Neurophysiol Clin.* 33(4):180-4 (2003), Saletu M. et al., *Hum Psychopharmacol.* 16(2):177-187 (2001)). Therefore, because PLMD and PLMS are characterized by a dysfunction in dopamine signaling and are treatable with L-dopa, it is believed that the use of PDE7 inhibitory agents may be useful to treat PLMD and/or PLMS when administered to a subject in need thereof either alone, or in conjunction with L-dopa or other dopamine receptor agonist(s), either concurrently or sequentially. The aged rat animal model, described by Baier P. C. et al., *J Neurol Sci.* 15; 198(1-2):71-7 (2002), may be used to assess the efficacy of PDE7 inhibitory agents for treatment of PLMS.

Multiple System Atrophy Including Shy-Drager Syndrome

Multiple System Atrophy is a group of progressive neurodegenerative disorders that include Shy-Drager syndrome, olivopontocerebellar atrophy, and striatonigral degeneration. Characteristic symptoms include Parkinson's-like motor abnormalities, orthostatic hypotension, bladder dysfunction, and cerebellar dysfunction (Vanacore N., *J Neural Transm.* 112(12):1605-12 (2005). A pathological similarity with Parkinson's disease is suggested by the finding of alpha synuclein deposits in autopsy specimens from both diseases (Yoshida M., *Neuropathology* 27(5):484-93 (2007); Wenning G. K. et al., *Acta Neuropathol.* 109(2):129-40 (2005); Moore D. J. et al., *Annu Rev Neurosci.* 28:57-87 (2005). L-dopa is used commonly in therapy to alleviate parkinsonian symptoms with a response rate estimated between 33% and 60% (Gilman S. et al., J Neural Transm. 112(12):1687-94 (2005); Colosimo C. et al., J Neural Transm. 112(12):1695-704 (2005)). Therefore, because some multiple system atrophy disorders (including Shy-Drager syndrome) are treatable with L-dopa, it is believed that the use of PDE7 inhibitory agents may be useful to treat those types of multiple system atrophy disorders, such as Shy-Drager syndrome, that are therapeutically responsive to treatment with dopaminergic agents, when administered to a subject in need thereof either alone, or in conjunction with L-dopa, dopamine receptor agonist(s) or other dopaminergic agents, either concurrently or sequentially. It is known that the MPTP model is a model that is predictive for Multiple System Atrophy, including Shy-Drager syndrome. Stefanova N. et al., *Trends Neurosci.* 28(9):501-6 (2005). The animal model of multiple system atrophy, as described by Stefanova N. et al., *Trends Neurosci.* 28(9):501-6 (2005) may be also be used to assess the efficacy of PDE7 inhibitory agents for treatment of multiple system atrophy disorders, such as Shy-Drager syndrome.

Therefore, based on the studies described herein, it is believed that the use of PDE7 inhibitory agents may be useful to treat multiple system atrophy disorders that are therapeutically responsive to treatment with dopaminergic agent(s), including Shy-Drager syndrome, when administered to a subject in need thereof either alone, or in conjunction with a dopamine receptor agonist(s), either concurrently or sequentially.

Tourette's Syndrome

Tourette's syndrome is a neurodevelopmental disorder in which the prominent symptoms are stereotyped movements and vocalizations or "tics" (Müller N. *Dialogues Clin Neurosci.* 9(2):161-71 (2007); Leckman J F, et al *J Child Neurol.* 21(8):642-9 (2006)). There is anatomical and neuroimaging evidence for the involvement of the dopaminergic system in the basal ganglia in this disease (Müller N. Dialogues Clin Neurosci. 9(2):161-71 (2007)). While anti-psychotics, which block D2 dopamine receptors, are one of the drug classes used to treat disabling tics in Tourette's syndrome, a double-blind crossover clinical study with the dopamine receptor agonist pergolide demonstrated that this drug significantly improved tics (Gilbert D L, et al *Neurology.* 28; 54(6):1310-5 (2000)).

Therefore, because Tourette's syndrome is characterized by a dysfunction in dopamine signaling and are treatable with the dopamine agonist pergolide, it is believed that the use of PDE7 inhibitory agents may be useful to treat Tourette's syndrome when administered to a subject in need thereof either alone, or in conjunction with dopamine receptor agonist(s) or other dopaminergic agent(s), either concurrently or sequentially.

Huntington's Disease

Huntington's disease is a progressive, genetically determined, and fatal neurological disease that is characterized by jerking movements (chorea) that increase in severity and, in combination with cognitive impairments, eventually lead to complete immobility and loss of function in activities of daily living. The selective loss of medium spiny neurons in the striatum is a prominent pathological feature and is believed to be a primary cause of choreic movements (Standaert D G and Young A B in Goodman and Gilman's Pharmacological Basis of Therapeutics 10$^{th}$ ed McGraw-Hill New York 2001; Chapter 22, pp 562-564). There are no drugs that are useful in slowing the rate of progression of Huntington's and very few that are consistently useful in the amelioration of symptoms. A recent review cited anti-psychotic agents such as haloperidol as "possibly useful" in the treatment of choreic movements. The same review stated that L-dopa and the dopamine agonist pramipexole were "possibly useful" for the treatment of rigidity (Bonelli R M et al. *Curr Pharm Des.* 12(21):2701-20. (2006)). A few reports suggest that L-dopa or pramipexole may be useful in a specific variant (Westphal variant) of Huntington's in which parkinsonian symptoms are prominent (Bonelli R M et al *Clin Neuropharmacol.* 25(1):58-60 (2002); Reuter I, *J Neurol Neurosurg Psychiatry.* 68(2):238-41 (2000)). However, controlled trials have not been performed. Therefore, it is possible that a PDE7 inhibitory compound could be useful in Huntington's patients who are responsive to L-dopa, other dopamine agonists or precursors, or other dopaminergic agents.

Dopamine-Responsive Dystonia:

Dopamine-responsive dystonia (DRD) is an early onset, progressive, and largely genetically determined neurological disease characterized by diffuse rigidity and other Parkinson's-like symptoms. Segawa M et al., *Adv Neurol.* 14:215-33 (1976). Depletion of dopamine in the striatum is observed but nerve terminals are intact. A major cause of DRD is an inherited deficiency in the enzyme GTP cyclohydrolase, the rate-limiting enzyme in the synthesis of tetrahydrobiopterin (Segawa disease), which is in turn an essential co-factor for tyrosine hydroxylase. Ichinose H et al., *J Biol. Chem.* 380 (12):1355-64 (1999). This deficiency leads to the depletion of dopa and dopamine in nigro-striatal terminals. Treatment with L-dopa/carbidopa combinations (e.g., Sinemet) is highly successful and is the standard of care in this disease. Jeon B, *J Korean Med. Sci.* 12(4):269-79 (1997). Because of the responsiveness of this disease to L-dopa and the intactness of the dopamine signaling pathway in medium spiny neurons, it is believed that PDE7 inhibitory compounds of the present invention may also prove to be effective treatments for DRD.

III. PDE7 Inhibitory Agents

Cyclic nucleotide phosphodiesterase type 7 (PDE7) is identified as a unique family based on its primary amino acid sequence and distinct enzymatic activity. The PDE genes identified as PDE7 (PDE7A and PDE7B), code for cAMP-specific PDEs. The biochemical and pharmacological characterization of PDE7 shows a high-affinity cAMP-specific PDE (Km=0.2 μM) that is not affected by cGMP nor by selective inhibitors of other PDEs. The PDE7 enzyme selectively decomposes cAMP and is characterized as an enzyme that is not inhibited by rolipram, a selective inhibitor of PDE4, which is a distinct, cAMP-specific PDE family. Two sub-types have been identified within the PDE7 family, PDE7A (Michael, T., et al., *J Biol. Chem.* 268(17):12925-12932, 1993; Han, P., et al., *J Biol. Chem.* 272(26):16152-16157, 1997) and PDE7B (U.S. Pat. No. 6,146,876; Gardner, C., et al., *Biochem. Biophys. Res. Commun.* 272(1):186-192, 2000; and Saski, T., et al., *Biochem. Biophys. Res. Commun.* 271(3):575-583, 2000). The two gene products exhibit 70% identity in their C-terminal catalytic domains (Hetman J. M., et al., *PNAS* 97(1):472-476 (2000).

PDE7A has three splice variants (PDE7A1, PDE7A2 and PDE7A3); these variants are generated via alternative splicing at both the N- and C-termini (Bloom, T. J., and J. A. Beavo, *Proc. Natl. Acad. Sci. USA.* 93:14188-14192, 1996). The nucleotide sequence of PDE7A, transcript variant 1, is accessible in public databases by the accession number NM_002603. Human PDE7A1 protein (SEQ ID NO: 2, encoded by SEQ ID NO:1) has 456 amino acids and migrates at an apparent molecular weight of 53-55 kDa on reduced SDS-PAGE.

The nucleotide sequence of PDE7A, transcript variant 2, is accessible in public databases by the accession number NM_002604. Human PDE7A2 protein (SEQ ID NO:4, encoded by SEQ ID NO:3) has 424 amino acids.

The PDE7A protein has a region of about 270 amino acids at the carboxy terminal end that displays significant similarity (~23% homology) to the analogous regions of other cAMP-hydrolyzing PDEs. This region serves as the catalytic domain. The amino-terminal region of this protein is divergent from that of other PDEs and presumably mediates the distinctive and regulatory properties unique to this enzyme family.

The nucleotide sequence of human PDE7B is accessible in public databases by the accession number NM_018945, provided as SEQ ID NO:6, encoded by SEQ ID NO:7. Three splice variants of PDE7B have been reported: PDE7B1, PDE7B2 and PDE7B3. PDE7B is published in WO 01/62904, U.S. Pat. No. 6,146,876.

Both PDE7B2 and PDE7B3 possess unique N-terminal sequences. Human PDE7B gene products have an apparent molecular weight of 53-55 kDa on reduced SDS-PAGE (Sasaki, T., Kotera, J., Omori, K., *Biochemical J.* 361:211-220, 2002). As in PDE7A, the PDE7B has a significantly conserved region of about 270 amino acids common to all PDEs at the carboxy terminal, which serves as the catalytic domain. Similar to the PDE7A protein, the amino-terminal region of PDE7B protein is divergent and presumably accounts for the distinctive and regulatory properties unique to the individual PDE families. The PDE7B protein shows homology to other cAMP-dependent PDEs (23%) within the catalytic domain. The PDE7B polypeptide is 61% homologous to PDE7A, according to WO 2004/044196.

PDE7 is also uniquely localized in mammalian subjects relative to other PDE families. PDE7A expression has been detected in the majority of tissues analyzed, including the brain, heart, kidney, skeletal muscle, spleen and uterus (Bloom, et al., *PNAS* 93:14188, 1996). Within the brain, PDE7A is widely distributed in both neuronal and non-neuronal cell populations (Miro, et al., *Synapse* 40:201, 2001). PDE7A's wide expression in the brain, including the basal ganglia and substantia nigra, provides a theoretical basis for a role for PDE7A in motor control as well as other brain functions.

Whereas PDE7A expression is widely distributed in brain tissue, PDE7B brain expression is more restricted and highly enriched in areas linked to motor control, such as the striatum (Reyes-Irisarri, et al, *Neuroscience* 132:1173, 2005). However, despite the presence of PDE7 in the brain tissue, prior to the data disclosed in the present application, there have been no data linking PDE7 with any specific CNS disease, such as Parkinson's disease. Rather, the use of PDE7 inhibitors has been focused on immunological applications based on work demonstrating that PDE7 inhibition with small interfering RNAs (siRNA) could regulate T-cell proliferation. See Rotella, D. P., *Drug Discovery* 2007, 22-23.

Consistent with the dopamine signaling model shown in FIGS. 2A-2C, the expression pattern of PDE7A and PDE7B overlaps that of the dopaminergic system, supporting the theory that PDE7 is involved in the regulation of motor function. Therefore, while not wishing to be bound by theory, it is believed that treating PD by inhibiting PDE7 functions to boost dopamine signaling, which may be an alternative mechanism for treating PD compared to dopamine receptor agonists. It is also believed that a PDE7 inhibitor may be useful as a therapeutic agent for administration in conjunction (i.e., in combination, concurrently or sequentially) with one or more dopamine receptor agonist(s) or other dopaminergic agent(s).

In the practice of the methods of the invention, representative PDE7 inhibitory agents that inhibit the phosphodiesterase activity of PDE7 include: molecules that bind to PDE7 and inhibit the enzyme activity of PDE7 (such as small molecule inhibitors or blocking peptides that bind to PDE7 and reduce enzymatic activity), and molecules that decrease the expression of PDE7 at the transcriptional and/or translational level (such as PDE7 antisense nucleic acid molecules, PDE7 specific RNAi molecules and PDE7 ribozymes), thereby preventing PDE7 from cleaving cAMP. The PDE7 inhibitory agents can be used alone as a primary therapy or in combination with other therapeutics (such as dopamine receptor agonists) as an adjuvant therapy to enhance the therapeutic benefits, as discussed supra.

The inhibition of PDE7 is characterized by at least one of the following changes that occur as a result of administration of a PDE7 inhibitory agent in accordance with the methods of the invention: the inhibition of PDE7-dependent enzymatic cleavage of the 3'-phosphodiester bond in cAMP to form 5'-adenosine monophosphate (5'-AMP) (measured, for example, as described in Example 1), a reduction in the gene or protein expression level of PDE7, measured, for example, by gene expression analysis (e.g., RT-PCR analysis) or protein analysis (e.g., Western blot).

In some embodiments, a PDE7 inhibitory agent is a molecule or composition that inhibits the expression of PDE7A, PDE7B, or both PDE7A and PDE7B, such as an antisense or small inhibitory nucleotide (e.g., siRNA) that specifically hybridizes with the cellular mRNA and/or genomic DNA corresponding to the gene(s) of the target PDE7 so as to inhibit their transcription and/or translation, or a ribozyme that specifically cleaves the mRNA of a target PDE7.

Potency of PDE7 Inhibitory Agents

In one embodiment, a PDE7 inhibitory agent useful in the methods of the invention is a compound that is sufficiently potent to inhibit the enzymatic activity of PDE7 (PDE7A, PDE7B, or PDE7A and PDE7B) at an $IC_{50} \leq 1$ µM, preferably less than or about 0.1 µM. In one embodiment, the PDE7 inhibitory agent is sufficiently potent to inhibit the enzymatic activity of PDE7 (PDE7A, PDE7B, or PDE7A and PDE7B) at an $IC_{50}$ of from about 0.1 to about 500 nM. In one embodiment, the PDE7 inhibitory agent is potent to inhibit the enzymatic activity of PDE7 (PDE7A, PDE7B, or PDE7A and PDE7B) at an $IC_{50}$ of from about 1 to about 100 nM.

Representative methods for determining the $IC_{50}$ for a PDE7 (PDE7A or PDE7B) inhibitory agent are provided in Example 1 herein, and are well known in the art, such as the Scintillation Proximity Assay (SPA) disclosed in Bardelle et al., Anal Biochem 15:275(2):148-55 (1999).

PDE7A or PDE7B Selective Inhibitory Agents

In one embodiment, the PDE7 inhibitor useful in the method of the invention is a PDE7A inhibitory agent. In one embodiment, the PDE7A inhibitory agent is potent to inhibit the enzymatic activity of PDE7A at an $IC_{50}$ of from about 0.1 to about 500 nM. In one embodiment, the PDE7A inhibitor has an $IC_{50}$ of from about 1 to about 100 nM. A suitable assay for determining the $IC_{50}$ for a PDE7A inhibitor uses recombinant human PDE7A2 enzymes expressed in a baculoviral system. This assay method is a modification of the SPA assay reported by Bardelle et al. supra. An exemplary assay for measuring PDE7A inhibition is provided in Example 1.

In some embodiments, the PDE7 inhibitory agent exhibits isozyme-selective activity against PDE7A. A PDE7A selective inhibitory agent reduces PDE7A activity at least two-fold more than PDE7B activity, more preferably at least 10-fold, at least 20-fold, at least 50-fold, or at least 100-fold. In some embodiments, the PDE7A inhibitory agent is an inhibitory agent that is at least 10-fold (such as at least 20-fold, or at least 50-fold or at least 100-fold) more selective for inhibiting PDE 7A activity than for the enzyme activity of any other PDE (PDE1-6, 7B, and 8-11).

In another embodiment, the PDE7 inhibitor useful in the method of the invention is a PDE7B inhibitor. Due to the potential for reduced side effects due to the restricted expression of PDE7B, and high levels of expression in areas of the brain linked to motor control (e.g., the striatum), inhibitors for PDE7B may be useful for treatment of neurological movement disorders such as Parkinson's disease.

In one embodiment, the PDE7B inhibitor has an $IC_{50}$ of from about 0.1 to about 500 nM. In one embodiment, the PDE7B inhibitory agent is sufficiently potent to inhibit the enzymatic activity of PDE7B at an $IC_{50}$ of from about 0.1 to about 500 nM. In one embodiment, the PDE7B inhibitor has an $IC_{50}$ of from about 1 to about 100 nM. Methods for determining the $IC_{50}$ for a PDE7B inhibitor are well known in the art, such as the assays disclosed in Bardelle et al., supra. An exemplary assay for measuring PDE7AB inhibition is provided in Example 1.

In some embodiments, the PDE7 inhibitor exhibits isozyme-selective activity against PDE7B. A PDE7B selective inhibitory agent reduces PDE7B activity at least two-fold more than PDE7A activity, more preferably at least 10-fold, at least 20-fold, at least 50-fold, or at least 100-fold. In some embodiments, the PDE7B inhibitory agent is an inhibitory agent that is at least 10-fold (such as at least 20-fold, or at least 50-fold or at least 100-fold) more selective for inhibiting PDE7B activity than for the enzyme activity of any other PDE (PDE1-6, 7A, and 8-11).

PDE7 Selectivity as Compared to Other PDEs

In some embodiments, the PDE7 inhibitory agent has an $IC_{50}$ for inhibiting PDE1B activity of greater than 5 times (such as at least 10-fold, at least 20-fold, or at least 50-fold or at least 100-fold) the lesser of the $IC_{50}$ for inhibiting PDE7A activity and the $IC_{50}$ for inhibiting PDE7B activity. Stated differently, the PDE7 inhibitor is more potent (by 5 times, 10 times, 20 times, 50 times or 100 times) at inhibiting the activity of PDE7A or PDE7B (whichever PDE7A or PDE7B isozyme upon which the PDE7 inhibitor has the most effect), than it is at inhibiting the activity of PDE1B. For purposes of the present specification, by way of example, this property may be still more simply stated as the PDE7 inhibitor is more potent (by 5 times, 10 times, 20 times, 50 times or 100 times) at inhibiting the activity of PDE7 than it is at inhibiting the activity of PDE1B.

Dual inhibition of both PDE7 and PDE1B may confer additional benefit in the treatment of movement disorders based on a report that deletion of the gene for PDE in mice stimulated the metabolism of dopamine and sensitized the animals to the effects of dopaminergic agonists (Siuciak, et al., Neuropharmacology 53(1): 113-23 (2007)).

In some embodiments, the PDE7 inhibitory agent has an $IC_{50}$ for inhibiting PDE10 activity of greater than 5 times (such as at least 10-fold, or at least 20-fold, or at least 50-fold or at least 100-fold) the lesser of the $IC_{50}$ for inhibiting PDE7A activity and the $IC_{50}$ for inhibiting PDE7B activity. Dual inhibition of both PDE7 and PDE10 may confer additional benefit in the treatment of movement disorders based on a report that selective inhibitors of PDE10 cause an increase in cAMP levels in the striatum (Siuciak J. A. et al., Neuropharmacology 51(2):386-96 (2006)).

In some embodiments, the PDE7 inhibitory agent has an $IC_{50}$ for inhibiting PDE3 activity of greater than 10 times (such as at least 20-fold, at least 50-fold or at least 100-fold) the lesser of the $IC_{50}$ for inhibiting PDE7A activity and the $IC_{50}$ for inhibiting PDE7B activity. This is because the administration of selective inhibitors of PDE3 to patients in heart failure was shown to increase their rate of mortality (Packer M. et al., N Engl J. Med. 325(21):1468-75 (1991)).

In some embodiments, the PDE7 inhibitory agent has an $IC_{50}$ for inhibiting PDE4 activity of greater than 10 times (such as at least 20-fold, at least 50-fold or at least 100-fold) the lesser of the $IC_{50}$ for inhibiting PDE7A activity and the IC50 for inhibiting PDE7B activity. This is because deletion of one of the PDE4 genes in mice has been shown to lead to cardiac myopathy (Lehnart S. E. et al., Cell 123(1):25-35 (2005)).

In some embodiments, the PDE7 inhibitory agent has a half maximally effective dose ("$ED_{50}$") in an in vivo assay of PDE4 inhibition (for example, sedation or inhibition of TNF alpha levels after endotoxin treatment) of greater than 10 times (such as at least 20-fold, at least 50-fold or at least 100-fold) the lesser of the $ED_{50}$ in an in vivo assay of PDE7A and PDE7B inhibition (for example, restoration of stride length in an MPTP-treated animal). In accordance with such embodiments, it has been determined that some compounds having dual PDE4/PDE7 inhibitory activity possess greater selectivity against PDE7 than PDE4 in vivo, as compared to the PDE4/PDE7 selectivity of the compound as determined in an in vitro assay.

In some embodiments, the PDE7 inhibitory agent has an $IC_{50}$ for inhibiting PDE3 activity and PDE4 activity of greater than 10 times (such as at least 20-fold, at least 50-fold or at least 100-fold) the lesser of the $IC_{50}$ for inhibiting PDE7A activity and the IC50 for inhibiting PDE7B activity.

In some embodiments, the PDE7 inhibitory agent has an $IC_{50}$ for inhibiting PDE8 activity of greater than 10 times (such as at least 20-fold, at least 50-fold or at least 100-fold) the lesser of the $IC_{50}$ for inhibiting PDE7A activity and the $IC_{50}$ for inhibiting PDE7B activity.

In some embodiments, the PDE7 inhibitory agent has an $IC_{50}$ for inhibiting PDE4 activity and PDE8 activity of greater than 10 times (such as at least 20-fold, at least 50-fold or at least 100-fold) the lesser of the $IC_{50}$ for inhibiting PDE7A activity and the $IC_{50}$ for inhibiting PDE7B activity. In accordance with this embodiment, it is known that the PDE families that specifically/preferentially hydrolyze cAMP include PDE4, PDE7, and PDE8.

In some embodiments, the PDE7 inhibitory agent has an $IC_{50}$ for inhibiting the activity of PDE1, PDE2, PDE3, PDE4, and PDE8, PDE10, and PDE11 of greater than 10 times the lesser of the $IC_{50}$ for inhibiting PDE7A activity and the IC50 for inhibiting PDE7B activity. In accordance with this embodiment, it is known that the PDE families that specifically/preferentially hydrolyze cAMP include PDE4, PDE7, and PDE8 and the PDE1, PDE2, PDE3, PDE10, and PDE11 families show substantial activity against both cAMP and cGMP.

In some embodiments, the PDE inhibitory agent is a selective PDE7 inhibitor for which the lesser of the $IC_{50}$ for inhibiting PDE7A activity and the IC50 for inhibiting PDE7B activity is less than one-tenth (such as one-twentieth, one-fiftieth, or one-hundredth) the $IC_{50}$ that the agent has for inhibiting any other PDE enzyme from the PDE1-6 and PDE8-11 enzyme families.

A selective PDE7 inhibitor can be identified, for example, by comparing the ability of an agent to inhibit PDE7 (PDE7A, PDE7B or PDE7A and PDE7B) enzyme activity to its ability to inhibit PDE enzymes from the other PDE families. For example, an agent may be assayed for its ability to inhibit PDE7 activity as well as PDE1, PDE2, PDE3, PDE4, PDE5, PDE6, PDE8, PDE9, PDE10, and PDE11. Exemplary methods for comparing the ability of an agent to inhibit PDE7 enzyme activity to its ability to inhibit PDE enzymes from the other PDE families are provided in Example 2 herein. The ratio of the $IC_{50}$ inhibition for each of the PDE(1-6 and 8-11) isozymes to the $IC_{50}$ inhibition of PDE7 (i.e., the more sensitive of PDE7A or PDE7B) may be determined by a standard in vitro, in vivo, or ex vivo assay, such as those described herein.

In some embodiments, a PDE7 inhibitor is selective for PDE7 and substantially inactive against other PDEs (e.g., PDE1, PDE2, PDE3, PDE4, and PDE8, PDE10, and PDE11) due to targeting of the PDE7 inhibitor to one or more target tissues, such as the brain and/or skeletal muscle. As described herein, PDE7 is uniquely localized in mammalian subjects relative to other PDE families. Within the brain, PDE7A is widely distributed in both neuronal and non-neuronal cell populations, including the basal ganglia and substantia nigra (Miro et al., Synapse 40:201, 2001). PDE7B is expressed in the brain in the striatum (Reyes-Irisarri et al., Neuroscience 132:1173, 2005).

PDE7 Selectivity as Compared to Other Non-PDE Molecular Targets Known to be Involved with a Neurological Movement Disorder In some embodiments, the PDE7 inhibitory agent is selective for PDE7 and substantially inactive against non-PDE molecular targets known or believed to be involved with the pathology of a neurological movement disorder. In some embodiments, the PDE7 inhibitory agent is a PDE7 inhibitory agent for which the lesser of the $IC_{50}$ for inhibiting PDE7A activity and the IC50 for inhibiting PDE7B activity is less than one-half (such as less than one-fifth, less than one-tenth, such as less than one-twentieth, less than one-fiftieth, or less than one-hundredth) of the $IC_{50}$ that the agent has for inhibiting activity at other molecular targets (i) known to be involved with the pathology of a neurological movement disorder selected from the group consisting of Parkinson's disease, Post-Encephalitic Parkinsonism, Dopamine-Responsive Dystonia, Shy-Drager Syndrome, Period Limb Movement Disorder (PLMD), Periodic Limb Movements in Sleep (PLMS), and Restless Leg(s) Syndrome (RLS), or (ii) at which other drug(s) that are therapeutically effective to treat the disorder act.

In other embodiments, the PDE7 inhibitory agent is selective for PDE7 and substantially inactive against non-PDE molecular targets known to be involved with the pathology of Parkinson's disease. In some embodiments, the PDE7 inhibitory agent is a PDE7 inhibitory agent for which the lesser of the $IC_{50}$ for inhibiting PDE7A activity and the $IC_{50}$ for inhibiting PDE7B activity is less than one-half (such as less than one-fifth, less than one-tenth, less than one-twentieth, less than one-fiftieth, or less than one-hundredth) of the $IC_{50}$ that the agent has for inhibiting activity at other molecular targets (i) known to be involved with the pathology of Parkinson's disease, such as catechol-O-methyltransferase (COMT), monamine oxidase B (MAO-B), dopamine transporters (DAT), tyrosine hydroxylase, dopamine receptors, adenosine $A_{2A}$ receptors, muscarinic acetylcholine receptors, N-methyl D-aspartate (NMDA) receptors, gamma amino butyric acid (GABA) receptors and gabapentin receptors, or (ii) at which other drug(s) that are therapeutically effective to treat Parkinson's disease act. Exemplary methods for comparing the ability of an agent to inhibit PDE7 enzyme activity to its ability to inhibit other molecular targets known to be involved with the pathology of Parkinson's disease are provided in Example 4 herein.

In other embodiments, the PDE7 inhibitory agent is selective for PDE7 and substantially inactive against non-PDE molecular targets known to be associated with the dopamine signaling pathway. In some embodiments, the PDE7 inhibitory agent is a PDE7 inhibitory agent for which the lesser of the $IC_{50}$ for inhibiting PDE7A activity and the IC50 for inhibiting PDE7B activity is less than one-half (such as less than one-fifth, less than one-tenth, such as less than one-twentieth, less than one-fiftieth, or less than one-hundredth) of the $IC_{50}$ that the agent has for inhibiting activity at other molecular targets known to be associated with the dopamine signaling pathway, such as catechol-O-methyltransferase (COMT), monamine oxidase B (MAO-B), dopamine transporters (DAT), tyrosine hydroxylase, dopa decarboxylase, dopamine receptors, adenylyl cyclase, protein kinase A (PKA), dopamine and cyclic AMP-regulated phosphoprotein of molecular weight 32,000 (DARPP32), and protein phosphatase-1. Exemplary methods for comparing the ability of an agent to inhibit PDE7 enzyme activity to its ability to inhibit other molecular targets known to be associated with the dopamine signaling pathway are provided in Example 4 herein.

Types of PDE7 Inhibitory Agents

The PDE7 inhibitory agent can be any type of agent including, but not limited to, a chemical compound, a protein or polypeptide, a peptidomimetic, a nucleic acid molecule, or ribozyme. In some embodiments, PDE7 inhibitory agents are small molecule inhibitors including natural and synthetic substances that have a low molecular weight (i.e., less than about 450 g/mole), such as, for example, peptides, peptidomimetics and nonpeptide inhibitors such as chemical compounds.

Chemical Compounds:

The PDE7 inhibitors useful in the methods of the invention include agents that are administered by a conventional route (e.g., oral, intramuscular, subcutaneous, transdermal, transbucal, intravenous, etc.) into the bloodstream and are ultimately transported through the vascular system across the blood brain barrier to inhibit PDE7 in the brain. Accordingly, for these methods of administration, the PDE7 inhibitors have the ability to cross the blood brain barrier. Those PDE inhibitors described below that have the ability to cross the blood brain barrier (e.g., those having a molecular weight less than about 450 g/mole and that are sufficiently lipophilic) are useful in the methods of the invention when the inhibitors are administered by a route that ultimately transports the inhibitors to the brain in the bloodstream.

The following is a description of exemplary PDE7 inhibitors useful in the methods of the invention.

In one embodiment, PDE7 inhibitors useful in the methods of the invention are selected from those compounds generally or specifically disclosed in EP 1 454 897, WO 2003/053975, and US 20050148604, each expressly incorporated herein by reference in its entirety. In one embodiment, PDE7 inhibitors useful in the methods of the invention have the formulas:

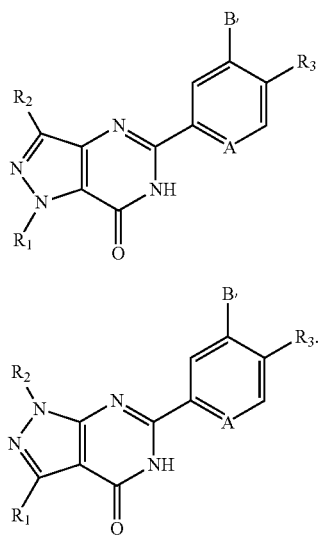

The substituents for the above compounds are defined as follows:

A represents N or $CR_4$,

B represents a hydrogen atom or a halogen atom, $R_1$ represents optionally substituted $C_{3-7}$ cycloalkyl or tert-butyl, $R_2$ represents hydrogen, methyl, or ethyl, $R_3$ represents a hydrogen, nitro, cyano or halogen atom, $NR_5R_6$, $C(=X)R_7$, $SO_2NR_5R_6$, $OR_8$, $NR_8CONR_5R_6$, $NR_8SO_2R_9$, $NR_8CO_2R_9$, a heteroaryl group, optionally substituted $C_{1-3}$ alkyl, optionally substituted $C_{1-6}$ alkenyl, or optionally substituted saturated or unsaturated heterocycloalkyl, $R_4$ represents hydrogen, or $C_{1-3}$ alkoxy substituted, if desired, by one or more fluorine atoms, $R_5$ and $R_6$ are the same or different, and represent a hydrogen atom, optionally substituted $C_{1-6}$ alkyl, optionally substituted heterocycloalkyl, or optionally substituted acyl or, together with the nitrogen atom which they are bound to, form azetidinyl, pyrrolidinyl, piperidinyl, morpholino, thiomorpholino, piperazinyl, or homopiperazinyl, each of these groups being optionally substituted by optionally substituted $C_{1-4}$ alkyl, OH, $C_{1-3}$ alkoxy, $CO_2H$, $NR_5R_6$, an oxo group, $NR_9COR_7$, or $C(=O)R_7$, $R_7$ represents optionally substituted $C_{1-6}$ alkyl, OH, $OR_8$, or $NR_5R_6$, $R_8$ represents hydrogen, an optionally substituted $C_{1-6}$ alkyl group, or optionally substituted heterocycloalkyl, $R_9$ represents an optionally substituted $C_{1-6}$ alkyl group, and X represents O, S, or NH.

In regard to the above compounds, "optionally substituted" refers to optionally substituted linear, branched or cyclic alkyl group such as methyl, ethyl, propyl or cyclohexyl; a hydroxyl group; a cyano group; an alkoxy group such as methoxy or ethoxy; an optionally substituted amino group such as amino, methylamino or dimethylamino; an optionally substituted acyl group such as acetyl or propionyl; a carboxyl group; an optionally substituted aryl group such as phenyl or naphthyl; an optionally substituted heteroaryl group such as pyridinyl, thiazolyl, imidazolyl or pyrazyl; an optionally substituted saturated or unsaturated heterocycloalkyl group such as piperazinyl or morphonyl; an optionally substituted carbamoyl group; an optionally substituted amido group; a halogen atom such as chlorine, fluorine or bromine; a nitro group; an optionally substituted sulfone group; an optionally substituted sulfonylamido group; an oxo group; a urea group; and an optionally substituted linear, branched or cyclic alkenyl group such as ethenyl, propenyl or cyclohexenyl.

Examples of the heteroaryl group as $R^3$ include a 5- to 7-membered monocyclic heteroaryl group having 2 to 8 carbon atoms and containing 1 to 4 hetero atoms consisting of oxygen atoms, nitrogen atoms or sulfur atoms, and a polycyclic heteroaryl group comprising two or more such identical or different monocyclic compounds fused together, examples of the monocyclic and polycyclic heteroaryl groups being pyrrole, furyl, thienyl, imidazolyl, thiazolyl, pyridyl, pyrazyl, indolyl, quinolyl, isoquinolyl, and tetrazolyl.

In one embodiment, a PDE7 inhibitor useful in the invention has the formula:

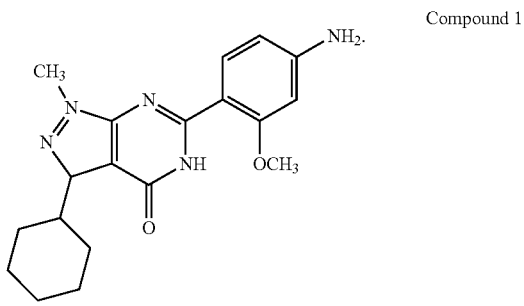

The activity of Compound 1 in inhibiting select PDEs is described in Examples 1 and 2. The effectiveness of Compound 1 in the MPTP Parkinson's model is described in Examples 5 and 6.

In others embodiments, PDE7 inhibitors useful in the methods of the invention have the formulas:

In another embodiment, a PDE7 inhibitor useful in the methods of the invention has the formula:

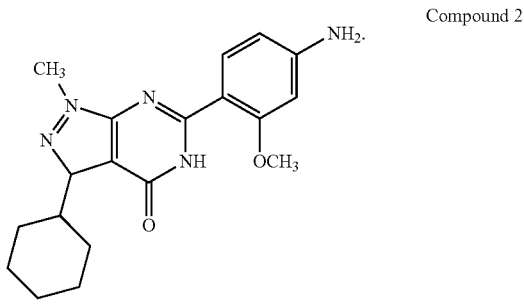

The activity of Compound 2 in inhibiting select PDEs is described in Examples 1 and 2. The effectiveness of Compound 2 in the MPTP Parkinson's model is described in Example 7.

In other embodiments, PDE7 inhibitors useful in the methods of the invention have the formulas:

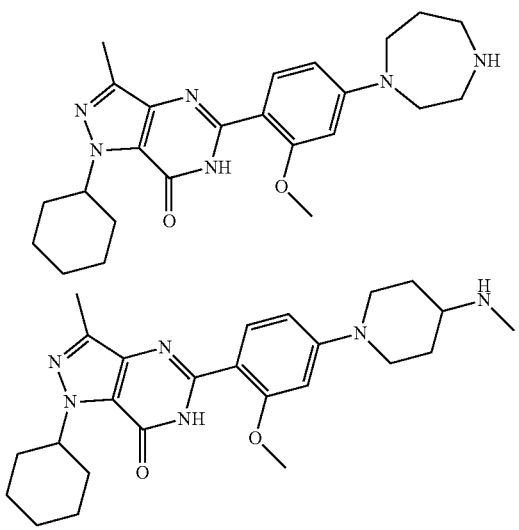

The preparation of the above compounds is described in EP 1 454 897, WO 2003/053975, and US 20050148604.

In another embodiment, PDE7 inhibitors useful in the methods of the invention are selected from those compounds generally or specifically disclosed in US 2002/0198198, WO 2002/076953, WO 2002/074754, WO 2006/092691, *Bioorganic & Medicinal Chemistry Letters* 14 (2004) 4623-4626, and *Bioorganic & Medicinal Chemistry Letters* 14 (2004) 4627-4631, each expressly incorporated herein by reference in its entirety. In one embodiment, PDE7 inhibitors useful in the methods of the invention have the formulas:

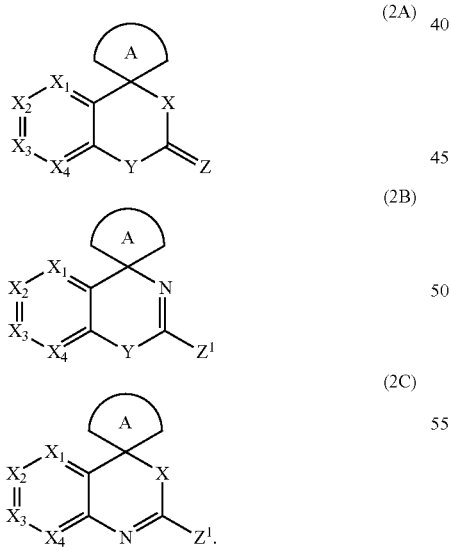

The substituents for the above compounds are defined as follows:

(a) $X_1$, $X_2$, $X_3$, and $X_4$ are the same or different and are selected from:

N, provided that not more than two of the groups $X_1$, $X_2$, $X_3$, and $X_4$ simultaneously represent a nitrogen atom, or, C—$R_1$, in which $R_1$ is selected from:

$Q_1$, or lower alkyl, lower alkenyl, or lower alkynyl, these groups being unsubstituted or substituted with one or several groups $Q_2$;

the group $X_5$—$R_5$ in which, $X_5$ is selected from:

a single bond, lower alkylene, lower alkenylene, or lower alkynylene; optionally interrupted with 1 or 2 heteroatoms chosen from O, S, S(=O), $SO_2$, or N, the carbon atoms of these groups being unsubstituted or substituted with one or several groups, identical or different, selected from $SR_6$, $OR_6$, $NR_6R_7$, =O, =S, or =$NR_6$ in which $R_6$ and $R_7$ are the same or different and are selected from hydrogen or lower alkyl, and, $R_5$ is selected from aryl, heteroaryl, cycloalkyl optionally interrupted with C(=O) or with 1, 2, or 3 heteroatoms chosen from O, S, S(=O), $SO_2$, or N, cycloalkenyl optionally interrupted with C(=O) or with 1, 2, or 3 heteroatoms chosen from O, S, S(=O), $SO_2$ or N, or a bicyclic group, these groups being unsubstituted or substituted with one or several groups selected from $Q_3$, heteroaryl, or lower alkyl optionally substituted with $Q_3$;

in which $Q_1$, $Q_2$, and $Q_3$ are the same or different and are selected from:

hydrogen, halogen, CN, $NO_2$, $SO_3H$, P(=O)(OH)$_2$, $OR_2$, OC(=O)$R_2$, C(=O)$OR_2$, $SR_2$, S(=O)$R_2$, $NR_3R_4$, Q-$R_2$, Q-$NR_3R_4$, $NR_2$-Q-$NR_3R_4$, or $NR_3$-Q-$R_2$ in which Q is selected from C(=NR), C(=O), C(=S), or $SO_2$, R is selected from hydrogen, or lower alkyl, and $R_2$, $R_3$, and $R_4$ are the same or different and are selected from:

hydrogen, lower alkyl optionally interrupted with C(=O), $(CH_2)_n$-aryl, $(CH_2)_n$-heteroaryl, $(CH_2)_n$-cycloalkyl optionally interrupted with C(=O) or with 1 or 2 heteroatoms chosen from O, S, S(=O), $SO_2$, or N, in which n is an integer selected from 0, 1, 2, 3 or 4;

these groups being unsubstituted or substituted with one or several groups selected from lower alkyl, halogen, CN, $CH_3$, $SO_3H$, $SO_2CH_3$, $CF_3$, C(=O)$NHSO_2CH_3$, $OR_6$, $COOR_6$, C(=O)$R_6$, $NR_6R_7$, C(=O)$NR_6R_7$, or $SO_2NR_6R_7$, in which $R_6$ and $R_7$ are the same or different and are selected from hydrogen or lower alkyl optionally substituted with one or two groups selected from OR, COOR or $NRR_8$ in which R and $R_8$ are hydrogen or lower alkyl, and, $R_6$ and $R_7$, and/or, $R_3$ and $R_4$, together with the nitrogen atom to which they are linked, can form a 4- to 8-membered heterocyclic ring, which may contain one or two heteroatoms selected from O, S, S(=O), $SO_2$, or N, and which may be substituted with, a 4- to 8-membered heterocyclic ring, which may contain one or two heteroatoms selected from O, S, or N, and which may be substituted with a lower alkyl, or, a lower alkyl optionally substituted with OR', NR'R", C(=O)NR'R" or COOR' in which R' and R" are the same or different and are selected from H, lower alkyl optionally substituted with OR or COOR in which R is hydrogen or lower alkyl, and R' and R" together with the nitrogen atom to which they are linked, can form a 4- to 8-membered heterocyclic ring, which may contain one or two heteroatoms selected from O, S, or N; or, (b) X is O, S, or $NR_9$, in which $R_9$ is selected from hydrogen, CN, OH, $NH_2$, lower alkyl, lower alkenyl, or lower alkynyl, these groups being unsubstituted or substituted with cycloalkyl optionally interrupted with 1 or 2 heteroatoms chosen from O, S, S(=O), $SO_2$, or N, cycloalkenyl optionally interrupted with 1 or 2 heteroatoms chosen from O, S, S(=O), $SO_2$, or N, aryl, heteroaryl, $OR_{10}$, or $NR_{10}R_{11}$ in which $R_{10}$ and $R_{11}$ are the same or different and are selected from hydrogen or lower alkyl;

(c) Y is selected from O, S, or N—$R_{12}$, in which $R_{12}$ is selected from hydrogen, CN, OH, $NH_2$, lower alkyl, lower alkenyl, or lower alkynyl, these groups being unsubstituted or substituted with cycloalkyl optionally interrupted with 1 or 2 heteroatoms chosen from O, S, S(=O), $SO_2$, or N, cycloalkenyl optionally interrupted with 1 or 2 heteroatoms chosen from O, S, S(=O), $SO_2$, or N, aryl, heteroaryl, $OR_{10}$, or $NR_{10}R_{11}$ in which $R_{10}$ and $R_{11}$ are the same or different and are selected from hydrogen or lower alkyl;

(d) Z is chosen from CH—$NO_2$, O, S, or $NR_{13}$ in which $R_{13}$ is selected from hydrogen, CN, OH, $NH_2$, aryl, heteroaryl, cycloalkyl optionally interrupted with one or several heteroatoms chosen from O, S, S(=O), $SO_2$, or N, cycloalkenyl optionally interrupted with one or several heteroatoms chosen from O, S, S(=O), $SO_2$, or N, C(=O)$R_{14}$, C(=O)$NR_{14}R_{15}$, $OR_{14}$, or, lower alkyl, unsubstituted or substituted with one or several groups which are the same or different and which are selected $OR_{14}$ or $NR_{14}R_{15}$;

$R_{14}$ and $R_{15}$ being independently selected from hydrogen or lower alkyl, or, $R_{14}$ and $R_{15}$, together with the nitrogen atom to which they are linked, can form a 4- to 8-membered heterocyclic ring which may contain one or two heteroatoms chosen from O, S, or N, and which may be substituted with a lower alkyl;

(e) $Z_1$ is chosen from H, $CH_3$, or $NR_{16}R_{17}$ in which $R_{16}$ and $R_{17}$ are the same or different and are selected from hydrogen, CN, aryl, heteroaryl, cycloalkyl optionally interrupted with one or several heteroatoms chosen from O, S, S(=O), $SO_2$, or N, cycloalkenyl optionally interrupted with one or several heteroatoms chosen from O, S, S(=O), $SO_2$, or N, C(=O)$R_{14}$, C(=O)$NR_{14}R_{15}$, $OR_{14}$, or, lower alkyl unsubstituted or substituted with one or several groups selected from $OR_{14}$ or $NR_{14}R_{15}$, $R_{14}$ and $R_{15}$ being chosen from hydrogen or lower alkyl, and, $R_{14}$ and $R_{15}$, and/or, $R_{16}$ and $R_{17}$, together with the nitrogen atom to which they are linked, can form a 4- to 8-membered heterocyclic ring which may contain one or two heteroatoms chosen from O, S, or N, and which may be substituted with a lower alkyl;

(f) A is a cycle selected from:

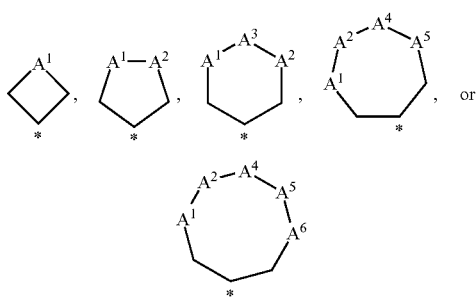

in which
$A_1, A_2, A_3, A_4, A_5,$ and $A_6$ are the same or different and are selected from O, S, C, C(=O), SO, $SO_2$, or $NR_{18}$ in which $R_{18}$ is selected from hydrogen, aryl, heteroaryl, cycloalkyl optionally interrupted with one or several heteroatoms chosen from O, S, S(=O), $SO_2$, or N, cycloalkenyl optionally interrupted with one or several heteroatoms chosen from O, S, S(=O), $SO_2$, or N, lower alkyl unsubstituted or substituted with aryl, heteroaryl, cycloalkyl optionally interrupted with one or several heteroatoms chosen from O, S, S(=O), $SO_2$, or N, cycloalkenyl optionally interrupted with one or several heteroatoms chosen from O, S, S(=O), $SO_2$, or N, CN, $NR_{19}R_{20}$, C(=O)$NR_{19}R_{20}$, $OR_{19}$, C(=O)$R_{19}$ or C(=O)$OR_{19}$ in which $R_{19}$ and $R_{20}$ are identical or different and are selected from hydrogen or lower alkyl;

* represents the carbon atom which is shared between the cycle A and the backbone cycle containing X and/or Y;

each carbon atom of the cycle A is unsubstituted or substituted with 1 or 2 groups, identical or different, selected from lower alkyl optionally substituted with $OR_{21}$, $NR_{21}R_{22}$, $COOR_{21}$, or $CONR_{21}R_{22}$, lower haloalkyl, CN, F, =O, $SO_2NR_{19}R_{20}$, $OR_{19}$, $SR_{19}$, C(=O)$OR_{19}$, C(=O)$NR_{19}R_{20}$, or $NR_{19}R_{20}$ in which $R_{19}$ and $R_{20}$ are identical or different and are selected from hydrogen or lower alkyl optionally substituted with $OR_{21}$, $NR_{21}R_{22}$, $COOR_{21}$, or $CONR_{21}R_{22}$, in which $R_{21}$ and $R_{22}$ are identical or different and are selected from hydrogen or lower alkyl, and, $R_{19}$ and $R_{20}$, and/or, $R_{21}$ and $R_{22}$, together with the nitrogen atom to which they are linked, can form a 4- to 8-membered heterocyclic ring;

two atoms of the cycle A, which are not adjacent, may be linked by a 2, 3 or 4 carbon atom chain which may be interrupted with 1 heteroatom chosen from O, S or N; provided that not more than two of the groups $A_1, A_2, A_3, A_4, A_5,$ and $A_6$ simultaneously represent a heteroatom; and their tautomeric forms, their racemic forms, their isomers, and their pharmaceutically acceptable derivatives.

In regard to the above compounds, halogen includes fluoro, chloro, bromo, and iodo. Preferred halogens are F and Cl. Lower alkyl includes straight and branched carbon chains having from 1 to 6 carbon atoms. Examples of such alkyl groups include methyl, ethyl, isopropyl, and tert-butyl. Lower alkenyl includes straight and branched hydrocarbon radicals having from 2 to 6 carbon atoms and at least one double bond. Examples of such alkenyl groups are ethenyl, 3-buten-1-yl, 2-ethenylbutyl, and 3-hexen-1-yl. Lower alkynyl includes straight and branched hydrocarbon radicals having from 2 to 6 carbon atoms and at least one triple bond. Examples of such alkynyl groups are ethynyl, 3-butyn-1-yl, propynyl, 2-butyn-1-yl, and 3-pentyn-1-yl. Lower haloalkyl includes a lower alkyl as defined above, substituted with one or several halogens. An example of haloalkyl is trifluoromethyl. Aryl is understood to refer to an aromatic carbocycle containing between 6 and 10 carbon atoms. An example of an aryl group is phenyl. Heteroaryl includes aromatic cycles which have from 5 to 10 ring atoms, from 1 to 4 of which are independently selected from the group consisting of O, S, and N. Representative heteroaryl groups have 1, 2, 3 or 4 heteroatoms in a 5- or 6-membered aromatic ring. Examples of such groups are tetrazole, pyridyl, and thienyl. Representative cycloalkyl contain from 3 to 8 carbon atoms. Examples of such groups are cyclopropyl, cyclobutyl, cyclopentyl, cyclohexyl, cycloheptyl and cyclooctyl. The term "interrupted" means that in a backbone chain, a carbon atom is replaced by an heteroatom or a group as defined herein. For example, in "cycloalkyl or cycloalkenyl optionally interrupted with C(=O) or with 1 heteroatom chosen from O, S, S(=O), $SO_2$ or N", the term "interrupted" means that C(=O) or a heteroatom can replace a carbon atom of the ring. Example of such groups are morpholine or piperazine. Cycloalkenyl includes 3- to 10-membered cycloalkyl containing at least one double bond. Heterocyclic rings include heteroaryl as defined above and cycloalkyl or cycloalkenyl, as defined above, interrupted with 1, 2 or 3 heteroatoms chosen from O, S, S(=O), $SO_2$, or N. Bicyclic substituents refer to two cycles, which are the same or different and which are chosen from aryl, heterocyclic ring, cycloalkyl or cycloalkenyl, fused together to form said bicyclic substituents. An example of a bicyclic substituent is indolyl.

In one embodiment, a PDE7 inhibitor useful in the methods of the invention has the formula:

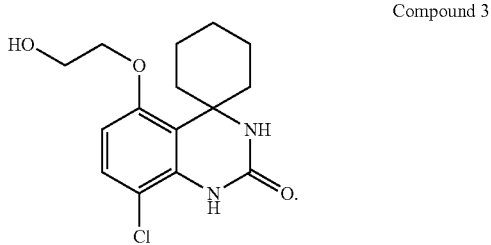 [SMILES: O=C1Nc2c(Cl)ccc(OCCO)c2C2(CCCCC2)N1]

Compound 3

The activity of Compound 3 in inhibiting select PDEs is described in Examples 1 and 2. The effectiveness of Compound 3 in the MPTP Parkinson's model is described in Example 7.

In other embodiments, PDE7 inhibitors useful in the methods of the invention have the formulas:

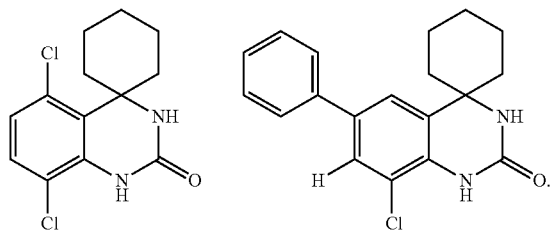 [SMILES: O=C1Nc2c(Cl)ccc(Cl)c2C2(CCCCC2)N1 ; O=C1Nc2c(Cl)cc(-c3ccccc3)cc2C2(CCCCC2)N1]

The preparation of the above compounds is described in US 2002/0198198, WO 2002/076953, WO 2002/074754, WO 2006/092691, *Bioorganic & Medicinal Chemistry Letters* 14 (2004) 4623-4626, and *Bioorganic & Medicinal Chemistry Letters* 14 (2004) 4627-4631.

In another embodiment, PDE7 inhibitors useful in the methods of the invention are selected from those compounds generally or specifically disclosed in EP 1 193 261, WO 2002/28847, US 20030045557, U.S. Pat. No. 7,122,565, *Bioorganic & Medicinal Chemistry Letters* 14 (2004) 4607-4613, and *Bioorganic & Medicinal Chemistry Letters* 14 (2004) 4615-4621, each expressly incorporated herein by reference in its entirety. In one embodiment, PDE7 inhibitors useful in the methods of the invention have the formula:

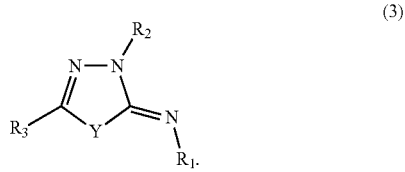

(3)

The substituents for the above compounds are defined as follows:

Y is S or O;

$R_1$ is $C_1$-$C_{10}$ alkyl, $C_2$-$C_{10}$ alkenyl, $C_2$-$C_{10}$ alkynyl, cycloalkyl, cycloalkenyl, heterocycle, aryl, or a polycyclic group; each optionally substituted with one or several groups $X_1$—$R_4$, identical or different, in which $X_1$ is a single bond, lower alkylene, $C_2$-$C_6$ alkenylene, cycloalkylene, arylene, or divalent heterocycle, and $R_4$ is:
  (1) H, =O, $NO_2$, CN, halogen, lower haloalkyl, lower alkyl, carboxylic acid bioisostere;
  (2) $COOR_5$, $C(=O)R_5$, $C(=S)R_5$, $SO_2R_5$, $SOR_5$, $SO_3R_5$, $SR_5$, $OR_5$;
  (3) $C(=O)NR_7R_8$, $C(=S)NR_7R_8$, $C(=CH-NO_2)NR_7R_8$, $C(=N-CN)NR_7R_8$, $C(=N-SO_2NH_2)NR_7R_8$, $C(=NR_7)NHR_8$, $C(=NR_7)R_8$, $C(=NR_9)NHR_8$, $C(=NR_9)R_8$, $SO_2NR_7R_8$, or $NR_7R_8$, wherein $R_7$ and $R_8$ are the same or different and are selected from OH, $R_5$, $R_6$, $C(=O)NR_5R_6$, $C(=O)R_5$, $SO_2R_5$, $C(=NR_9)NHR_{10}$, $C(=NR_9)R_{10}$, $C(=CH-NO_2)NR_9R_{10}$, $C(=N-SO_2NH_2)NR_9R_{10}$, $C(=N-CN)NR_9R_{10}$, or $C(=S)NR_9R_{10}$;

$R_2$ is lower alkyl, $C_2$-$C_{10}$ alkenyl, $C_2$-$C_{10}$ alkynyl, cycloalkyl, cycloalkenyl, heterocycle, aryl; each optionally substituted with one or several groups which are the same or different and which are selected from:
  (1) H, carboxylic acid bioisostere, lower haloalkyl, halogen,
  (2) $COOR_5$, $OR_5$, $SO_2R_5$,
  (3) $SO_2NR_{11}R_{12}$, $C(=O)NR_{11}R_{12}$, $NR_{11}R_{12}$, wherein $R_{11}$ and $R_{12}$ are the same or different and are selected from OH, $R_5$, $R_6$, $C(=O)NR_5R_6$, $C(=O)R_5$, $SO_2R_5$, $C(=S)NR_9R_{10}$, $C(=CH-NO_2)NR_9R_{10}$, $C(=N-CN)NR_9R_{10}$, $C(=N-SO_2NH_2)NR_9R_{10}$, $C(=NR_9)NHR_{10}$, or $C(=NR_9)R_{10}$;

$R_3$ is $X_2$—$R'_3$, wherein $X_2$ is a single bond or, a group selected from $C_1$-$C_4$ alkylene, $C_2$-$C_6$ alkenylene, $C_2$-$C_6$ alkynylene, each optionally substituted with one or several groups which are the same or different and which are selected from:
  (1) H, $C_1$-$C_3$ alkyl, $C_3$-$C_4$ cycloalkyl, aryl, heterocycle, =O, CN,
  (2) $OR_5$, =$NR_5$; or
  (3) $NR_{13}R_{14}$, wherein $R_{13}$ and $R_{14}$ are the same or different and are selected from $R_5$, $R_6$, $C(=O)NR_5R_6$, $C(=O)R_5$, $SO_2R_5$, $C(=S)NR_9R_{10}$, $C(=CH-NO_2)NR_9R_{10}$, $C(=NR_9)NHR_{10}$, or $C(=NR_9)R_{10}$;

$R'_3$ is cycloalkyl, cycloalkenyl, aryl, heterocycle, or a polycyclic group; each optionally substituted with one or several groups $X_3$—$R_{17}$ wherein $X_3$ is a single bond, lower alkylene, $C_2$-$C_6$ alkenylene, $C_2$-$C_6$ alkynylene, cycloalkylene, arylene, divalent heterocycle or a divalent polycyclic group, and, $R_{17}$ is:
  (1) H, =O, $NO_2$, CN, lower haloalkyl, halogen, carboxylic acid bioisostere, cycloalkyl,
  (2) $COOR_5$, $C(=O)R_5$, $C(=S)R_5$, $SO_2R_5$, $SOR_5$, $SO_3R_5$, $SR_5$, $OR_5$;
  (3) $C(=O)NR_{15}R_{16}$, $C(=S)NR_{15}R_{16}$, $C(=N-CN)NR_{15}R_{16}$, $C(=N-SO_2NH_2)NR_{15}R_{16}$, $C(=CH-NO_2)NR_{15}R_{16}$, $SO_2NR_{15}R_{16}$, $C(=NR_{15})NHR_{16}$, $C(=NR_{15})R_{16}$, $C(=NR_9)NHR_{16}$, $C(=NR_9)R_{16}$, or $NR_{15}R_{16}$ wherein $R_{15}$ and $R_{16}$ are the same or different and are selected from OH, $R_5$, $R_6$, $C(=O)NR_5R_6$, $C(=O)R_5$, $SO_2R_5$, $C(=S)NR_9R_{10}$, $C(=CH-NO_2)NR_9R_{10}$, $C(=N-CN)NR_9R_{10}$, $C(=N-SO_2NH_2)NR_9R_{10}$, $C(=NR_9)NHR_{10}$ or $C(=NR_9)R_{10}$,
  (4) heterocycle optionally substituted with one or several groups $R_5$;

wherein $R_5$ and $R_6$ are the same or different and are selected from H, lower alkyl, $C_2$-$C_6$ alkenyl, $C_2$-$C_6$ alkynyl, $X_4$-cycloalkyl, $X_4$-cycloalkenyl, $X_4$-aryl, $X_4$-heterocycle or $X_4$-polycyclic group, wherein $X_4$ is a single bond, lower alkylene, or $C_2$-$C_6$ alkenylene; each optionally substituted with one or several groups that are the same or different and selected from halogen, =O, $COOR_{20}$, CN, $OR_{20}$, O-lower alkyl optionally substituted with $OR_{20}$, C(=O)-lower alkyl, lower haloalkyl,

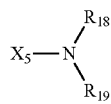

in which $X_5$ is a single bond or lower alkylene and $R_{18}$, $R_{19}$, and $R_{20}$, are the same or different and are selected from H or lower alkyl;

$X_6$-heterocycle, $X_6$-aryl, $X_6$-cycloalkyl, $X_6$-cycloalkenyl, or $X_6$-polycyclic group, wherein $X_6$ is a single bond or lower alkylene, these groups being optionally substituted with one or several groups, identical or different, selected from halogens, $COOR_{21}$, $OR_{21}$, or $(CH_2)_nNR_{21}R_{22}$ in which n is 0, 1, or 2 and $R_{21}$ and $R_{22}$ are the same or different and are selected from H or lower alkyl;

$R_9$ is selected from H, CN, OH, lower alkyl, O-lower alkyl, aryl, heterocycle, $SO_2NH_2$, or

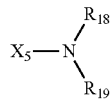

in which $X_5$ is a single bond or lower alkylene and $R_{18}$ and $R_{19}$ are the same or different and are selected from H or lower alkyl;

$R_{10}$ is selected from hydrogen, lower alkyl, cyclopropyl, or heterocycle;

or their pharmaceutically acceptable derivatives.

In regard to the above compounds, aryl refers to an unsaturated carbocycle, exclusively comprising carbon atoms in the cyclic structure, the number of which is between 5 and 10, including phenyl, naphthyl, or tetrahydronaphthyl. Heterocycle refers to a nonsaturated or saturated monocycle containing between 1 and 7 carbon atoms in the cyclic structure and at least one heteroatom in the cyclic structure, such as nitrogen, oxygen, or sulfur, preferably from 1 to 4 heteroatoms, identical or different, selected from nitrogen, sulfur and oxygen atoms. Suitable heterocycles include morpholinyl, piperazinyl, pyrrolidinyl, piperidinyl, pyrimidinyl, 2- and 3-furanyl, 2- and 3-thienyl, 2-pyridyl, 2- and 3-pyranyl, hydroxypyridyl, pyrazolyl, isoxazolyl, tetrazole, imidazole, triazole, and the like. Polycyclic groups include at least two cycles, identical or different, selected from aryl, heterocycle, cycloalkyl, cycloalkenyl groups fused together to form said polycyclic group such as 2- and 3-benzothienyl, 2- and 3-benzofuranyl, 2-indolyl, 2- and 3-quinolinyl, acridinyl, quinazolinyl, indolyl benzo[1,3]dioxolyl, and 9-thioxantanyl. Bicyclic groups refer to two cycles, which are the same or different and which are chosen from aryl, heterocycle, cycloalkyl or cycloalkenyl, fused together to form said bicyclic groups. Halogen refers to fluorine, chlorine, bromine, or iodine. Lower alkyl refers to an alkyl is linear or branched and contains 1 to 6 carbon atoms. Examples of lower alkyl groups include methyl, ethyl, propyl, butyl, isopropyl, tert-butyl, isobutyl, n-butyl, pentyl, hexyl and the like. Alkenyl refers to a linear or branched unsaturated carbon atom chain, comprising one or several double bonds, preferably one or two double bonds. Alkynyl refers to a linear or branched unsaturated carbon atom chain, comprising one or several triple bonds, preferably one or two triple bonds. Lower haloalkyl refers to a lower alkyl substituted with one or several halogens; preferred lower haloalkyl groups include perhaloalkyl groups such as $CF_3$. Cycloalkyl refers to saturated monocarbocyle containing from 3 to 10 carbon atoms; including cyclopropyl, cyclobutyl, cyclopentyl, cyclohexyl, and cycloheptyl. Cycloalkenyl refers to unsaturated monocarbocyle containing from 3 to 10 carbon atoms. Examples of suitable cycloalkenyl are 3-cyclohexene, and 3-cycloheptene. Carboxylic acid bioisostere has the classical meaning; common carboxylic acid bioisostere are tetrazole-5-yl, C(=O)N(H)OH, isoxazol-3-yl, hydroxythiadiazolyl, sulfonamido, sulfonylcarboxamido, phosphonic acid, phosphonamido, phosphinic acid, sulfonic acids, acyl sulfonamido, mercaptoazole, acyl cyanamides.

In one embodiment, a PDE7 inhibitor useful in the methods of the invention has the formula:

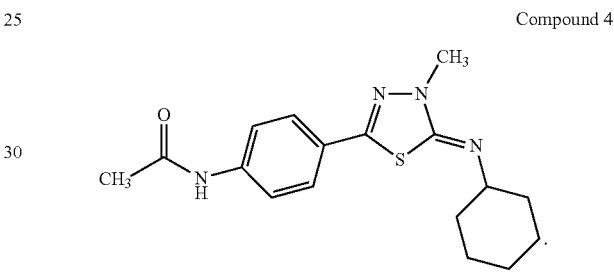

Compound 4

The activity of Compound 4 in inhibiting several PDEs is described in Examples 1 and 2. The effectiveness of Compound 4 in the MPTP Parkinson's model is described in Example 7.

In other embodiments, PDE7 inhibitors useful in the methods of the invention have the formulas:

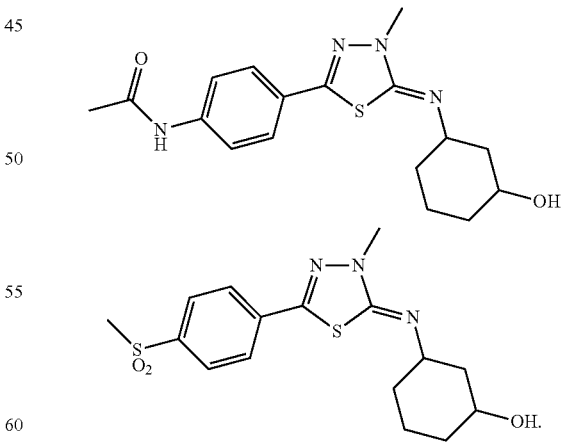

The preparation of the above compounds is described in EP 1 193 261, WO 02/28847, US 20030045557, U.S. Pat. No. 7,122,565, *Bioorganic & Medicinal Chemistry Letters* 14 (2004) 4607-4613, and *Bioorganic & Medicinal Chemistry Letters* 14 (2004) 4615-4621.

In another embodiment, PDE7 inhibitors useful in the methods of the invention are selected from those compounds generally or specifically disclosed in WO 2004/111054, US 20060128728, and US 20070270419, each expressly incorporated herein by reference in its entirety. In one embodiment, PDE7 inhibitors useful in the methods of the invention have the formulas:

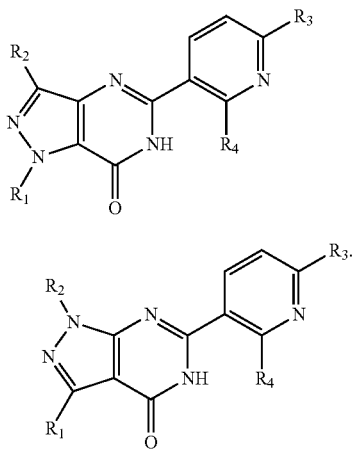

The substituents for the above compounds are defined as follows:

$R_1$ is a substituted or unsubstituted $C_{3-8}$ cycloalkyl group or tert-butyl group;

$R_2$ is a hydrogen atom or $C_{1-3}$ alkyl group;

$R_3$ is a group: $NR_5R_6$, $C(=O)R_7$, or $S(O)_{0-2}R_8$;

$R_4$ is a hydrogen atom or $C_{1-3}$ alkoxyl group which is unsubstituted or substituted by one or more fluorine atom(s);

$R_5$ and $R_6$ are, same or different from each other, a hydrogen atom, substituted or unsubstituted $C_{1-6}$ alkyl group, substituted or unsubstituted acyl group, substituted or unsubstituted heterocycloalkyl group, and substituted or unsubstituted heterocycloalkyl ring formed with a nitrogen atom which is binding $R_5$ and $R_6$;

$R_7$ is a group: $OR_9$ or $NR_5R_6$;

$R_8$ is a hydrogen atom, a halogen atom, a group: $NR_5R_6$, substituted or unsubstituted $C_{1-6}$ alkyl group, or substituted or unsubstituted aryl group;

$R_9$ is a hydrogen atom or substituted or unsubstituted $C_{1-6}$ alkyl group;

or pharmaceutically acceptable salts or solvates thereof.

In regard to the above compounds, the term "$C_1$-$C_3$ alkyl group" includes a straight or branched-chained alkyl group having 1 to 3 carbon atoms. The term "$C_3$-$C_8$ cycloalkyl group" includes a cycloalkyl group having 3 to 8 carbon atoms such as cyclopropyl, cyclobutyl, cyclopentyl, cyclohexyl and cyclooctyl. The term "heterocycloalkyl group" is 3 to 7 membered heterocyclic group containing the same or different 1 to 4 hetero atom(s) such as oxygen, nitrogen or sulfur atom(s), and examples may include pyrrolidinyl, piperidinyl, piperazinyl, homopiperazinyl, tetrahydrofuryl, tetrahydrophyranyl, morpholinyl and azetidinyl. The term "$C_1$-$C_3$ alkoxy group" means alkoxy group having 1 to 3 carbon atoms. The term "acyl group" means acyl group having 1 to 8 carbon atoms. The term "aryl group" is phenyl, naphthyl, biphenyl group, having 6 to 12 carbon atoms, and the term "heteroaryl group" is 5 to 7 membered monocyclic or polycyclic group thereof containing 2 to 8 carbon atoms and the same or different 1 to 4 hetero atom(s) such as oxygen, nitrogen, sulfur atom(s). The examples include pyrrole, furyl, thienyl, imidazolyl, thiazolyl, pyrazinyl, indolyl, quinolinyl, isoquinolinyl, tetrazolyl, pyridinyl, pyrazolyl pyridazinyl and pyrimidinyl. Examples of suitable substituent of "substituted or unsubstituted $C_1$-$C_6$ alkyl group" include hydroxyl group and halogen atom, and examples of suitable substituent of "substituted or unsubstituted acyl group" include halogen atom and nitro group. Further, examples of suitable substituent of "substituted or unsubstituted aryl group" include $C_1$-$C_3$ alkyl, halogen atom, amino group, acyl group, amide group, hydroxyl group, acylamino group, carboxyl group and sulfonyl group. Examples of suitable substituent of "substituted or unsubstituted $C_3$-$C_8$ cycloalkyl group" is $C_1$-$C_3$ alkyl, hydroxyl group and oxo group, and examples of suitable substituent of "substituted or unsubstituted heterocycloalkyl group" may include carboxy group, acyl group, alkoxy group, amino group, alkylamino group, acylamino group, hydroxyl group, oxo group, ethylenedioxy group, methyl group, ethyl group and hydroxyethyl group.

In other embodiments, PDE7 inhibitors useful in the methods of the invention have the formulas:

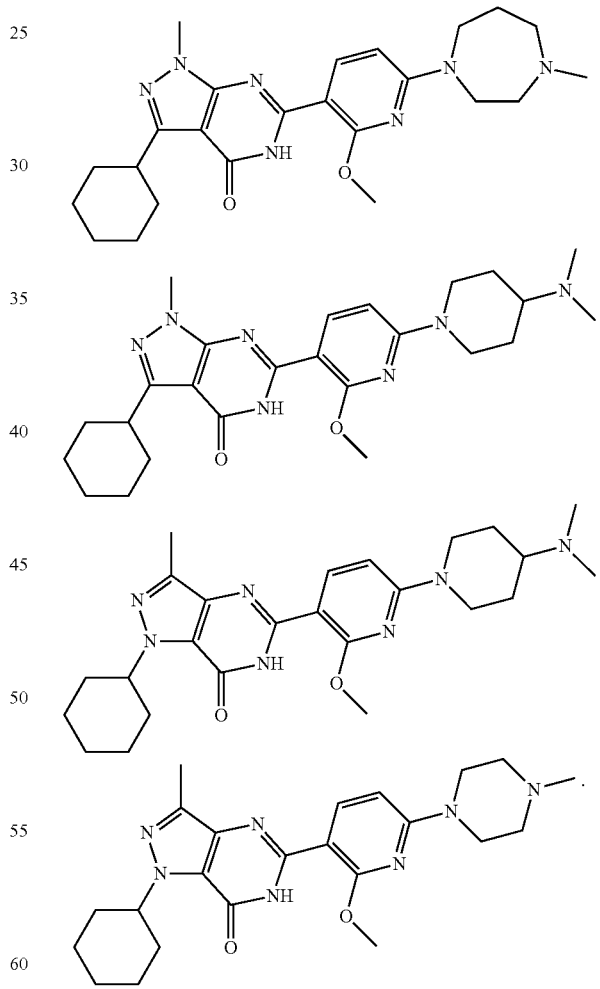

The preparation of the above compounds is described in WO 2004/111054, US 20060128728, and US 20070270419.

In another embodiment, PDE7 inhibitors useful in the methods of the invention are selected from those compounds generally or specifically disclosed in U.S. Pat. No. 6,903,109, US 20040082578, WO 2003/088963, and US 20060154949, each expressly incorporated herein by reference in its entirety. In one embodiment, PDE7 inhibitors useful in the methods of the invention have the formula:

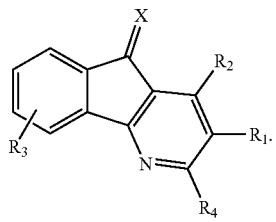

(5)

The substituents for the above compounds are defined as follows:

(a) $R_1$ is selected from the group consisting of:
  (i) $COR_5$, wherein $R_5$ is selected from H, optionally substituted $C_{1-8}$ straight or branched chain alkyl, optionally substituted aryl and optionally substituted arylalkyl; wherein the substituents on the alkyl, aryl and arylalkyl group are selected from $C_{1-8}$ alkoxy, phenylacetyloxy, hydroxy, halogen, p-tosyloxy, mesyloxy, amino, cyano, carboalkoxy, or $NR_{20}R_{21}$ wherein $R_{20}$ and $R_{21}$ are independently selected from the group consisting of hydrogen, $C_{1-8}$ straight or branched chain alkyl, $C_{3-7}$ cycloalkyl, benzyl, or aryl;
  (ii) $COOR_6$, wherein $R_6$ is selected from H, optionally substituted $C_{1-8}$ straight or branched chain alkyl, optionally substituted aryl and optionally substituted arylalkyl; wherein the substituents on the alkyl, aryl and arylalkyl group are selected from $C_{1-8}$ alkoxy, phenylacetyloxy, hydroxy, halogen, p-tosyloxy, mesyloxy, amino, cyano, carboalkoxy, or $NR_{20}R_{21}$ wherein $R_{20}$ and $R_{21}$ are independently selected from the group consisting of hydrogen, $C_{1-8}$ straight or branched chain alkyl, $C_{3-7}$ cycloalkyl, benzyl, or aryl;
  (iii) cyano;
  (iv) a lactone or lactam formed with $R_4$;
  (v) $CONR_7R_8$ wherein $R_7$ and $R_8$ are independently selected from H, $C_{1-8}$ straight or branched chain alkyl, $C_{3-7}$ cycloalkyl, trifluoromethyl, hydroxy, alkoxy, acyl, alkylcarbonyl, carboxyl, arylalkyl, aryl, heteroaryl, and heterocyclyl; wherein the alkyl, cycloalkyl, alkoxy, acyl, alkylcarbonyl, carboxyl, arylalkyl, aryl, heteroaryl, and heterocyclyl groups may be substituted with carboxyl, alkyl, aryl, substituted aryl, heterocyclyl, substituted heterocyclyl, heteroaryl, substituted heteroaryl, hydroxamic acid, sulfonamide, sulfonyl, hydroxy, thiol, alkoxy, or arylalkyl;
  or $R_7$ and $R_8$ taken together with the nitrogen to which they are attached form a heterocyclyl or heteroaryl group;
  (vi) a carboxylic ester or carboxylic acid bioisostere including optionally substituted heteroaryl groups;

(b) $R_2$ is selected from the group consisting of optionally substituted alkyl, optionally substituted aryl, optionally substituted heteroaryl, optionally substituted $C_{3-7}$ cycloalkyl, optionally substituted heterocyclyl, wherein the heterocyclyl is 1,3-dioxolane or furan, or $R_2$ is

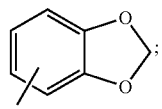

(c) $R_3$ is from one to four groups independently selected from the group consisting of:
  (i) hydrogen, halo, $C_{1-8}$ straight or branched chain alkyl, arylalkyl, $C_{3-7}$ cycloalkyl, $C_{1-8}$ alkoxy, cyano, $C_{1-4}$ carboalkoxy, trifluoromethyl, $C_{1-8}$ alkylsulfonyl, halogen, nitro, hydroxy, trifluoromethoxy, $C_{1-8}$ carboxylate, aryl, heteroaryl, and heterocyclyl;
  (ii) $NR_{10}R_{11}$ wherein $R_{10}$ and $R_{11}$ are independently selected from H, $C_{1-8}$ straight or branched chain alkyl, arylalkyl, $C_{3-7}$ cycloalkyl, carboxyalkyl, aryl, heteroaryl, or heterocyclyl, or $R_{10}$ and $R_{11}$ taken together with the nitrogen to which they are attached form a heterocyclyl or heteroaryl group;
  (iii) $NR_{12}COR_{13}$ wherein $R_{12}$ is selected from hydrogen or alkyl and $R_{13}$ is selected from hydrogen, alkyl, substituted alkyl, $C_{1-3}$ alkoxyl, carboxyalkyl, $R_{30}R_{31}N(CH_2)_p$, $R_{30}R_{31}NCO(CH_2)_p$, aryl, arylalkyl, heteroaryl, or heterocyclyl, or $R_{12}$ and $R_{13}$ taken together with the carbonyl group form a carbonyl containing heterocyclyl group, wherein $R_{30}$ and $R_{31}$ are independently selected from H, OH, alkyl, and alkoxy, and p is an integer from 1-6, wherein the alkyl group may be substituted with carboxyl, alkyl, aryl, substituted aryl, heterocyclyl, substituted heterocyclyl, heteroaryl, substituted heteroaryl, hydroxamic acid, sulfonamide, sulfonyl, hydroxy, thiol, alkoxy, or arylalkyl;

(d) $R_4$ is selected from the group consisting of (i) hydrogen, (ii) $C_{1-3}$ straight or branched chain alkyl, (iii) benzyl, and (iv) $NR_{13}R_{14}$, wherein $R_{13}$ and $R_{14}$ are independently selected from hydrogen and $C_{1-6}$ alkyl; wherein the $C_{1-3}$ alkyl and benzyl groups are optionally substituted with one or more groups selected from $C_{3-7}$ cycloalkyl, $C_{1-8}$ alkoxy, cyano, $C_{1-4}$ carboalkoxy, trifluoromethyl, $C_{1-8}$ alkylsulfonyl, halogen, nitro, hydroxy, trifluoromethoxy, $C_{1-8}$ carboxylate, amino, $NR_{13}R_{14}$, aryl, and heteroaryl; and (e) X is selected from S and O;
and the pharmaceutically acceptable salts, esters and prodrug forms thereof.

In an alternative embodiment, $R_1$, $R_3$, and $R_4$ are as above and $R_2$ is $NR_{15}R_{16}$, where $R_{15}$ and $R_{16}$ are independently selected from hydrogen, $C_{1-8}$ straight or branched chain alkyl, arylalkyl, $C_{3-7}$ cycloalkyl, aryl, heteroaryl, and heterocyclyl, or $R_{15}$ and $R_{16}$ taken together with the nitrogen to which they are attached form a heterocyclyl or heteroaryl group.

In regard to the above compounds, "alkyl" refers to straight, cyclic and branched-chain alkyl. The alkyl group may be optionally substituted with one or more groups such as halogen, OH, CN, mercapto, nitro, amino, $C_1$-$C_8$-alkyl, $C_1$-$C_8$-alkoxy, $C_1$-$C_8$-alkylthio, $C_1$-$C_8$-alkyl-amino, di($C_1$-$C_8$-alkyl)amino, (mono-, di-, tri-, and per-) halo-alkyl, formyl, carboxy, alkoxycarbonyl, $C_1$-$C_8$-alkyl-CO—O—, $C_1$-$C_8$-alkyl-CO—NH—, carboxamide, hydroxamic acid, sulfonamide, sulfonyl, thiol, aryl, aryl($c_1$-$c_8$)alkyl, heterocyclyl, and heteroaryl. The term "bioisostere" is defined as "groups or molecules which have chemical and physical properties producing broadly similar biological properties." (Burger's Medicinal Chemistry and Drug Discovery, M. E. Wolff, ed. Fifth Edition, Vol. 1, 1995, Pg. 785). The term "acyl" as used herein, whether used alone or as part of a substituent group, means an organic radical having 2 to 6 carbon atoms (branched or straight chain) derived from an organic acid by removal of the hydroxyl group. "Aryl" or "Ar," whether used alone or as part of a substituent group, is a carbocyclic aromatic radical including, but not limited to, phenyl, 1- or 2-naphthyl and the like. The carbocyclic aromatic radical may be substituted by independent replacement of 1 to 5 of the hydrogen atoms thereon with halogen, OH, CN, mercapto, nitro, amino, $C_1$-$C_8$-alkyl, $C_1$-$C_8$-alkoxyl, $C_1$-$C_8$-alkylthio, $C_1$-$C_8$-alkyl-amino, di($C_1$-$C_8$-alkyl)amino, (mono-, di-, tri-, and per-) halo-alkyl, formyl, carboxy, alkoxycarbonyl, $C_1$-$C_8$-alkyl-CO—O—, $C_1$-$C_8$-alkyl-CO—NH—, or carboxamide. Illustrative aryl radicals include, for example, phenyl, naphthyl, biphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. The term "heteroaryl" refers to a cyclic, fully unsaturated radical having from five to ten ring atoms of which one ring atom is selected from S, O, and N; 0-2 ring atoms are additional heteroatoms independently selected from S, O, and N; and the remaining ring atoms are carbon. The radical may be joined to the rest of the molecule via any of the ring atoms. The terms "heterocycle," "heterocyclic," and "heterocycle" refer to an optionally substituted, fully or partially saturated cyclic group which is, for example, a 4- to 7-membered monocyclic, 7- to 11-membered bicyclic, or 10- to 15-membered tricyclic ring system, which has at least one heteroatom in at least one carbon atom containing ring. Each ring of the heterocyclic group containing a heteroatom may have 1, 2, or 3 heteroatoms selected from nitrogen atoms, oxygen atoms, and sulfur atoms, where the nitrogen and sulfur heteroatoms may also optionally be oxidized. The nitrogen atoms may optionally be quaternized. The heterocyclic group may be attached at any heteroatom or carbon atom.

In other embodiments, PDE7 inhibitors useful in the methods of the invention have the formulas:

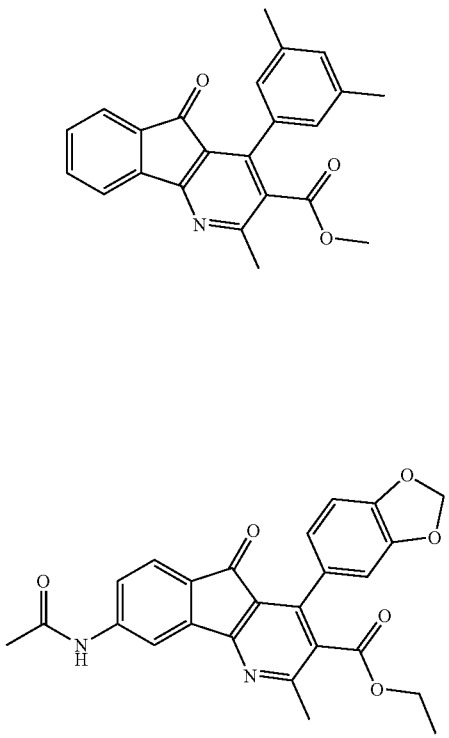

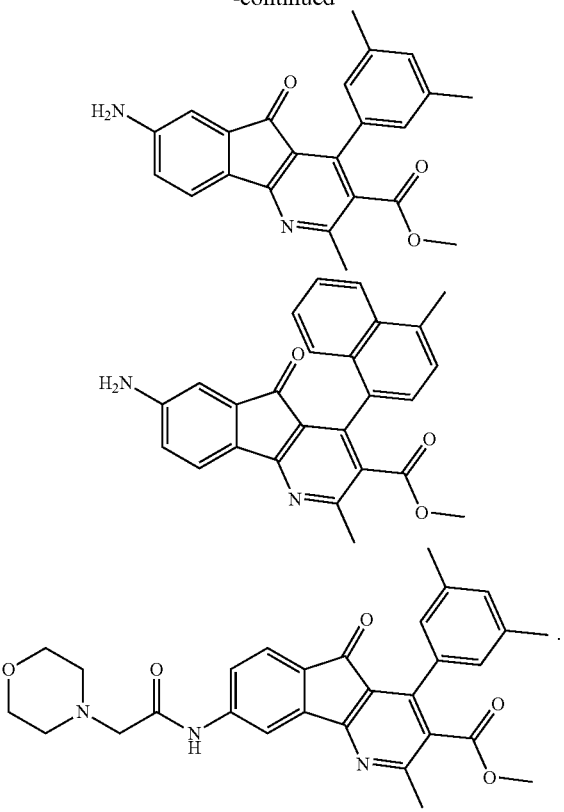

The preparation of the above compounds is described in U.S. Pat. No. 6,903,109, US 20040082578, WO 2003/088963, and US 20060154949.

In another embodiment, PDE7 inhibitors useful in the methods of the invention are selected from those compounds generally or specifically disclosed in U.S. Pat. No. 6,958,328, WO 2002/085894, and US 20030212089, each expressly incorporated herein by reference in its entirety. These PDE7 inhibitors have the same formula as those described above (e.g., U.S. Pat. No. 6,903,109), except that $R_1$ is not a carboxylic ester or carboxylic acid bioisostere. The preparation of these compounds is described in U.S. Pat. No. 6,958,328, US 20030212089, and WO 2002/085894.

In another embodiment, PDE7 inhibitors useful in the methods of the invention are selected from those compounds generally or specifically disclosed in WO 2006/004040 and EP 1 775 298, each expressly incorporated herein by reference in its entirety. In one embodiment, PDE7 inhibitors useful in the methods of the invention have the formula:

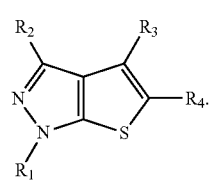

(6)

The substituents for the above compounds are defined as follows:

$R_1$ is substituted or unsubstituted $C_{3-8}$ alkyl group, substituted or unsubstituted cycloalkyl group, or substituted or unsubstituted heterocycloalkyl group (e.g., cyclohexyl, cycloheptyl, or tetrahydropyranyl);

$R_2$ is a hydrogen atom or substituted or unsubstituted $C_{1-3}$ alkyl group (e.g., methyl);

$R_3$ is a hydrogen atom, substituted or unsubstituted $C_{1-3}$ alkyl group, or a halogen atom; and $R_4$ is substituted or unsubstituted aryl group, substituted or unsubstituted heteroaryl group, or a group $CONR_5R_6$, or $CO_2R_7$, wherein $R_5$ and $R_6$ are, same or different from each other, a hydrogen atom; $C_{1-6}$ alkyl group which may be substituted by a halogen atom, substituted or unsubstituted aryl group, substituted or unsubstituted heteroaryl group, substituted or unsubstituted heterocycloalkyl group, substituted or unsubstituted cycloalkyl group, a group $NR_7COR_8$, $COR_5$, $NR_9R_{10}$; substituted or unsubstituted cycloalkyl group; substituted or unsubstituted heterocycloalkyl group; substituted or unsubstituted aryl group; substituted or unsubstituted heteroaryl group; or substituted or unsubstituted heterocycloalkyl group in which the ring is formed together with the nitrogen atom binding $R_5$ and $R_6$;

wherein $R_7$ is a hydrogen atom or substituted or unsubstituted $C_{1-3}$ alkyl group;

wherein $R_8$ is substituted or unsubstituted heterocycloalkyl group, or a group OH, $OR_7$, or $NR_9R_{10}$;

wherein $R_9$ and $R_{10}$ are, same or different from each other, a hydrogen atom; substituted or unsubstituted $C_{1-3}$ alkyl group, substituted or unsubstituted heterocycloalkyl group; substituted or unsubstituted acyl; a group $SO_2R_7$, or substituted or unsubstituted heterocycloalkyl group in which the ring is formed together with the nitrogen atom binding $R_5$ and $R_6$;

or pharmaceutically acceptable salts or solvates thereof.

In regard to the above compounds, the term "cycloalkyl group" means cycloalkyl group having 3 to 8 carbon atoms. The term "heterocycloalkyl group" may be 3 to 7 membered monocyclic or polycyclic heterocyclic group containing the same or different 1 to 4 hetero atom(s) such as oxygen, nitrogen or sulfur atom(s), and examples may include piperidinyl, pyrrolidinyl, piperazinyl, tetrahydrofuryl, tetrahydropyranyl, morpholinyl, azetidinyl, imidazolidinyl, oxazolidinyl, hexahydropyrrolidinyl, octahydroindolidinyl, octahydroquinolidinyl, octahydroindolyl, and oxo-derivatives thereof. The term "aryl group" may be aromatic hydrocarbon group, which consists of mono-benzene ring, or binding or condensed benzene ring, such as phenyl, naphthyl, biphenyl and the like; and dicyclic or tricyclic group, which consists of benzene ring condensed with cycloalkyl or heterocyclic ring, such as 1,2,3,4-tetrahydronaphthalene, 2,3-dihydroindene, indoline, coumarone and the like. The term "heteroaryl group" may be 5 to 7 membered monocyclic heteroaryl group or polycyclic heteroaryl group, and having 2 to 8 carbon atoms with 1 to 4 hetero atom(s) such as oxygen, nitrogen, sulfur atom(s), in which the polycyclic heteroaryl group has condensed ring system by the same or different monocyclic heteroaryl or benzene ring each other; or polycyclic group which is consisted of heteroaryl group condensed with cycloalkyl or heterocycloalkyl ring. Examples of suitable substituent of the present invention may include straight, branched-chained or cyclic $C_1$-$C_8$ alkyl group, which may be substituted by one or more methyl, ethyl, propyl, isopropyl, n-butyl, t-butyl, cyclohexyl, cycloheptyl, methoxymethyl, hydroxymethyl, trifluoromethyl, $C_1$-$C_3$ alkoxy group, halogen atom, and hydroxyl group; hydroxyl group; cyano group; substituted or unsubstituted alkoxy group such as methoxy, ethoxy group; amino group which may be substituted by $C_1$-$C_6$ alkyl group or acyl group such as amino, methylamino, ethylamino, dimethylamino, acylamino and the like; carboxylic group; substituted or unsubstituted ester group; phosphate group; sulfonic group; substituted or unsubstituted aryl group; substituted or unsubstituted heteroaryl group; saturated or unsaturated heterocycloalkyl group which may be substituted; substituted or unsubstituted carbamoyl group; substituted or unsubstituted amide group; substituted or unsubstituted thioamide group; halogen atom; nitro group; substituted or unsubstituted sulfone group; substituted or unsubstituted sulfonylamide group; oxo group; substituted or unsubstituted urea group; straight, branched-chained or cyclic alkenyl group such as ethenyl, propenyl, cyclohexenyl and the like.

In other embodiments, PDE7 inhibitors useful in the methods of the invention have the formulas:

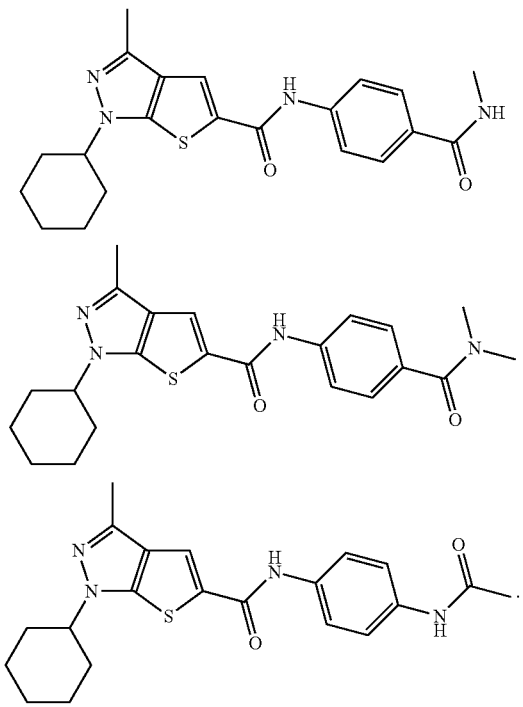

The preparation of the above compounds is described in EP 1 775 298 and WO 2006/004040.

In another embodiment, PDE7 inhibitors useful in the methods of the invention are selected from those compounds generally or specifically disclosed in WO 2004/111053 and US 20060128707, each expressly incorporated herein by reference in its entirety. In one embodiment, PDE7 inhibitors useful in the methods of the invention have the formulas:

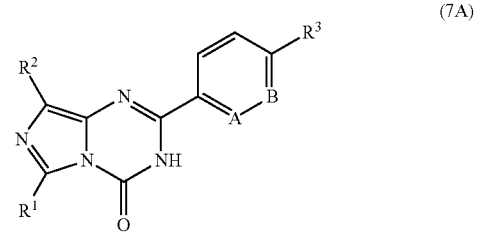

(7A)

-continued

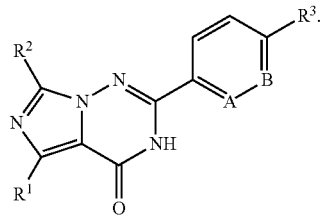
(7B)

The substituents for the above compounds are defined as follows:

A is N or $CR_4$;
B is N or CH;
$R_1$ is substituted or unsubstituted $C_{3-8}$ cycloalkyl group or tert-butyl group;
$R_2$ is a hydrogen atom or $C_{1-6}$ alkyl group;
$R_3$ is a hydrogen atom; nitro group; cyano group; a halogen atom; heteroaryl group; substituted or unsubstituted $C_{1-6}$ alkyl group; substituted or unsubstituted $C_{2-6}$ alkenyl group; saturated or unsaturated heterocycloalkyl group which is substituted or unsubstituted; a group: $NR_5R_6$, $C(O)R_7$, $SO_2R_7$, $OR_8$, $NR_8COR_7$, $NR_8SO_2R_7$;
$R_4$ is a hydrogen atom or $C_{1-3}$ alkoxy group which is unsubstituted or substituted by one or more fluorine atom(s);
$R_5$ and $R_6$ are, same or different from each other, a hydrogen atom; substituted or unsubstituted $C_{1-6}$ alkyl group; substituted or unsubstituted acyl group; or substituted or unsubstituted heterocycloalkyl group;
$R_7$ is a hydrogen atom; substituted or unsubstituted $C_{1-6}$ alkyl group; substituted or unsubstituted heterocycloalkyl group; OH; $OR_8$ or $NR_5R_6$;
$R_8$ is a hydrogen atom, substituted or unsubstituted $C_{1-6}$ alkyl group; or substituted or unsubstituted heterocycloalkyl group;
or pharmaceutically acceptable salts or solvates thereof.

In regard to the above compounds, the term "$C_1$-$C_6$ alkyl group" refers to a straight or branched-chained alkyl group having 1 to 6 carbon atoms, and the term "$C_2$-$C_6$ alkenyl group" refers to a straight or branched-chained alkenyl group having 2 to 6 carbon atoms. The term "cycloalkyl group" refers to a cycloalkyl group having 3 to 8 carbon atoms such as cyclopropyl, cyclobutyl, cyclopentyl, cyclohexyl, cycloheptyl, and cyclooctyl. The term "heterocycloalkyl group" is 3 to 7 membered heterocyclic group containing the same or different 1 to 4 hetero atom(s) such as oxygen, nitrogen or sulfur atom(s), and examples may include piperidinyl, pyrrolidinyl, piperazinyl, tetrahydrofuryl, tetrahydropyranyl, morpholinyl, azetidinyl, and homopiperazinyl. The term "heteroaryl group" is 5 to 7 membered monocyclic or polycyclic group thereof containing 2 to 8 carbon atoms and the same or different 1 to 4 hetero atom(s) such as oxygen, nitrogen or sulfur atom(s). The examples include pyrrole, furyl, thienyl, imidazolyl, thiazolyl, pyrazinyl, indolyl, quinolinyl, isoquinolinyl, tetrazolyl, pyridinyl, pyrazolyl, pyridazinyl, and pyrimidinyl. The "halogen atom" includes fluorine, chlorine, bromine and iodine. Examples of the suitable substituent of "substituted or unsubstituted $C_1$-$C_6$ alkyl group", "substituted or unsubstituted $C_3$-$C_8$ cycloalkyl group", "substituted or unsubstituted alkenyl group", "substituted or unsubstituted heterocycloalkyl group" and "substituted or unsubstituted acyl group" include a straight or branched-chained, or substituted or unsubstituted alkyl group such as methyl, ethyl, propyl, isopropyl, n-butyl, tert-butyl, substituted or unsubstituted cycloalkyl group such as cyclopropyl, cyclobutyl, cyclopentyl, cyclohexyl, and cycloheptyl; hydroxyl group; cyano group; alkoxy group such as methoxy and ethoxy; substituted or unsubstituted amino group such as amino, methylamino, ethylamino, and dimethylamino; substituted or unsubstituted acyl group such as acetyl, and propionyl; substituted or unsubstituted aryl group; substituted or unsubstituted heteroaryl group; saturated or unsaturated heterocycloalkyl group which is substituted or unsubstituted; substituted or unsubstituted carbamoyl group; substituted or unsubstituted amide group; halogen atom; nitro group; substituted or unsubstituted sulfone group; oxo group; urea group; a straight or branched-chained, or cyclic alkenyl group which is substituted or unsubstituted such as ethenyl, propenyl, and cyclohexenyl.

In other embodiments, PDE7 inhibitors useful in the methods of the invention have the formulas:

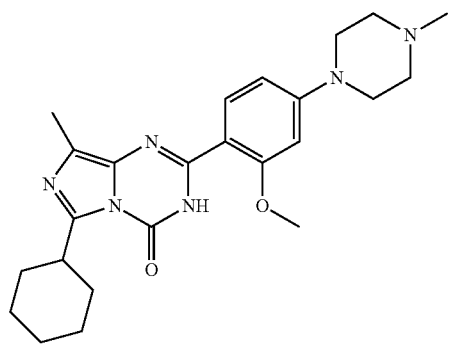

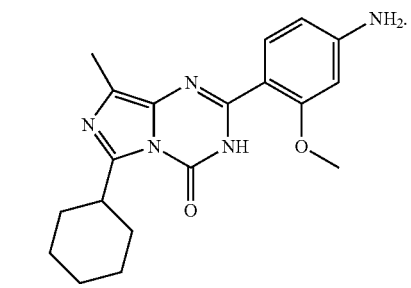

The preparation of the above compounds is described in US 20060128707 and WO 2004/111053.

In another embodiment, PDE7 inhibitors useful in the methods of the invention are selected from those compounds generally or specifically disclosed in U.S. Pat. No. 6,617,357, US 20020156064, and *Molecular Pharmacology*, 66:1679-1689, 2004, each expressly incorporated herein by reference in its entirety. In one embodiment, PDE7 inhibitors useful in the methods of the invention have the formula:

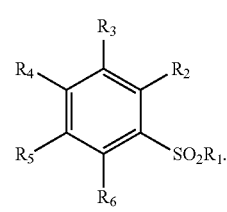
(8)

The substituents for the above compounds are defined as follows:

$R_1$ is $NR_aR_b$ where $R_a$ and $R_b$ are independently H or $C_{1-6}$ alkyl, or represents a 5 to 7 member ring comprised of carbon or carbon and one or more additional heteroatoms selected from O, N, or S;

$R_2$ is H, $C_{1-8}$ alkyl, $C_{1-3}$ alkyl-Ar, $C_{1-3}$ alkyl-$C_{3-6}$ cycloalkyl, $C_{2-8}$ alkenyl, $C_{2-4}$ alkenyl-Ar, or $C_{2-4}$ alkenyl-$C_{3-6}$ cycloalkyl, wherein Ar is substituted or unsubstituted phenyl;

$R_3$ is $NO_2$, halo, CN, $C(O)OR_7$, $COR_1$, or $NR_aR_b$ where $R_a$ and $R_b$ are independently H or $C_{1-6}$ alkyl;

$R_4$ is H, $OC_{1-6}$ alkyl, halo, $C(O)NR_aR_b$, $C(O)OR_7$, $C_{1-8}$ alkyl, $OCHF_2$, $CH_2OR_8$, $OC_{1-3}$ alkyl-Ar, or $CH_2NHC(O)CH_3$;

$R_5$ is H, halo, or alkyl;

$R_6$ is $C_{1-8}$ alkyl, $OC_{1-4}$ alkyl, or halo;

$R_7$ is hydrogen or an ester or amide-forming group;

$R_8$ is hydrogen or $C_{1-6}$ alkyl;

or a pharmaceutically acceptable salt or solvate thereof.

In one embodiment, a PDE7 inhibitor useful in the methods of the invention has the formula:

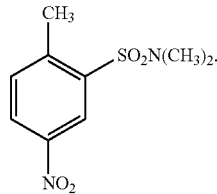

The preparation of the above compounds is described in U.S. Pat. No. 6,617,357, US 20020156064, and *Molecular Pharmacology,* 66:1679-1689, 2004.

In another embodiment, PDE7 inhibitors useful in the methods of the invention are selected from those compounds generally or specifically disclosed in U.S. Pat. No. 6,852,720, EP 1 348 433, and WO 2003/082277, each expressly incorporated herein by reference in its entirety. In one embodiment, PDE7 inhibitors useful in the methods of the invention have the formula:

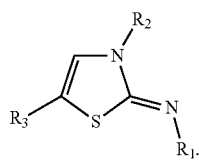

(9)

The substituents for the above compounds are defined as follows:

$R_1$ is a group selected from cycloalkyl, heterocycloalkyl, aryl and heteroaryl, those groups being optionally substituted by one or more groups, identical or different, selected independently of each other from halogen, trifluoromethyl, nitro, cyano, oxo, $NR_4R_5$, $CO_2R_4$, $CONR_4R_5$, $OR_4$, $S(O)_nR_4$, $S(O)_n$ $NR_4R_5$, tetrazolyl and $(C_1-C_6)$ alkyl which is optionally substituted by 1 to 3 groups, identical or different, selected independently of each other from $OR_4$, $NR_4R_5$, and $CO_2R_4$; wherein n is an integer from 0 to 2 inclusive, $R_4$ and $R_5$ are identical or different and independently of each other are a hydrogen atom or a group of formula $X_1$—$R_a$, wherein $X_1$ is a single bond or a $(C_1-C_6)$ alkylene group, and $R_a$ is a group selected from $(C_1-C_6)$ alkyl, cycloalkyl, heterocycloalkyl, aryl, and heteroaryl, $R_2$ is a group selected from $(C_1-C_6)$ alkyl, $(C_2-C_6)$ alkenyl, $(C_2-C_6)$ alkynyl, aryl, and cycloalkyl, $R_3$ is a group selected from cycloalkyl, heterocycloalkyl, aryl and heteroaryl, these groups being optionally substituted by one or more groups, identical or different, selected independently of each other from halogen, nitro, cyano, trifluoromethyl, oxo, $(C_1-C_6)$ alkyl, $OR_6$, $NR_6R_7$, $COR_6$, $CO_2R_6$, $CONHOH$, $CONR_6R_7$, $S(O)_mR_6$, $S(O)_mNR_6R_7$, $NR_6COR_7$, $NR_6SO_2R_7$, $N(SO_2R_7)_2$, $NR_6CONR_7R_8$, $C(=NCN)NR_6R_7$, $NR_8C(=NCN)NR_6R_7$, and tetrazolyl optionally substituted with a $(C_1-C_4)$ alkyl, wherein m is an integer from 0 to 2 inclusive, $R_6$ and $R_7$ are identical or different and independently of each other are a hydrogen atom or a group of formula $X_2R_b$, wherein $X_2$ is a single bond or a $(C_1-C_6)$ alkylene group, $R_b$ is a group selected from $(C_1-C_6)$ alkyl, cycloalkyl, heterocycloalkyl, aryl and heteroaryl, these groups being optionally substituted by 1 to 3 groups, identical or different, selected independently of each other from hydroxy, $(C_1-C_6)$ alkoxy, $(C_1-C_6)$ alkyl, amino, mono$(C_1-C_6)$ alkylamino, di$(C_1-C_6)$ alkylamino (each alkyl amino being identical or different, independently of each other), carboxy, $(C_1-C_6)$ alkoxycarbonyl, and benzyl, and $R_8$ represents a hydrogen atom or a $(C_1-C_6)$ alkyl group;

a racemic form thereof, an isomer thereof, an N-oxide thereof, or a pharmaceutically acceptable acid or base salt thereof.

The preparation of the above compounds is described in U.S. Pat. No. 6,852,720, EP 1 348 433, and WO 2003/082277.

In another embodiment, PDE7 inhibitors useful in the methods of the invention are selected from those compounds generally or specifically disclosed in U.S. Pat. No. 6,753,340, US 20030191167, EP 1 348 701, and WO 2003/082839, each expressly incorporated herein by reference in its entirety. In one embodiment, PDE7 inhibitors useful in the methods of the invention have the formula:

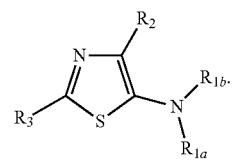

(10)

The substituents for the above compounds are defined as follows:

$R_{1a}$ is a group selected from hydrogen, $(C_1-C_6)$ alkyl and aryl$(C_1-C_6)$ alkyl, $R_{1b}$ is a group selected from cycloalkyl, heterocycloalkyl, aryl and heteroaryl, those groups being optionally substituted by one or more groups, identical or different, selected independently of each other from halogen, trifluoromethyl, nitro, cyano, oxo, $NR_4R_5$, $CO_2R_4$, $CONR_4R_5$, $OR_4$, $S(O)_bR_4$, $S(O)_n$ $NR_4R_5$, tetrazolyl, and $(C_1-C_6)$ alkyl which is optionally substituted by 1 to 3 groups, identical or different, selected independently of each other from $OR_4$, $NR_4$, $R_5$, and $CO_2R_4$, wherein n is an integer from 0 to 2 inclusive, $R_4$ and $R_5$ are identical or different and independently of each other are a hydrogen atom or a group of formula $X_1$—$R_a$, wherein $X_1$ is a single bond or a $(C_1-C_6)$ alkylene group, and $R_a$ is a group selected from $(C_1-C_6)$ alkyl, cycloalkyl, heterocycloalkyl, aryl and heteroaryl, $R_2$ is a group selected from $(C_1-C_6)$ alkyl, $(C_2-C_6)$ alkenyl, $(C_2-C_6)$ alkynyl, aryl and cycloalkyl, R$_3$ is a group selected from cycloalkyl, heterocycloalkyl, aryl and heteroaryl, these groups being optionally substituted by one or more groups, identical or different, selected independently of each other from halogen, nitro, cyano, trifluoromethyl, oxo, (C$_1$-C$_6$) alkyl, OR$_6$, NR$_6$R$_7$, COR$_6$, CO$_2$R$_6$, CONHOH, CONR$_6$R$_7$, S(O)$_m$R$_6$, S(O)$_m$NR$_6$R$_7$, NR$_6$COR$_7$, NR$_6$SO$_2$R$_7$, N(SO$_2$R$_7$)$_2$, NR$_6$CONR$_7$R$_8$, C(=N—CN)NR$_6$R$_7$, NR$_8$C(=N—CN)NR$_6$R$_7$, and tetrazolyl optionally substituted with a (C$_1$-C$_4$) alkyl, wherein m is an integer from 0 to 2 inclusive, R$_6$ and R$_7$ are identical or different and independently of each other are a hydrogen atom or a group of formula X$_2$—R$_b$, wherein X$_2$ is a single bond or a (C$_1$-C$_6$) alkylene group, R$_b$ is a group selected from (C$_1$-C$_6$) alkyl, cycloalkyl, heterocycloalkyl, aryl and heteroaryl, these groups being optionally substituted by 1 to 3 groups, identical or different, selected independently of each other from hydroxy, (C$_1$-C$_6$) alkoxy, (C$_1$-C$_6$) alkyl, amino, mono(C$_1$-C$_6$) alkylamino, di(C$_1$-C$_6$) alkylamino (each alkyl amino being identical or different, independently of each other), carboxy, (C$_1$-C$_6$) alkoxycarbonyl, and benzyl, and R$_8$ is a hydrogen atom or a (C$_1$-C$_6$) alkyl group, or a racemic form thereof, an isomer thereof, an N-oxide thereof or a pharmaceutically acceptable acid or base salt thereof.

The preparation of these compounds is described in U.S. Pat. No. 6,753,340, US 20030191167, EP 1 348 701, and WO 2003/082839.

In another embodiment, PDE7 inhibitors useful in the methods of the invention are selected from those compounds generally or specifically disclosed in U.S. Pat. No. 6,849,638, US 20030119829, and WO 2002/088138, each expressly incorporated herein by reference in its entirety. In one embodiment, PDE7 inhibitors useful in the methods of the invention have the formula:

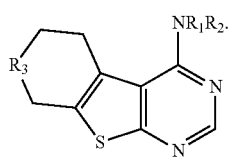

(11)

The substituents for the above compounds are defined as follows:

R$_1$ and R$_2$ are independently selected from the group consisting of hydrogen, alkyl of 1-8 carbon atoms, alkenyl of 2-8 carbon atoms, alkynyl of 2-8 carbon atoms, cycloalkyl of 3-7 carbon atoms, fully saturated heterocycle of 2-6 carbon atoms and 1-2 heteroatoms selected from NH, S and O, aryl of 6-12 carbon atoms, that may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms or heteroaryl of 4-11 carbon atoms and 1, 2 heteroatoms selected from N, S, and O, heteroaryl of 4-11 carbon atoms and 1-2 heteroatoms selected from N, S and O, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms or heteroaryl of 4-11 carbon atoms and 1-2 heteroatoms selected from N, S and O, and R$_4$—R$_5$, or R$_1$ and R$_2$ combine to form, together with the nitrogen atom to which they are attached, a 5-7 membered saturated ring which may contain 1-2 additional heteroatoms selected from the group consisting of NH, NR$_8$, S and O, or combine to form, together with the nitrogen atom to which they are attached, a 5-7 membered unsaturated ring that may contain 1-2 additional heteroatoms selected from the group consisting of N, S and O, wherein said saturated or unsaturated ring may be substituted with 1-2 substituents selected from the group consisting of OH, alkyl of 1-6 carbon atoms, alkenyl of 2-6 carbon atoms, alkynyl of 2-6 carbon atoms, cycloalkyl of 3-7 carbon atoms, fully saturated heterocycle of 2-6 carbon atoms and 1-2 heteroatoms selected from NH, S, and O, halogen, haloalkyl of 1-2 carbon atoms and a number of halogen atoms up to the perhalo level, alkoxy of 1-6 carbon atoms, haloalkoxy of 1-6 carbon atoms and a number of halogen atoms up to the perhalo level, and R$_9$-R$_{10}$; or R$_1$ and R$_2$ combine to form, together with the nitrogen atom to which they are attached, an 8-10 membered bicyclic saturated ring;

R$_3$ is selected from the group consisting of NH, S, S(=O)$_2$, and O;

R$_4$ is selected from alkyl of 1-8 carbon atoms, alkenyl of 2-8 carbon atoms, alkynyl of 2-8 carbon atoms, C(=C), S(=O)$_2$, and C(=O)O;

R$_5$ is selected from hydrogen, OH, alkyl of 1-8 carbon atoms, alkenyl of 2-8 carbon atom, alkynyl of 2-8 carbon atoms, alkoxy of 1-8 carbon atoms, aryl of 6-12 carbon atoms, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkyl of 1-6 carbon atoms and a number of halogen atoms up to the perhalo level, aryl of 6-12 carbon atoms and heteroaryl of 4-11 carbon atoms and 1-2 heteroatoms selected from N, S, and O, heteroaryl of 4-11 carbon atoms and 1-2 heteroatoms selected from N, S, and O, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms and heteroaryl of 4-11 carbon atoms and 1-2 heteroatoms selected from N, S, and O, cycloalkyl of 3-7 carbon atoms, fully saturated heterocycle of 2-6 carbon atoms and 1-2 heteroatoms selected from NH, S and O, and NR$_6$R$_7$, R$_6$ and R$_7$ are independently selected from hydrogen, alkyl of 1-8 carbon atoms, alkenyl of 2-8 carbon atoms, and alkynyl of 2-8 carbon atoms, or R$_6$ and R$_7$ combine together with the nitrogen atom to which they are attached to form a 5-7 membered, unsaturated ring which may contain 1-2 additional heteroatoms selected from N, S and O or to form a 5-7 membered, saturated ring which may contain 1-2 additional heteroatoms selected from NH, S, and O;

R$_8$ is selected from alkyl of 1-8 carbon atoms, alkenyl of 2-8 carbon atoms, alkynyl of 2-8 carbon atoms, R$_{11}$-R$_{12}$, cycloalkyl of 3-7 carbon atoms, fully saturated heterocycle of 2-6 carbon atoms and 1-2 heteroatoms selected from NH, S, and O, aryl of 6-12 carbon atoms, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms or heteroaryl of 4-11 carbon atoms and 1-2 heteroatoms selected from N, S, and O, heteroaryl of 4-11 carbon atoms and 1-2 heteroatoms selected from N, S, and O, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms or heteroaryl of 4-11 carbon atoms and 1-2 heteroatoms selected from N, S, and O;

$R_9$ is selected from alkyl of 1-8 carbon atoms, alkenyl of 2-8 carbon atoms, and alkynyl of 2-8 carbon atoms, $R_{10}$ is selected from OH, aryl of 6-12 carbon atoms, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms or heteroaryl of 4-11 carbon atoms and 1-2 heteroatoms selected from N, S, and O, and heteroaryl of 4-11 carbon atoms and 1-2 heteroatoms selected from N, S, and O, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms or heteroaryl of 4-11 carbon atoms and 1-2 heteroatoms selected from N, S, and O;

$R_{11}$ is selected from alkyl of 1-8 carbon atoms, alkenyl of 2-8 carbon atoms, and alkynyl of 2-8 carbon atoms; and $R_{12}$ is selected from cycloalkyl of 3-7 carbon atoms, fully saturated heterocycle of 2-6 carbon atoms and 1-2 heteroatoms selected from NH, S, and O, aryl of 6-12 carbon atoms, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms or heteroaryl of 4-11 carbon atoms and 1-2 heteroatoms selected from N, S, and O, and heteroaryl of 4-11 carbon atoms and 1-2 heteroatoms selected from N, S and O, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms or heteroaryl of 4-11 carbon atoms and 1-2 heteroatoms selected from N, S and O;

and pharmaceutically acceptable salts thereof.

The preparation of these compounds is described in U.S. Pat. No. 6,849,638, US 20030119829, and WO 2002/088138.

In another embodiment, PDE7 inhibitors useful in the methods of the invention are selected from those compounds generally or specifically disclosed in US 2005222138 and WO 2003/064389, each expressly incorporated herein by reference in its entirety. In one embodiment, PDE7 inhibitors useful in the methods of the invention have the formula:

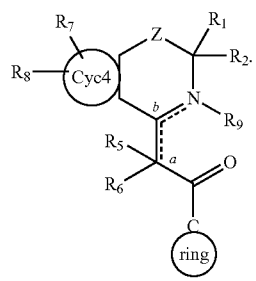

(12)

The substituents for the above compounds are defined as follows:

$R_1$ and $R_2$ are each independently, (1) hydrogen atom, or (2) $C_{1-8}$ alkyl, or $R_1$ and $R_2$ may be taken together with the carbon atom to which they are attached to form Cyc1, wherein $R_1$ and $R_2$ do not represent hydrogen atom at the same time;

Z is (1) $CR_3R_4$, (2) O, (3) S, or (4) a bond;

$R_3$ and $R_4$ are each independently, (1) hydrogen atom, (2) $C_{1-8}$ alkyl, (3) $C_{1-8}$ alkoxy, or (4) hydroxy, or $R_3$ and $R_4$ may be taken together with the carbon atom to which they are attached to form Cyc1 or C(O);

$R_5$ and $R_6$ are each independently, (1) hydrogen atom, or (2) $C_{1-8}$ alkyl, or $R_5$ and $R_6$ may be taken together with the carbon atom to which they are attached to form Cyc1;

Cyc1, which is represented by $R_1$ and $R_2$, $R_3$ and $R_4$, $R_5$ and $R_6$, is, each independently, (1) $C_{3-10}$ cycloalkyl, or (2) 3-10 membered monocyclic hetero-ring comprising 1-2 of heteroatom selected from oxygen, nitrogen and sulfur, and Cyc1 may be substituted with $R_{10}$;

$R_{10}$ is (1) $C_{1-8}$ alkyl, (2) $C_{1-8}$ alkoxy, (3) hydroxy, (4) $COOR_{11}$, (5) oxo, (6) $SO_2R_{12}$, or (7) $COR_D$;

$R_{11}$ is hydrogen atom, or $C_{1-8}$ alkyl;

$R_{12}$ and $R_{13}$ are (1) $C_{1-8}$ alkyl, or (2) phenyl which may be substituted with $C_{1-8}$ alkyl;

$R_7$ and $R_8$ are each independently, (1) hydrogen atom, (2) $C_{1-8}$ alkyl, (3) $C_{1-8}$ alkoxy, (4) hydroxy, (5) cyano, (6) halogen atom, (7) $COOR_{14}$, (8) $CONR_{15}R_{16}$, (9) Cyc2, (10) $C_{2-8}$ alkenyl, (11) $C_{2-8}$ alkynyl, (12) $NR_{51}R_{52}$, (13) nitro, (14) formyl, (15) $C_{2-8}$ acyl, (16) $C_{1-8}$ alkyl substituted with hydroxy, $C_{1-8}$ alkoxy, Cyc2, $NR_{51}R_{52}$, or $NR_{53}$—Cyc2, (17) $NR_{54}COR_{55}$, (18) $NR_{56}SO_2R_{57}$, (19) $SO_2NR_{58}R_{59}$, (20) $C_{2-8}$ alkenyl substituted with $COOR_{14}$, (21) CH=N—OH, (22) $C_{1-8}$ alkylene-$NR_{60}$—($C_{1-8}$ alkylene)-$R_{61}$, (23) $C_{1-8}$ alkylthio, (24) $C_{1-8}$ alkyl substituted with 1-3 of halogen atom, (25) $C_{1-8}$ alkoxy substituted with 1-3 of halogen atom, (26) $C_{1-8}$ alkoxy substituted with Cyc2, (27) O-Cyc2, (28) $OSO_2R_{65}$, or (29) CH=N—$OR_{137}$;

$R_{14}$ is hydrogen atom, or $C_{1-8}$ alkyl;

$R_{15}$ and $R_{16}$ are each independently hydrogen atom or $C_{1-8}$ alkyl;

$R_{51}$ and $R_{52}$, $R_{58}$ and $R_{59}$ are each independently, hydrogen atom, or $C_{1-8}$ alkyl;

$R_{53}$, $R_{54}$, $R_{56}$, and $R_{60}$ are each independently, hydrogen atom, or $C_{1-8}$ alkyl;

$R_{55}$ is hydrogen atom, $C_{1-8}$ alkyl, or $C_{1-8}$ alkoxy; $R_{57}$ is $C_{1-8}$ alkyl;

$R_{61}$ is $NR_{62}R_{63}$ or hydroxy;

$R_{62}$ and $R_{63}$ are each independently, hydrogen atom, or $C_{1-8}$ alkyl;

$R_{65}$ is $C_{1-8}$ alkyl;

$R_{137}$ is $C_{1-8}$ alkyl;

(hereinafter it is abbreviated as ring) is Cyc2 wherein the group which attaches to carbonyl is carbon;

$R_7$, $R_8$, and Cyc2 represented by ring are each independently, (1) $C_{3-15}$ mono-, bi- or tri-cyclic (fused or spiro)carboring, or (2) 3-15 membered mono-, bi- or tri-cyclic (fused or spiro)heterosing comprising 1-4 of heteroatom selected from oxygen, nitrogen and sulfur;

Cyc2 may be substituted with 1-5 of $R_{17}$ or $R_{17'}$;

$R_{17}$ is (1) $C_{1-8}$ alkyl, (2) $C_{2-8}$ alkenyl, (3) $C_{2-8}$ alkynyl, (4) $C_{1-8}$ alkoxy, (5) $C_{1-8}$ alkylthio, (6) hydroxy, (7) halogen atom, (8) nitro, (9) oxo, (10) carboxy, (11) formyl, (12) cyano, (13) $NR_{18}R_{19}$, (14) phenyl, phenoxy or phenylthio, which may be substituted with 1-5 of $R_{20}$, (15) $C_{1-8}$ alkyl, $C_{2-8}$ alkenyl, $C_{1-8}$ alkoxy or $C_{1-8}$ alkylthio, which may be substituted with 1-5 of $R_{21}$ (16) $OCOR_{22}$, (17) $CONR_{23}R_{24}$, (18) $SO_2NR_{25}R_{26}$ (19) $COOR_{27}$, (20) $COCOOR_{28}$, (21) $COR_{29}$, (22) $COCOR_{30}$, (23) $NR_{31}COR_{32}$, (24) $SO2R_{33}$, (25) $NR_{34}SO_2R_{35}$, or (26) $SOR_{64}$;

$R_{18}$ and $R_{19}$, $R_{31}$ and $R_{34}$ are each independently, hydrogen atom, or $C_{1-8}$ alkyl;

$R_{20}$ and $R_{21}$ are $C_{1-8}$ alkyl, $C_{1-8}$ alkoxy, hydroxy, halogen atom, nitro, or $COOR_{36}$;

$R_{22}$ and $R_{64}$ are each independently $C_{1-8}$ alkyl;

$R_{23}$, $R_{24}$, $R_{25}$ and $R_{26}$ are each independently hydrogen atom, $C_{1-8}$ alkyl, or phenyl;

$R_{27}$, $R_{28}$, $R_{29}$, $R_{30}$, $R_{32}$, $R_{33}$ and $R_{35}$ are (1) $C_{1-8}$ alkyl, (2) $C_{2-8}$ alkenyl, (3) $C_{1-8}$ alkyl substituted with 1-5 of $R_{37}$, (4) diphenylmethyl, (5) triphenylmethyl, (6) Cyc3, (7) $C_{1-8}$ alkyl or $C_{2-8}$ alkenyl substituted with Cyc3, (8) $C_{1-8}$ alkyl substituted with O-Cyc3, S-Cyc3 or $SO_2$-Cyc3;

$R_{36}$ is hydrogen atom, or $C_{1-8}$ alkyl;

$R_{37}$ is $C_{1-8}$ alkoxy, $C_{1-8}$ alkylthio, benzyloxy, halogen atom, nitro or $COOR_{38}$;

$R_{38}$ is hydrogen atom, $C_{1-8}$ alkyl or $C_{2-8}$ alkenyl;

Cyc3 is (1) $C_{3-15}$ mono-, bi- or tri-cyclic (fused or spiro) carboring, or (2) 3-15 membered mono-, bi- or tri-cyclic (fused or spiro)heterosing comprising 1-4 of heteroatom selected from oxygen, nitrogen and sulfur;

Cyc3 may be substituted with 1-5 of $R_{39}$;

$R_{39}$ is (1) $C_{1-8}$ alkyl, (2) $C_{2-8}$ alkenyl, (3) $C_{2-8}$ alkynyl, (4) $C_{1-8}$ alkoxy, (5) $C_{1-8}$ alkylthio, (6) hydroxy, (7) halogen atom, (8) nitro, (9) oxo, (10) cyano, (11) benzyl, (12) benzyloxy, (13) $C_{1-8}$ alkyl, $C_{1-8}$ alkoxy or $C_{1-8}$ alkylthio substituted with 1-5 of $R_{40}$, (14) phenyl, phenoxy, phenylthio, phenylsulfonyl or benzoyl which may be substituted with 1-5 of $R_{41}$, (15) $OCOR_{42}$, (16) $SO_2R_{43}$, (17) $NR_{44}COR_{45}$, (18) $SO_2NR_{46}R_{47}$, (19) $COOR_{48}$, or (20) $NR_{49}R_{50}$;

$R_{40}$ is halogen atom;

$R_{41}$ is $C_{1-8}$ alkyl, $C_{1-8}$ alkoxy, halogen atom, or nitro;

$R_{42}$, $R_{43}$ and $R_{45}$ are $C_{1-8}$ alkyl;

$R_{44}$ and $R_{48}$ are hydrogen atom or $C_{1-8}$ alkyl;

$R_{46}$ and $R_{47}$, $R_{49}$ and $R_{50}$ are each independently, hydrogen atom or $C_{1-8}$ alkyl;

$R_{17'}$ is (1) SH, (2) $NR_{66}CHO$, (3) Cyc5, (4) $C_{1-8}$ alkyl, $C_{2-8}$ alkenyl or $C_{2-8}$ alkynyl substituted with Cyc5, (5) CO—(NH-amino acid residue-CO)$_n$—OH, (6) $NR_{67}CONR_{68}R_{69}$, (7) $CONR_{70}NR_{71}R_{72}$, (8) $CONR_{73}OR_{74}$, (9) $CONR_{75}COR_{76}$, (10) C(S)$NR_{77}R_{78}$, (11) $CONR_{79}C(S)COOR_{80}$, (12) $NR_{81}COCOOR_{82}$, (13) $NR_{83}COOR_{84}$, (14) $CONR_{85}C(S)R_{86}$, (15) $OCOR_{87}$, (16) $SOR_{88}$, (17) $CONR_{89}R_{90}$, (18) $SO_2NR_{91}R_{92}$, (19) $COOR_{93}$, (20) $COCOOR_{94}$, (21) $COR_{95}$, (22) $COCOR_{96}$, (23) $NR_{97}COR_{98}$, (24) $SO_2R_{99}$, (25) $NR_{100}SO_2R_{101}$, or (26) $NR_{102}R_{103}$;

n is an integer of 1 or 2;

$R_{66}$, $R_{73}$, $R_{75}$, $R_{77}$, $R_{79}$, $R_{81}$, $R_{83}$, $R_{85}$, $R_{97}$, $R_{100}$ and $R_{102}$ are hydrogen atom, or $C_{1-8}$ alkyl;

$R_{67}$ and $R_{68}$, $R_{70}$ and $R_{71}$ are each independently hydrogen atom, or $C_{1-8}$ alkyl;

$R_{89}$ and $R_{91}$ are (1) hydrogen atom, (2) $C_{1-8}$ alkyl, (3) phenyl, or (4) $C_{1-8}$ alkyl substituted with cyano or $C_{1-8}$ alkoxy;

$R_{103}$ is Cyc6;

$R_{69}$, $R_{72}$, $R_{74}$, $R_{76}$, $R_{78}$, $R_{80}$, $R_{82}$, $R_{84}$, $R_{86}$, $R_{87}$, $R_{88}$, $R_{90}$ and $R_{92}$ are (1) hydrogen atom, (2) $C_{1-8}$ alkyl, (3) $C_{2-8}$ alkenyl, (4) $C_{2-8}$ alkynyl, (5) $C_{1-8}$ alkyl substituted with 1-5 of $R_{104}$, (6) diphenylmethyl, (7) triphenylmethyl, (8) Cyc6, (9) $C_{1-8}$ alkyl or $C_{2-8}$ alkenyl substituted with Cyc6, or (10) $C_{1-8}$ alkyl substituted with O-Cyc6, S-Cyc6 or $SO_2$-Cyc6;

$R_{104}$ is (1) $C_{1-8}$ alkoxy, (2) $C_{1-8}$ alkylthio, (3) benzyloxy, (4) halogen atom, (5) nitro, (6) $COOR_{105}$, (7) cyano, (8) $NR_{106}R_{107}$, (9) $N_{108}COR_{109}$, (10) hydroxy, (11) SH, (12) $SO_3H$, (13) S(O)OH, (14) $OSO_3H$, (15) $C_{2-8}$ alkenyloxy, (16) $C_{2-8}$ alkynyloxy, (17) $COR_{110}$, (18) $SO_2R_{111}$, or (19) $C_{1-8}$ alkoxy or $C_{1-8}$ alkylthio substituted with hydroxy;

$R_{105}$ is hydrogen atom, $C_{1-8}$ alkyl, or $C_{2-8}$ alkenyl;

$R_{106}$ and $R_{107}$ are each independently, hydrogen atom, or $C_{1-8}$ alkyl;

$R_{108}$ is hydrogen atom, or $C_{1-8}$ alkyl;

$R_{109}$ and $R_{111}$ are $C_{1-8}$ alkyl;

$R_{110}$ is $C_{1-8}$ alkyl, or halogen atom;

$R_{93}$, $R_{94}$, $R_{95}$, $R_{96}$, $R_{98}$, $R_{99}$ and $R_{101}$ are (1) $C_{2-8}$ alkynyl, (2) $C_{1-8}$ alkyl substituted with $R_{128}$ which may be substituted with 1-4 of $R_{29}$, (3) Cyc8, (4) $C_{1-8}$ alkyl or $C_{2-8}$ alkenyl substituted with Cyc8, or (5) $C_{1-8}$ alkyl substituted with O-Cyc8, S-Cyc8 or $SO_2$-Cyc8; $R_{128}$ is (1) cyano, (2) $NR_{106}R_{107}$, (3) $NR_{108}COR_{109}$, (4) hydroxy, (5) SH, (6) $SO_3H$, (7) S(O)OH, (8) $OSO_3H$, (9) $C_{2-8}$ alkenyloxy, (10) $C_{2-8}$ alkynyloxy, (11) $COR_{110}$, (12) $SO_2R_{111}$, or (13) $C_{1-8}$ alkoxy or $C_{1-8}$ alkylthio substituted with hydroxy;

$R_{129}$ has the same meaning as $R_{104}$;

Cyc5 and Cyc6 may be substituted with 1-5 of $R_{112}$;

$R_{112}$ is (1) $C_{1-8}$ alkyl, (2) $C_{2-8}$ alkenyl, (3) $C_{2-8}$ alkynyl, (4) $C_{1-8}$ alkoxy, (5) $C_{1-8}$ alkylthio, (6) hydroxy, (7) halogen atom, (8) nitro, (9) oxo, (10) cyano, (11) benzyl, (12) benzyloxy, (13) $C_{1-8}$ alkyl, $C_{1-8}$ alkoxy or $C_{1-8}$ alkylthio substituted with 1-5 of $R_{113}$, (14) phenyl, phenoxy, phenylthio or benzoyl, which may be substituted with 1-5 of $R_{114}$, (15) $COR_{115}$, (16) $SO_2R_{116}$, (17) $NR_{117}COR_{118}$, (18) $SO_2NR_{119}R_{120}$, (19) $COOR_{121}$, (20) $NR_{122}R_{123}$, (21) $COR_{124}$, (22) $CONR_{125}R_{126}$, (23) SH, (24) $C_{1-8}$ alkyl substituted with hydroxy or $NR_{127}$-benzoyl, or (25) Cyc7;

$R_{113}$ is halogen atom;

$R_{114}$ is $C_{1-8}$ alkyl, $C_{1-8}$ alkoxy, halogen atom, or nitro;

$R_{115}$, $R_{116}$ and $R_{118}$ are $C_{1-8}$ alkyl;

$R_{117}$, $R_{121}$, $R_{124}$ and $R_{127}$ are hydrogen atom, or $C_{1-8}$ alkyl;

$R_{119}$ and $R_{120}$, $R_{122}$ and $R_{123}$, $R_{125}$ and $R_{126}$ are each independently, hydrogen atom or $C_{1-8}$ alkyl;

Cyc7 may be substituted with 1-5 group selected from (1) $C_{1-8}$ alkyl, (2) $C_{1-8}$ alkoxy, (3) halogen atom, or (4) nitro;

Cyc8 may be substituted with $R_{130}$, and it further may be substituted with 1-4 of $R_{131}$;

$R_{130}$ is (1) $COR_{124}$, (2) $CONR_{125}R_{126}$, (3) SH, (4) $C_{1-8}$ alkyl substituted with hydroxy or $NR_{127}$-benzoyl, or (5) Cyc7;

$R_{131}$ has the same meaning as $R_{112}$;

Cyc5, Cyc6, Cyc7 and Cyc8 are (1) $C_{3-15}$ mono-, bi- or tri-cyclic (fused or spiro)carboring, or (2) 3-15 membered mono-, bi- or tri-cyclic (fused or spiro)heterosing comprising 1-4 of heteroatom selected from 1-4 of oxygen, nitrogen or sulfur;

wherein when $R_{17'}$ is Cyc5, Cyc5 is not phenyl which may be substituted with 1-5 selected from $C_{1-8}$ alkyl, $C_{1-8}$ alkoxy, hydroxy, halogen atom, nitro, COOH, or COO($C_{1-8}$ alkyl);

wherein Cyc7 is not phenyl;

Cyc4 is (1) $C_{5-7}$ monocyclic carboring, or (2) 5-7 membered monocyclic heteroring comprising 1-2 of heteroatom selected from oxygen, nitrogen and sulfur; (abbreviated as dashed line a hereafter) and (abbreviated as dashed line b hereafter) are (1) a bond, or (2) a double bond;

$R_9$ (1) absent or (2) is hydrogen atom;

wherein (1) when dashed line a is a bond, dashed line b is a double bond, and $R_9$ is absent, (2) when dashed line a is a double bond, dashed line b is a bond, and $R_9$ is hydrogen atom and $R_6$ is absent, and (3) 2-(3,3-dimethyl-3,4-dihydro-(2H)-isoquinolin-1-ylidene)-1-phenylethan-1-one is excluded, or a pharmacologically acceptable salt thereof.

The preparation of these compounds is described in US 2005222138 and WO 2003/064389.

In another embodiment, PDE7 inhibitors useful in the methods of the invention are selected from those compounds generally or specifically disclosed in WO 2003/057149, expressly incorporated herein by reference in its entirety. In one embodiment, PDE7 inhibitors useful in the methods of the invention have the formula:

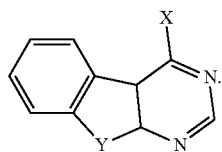

(13)

The substituents for the above compounds are defined as follows:

(1) X is selected from halogen and $NR_1R_2$, (2) Y is selected from $NR_3$, S, and O, with the proviso that Y is not S when X is Cl, (3) $R_1$ and $R_2$ are independently selected from hydrogen, alkyl of 1-8 carbon atoms, alkenyl of 2-8 carbon atoms, alkynyl of 2-8 carbon atoms, cycloalkyl of 3-7 carbon atoms, polycycloalkyl of 5-9 carbon atoms, heterocycloalkyl of 2-6 carbon atoms and 1-2 heteroatoms selected from NH, S, and O, aryl of 6-12 carbon atoms, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms, or heteroaryl of 4-11 carbon atoms and 1-2 heteroatoms selected from N, S, and O, heteroaryl of 4-11 carbon atoms and 1-2 heteroatoms selected from N, S and O, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms, or heteroaryl of 4-11 carbon atoms and 1-2 heteroatoms selected from N, S, and O, and $R_4R_5$, or $R_1$ and $R_2$ combine to form, together with the nitrogen atom to which they are attached, a 5-7 membered monocyclic saturated ring, which optionally contains 1-2 additional heteroatoms selected from the group consisting of NH, $NR_6$, S, and O, or combine to form, together with the nitrogen atom to which they are attached, a 6-10 membered fused polycyclic saturated ring, which optionally contains 1-2 additional heteroatoms selected from the group consisting of NH, $NR_6$, S, and O, or combine to form, together with the nitrogen atom to which they are attached, a 5-7 membered unsaturated ring, which optionally contains 1-2 additional heteroatoms selected from the group consisting of N, S, and O, wherein said monocyclic saturated ring, polycyclic saturated ring or unsaturated ring may be substituted with 1-2 substituents selected from the group consisting of OH, alkyl of 1-6 carbon atoms, alkenyl of 2-6 carbon atoms, alkynyl of 2-6 carbon atoms, cycloalkyl of 3-7 carbon atoms, heterocycloalkyl of 2-6 carbon atoms and 1-2 heteroatoms selected from NH, S, and O, halogen, haloalkyl of 1-2 carbon atoms and a number of halogen atoms up to the perhalo level, alkoxy of 1-6 carbon atoms, haloalkoxy of 1-6 carbon atoms and a number of halogen atoms up to the perhalo level, and $R_7R_8$, (4) $R_3$ is selected from hydrogen, alkyl of 1-8 carbon atoms, alkenyl of 2-8 carbon atoms, alkynyl of 2-8 carbon atoms, cycloalkyl of 3-7 carbon atoms, and heteroaryl of 4-11 carbon atoms and 1-2 heteroatoms selected from N, S, and O, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atom sup to the perhalo level, haloalkoxy of 1-6 carbon atoms and a number of halogen atoms up to the perhalo level, aryl of 6-12 carbon atoms, or heteroaryl of 4-11 carbon atoms and 1-2 heteroatoms selected from N, S, and O, (5) $R_4$ is selected from alkyl of 1-8 carbon atoms, alkenyl of 2-8 carbon atoms, alkynyl of 2-8 carbon atoms, C(=O), S(=O)$_2$, and C(=O)O, (6) $R_5$ is selected from hydrogen, OH, alkyl of 1-8 carbon atoms, alkenyl of 2-8 carbon atoms, alkynyl of 2-8 carbon atoms, alkoxy of 1-8 carbon atoms, thioxy of 1-8 carbon atoms, aryl of 6-12 carbon atoms, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms, or heteroaryl of 4-11 carbon atoms and 1-2 heteroatoms selected from N, S, and O, heteroaryl of 4-11 carbon atoms and 1-2 heteroatoms selected from N, S, and O, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms, or heteroaryl of 4-11 carbon atoms and 1-2 heteroatoms selected from N, S, and O, cycloalkyl of 3-7 carbon atoms, heterocycloalkyl of 2-6 carbon atoms and 1-2 heteroatoms selected from NH, S, and O, and $NR_9R_{10}$, (7) $R_6$ and $R_7$ are independently selected from alkyl of 1-8 carbon atoms, alkenyl of 2-8 carbon atoms, and alkynyl of 2-8 carbon atoms, (8) $R_8$ is selected from OH, aryl of 6-12 carbon atoms, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, haloalkoxy of 1-6 carbon atoms and a number of halogen atoms up to the perhalo level, aryl of 6-12 carbon atoms or heteroaryl of 4-11 carbon atoms and 1-2 heteroatoms selected from N, S, and O, and heteroaryl of 4-11 carbon atoms and 1-2 heteroatoms selected from N, S, and O, which may be substituted with alkyl of 1-6 carbon atoms, alkenyl of 2-6 carbon atoms, alkynyl of 2-6 carbon atoms, alkoxy of 1-6 carbon atoms, halogen, haloalkyl of 1-6 carbon atoms and a number of halogen atoms up to the perhalo level, aryl of 6-12 carbon atoms or heteroaryl of 4-11 carbon atoms and 1-2 heteroatoms selected from N, S, and O;

(9) $R_9$ and $R_{10}$ are independently selected from hydrogen, alkyl of 1-8 carbon atoms, alkenyl of 2-8 carbon atoms, and alkynyl of 2-8 carbon atoms, or $R_9$ and $R_{10}$ combine together with the nitrogen atom to which they are attached to form a 5-7 membered, unsaturated ring which may contain 1-2 additional heteroatoms selected from N, S, and O, or to form a 5-7 membered, saturated ring which may contain 1-2 additional heteroatoms selected from NH, $NR_{11}$, S, and O;

(10) $R_1$ is selected from alkyl of 1-8 carbon atoms, alkenyl of 2-8 carbon atoms, and alkynyl of 2-8 carbon atoms, and pharmaceutically acceptable salts thereof.

The preparation of these compounds is described in WO 2003/057149.

In another embodiment, PDE7 inhibitors useful in the methods of the invention are selected from those compounds generally or specifically disclosed in US 20030092721, U.S. Pat. No. 7,022,849, WO 2002/102315, and US 2006116516, each expressly incorporated herein by reference in its entirety. In one embodiment, PDE7 inhibitors useful in the methods of the invention have the formula:

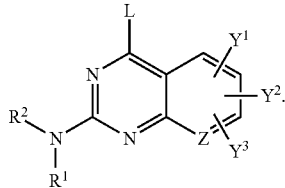

(14)

The substituents for the above compounds are defined as follows: $R_1$ is H or alkyl;

$R_2$ is (a) heteroaryl or heterocyclo, either of which may be optionally substituted with one to three groups T1, T2, T3; or (b) aryl fused to a heteroaryl or heterocyclo ring wherein the combined ring system may be optionally substituted with one to three groups T1, T2, T3;

L is (a) $OR_4$, $C(O)R_4$, $C(O)OR_4$, $SR_4$, $NR_3R_4$, $C(O)NR_3R_4$, $NR_3SO_2R_{4b}$, halogen, nitro, or haloalkyl; or (b) alkyl, aryl, heteroaryl, heterocyclo, or cycloalkyl any of which may be optionally substituted with one to three groups T1a, T2a and/or T3a;

$Y_1$, $Y_2$ and $Y_3$ are independently (a) hydrogen, halo, or $-OR_{4a}$; or (b) alkyl, alkenyl, or alkynyl, any of which may be optionally substituted with one to three groups T1b, T2b and/or T3b;

$R_3$ and $R_4$ are independently H, alkyl, alkenyl, aryl, (aryl)alkyl, heteroaryl, (heteroaryl) alkyl, cycloalkyl, (cycloalkyl)alkyl, heterocyclo, or (heterocyclo) alkyl, any of which may be optionally substituted with one to three groups T1a, T2a and/or T3a; or $R_3$ and $R_4$ together with the nitrogen atom to which they are attached may combine to form a 4- to 8-membered heterocyclo ring optionally substituted with one to three groups T1a, T2a and/or T3a;

$R_{4a}$ is hydrogen, alkyl, alkenyl, aryl, heteroaryl, (aryl)alkyl, (heteroaryl) alkyl, heterocyclo, (heterocyclo) alkyl, cycloalkyl, or (cycloalkyl) alkyl, any of which may be optionally substituted with one to three groups T1b, T2b and/or T3b;

$R_{4b}$ is alkyl, alkenyl, aryl, (aryl) alkyl, heteroaryl, (heteroaryl) alkyl, cycloalkyl, (cycloalkyl) alkyl, heterocyclo, or (heterocyclo) alkyl, any of which may be optionally substituted with one to three groups T1a, T2a and/or T3a;

Z is N or CH;

T1-1b, T2-2b, and T3-3b are each independently;

(1) hydrogen or T6, where T6 is (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl) alkyl; (ii) a group (i) which is itself substituted by one or more of the same or different groups (i); or (iii) a group (i) or (ii) which is independently substituted by one or more of the following groups (2) to (13) of the definition of T1-1b, T2-2b and T3-3b;

(2) —OH or —OT6;

(3) —SH or —ST6;

(4) —C(O)$_t$H, —C(O)$_t$T6, or —O—C(O)T6, where t is 1 or 2;

(5) —SO$_3$H, —S(O)$_t$T6, or S(O)$_t$N(T9)T6;

(6) halo;

(7) cyano;

(8) nitro;

(9) -T4-NT7T8;

(10) -T4-N(T9)-T5-NT7T8;

(11) -T4-N(T10)-T5-T6;

(12) -T4-N(T10)-T5-H; and

(13) oxo;

T4 and T5 are each independently a single bond, T11S(O)$_t$T12-, T11C(O)T12-, T11C(S)T12, T11OT12, T11ST12, T11OC(O)T12, T11C(O)OT12, T11C(=NT9a)T12, or T11C(O)C(O)T12;

T7, T8, T9, T9a and T10 are:

(1) each independently hydrogen or a group provided in the definition of T6, or (2) T7 and T8 may together be alkylene or alkenylene, completing a 3- to 8-membered saturated or unsaturated ring together with the atoms to which they are attached, which ring is unsubstituted or substituted with one or more groups listed in the description of T1-1b, T2-2b and T3-3b, or (3) T7 or T8, together with T9, may be alkylene or alkenylene completing a 3- to 8-membered saturated or unsaturated ring together with the nitrogen atoms to which they are attached, which ring is unsubstituted or substituted with one or more groups listed in the description of T1-1b, T2-2b and T3-3b, or (4) T7 and T8 or T9 and T10 together with the nitrogen atom to which they are attached may combine to form a group N=CT13T14 where T13 and T14 are each independently H or a group provided in the definition of T6; and T11 and T12 are each independently a single bond, alkylene, alkenylene, or alkynylene.

The preparation of these compounds is described in US 20030092721, U.S. Pat. No. 7,022,849, WO 2002/102315, and US 2006116516.

In another embodiment, PDE7 inhibitors useful in the methods of the invention are selected from those compounds generally or specifically disclosed in U.S. Pat. No. 6,838,559, U.S. 20030100571, and WO 2002/102314, each expressly incorporated herein by reference in its entirety. In one embodiment, PDE7 inhibitors useful in the methods of the invention have the formulas:

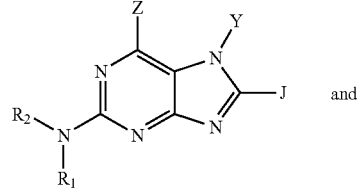

(15A)

and

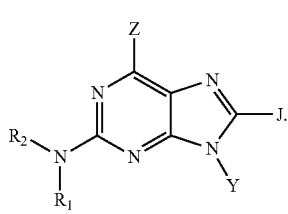

(15B)

The substituents for the above compounds are defined as follows:

$R_1$ is H or alkyl;

$R_2$ is (a) heteroaryl, or heterocyclo, either of which may be optionally substituted with one to three groups T1, T2, T3; (b) aryl substituted with one to three groups T1, T2, T3 provided that at least one of T1, T2, T3 is other than H; or (c) aryl fused to a heteroaryl or heterocyclo ring wherein the combined ring system may be optionally substituted with one to three groups T1, T2, T3;

Y is alkyl, alkenyl, alkynyl, cycloalkyl, aryl, heterocyclo, heteroaryl, (aryl)alkyl or (heteroaryl) alkyl any of which may be optionally substituted with one to three groups T1a, T2a, T3a;

J is (a) hydrogen, halo, or $OR_4$, or (b) alkyl, alkenyl, alkynyl, aryl, heteroaryl, heterocyclo, or, cycloalkyl any of which may be optionally substituted with one to three groups T1b, T2b, T3b;

Z is (a) $OR_4$, $SR_4$, $NR_3R_4$, $NR_3SO_2R_{4a}$ halogen, nitro, haloalkyl; or (b) alkyl, aryl, heteroaryl, heterocyclo, or cycloalkyl any of which may be optionally substituted with one to three groups T1c, T2c, T3c;

$R_3$ is H, alkyl, alkenyl, aryl, (aryl)alkyl, heteroaryl, (heteroaryl)alkyl, cycloalkyl, (cycloalkyl)alkyl, heterocyclo or (heterocyclo)alkyl any of which may be optionally independently substituted where valance allows with one to three groups T1c, T2c, T3c;

$R_4$ is alkyl, alkenyl, aryl, (aryl)alkyl, heteroaryl, (heteroaryl)alkyl, cycloalkyl, (cycloalkyl)alkyl, heterocyclo or (heterocyclo)alkyl any of which may be optionally independently substituted where valance allows with one to three groups T1d, T2d, or T3d; or $R_3$ and $R_4$ together with the nitrogen atom to which they are attached may combine to form a 4 to 8 membered heterocyclo ring optionally substituted with one to three groups T1c, T2c, or T3c;

$R_{4a}$ is hydrogen, alkyl, alkenyl, aryl, heteroaryl, (aryl)alkyl, (heteroaryl)alkyl, heterocyclo, (heterocyclo)alkyl, cycloalkyl or (cycloalkyl)alkyl any of which may be optionally substituted with one to three groups T1d, T2d or T3d;

T1, T1a, T1b, T1c, T1d, T2, T2a, T2b, T2c, T2d, T3, T3a, T3b, T3c, and T3d (hereinafter abbreviated as T1-1d, T2-2d, and T3-3d) are independently (1) hydrogen or T6, where T6 is
(a) alkyl, (hydroxy) alkyl, (alkoxy) alkyl, alkenyl, alkynyl, cycloalkyl, (cycloalkyl) alkyl, cycloalkenyl, (cycloalkenyl) alkyl, aryl, (aryl) alkyl, heterocyclo, (heterocyclo) alkyl, heteroaryl, or (heteroaryl) alkyl;
(b) a group (a) which is itself substituted by one or more of the same or different groups (a); or
(c) a group (a) or (b) which is independently substituted by one or more (preferably 1 to 3) of the following groups (2) to (13) of the definition of T1-1d, T2-2d and T3-3d,
(2) OH or OT6,
(3) SH or ST6,
(4) C(O)t H, C(O)t T6, or OC(O)T6, where t is 1 or 2;
(5) SO3 H, S(O)t T6, or S(O)t N(T9)T6,
(6) halo,
(7) cyano,
(8) nitro,
(9) T4NT7 T8,
(10) T4N(T9)-T5NT7 T8,
(11) T4N(T10)-T5-T6,
(12) T4N(T10)-T5H,
(13) oxo, T4 and T5 are each independently a single bond, T11-S(O)$_t$-T12, T11-C(O)-T12, T11-C(S)-T12, T11-O-T12, -T11S-T12, -T11OC(O)-T12, -T11-C(O)O-T12, -T11C(=NT9a)-T12, or T11-C(O)—C(O)-T12;

T7, T8, T9, T9a and T10 are (1) each independently hydrogen or a group provided in the definition of T6, or (2) T7 and T8 may together be alkylene or alkenylene, completing a 3- to 8-membered saturated or unsaturated ring together with the atoms to which they are attached, which ring is unsubstituted or substituted with one or more groups listed in the description of T1-1d, T2-2d and T3-3d, or (3) T7 or T8, together with T9, may be alkylene or alkenylene completing a 3- to 8-membered saturated or unsaturated ring together with the nitrogen atoms to which they are attached, which ring is unsubstituted or substituted with one or more groups listed in the description of T1-1d, T2-2d and T3-3d, or (4) T7 and T8 or T9 and T10 together with the nitrogen atom to which they are attached may combine to form a group N=CT13 T14 where T13 and T14 are each independently H or a group provided in the definition of T6; and T11 and T12 are each independently a single bond, alkylene, alkenylene, or alkynylene.

The preparation of these compounds is described in U.S. Pat. No. 6,838,559, U.S. 20030100571, and WO 2002/102314.

In another embodiment, PDE7 inhibitors useful in the methods of the invention are selected from those compounds generally or specifically disclosed in U.S. Pat. No. 7,087,614, U.S. 20030162802, and WO 2002/102313, each expressly incorporated herein by reference in its entirety. In one embodiment, PDE7 inhibitors useful in the methods of the invention have the formula:

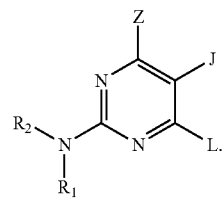

(16)

The substituents for the above compounds are described below.

In a related embodiment, PDE7 inhibitors useful in the methods of the invention have the formula:

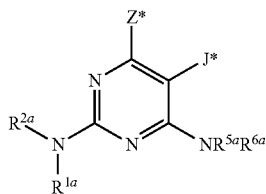
(16a)

The substituents for the above compounds are defined as follows:

$R_{1a}$ is hydrogen or alkyl; $R_{2a}$ is

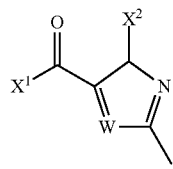

W is S; $X_1$ is alkoxy; and $X_2$ is alkyl;

Z* is halogen, haloalkyl, oxazolyl, $NR_{3a}R_{4a}$, C(O)—N(H)-alkylene-COOH, or phenyl which is unsubstituted or substituted with heteroaryl, $CO_tH$, or $CO_tT_6$;

$R_{3a}$ is hydrogen or alkyl;

$R_{4a}$ is alkyl, alkoxy, unsubstituted or substituted (heteroaryl) alkyl, unsubstituted or substituted heterocyclo, unsubstituted or substituted (heterocyclo) alkyl, or (aryl) alkyl wherein the aryl group is substituted with one or two groups T1 and/or T2 and/or further substituted with a group T3; or $R_{3a}$ and $R_{4a}$ together with the nitrogen atom to which they are attached combine to form an unsubstituted or substituted heterocyclo ring;

$R_{5a}$ is an unsubstituted or substituted (heteroaryl) alkyl, or (aryl) alkyl wherein the aryl group is substituted with one or two groups T1 and/or T2 and/or further substituted with a group T3; or $R_{5a}$ and $R_{6a}$ together with the nitrogen atom to which they are attached combine to form an unsubstituted or substituted heterocyclo ring; $R_{6a}$ is hydrogen or alkyl; J* is hydrogen or alkyl; T1 and T2 are independently alkoxy, alkoxycarbonyl, heteroaryl, $SO_3H$, or $SO_2R_{8a}$ where $R_{8a}$ is alkyl, amino, alkylamino or dialkylamino; or T1 and T2 together with the aryl ring to which they are attached combine to form a bicyclic ring; T3 is H, alkyl, halo, haloalkyl, or cyano; t is 1 or 2; and T6 is alkyl, haloalkyl, cycloalkyl, alkoxy, or heteroaryl.

The preparation of these compounds is described in U.S. Pat. No. 7,087,614, U.S. 20030162802, and WO 2002/102313.

In another embodiment, PDE7 inhibitors useful in the methods of the invention are selected from those compounds generally or specifically disclosed in US 20030104974, WO 2002/088080, and WO 2002/088079, each expressly incorporated herein by reference in its entirety. In one embodiment, PDE7 inhibitors useful in the methods of the invention have the formulas:

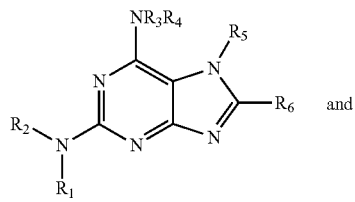
(17A)

and

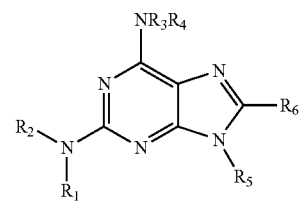
(17B)

The substituents for the above compounds are defined as follows:

$R_1$ is H or alkyl; $R_2$ is optionally substituted heteroaryl, or 4-substituted aryl; $R_3$ is hydrogen or alkyl; $R_4$ is alkyl, optionally substituted (aryl)alkyl, optionally substituted (heteroaryl)alkyl, optionally substituted heterocyclo, or optionally substituted (heterocyclo)alkyl; or $R_3$ and $R_4$ together with the nitrogen atom to which they are attached may combine to form an optionally substituted heterocyclo ring; $R_5$ is alkyl, optionally substituted (aryl)alkyl, or optionally substituted (heteroaryl)alkyl; and $R_6$ is hydrogen or alkyl.

In a related embodiment, PDE7 inhibitors useful in the methods of the invention have the formula:

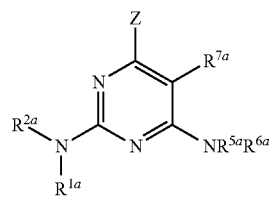

wherein $R_{1a}$ is H or alkyl; $R_{2a}$ is optionally substituted heteroaryl; Z is halogen, alkyl, substituted alkyl, haloalkyl, or $NR_{3a}R_{4a}$; $R_{3a}$ is hydrogen or alkyl; $R_{4a}$ is alkyl, optionally substituted (heteroaryl) alkyl, optionally substituted heterocyclo, optionally substituted (heterocyclo) alkyl, or (aryl) alkyl wherein the aryl group is substituted with one or two groups T1 and T2 and optionally further substituted with a group T3; or $R_{3a}$ and $R_{4a}$ together with the nitrogen atom to which they are attached may combine to form an optionally substituted heterocyclo ring; $R_{5a}$ is (aryl) alkyl wherein the aryl group is substituted with one or two groups T1 and T2 and optionally further substituted with a group T3; $R_{6a}$ is hydrogen or alkyl; $R_{7a}$ is hydrogen or alkyl; T1 and T2 are independently alkoxy, alkoxycarbonyl, heteroaryl or $SO_2R_{8a}$ where $R_{8a}$ is alkyl, amino, alkylamino or dialkylamino; or T1 and T2 together with the atoms to which they are attached may combine to form a ring (e.g., benzodioxole); T3 is H, alkyl, halo, haloalkyl or cyano.

In another related embodiment, PDE7 inhibitors useful in the methods of the invention have the formula:

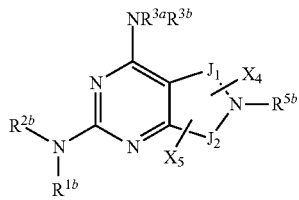

wherein $R_{1b}$ is H or alkyl; $R_{2b}$ is optionally substituted heteroaryl; $R_{3b}$ is H or alkyl; $R_{4b}$ is optionally substituted (aryl)alkyl; $R_{5b}$ is H, alkyl, or $C(O)(CH_2)_vOYR_{6b}$, where Y is a bond or C(O), $R_{6b}$ is hydrogen or alkyl, and v is an integer from 0 to 2; $J_1$ and $J_2$ are independently optionally substituted $C_{1-13}$ alkylene, provided that $J_1$ and $J_2$ are not both greater than $C_2$ alkylene; $X_4$ and $X_5$ are optional substituents bonded to any available carbon atom in one or both of $J_1$ and $J_2$, independently selected from hydrogen, $OR_7$, $NR_8R_9$, alkyl, substituted alkyl, alkenyl, substituted alkenyl, alkynyl, substituted alkynyl, cycloalkyl, substituted cycloalkyl, aryl, substituted aryl, heterocycloalkyl, or heteroaryl; R7 is hydrogen, alkyl, substituted alkyl, alkenyl, alkynyl, cycloalkyl, substituted cycloalkyl, C(O)alkyl, C(O)substituted alkyl, C(O)cycloalkyl, C(O) substituted cycloalkyl, C(O)aryl, C(O)substituted aryl, C(O)O-alkyl, C(O)O-substituted alkyl, C(O) heterocycloalkyl, C(O)heteroaryl, aryl, substituted aryl, heterocycloalkyl and heteroaryl; and $R_8$ and $R_9$ are independently selected from the group consisting of hydrogen, alkyl, substituted alkyl, cycloalkyl, substituted cycloalkyl, alkenyl, alkynyl, C(O) alkyl, C(O) substituted alkyl, C(O) cycloalkyl, C(O)substituted cycloalkyl, C(O)aryl, C(O)substituted aryl, C(O)O alkyl, C(O)O substituted alkyl, C(O) heterocycloalkyl, C(O) heteroaryl, $S(O)_2$alkyl, $S(O)_2$ substituted alkyl, $S(O)_2$ cycloalkyl, $S(O)_2$ substituted cycloalkyl, $S(O)_2$ aryl, $S(O)_2$ substituted aryl, $S(O)_2$ heterocycloalkyl, $S(O)_2$ heteroaryl, aryl, substituted aryl, heterocycloalkyl, and heteroaryl, or $R_8$ and $R_9$ taken together with the nitrogen atom to which they are attached complete an optionally substituted heterocycloalkyl or heteroaryl ring.

In a further related embodiment, PDE7 inhibitors useful in the methods of the invention have the formula:

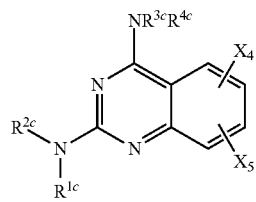

wherein $R_{1c}$ is H or alkyl; $R_{2c}$ is optionally substituted heteroaryl; $R_{3c}$ is H or alkyl; $R_{4c}$ is optionally substituted (aryl)alkyl; and $X_4$ and $X_5$ are optional substituents bonded to any available carbon atom in one or both of $J_1$ and $J_2$, independently selected from hydrogen, $OR_7$, $NR_8R_9$, alkyl, substituted alkyl, alkenyl, substituted alkenyl, alkynyl, substituted alkynyl, cycloalkyl, substituted cycloalkyl, aryl, substituted aryl, heterocycloalkyl, or heteroaryl.

The preparation of these compounds is described in US 20030104974, WO 2002/088080, and WO 2002/088079.

In another embodiment, PDE7 inhibitors useful in the methods of the invention are selected from those compounds generally or specifically disclosed in US 20030092908 and WO 2002/087513, each expressly incorporated herein by reference in its entirety. In one embodiment, PDE7 inhibitors useful in the methods of the invention have the formula:

(18)

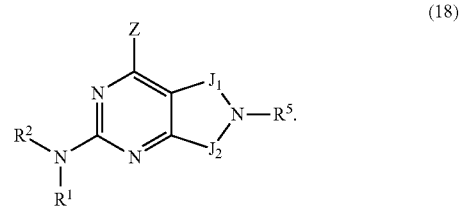

The substituents for the above compounds are defined as follows:

$R_1$ is hydrogen or alkyl;

$R_2$ is (a) heteroaryl, or heterocyclo, either of which may be optionally substituted with one to three groups T1, T2, T3; (b) aryl substituted with one to three groups T1, T2, T3 provided that at least one of T1, T2, T3 is other than H; or (c) aryl fused to a heteroaryl or heterocyclo ring wherein the combined ring system may be optionally substituted with one to three groups T1, T2, T3;

Z is $NR_3R_4$, $NR_3SO_2R_{4a}$, $OR_4$, $SR_4$, haloalkyl, or halogen;

$R_3$ and $R_4$ are independently H, alkyl, alkenyl, aryl, (aryl) alkyl, heteroaryl, (heteroaryl)alkyl, cycloalkyl, (cycloalkyl) alkyl, heterocyclo or (heterocyclo)alkyl any of which may be optionally independently substituted where valance allows with one to three groups T1a, T2a, or T3a; or $R_3$ and $R_4$ may be taken together with the nitrogen atom to which they are attached to form a heterocyclo or heteroaryl ring optionally independently substituted where valance allows with one to three groups T1a, T2a, or T3a;

$R_{4a}$ is alkyl, alkenyl, aryl, (aryl)alkyl, heteroaryl, (heteroaryl)alkyl, cycloalkyl, (cycloalkyl)alkyl, heterocyclo or (heterocyclo)alkyl any of which may be optionally independently substituted where valance allows with one to three groups T1a, T2a, or T3a;

$R_{3b}$ and $R_{4b}$ are independently H, alkyl, alkenyl, aryl, (aryl) alkyl, heteroaryl, (heteroaryl)alkyl, cycloalkyl, (cycloalkyl) alkyl, heterocyclo or (heterocyclo)alkyl;

$R_5$ is (1) hydrogen, or cyano;

(2) alkyl, alkenyl, alkynyl, cycloalkyl, (cycloalkyl)alkyl, aryl, (aryl)alkyl, heterocyclo, (heterocyclo)alkyl, heteroaryl or (heteroaryl)alkyl, any of which may be optionally independently substituted where valance allows with one to three groups T1b, T2b, or T3b; or (3) $C(O)R_6$, $C(O)OR_6$, $C(O)$—$C(O)OR$, or $SO_2R_{6a}$;

$R_6$ is H, alkyl, alkenyl, $NR_{3b}R_{4b}$, heterocyclo, (heterocyclo)alkyl, (hydroxy)alkyl, (alkoxy)alkyl, (aryloxy)alkyl, $(NR_{3b}R_{4b})$alkyl, heteroaryl, aryl or (aryl)alkyl, any of which may be optionally independently substituted where valance allows with one to three groups T1b, T2b, or T3b;

$R_{6a}$ is alkyl, alkenyl, $NR_{3b}R_{4b}$, heterocyclo, (heterocyclo) alkyl, (hydroxy)alkyl, (alkoxy)alkyl, (aryloxy)alkyl, $(NR_{3b}R_{4b})$alkyl, heteroaryl, aryl or (aryl)alkyl, any of which may be optionally independently substituted where valance allows with one to three groups T1b, T2b, or T3b;

J₁ and J₂ are independently optionally substituted $C_{1-3}$ alkylene, provided that J₁ and J₂ are not both greater than $C_2$ alkylene; and T1-1b, T2-2b, and T3-3b are each independently (1) hydrogen or T6, where T6 is (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl) alkyl, heterocyclo, (heterocyclo)alkyl, heteroaryl, or (heteroaryl) alkyl; (ii) a group (i) which is itself substituted by one or more of the same or different groups (i); or (iii) a group (i) or (ii) which is independently substituted by one or more (preferably 1 to 3) of the following groups (2) to (13) of the definition of T1-1b, T2-2b, and T3-3b, (2) OH or OT6, (3) SH or ST6, (4) C(O)$_t$H, C(O)$_t$T6, or OC(O)T6, where t is 1 or 2, (5) SO₃H, S(O)$_t$T6, or S(O)$_t$N(T9)T6, (6) halo, (7) cyano, (8) nitro, (9) T4-NT7T8,

(10) T4-N(T9)-T5-NT7T8,

(11) T4-N(T10)-T5-T6,

(12) T4-N(T10)-T5H,

(13) oxo,

T4 and T5 are each independently (1) a single bond, (2) T11-S(O)$_t$-T12, (3) T11-C(O)-T12, (4) T11-C(S)-T12, (5)-T11-O-T12, (6) T11-S-T12, (7) T11-O—C(O)-T12, (8) T11-C(O)—O-T12, (9) T11-C(=NT9a)-T12, or (10) T11-C(O)—C(O)-T12, T7, T8, T9, T9a and T10, (1) are each independently hydrogen or a group provided in the definition of T6, or (2) T7 and T8 may together be alkylene or alkenylene, completing a 3- to 8-membered saturated or unsaturated ring together with the atoms to which they are attached, which ring is unsubstituted or substituted with one or more groups listed in the description of T1-1b, T2-2b, and T3-3b, or (3) T7 or T8, together with T9, may be alkylene or alkenylene completing a 3- to 8-membered saturated or unsaturated ring together with the nitrogen atoms to which they are attached, which ring is unsubstituted or substituted with one or more groups listed in the description of T1-1b, T2-2b, and T3-3b, or (4) T7 and T8 or T9 and T10 together with the nitrogen atom to which they are attached may combine to form a group N=CT13T14 where T13 and T14 are each independently H or a group provided in the definition of T6; and T11 and T12 are each independently a single bond, alkylene, alkenylene, or alkynylene.

The preparation of these compounds is described in US 20030092908 and WO 2002/087513.

In another embodiment, PDE7 inhibitors useful in the methods of the invention are selected from those compounds generally or specifically disclosed in US 20040127707 and WO 2002/085906, each expressly incorporated herein by reference in its entirety. In one embodiment, PDE7 inhibitors useful in the methods of the invention have the formula:

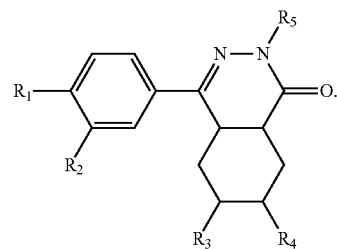

(19)

The substituents for the above compounds are defined as follows:

$R_1$ is 1-2C-alkoxy or 1-2C-alkoxy which is completely or predominantly substituted by fluorine, $R_2$ is fluorine, bromine, or chlorine, $R_3$ and $R_4$ are both hydrogen or together form an additional bond, $R_5$ is $R_6$, $C_mH_{2m}$—$R_7$, $C_nH_{2n}$—C(O)$R_8$, CH($R_9$)₂, $C_pH_{2p}$—Y-Aryl1, $R_{12}$ or $R_{26}$, wherein $R_6$ 1-8C-alkyl, 3-10C-cycloalkyl, 3-7C-cycloalkylmethyl, 3-7C-alkenyl, 3-7C-alkinyl, phenyl-3-4C-alkenyl, 7-10C-polycycloalkyl, naphthyl, pyridyl, pyrazinyl, pyridazinyl, pyrimidyl, quinazolinyl, quinoxalinyl, cinnolinyl, isoquinolinyl, quinolinyl, indanyl, indazolyl, benzoxazolyl, benzothiazolyl, oxazolyl, thiazolyl, N-methylpiperidyl, tetrahydropyranyl, 6-methyl-3-trifluoromethyl-pyridin-2-yl, 1,3,4-trimethyl-1H-pyrazolo[3,4-b]pyridin-6-yl, 3-thiophen-2-yl [1,2,4]thiadiazol-5-yl, 1,1-dioxide-tetrahydrothiophen-3-yl, 1-oxo-1,3-dihydro-isobenzofuran-5-yl, 4-(4-yl-but-1-oxy) benzoic acid, or an unsubstituted or by $R_{61}$ and/or $R_{62}$ substituted phenyl radical, wherein $R_{61}$ is hydroxyl, 1-4C-alkyl, 1-4C-alkoxy, nitro, cyano, halogen, carboxyl, hydroxycarbonyl-1-4C-alkyl, 1-4C-alkoxycarbonyl, hydroxy-1-4C-alkyl, amino, mono- or di-1-4C-alkylamino, 1-4C-alkylcarbonylamino, aminocarbonyl, mono- or di-1-4C-alkylaminocarbon-yl, aminosulfonyl, mono- or di-1-4C-alkylaminosulfonyl, 4-methylphenylsulfonamido, imidazolyl; tetrazol-5-yl, 2-(1-4C-alkyl)tetrazol-5-yl or 2-benzyltetrazol-5-yl and $R_{62}$ is 1-4C-alkyl, 1-4C-alkoxy, nitro, or halogen, $R_7$ is hydroxyl, halogen, cyano, nitro, nitroxy(O—NO₂), carboxyl, carboxyphenyloxy, phenoxy, 1-4C-alkoxy, 3-7C-cydoalkoxy, 3-7C-cycloalkylmethoxy, 1-4C-alkylcarbonyl, 1-4C-alkylcarbonyloxy, 1-4C-alkylcarbonylamino, 1-4C-alkoxycarbonyl, aminocarbonyl, mono- or di-1-4C-alkylaminocarbonyl, amino, mono- or di-1-4C-alkylamino, or an unsubstituted or by $R_{71}$ and/or $R_{72}$ substituted piperidyl, piperazinyl, pyrrolidinyl or morpholinyl radical, wherein $R_{71}$ is hydroxyl, 1-4C-alkyl, hydroxy-1-4C-alkyl or 1-4C-alkoxycarbonyl, and $R_{72}$ is 1-4C-alkyl, carboxyl, aminocarbonyl or 1-4C-alkoxycarbonyl, $R_8$ is an unsubstituted or by $R_{81}$ and/or $R_{82}$ substituted phenyl, naphthyl, phenanthrenyl or anthracenyl radical, wherein $R_{81}$ is hydroxyl, halogen, cyano, 1-4C-alkyl, 1-4C-alkoxy, carboxyl, aminocarbonyl, mono- or di-1-4C-alkylaminocarbonyl, 1-4C-alkylcarbonyloxy, 1-4C-alkoxycarbonyl, amino, mono- or di-1-4C-alkylamino, 1-4C-alkylcarbonylamino, or 1-4C-alkoxy which is completely or predominantly substituted by fluorine, and $R_{82}$ is hydroxyl, halogen, 1-4C-alkyl, 1-4C-alkoxy or 1-4C-alkoxy which is completely or predominantly substituted by fluorine, $R_9$ is $C_qH_{2q}$-phenyl, Y is a bond or O (oxygen), $Aryl_1$ is an unsubstituted phenyl, naphthyl, pyridyl, pyrazinyl, pyridazinyl, pyrimidinyl, quinazolinyl, quinoxalinyl, cinnolinyl, isoquinolyl, quinolyl, coumarinyl, benzimidazolyl, benzoxazolyl, benzothiazolyl, benzotriazolyl, N-benzosuccinimidyl, imidazolyl, pyrazolyl, oxazolyl, thiazolyl, furyl, thienyl, pyrrolyl, a 2-(1-4C-alkyl)-thiazol-4-yl radical, or a phenyl radical substituted by $R_{10}$ and/or $R_{11}$, wherein $R_{10}$ is hydroxyl, halogen, nitro, cyano, 1-4C-alkyl, trifluoromethyl, 1-4C-alkoxy, carboxyl, hydroxycarbonyl-1-4C-alkyl, 1-4C-alkylcarbonyloxy, 1-4C-alkoxycarbonyl, amino, mono- or di-1-4C-alkylamino, 1-4C-alkylcarbonylamino, aminocarbonyl, mono- or di-1-4C-alkylamino-carbonyl, imidazolyl or tetrazolyl, and $R_{11}$ is hydroxyl, halogen, nitro, 1-4C-alkyl or 1-4C-alkoxy, m is an integer from 1 to 8, n is an integer from 1 to 4, p is an integer from 1 to 6, q is an integer from 0 to 2, $R_{12}$ is a radical of formula (a)

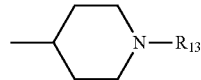

wherein $R_{13}$ is $S(O)_2$—$R_{14}$, $S(O)_2$—$(CH_2)_r$—R15, $(CH_2)_s$—$S(O)_2R16$, $C(O)R_{17}$, $C(O)$—$(CH_2)_r$—$R_{18}$, $(CH_2)_s$—$C(O)$—$R_{19}$, Hetaryl1, $Aryl_2$ or $Aryl_3$-1-4C-alkyl, $R_{14}$ is 1-4C-alkyl, 5-dimethylaminonaphthalin-1-yl, $N(R_{20})R_{21}$, phenyl or phenyl substituted by $R_{22}$ and/or $R_{23}$, $R_{15}$ is $N(R_{20})R_{21}$, $R_{16}$ is $N(R_{20})R_{21}$, $R_{17}$ is 1-4C-alkyl, hydroxycarbonyl-1-4C-alkyl, phenyl, pyridyl, 4-ethyl-piperazin-2,3-dion-1-yl, 2-oxo-imidazolidin-1-yl or $N(R_{20})R_{21}$, $R_{18}$ is $N(R_{20})R_{21}$, $R_{19}$ is $N(R_{20})R_{21}$, phenyl, phenyl substituted by $R_{22}$ and/or $R_{23}$ and/or $R_{24}$, $R_{20}$ and $R_{21}$ are independent from each other hydrogen, 1-7C-alkyl, 3-7C-cycloalkyl, 3-7C-cycloalkylmethyl or phenyl, or $R_{20}$ and $R_{21}$ together and with inclusion of the nitrogen atom to which they are bonded, form a 4-morpholinyl-ring, 1-pyrrolidinyl-ring, 1-piperidinyl-ring, 1-hexahydroazepino-ring or a 1-piperazinyl-ring of formula (b)

wherein $R_{25}$ is pyrid-4-yl, pyrid-4-ylmethyl, 1-4C-alkyldimethylamino, dimethylaminocarbonylmethyl, N-methylpiperidin-4-yl, 4-morpholino-ethyl or tetrahydrofuran-2-ylmethyl-, $R_{22}$ is halogen, nitro, cyano, carboxyl, 1-4C-alkyl, trifluoromethyl, 1-4C-alkoxy, 1-4C-alkoxycarbonyl, amino, mono- or di-1 4C-alkylamino, aminocarbonyl 1-4C-alkylcarbonylamino or mono- or di-1-4C-alkylaminocarbon-yl, $R_{23}$ is halogen, amino, nitro, 1-4C-alkyl or 1-4C-alkoxy, $R_{24}$ is halogen, $Hetaryl_1$ is pyrimidin-2-yl, thieno-[2,3-d]pyrimidin-4-yl, 1-methyl-1H-pyrazolo-[3,4-d]pyrimidin-4-yl, thiazolyl, imidazolyl or furanyl, $Aryl_2$ is pyridyl, phenyl or phenyl substituted by $R_{22}$ and/or $R_{23}$, $Aryl_3$ is pyridyl, phenyl, phenyl substituted by $R_{22}$ and/or $R_{23}$, 2-oxo-2H-chromen-7-yl or 4-(1,2,3-thiadiazol-4-yl)phenyl, r is an integer from 1 to 4, s is an integer from 1 to 4, $R_{26}$ is a radical of formula (c)

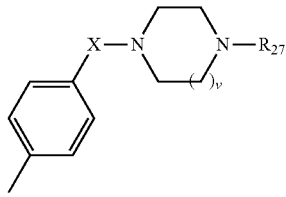

wherein $R_{27}$ is $C(O)R_{28}$, $(CH_2)_t$—$C(O)R_{29}$, $(CH_2)_uR_{30}$, $Aryl_4$, $Hetaryl_2$, phenylprop-1-en-3-yl or 1-methylpiperidin-4-yl, $R_{28}$ hydrogen, 1-4C-alkyl, $OR_{31}$, furanyl, indolyl, phenyl, pyridyl, phenyl substituted by $R_{34}$ and/or $R_{35}$ or pyridyl substituted by $R_{36}$ and/or $R_{37}$, $R_{29}$ is $N(R_{32})R_{33}$, $R_{30}$ is $N(R_{32})R_{33}$, tetrahydrofuranyl or pyridinyl, $R_{31}$ is 1-4C-alkyl, $R_{32}$ is hydrogen, 1-4C-alkyl, 3-7C-cycloalkyl or 3-7C-cycloalkylmethyl, $R_{33}$ is hydrogen, 1-4C-alkyl, 3-7C-cycloalkyl or 3-7C-cycloalkylmethyl, or $R_{32}$ and $R_{33}$ together and with inclusion of the nitrogen atom to which they are bonded, form a 4-morpholinyl-, 1-pyrrolidinyl-, 1-piperidinyl- or 1-hexahydroazepinyl-ring, $Aryl_4$ is phenyl, pyridyl, pyrimidinyl, phenyl substituted by $R_{34}$ and/or $R_{35}$, pyridyl substituted by $R_{36}$ and/or $R_{37}$, $R_{34}$ is halogen, nitro, 1-4C-alkyl, trifluoromethyl or 1-4C-alkoxy, $R_{35}$ is halogen or 1-4C-alkyl, $R_{36}$ is halogen, nitro, 1-4C-alkyl, trifluoromethyl or 1-4C-alkoxy, $R_{37}$ is halogen or 1-4C-alkyl, $Hetaryl_2$ is indol-4-yl, 2-methyl-quinolin-4-yl, 5-chloro-6-oxo-1-phenyl-1,6-dihydro-pyridazin-4-yl, 3-phenyl-1,2,4-thiadiazol-5-yl or 3-o-tolyl-1,2,4-thiadiazol-5-yl, t is an integer from 1 to 4, u is an integer from 1 to 4, v is an integer from 1 to 2, X is —C(O)— or —$S(O)_2$—, and the salts of these compounds.

The preparation of these compounds is described in US 20040127707 and WO 2002/085906.

In another embodiment, PDE7 inhibitors useful in the methods of the invention are selected from those compounds generally or specifically disclosed in U.S. Pat. No. 6,818,651, US 20040044212, and WO 2002/040450, each expressly incorporated herein by reference in its entirety. In one embodiment, PDE7 inhibitors useful in the methods of the invention have the formula:

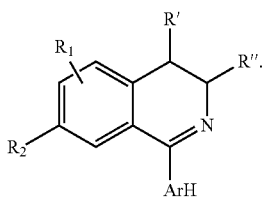

(20)

The substituents for the above compounds are defined as follows:

either $R_1$ denotes hydrogen, and $R_2$ denotes fluorine, chlorine, bromine, cyano, trifluoromethyl or phenoxy, or $R_1$ denotes hydrogen, fluorine, chlorine, bromine, trifluoromethyl or cyano, and $R_2$ denotes hydrogen, R' and R'' both denote hydrogen or together represent a bond, and Ar represents a phenyl radical of the formulae IIa, IIb, or IIc

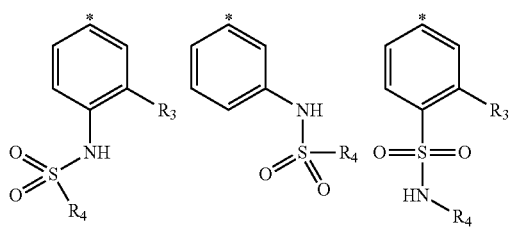

wherein $R_3$ denotes hydrogen, hydroxyl, nitro, amino, carboxyl, aminocarbonyl, 1-4C-alkoxy, trifluoromethoxy, 1-4C-alkoxycarbonyl or mono- or di-1-4C-alkylaminocarbonyl, $R_4$ represents 1-4C-alkyl, naphthalenyl, 5-dimethylaminonaphthalen-1-yl, phenylethen-2-yl, 3,5-dimethylisoxazol-4-yl, 5-chloro-3-methylbenzo[b]thiophen-2-yl, 6-chloro-imidazo[2,1b]-thiazol-5-yl, or represents a phenyl or thiophene radical which is unsubstituted or is substituted by one or more identical or different radicals selected from the group halogen, cyano, 1-4C-alkyl, trifluoromethyl, 1-4C-alkoxy which is substituted entirely or mainly by fluorine, 1-4C-alkoxy, 1-4C-alkylcarbonylamino, 1-4C-alkoxycarbonyl, phenylsulfonyl or isoxazolyl, or a hydrate, solvate, salt, hydrate of a salt, or solvate of a salt thereof.

The preparation of these compounds is described in U.S. Pat. No. 6,818,651, US 20040044212, and WO 2002/040450.

In another embodiment, PDE7 inhibitors useful in the methods of the invention are selected from those compounds generally or specifically disclosed in WO 2002/040449, expressly incorporated herein by reference in its entirety. In one embodiment PDE7 inhibitors in the methods of the invention have the formula:

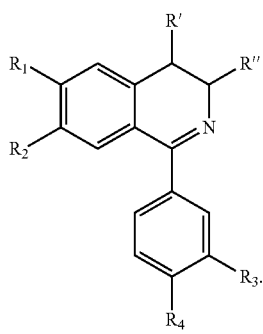

(21)

The substituents for the above compounds are defined as follows:

either $R_1$ denotes hydrogen and $R_2$ denotes fluorine, chlorine, bromine, cyano, trifluoromethyl or phenoxy, or $R_1$ denotes hydrogen, fluorine, chlorine, bromine, trifluoromethyl or cyano and $R_2$ denotes hydrogen, R' and R" both denote hydrogen or together represent a bond, $R_3$ denotes hydrogen, hydroxyl, nitro, amino, carboxyl, aminocarbonyl, 1-4C-alkoxy, trifluoromethoxy, 1-4C-alkoxycarbonyl or mono- or di-1-4C-alkylaminocarbonyl and $R_4$ denotes C(O)—X—$R_5$, N(H)—C(O)—$R_6$ or N(H)—C(O)—N(H)—$R_2$, wherein X denotes 0 or N(H), $R_5$ denotes hydrogen, 1-4C-alkyl, 3-7C-cycloalkylmethyl, 6,6-dimethylbicyclo[3,3,I]hept-2-yl, 3-7C-alkynyl, 1-4C-alkylcarbonyl-1-4C-alkyl, aminocarbonyl-1-4C-alkyl, furan-2-ylmethyl, 2-pyridin-2-yleth-1-yl, 2-pyridin-3-ylmethyl, N-methylpiperidin-3-yl, 1-benzylpiperidin-4-yl, morpholin-4-yl-eth-2-yl, morpholin-4-yl-eth-1-yl, 2-benzo[1,3]dioxol-4-yl-eth-1-yl, chroman-4-yl, 1-methoxycarbonyl-2-indol-3-yl-eth-1-yl, 1,3-bis-methoxycarbonylprop-1-yl, 1-methoxycarbonyl-3-methylsulfanyl-eth-1-yl, 1-methoxycarbonyl-2-thiazol-2-yl-eth-1-yl, or 4-methylthiazol-5-yl-eth-2-yl, or represents a benzyl-, phenyl-eth-1-yl or 1-methoxycarbonyl-2-phenyl-eth-2-yl radical which is unsubstituted or substituted by one or more radicals selected from the group halogen, trifluoromethyl and phenyl, $R_6$ denotes 2,4-dichlorophenoxymethyl, 2-tert-butoxycarbonylamino-eth-1-yl, 1-acetylpiperidin-4-yl, Ar1 or Ar2-CH=CH—, where Ar1 represents 3-chlorophenyl, 4-trifluoromethoxyphenyl, 3-phenoxyphenyl, indol5-yl, 2-methylpyridin-5-yl, quinolin-6-yl or 2-benzothiazol-6-yl, Ar2 represents furan-2-yl, furan-3-yl, thiophen-2-yl, indol-3-yl, 3-trifluoromethylphenyl, 3-methoxyphenyl or pyridin-3-yl, $R_7$ represents 1-4C-alkyl, 3-7C-alkenyl, 3-7C-cycloalkyl, 1-ethoxycarbonyl-2-phenyl-eth-1-yl, thiophen-2-yleth-1-yl or a phenyl radical which is unsubstituted or substituted by one or more radicals selected from the group halogen, cyano, 1-4C-alkyl, trifluoromethyl, 1-4C-alkylthio, 1-4C-alkoxy, 1-4C-alkoxy which is entirely or predominantly substituted by fluorine, 1-4C-alkylcarbonyl and phenoxy, or a salt thereof.

The preparation of these compounds is described in WO 2002/040449.

In another embodiment, PDE7 inhibitors useful in the methods of the invention are selected from those compounds generally or specifically disclosed in WO 2001/098274, expressly incorporated herein by reference in its entirety. In one embodiment. PDE7 inhibitors useful in the methods of the invention have the formula:

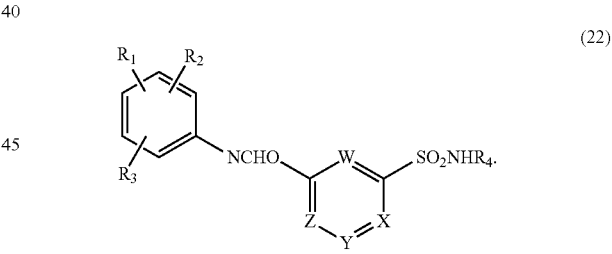

(22)

The substituents for the above compounds are defined as follows:

W, X, Y and Z, which may be the same or different, each represents a nitrogen atom or a $C(R^5)$ group [wherein $R_5$ is a hydrogen or halogen atom or an alkyl, haloalkyl, alkoxy, haloalkoxy, hydroxy, —$NO_2$ or —CN group] provided that two or more of W, X, Y, and Z are $C(R_5)$ groups;

$R_1$, $R_2$ and $R_3$, which may be the same or different, each is an atom or group -$L_1$(Alk$_1$)$_r$$L_2$($R_6$)$_s$ wherein $L_1$ and $L_2$, which may be the same or different, is each a covalent bond or a linker atom or group, r is zero or the integer 1, Alk$_1$ is an aliphatic or heteroaliphatic chain, s is an integer 1, 2 or 3 and $R_6$ is a hydrogen or halogen atom or a group selected from alkyl, —$OR_7$ [where $R_7$ is a hydrogen atom or an optionally substituted alkyl group], —$SR_7$, $NR_7R_8$ [where $R_8$ is as just defined for $R_7$ and may be the same or different], —$NO_2$, CN, $CO_2R_7$, $SO_3H$, $S(O)R_7$, $SO_2R_7$, $OCO_2R_7$, $CONR_7R_8$, OCONR$_7$R$_8$, CSNR$_7$R$_8$, OCR$_7$, OCOR$_7$, N(R$_7$)COR$_8$, N(R$_7$)CSR$_8$, S(O)NR$_7$R$_8$, SO$_2$NR$_7$R$_8$, N(R$_7$)SO$_2$R$_8$, N(R$_7$)CON(R$_8$)(R$_9$) [where R$_9$ is a hydrogen atom or an optionally substituted alkyl group], N(R$_7$)CSN(R$_8$)(R$_9$), N(R$_7$)SO$_2$N(R$_8$)(R$_9$), C(R$_7$)=NO(R$_8$), cycloaliphatic, heterocycloaliphatic, aryl or heteroaryl group]; provided that one or more of R$_1$, R$_2$, or R$_3$ is a substituent other than a hydrogen atom;

R$_4$ represents an optionally substituted phenyl, 1- or 2-naphthyl, pyridyl, pyrimidinyl, pyridazinyl, or pyrazinyl group; and the salts, solvates, hydrates and N-oxides thereof.

The preparation of these compounds is described in WO 2001/098274.

In another embodiment, PDE7 inhibitors useful in the methods of the invention are selected from those compounds generally or specifically disclosed in WO 2001/074786, expressly incorporated herein by reference in its entirety. In one embodiment. PDE7 inhibitors useful in the methods of the invention have the formula:

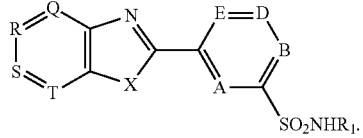

(23)

The substituents for the above compounds are defined as follows:

R$_1$ represents an aryl or heteroaryl group;

A, B, P, and E, which may be the same or different, each represents a nitrogen atom or a C(R$_2$) group [wherein R$_2$ is a hydrogen or halogen atom or an alkyl, haloalkyl, alkoxy, haloalkoxy, hydroxy, —NO$_2$ or —CN group] provided that two or more of A, B, D, and E are C(R$_2$) groups; X represents an oxygen or sulphur atom or a N(R$_3$) group wherein R$_3$ is a hydrogen atom or an alkyl group;

Q, R, S, and T, which may be the same or different each represents a nitrogen atom or a group C(R$_4$) [wherein R$_4$ is an atom or group -L$_1$(Alk$_1$)$_r$L$_2$(R$_5$)s wherein L$_1$ and L$_2$, which may be the same or different, is each a covalent bond or a linker atom or group, r is zero or the integer 1, Alkyl is an aliphatic or heteroaliphatic chain, s is an integer 1, 2 or 3 and R$_5$ is a hydrogen or halogen atom or a group selected from alkyl, OR$_6$ [where R$_6$ is a hydrogen atom or an optionally substituted alkyl group], SR$_6$, NR$_6$R$_7$ [where R$_7$ is as just defined for R$_6$ and may be the same or different], NO$_2$, CN, CO$_2$R$_6$, SO$_3$H, S(O)R$_6$, SO$_2$R$_6$, OCO$_2$R$_6$, CONR$_6$R$_7$, OCONR$_6$R$_7$, CSNR$_7$R$_7$, OCR$_6$, OCOR$_6$, N(R$_6$)COR$_7$, N(R$_6$)CSR$_7$, S(O)NR$_6$R$_7$, SO$_2$NR$_6$R$_7$, N(R$_6$)SO$_2$R$_7$; N(R$_6$)CON(R$_7$)(R$_8$) [where R$_8$ is a hydrogen atom or an optionally substituted alkyl group], N(R$_6$)CSN(R$_7$)(R$_8$), N(R$_6$)SO$_2$N(R$_7$)(R$_8$), C(R$_6$)=NO(R$_7$) cycloaliphatic, heterocycloaliphatic, aryl or heteroaryl group] provided that two or more of Q, R, S, and T are C(R$_4$) groups; and the salts, solvates, hydrates and N-oxides thereof.

The preparation of these compounds is described in WO 2001/074786.

In another embodiment, PDE7 inhibitors useful in the methods of the invention are selected from those compounds generally or specifically disclosed in WO 2000/068230, expressly incorporated herein by reference in its entirety. In one embodiment. PDE7 inhibitors useful in the methods of the invention have the formula:

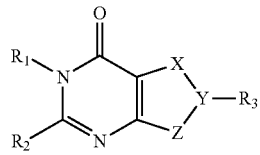

(24)

The substituents for the above compounds are defined as follows:

X—Y—Z represents NR$_4$—C=N or N=C—NR$_4$;

R$_1$ represents H, alkyl, cycloalkyl, cycloalkylalkyl, arylalkyl, heteroarylalkyl or heterocycloalkyl;

R$_2$ represents OR$_8$, NR$_8$R$_9$, SR$_{13}$, alkyl or CF$_3$;

R$_3$ represents halogen, alkyl, CF$_3$ or OR$_8$;

R$_4$, which can be attached to either X or Z, is a residue selected from

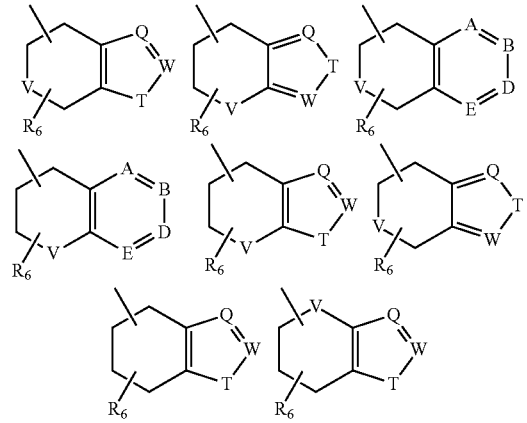

wherein attachment is through any position on the saturated ring, provided the attachment is not at a position adjacent to V, and the saturated ring may be substituted at any position with one or more R$_6$;

A, B, D, and E are the same or different and each represents Cl$_n$R$_5$, N or N—O;

V represents O, S, NR$_7$ or C(L$^1$$_m$R$_{14}$)(L$^2$$_n$R$_{14}$);

Q and W are the same or different and each represents CL$_n$R$_5$ or N;

T represents O, S or NR$_7$;

L$^1$ and L$^2$ are the same or different and each represents C(R$_{15}$)$_2$;

m and n are the same or different and each represents 0, 1, 2, 3, 4 or 5;

the R$_5$s are the same or different and each represents H, halogen, alkyl, cycloalkyl, OR$_8$, NR$_8$R$_9$, CO$_2$R$_{10}$, CONR$_{11}$R$_{12}$, CONHOH, SO$_2$NR$_{11}$R$_{12}$, SON$_{11}$R$_{12}$, COR$_{13}$, SO$_2$R$_{13}$, SOR$_{13}$, SR$_{13}$, CF$_3$, NO$_2$ or CN;

R$_6$ represents H, alkyl, cycloalkyl, OR$_8$, NR$_8$R$_9$, CO$_2$R$_{10}$, CONR$_{11}$R$_{12}$, SO$_2$NR$_{11}$R$_{12}$, SON$_{11}$R$_{12}$, COR$_{13}$, SO$_2$R$_{13}$, SOR$_{13}$, SR$_{13}$, CF$_3$, CN or =O;

R$_7$ represents H or alkyl;

R$_8$ represents H, alkyl, cycloalkyl, cycloalkylalkyl, aryl, arylalkyl, heteroaryl, heteroarylalkyl, heterocyclo or heterocycloalkyl;

R$_9$ represents R$_8$ or alkylcarbonyl, alkoxycarbonyl, alkylsulphonyl, cycloalkylcarbonyl, cycloalkoxycarbonyl, cycloalkylsulphonyl, cycloalkylalkylcarbonyl, cycloalkylalkoxycarbonyl, cycloalkylalkylsulphonyl, arylcarbonyl, arylsulphonyl, heteroarylcarbonyl, heteroarylsulphonyl, heterocyclocarbonyl, heterocyclosulphonyl, arylalkylcarbonyl, arylalkoxycarbonyl, arylalkylsulphonyl, heteroarylalkylcarbonyl, heteroarylalkoxycarbonyl, heteroarylsulphonyl, heterocycloalkylcarbonyl, heterocycloalkoxycarbonyl or heterocycloalkylsulphonyl; or $NR_8R_9$ represents a heterocyclic ring such as morpholine;

$R_{10}$ represents H, alkyl, cycloalkyl, cycloalkylalkyl, arylalkyl, heteroarylalkyl or heterocycloalkyl;

$R_{11}$ and $R_{12}$ are the same or different and are each $R_8$, or $NR_{11}R_{12}$ represents a heterocyclic ring such as morpholine;

$R_{13}$ represents alkyl, cycloalkyl, cycloalkylalkyl, aryl, arylalkyl, heteroaryl, heteroarylalkyl, heterocyclo or heterocycloalkyl;

the $R_{14}$s are the same or different and are each selected from H alkyl, cycloalkyl, $OR_8$, $NR_8R_9$, $CO_2R_{10}$, $CONR_{11}R_{12}$, CONHOH, $SO_2NR_{11}R_{12}$, $SON_{11}R_{12}$, $COR_{13}$, $SO_2R_{13}$, $SOR_{13}$, $SR_{13}$, $CF_3$, $NO_2$ and CN, provided that when both m and n represent 0, if one $R_{14}$ is $OR_8$, $NR_8R_9$ or $SR_{13}$, the other is not $OR_8$, $NR_8R_9$ or $SR_{13}$; and $R_{15}$ represents H, alkyl or F; or a pharmaceutically acceptable salt thereof.

The preparation of these compounds is described in WO 2000/068230, incorporated herein by reference in its entirety.

In another embodiment, PDE7 inhibitors useful in the methods of the invention are selected from those compounds generally or specifically disclosed in US 20040106631, EP 1 400 244, and WO 2004/026818, each expressly incorporated herein by reference in its entirety. In one embodiment, PDE7 inhibitors useful in the methods of the invention have the formula:

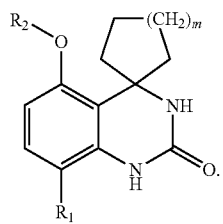

(25)

The substituents for the above compounds are defined as follows:

m is 1, 2 or 3; $R_1$ is methyl, chloro, bromo or fluoro; $R_2$ is $-Q^1-Q^2-Q^3-Q^4$ or $(C_1-C_6)$ alkyl, said $(C_1-C_6)$ alkyl is substituted with one to three $OR_4$, $COOR_4$, $NR_4R_5$, $NRC(=O)R_4$, $C(=O)NR_4R_5$ or $SO_2NR_4R_5$;

$R_4$ is $(C_1-C_6)$ alkyl substituted with one to three F, CN, $S(=O)R_6$, $SO_3H$, $SO_2R_6$, $SR_7$, $C(=O)-NH-SO_2-CH_3$, $C(=O)R_7$, $NR'C(=O)R_7$, $NR'SO_2R_6$, $C(=O)NR_7R_8$, $O-C(=O)NR_7R_8$ or $SO_2NR_7R_8$;

$R_5$ is H or $(C_1-C_6)$ alkyl optionally substituted with one to three F, CN, $S(=O)R_6$, $SO_3H$, $SO_2R_6$, $SR_7$, $C(=O)-NH-SO_2-CH_3$, $C(=O)R_7$, $NR'C(=O)R_7$, $NR'SO_2R_6$, $C(=O)NR_7R_8$, $O-C(=O)NR_7R_8$ or $SO_2NR_7R_8$; or said $(C_1-C_6)$ alkyl is (1) substituted with one to three $OC(=O)R_{4a}$, $SR_{4a}$, $S(=O)R_3$, $C(=NR_9)R_{4a}$, $C(=NR_9)-NR_{4a}R_{5a}$, $NR-C(=NR_9)-NR_{4a}R_{5a}$, $NRCOOR_{4a}$, $NR-C(=O)NR_{4a}R_{5a}$, $NR-SO_2-NR_{4a}R_{5a}$, $NR-C(=NR_9)-R_{4a}$ or $NR-SO_2-R_3$; and (2) optionally substituted with one or two $OR_{4a}$, $COOR_{4a}$, $C(=O)-R_{4a}$, $NR_{4a}R_{5a}$, $NRC(=O)R_{4a}$, $C(=O)NR_{4a}R_{5a}$ or $SO_2NR_{4a}R_{5a}$;

$R_9$ is H, CN, OH, $OCH_3$, $SO_2CH_3$, $SO_2NH_2$ or $(C_1-C_6)$ alkyl; and $R_3$ is $(C_1-C_6)$ alkyl optionally substituted with one to three F, CN, $S(=O)R_6$, $SO_3H$, $SO_2R_6$, $C(=O)-NH-SO_2-CH_3$, $OR_7$, $SR_7$, $COOR_7$, $C(=O)R_7$, $O-C(=O)NR_7R_8$, $NR_7R_8$, $NR'C(=O)R_7$, $NR'SO_2R_6$, $C(=O)NR_7R_8$ or $SO_2NR_7R_8$;

$R_{4a}$ and $R_{5a}$ are the same or different and are H or $(C_1-C_6)$ alkyl optionally substituted with one to three F, CN, $S(=O)R_6$, $SO_3H$, $SO_2R_6$, $C(=O)-NH-SO_2-CH_3$, $OR_7$, $SR_7$, $COOR_7$, $C(=O)R_7$, $O-C(=O)NR_7R_8$, $NR_7R_8$, $NR'C(=O)R_7$, $NR'SO_2R_6$, $C(=O)NR_7R_8$ or $SO_2NR_7R_8$;

$Q^1$ is a single bond or $(C_1-C_6)$ alkylene; $Q^2$ is a saturated 4- to 6-membered heterocyclyl comprising one or two O or N; $Q^3$ is $(C_1-C_6)$ alkylene; $Q^4$ is a 4 to 8-membered, aromatic or non aromatic heterocyclyl comprising 1 to 4 O, S, $S(=O)$, $SO_2$, or N, said heterocyclyl being optionally substituted with one to three OR, NRR', $-CN$ or $(C_1-C_6)$ alkyl;

R is H or $(C_1-C_6)$ alkyl;

$R_6$ is $(C_1-C_6)$ alkyl optionally substituted with one or two OR';

$R_7$ and $R_8$ are the same or different and are H or $(C_1-C_6)$ alkyl optionally substituted with one or two OR';

$R_9$ is H, CN, OH, $OCH_3$, $SO_2CH_3$, $SO_2NH_2$ or $(C_1-C_6)$ alkyl;

R' is H or $(C_1-C_6)$ alkyl; and R" is H or $(C_1-C_6)$ alkyl;

provided that (1) the atom of $Q^2$ bound to $Q^1$ is a carbon atom; and (2) the atom of $Q^4$ bound to $Q^3$ is a carbon atom;

or a racemic form, isomer, pharmaceutically acceptable derivative thereof.

The preparation of these compounds is described in US 20040106631, EP 1 400 244, and WO 2004/026818.

In another embodiment, PDE7 inhibitors useful in the methods of the invention are selected from those compounds generally or specifically disclosed in U.S. Pat. No. 6,936,609 and US 20040249148, each expressly incorporated herein by reference in its entirety. In one embodiment, PDE7 inhibitors useful in the methods of the invention have the formula:

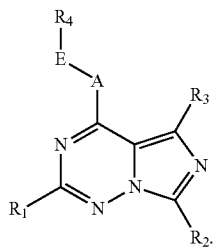

(26)

The substituents for the above compounds are defined as follows:

$R_1$ represents $(C_6-C_{10})$-aryl, which is optionally identically or differently substituted by radicals selected from the group consisting of halogen, formyl, carbamoyl, cyano, hydroxyl, trifluoromethyl, trifluoromethoxy, nitro, $(C_1-C_6)$-alkyl or $(C_1-C_6)$-alkoxy, and optionally by a radical of the formula $SO_2NR_5R_6$, wherein $R_5$ and $R_6$ independently of one another denote hydrogen or $(C_1-C_6)$-alkyl, or $NR_5R_6$ denotes 4- to 8-membered heterocyclyl, bonded via a nitrogen atom, optionally identically or differently substituted by radicals selected from the group consisting of oxo, halogen, $(C_1-C_6)$-alkyl and $(C_1-C_6)$-acyl, $R_2$ represents a saturated or partially unsaturated hydrocarbon radical having 1 to 10 carbon atoms, $R_3$ represents methyl or ethyl, A represents O, S, or NR₇, wherein R₇ denotes hydrogen or (C₁-C₆)-alkyl optionally substituted by (C₁-C₃)-alkoxy, E represents a bond or (C₁-C₃)-alkanediyl, R₄ represents (C₆-C₁₀)-aryl or 5- to 10-membered heteroaryl, where aryl and heteroaryl are optionally identically or differently substituted by radicals selected from the group consisting of halogen, formyl, carboxyl, carbamoyl, —SO₃H, aminosulphonyl, cyano, hydroxyl, trifluoromethyl, trifluoromethoxy, nitro, (C₁-C₆)-alkyl, (C₁-C₆)-alkoxy, 1,3-dioxa-propane-1,3-diyl, (C₁-C₆)-alkylthio, (C₁-C₆)-alkylsulphinyl and (C₁-C₆)-alkyl-sulphonyl, —NR₈R₉ end optionally methyl-substituted, 5- to 6-membered heteroaryl or phenyl, wherein R₈ and R₉ independently of one another denote hydrogen, (C₁-C₆)-alkyl or (C₁-C₆)-acyl, or salt thereof.

The preparation of these compounds is described in U.S. Pat. No. 6,936,609 and US 20040249148.

In another embodiment, PDE7 inhibitors useful in the methods of the invention are selected from those compounds generally or specifically disclosed in WO 2006/092692, expressly incorporated herein by reference in its entirety. In one embodiment, PDE7 inhibitors useful in the methods of the invention have the formulas:

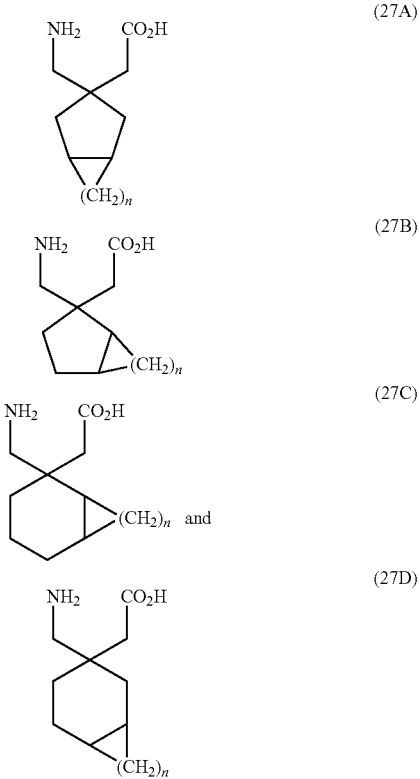

wherein n is an integer of from 1 to 4, and where there are stereocenters, each center may be independently R or S.

The preparation of these compounds is described in WO 2006/092692.

In another embodiment, PDE7 inhibitors useful in the methods of the invention are selected from those compounds generally or specifically disclosed in US 2006229306 and WO 2004/065391, each expressly incorporated herein by reference in its entirety. In one embodiment, PDE7 inhibitors useful in the methods of the invention have the formula:

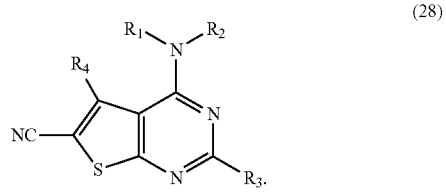

The substituents for the above compounds are defined as follows:

R₁ and R₂ either
(1) independently represent:
(a) a hydrogen atom;
(b) a group selected from alkyl, alkenyl and alkynyl groups, wherein each alkyl, alkenyl and alkynyl group is independently optionally substituted by one or more substituents selected from halogen atoms, hydroxy, alkoxy, aryloxy, alkylthio, hydroxycarbonyl, alcoxycarbonyl, mono- and di-alkylaminoacyl, oxo, amino, and mono- and di-alkylamino groups; or
(c) a group of formula (CH₂)ₙ—R₆, wherein n is an integer from 0 to 4 and R₆ represents a cycloalkyl or cycloalkenyl group;
(2) R₁ and R₂ form, together with the nitrogen atom to which they are attached, a 3- to 8-membered ring comprising from 1 to 4 heteroatoms selected from nitrogen, oxygen and sulphur, which ring is saturated or unsaturated and optionally substituted by one or more substituents selected from halogen atoms, alkyl, hydroxy, alkoxy, acyl, hydroxycarbonyl, alkoxycarbonyl, alkylenedioxy, amino, mono- and di-alkylamino, mono- and di-alkylaminoacyl, nitro, cyano and trifluoromethyl groups;

R₃ is a group of formula (CH₂)ₙ₋G′ wherein n is an integer from 0 to 4 and G represents a monocyclic or bicyclic aryl or heteroaryl group comprising from zero to four heteroatoms which group is optionally substituted by one or more substituents selected from:
(1) halogen atoms;
(2) alkyl and alkylene groups, wherein each alkyl and alkylene group is independently optionally substituted by one or more substituents selected from halogen atoms; and
(3) phenyl, hydroxy, hydroxyalkyl, alkoxy, alkylenedioxy, aryloxy, alkylthio, amino, mono- and di-alkylamino, acylamino, nitro, acyl, hydroxycarbonyl, alkoxycarbonyl, cyano, difluoromethoxy and trifluoromethoxy groups;

R₄ represents a hydrogen atom, an alkyl or an aryl group.

The preparation of these compounds is described in US 2006229306 and WO 2004/065391.

Other compounds useful in the methods of the invention include imidazopyridine derivatives (WO 2001/34601), dihydropurine derivatives (WO 2000/68203), pyrrole derivatives (WO 2001/32618), benzothiopyranoimidazolone derivatives (DE 19950647), heterocyclic compounds (WO 2002/87519), guanine derivatives (*Bioorg. Med. Chem. Lett.* 11:1081-1083, 2001), and benzothienothiadiazine derivatives (*Eur. J. Med. Chem.* 36:333, 2001). The disclosure of each published patent application and journal article listed above is expressly incorporated herein by reference in its entirety.

In another embodiment, PDE7 inhibitors useful in the methods of the invention are selected from those compounds generally or specifically disclosed in WO 2008/130619, expressly incorporated herein by reference in its entirety. In one embodiment, PDE7 inhibitors useful in the methods of the invention have the formula:

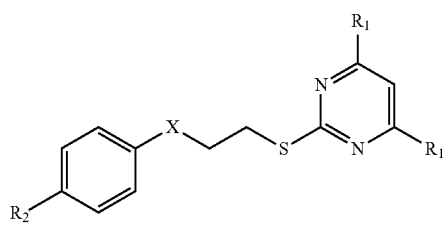
(29)

The substituents for the above compounds are defined as follows:

X is SO, or SO$_2$,

R1 is H, or alkyl,

R2 is alkyl, or halogen.

In specific embodiments, R1 is Me. In other specific embodiments R1 is F. In certain embodiments R2 is t-Bu. In specific embodiments, R1 is methyl. In more specific embodiments, the compounds are selected from:

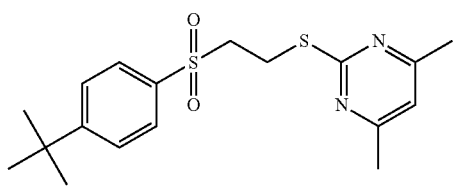

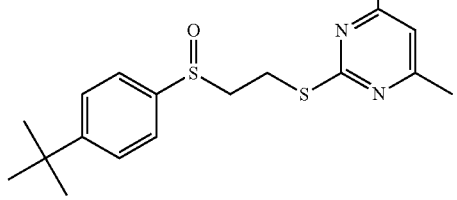

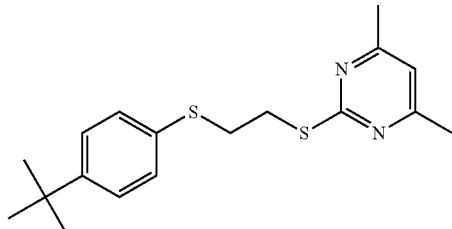

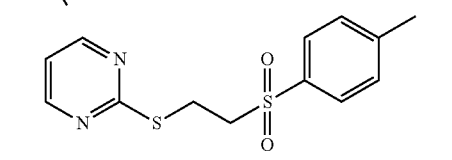

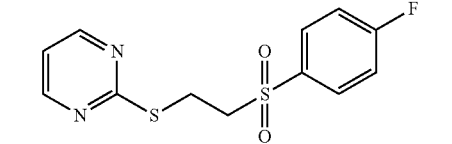

In a related embodiment, PDE7 inhibitors useful in the methods of the invention have the formula:

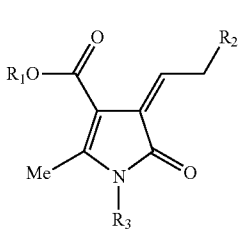
(30)

wherein

R1 is alkyl,

R2 is aryl or heteroaryl,

R3 is alkyl, aryl, cycloakyl, or alkylaryl.

In specific embodiments, R1 is methyl. In certain embodiments R2 is furanyl or thiophenyl. In other specific embodiments, R2 is substituted phenyl or benzyl. In preferred embodiments, R3 is iso-butyl. In more specific embodiments, the compounds are selected from:

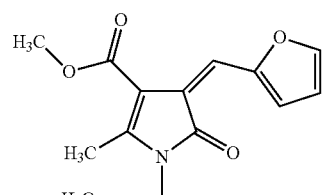

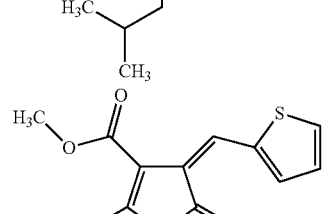

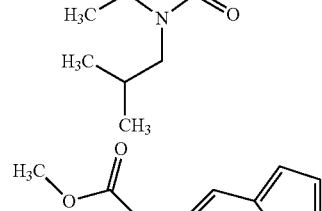

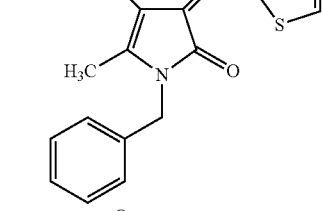

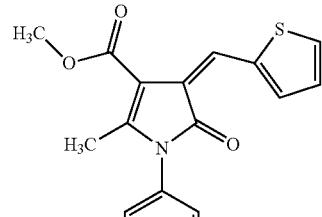
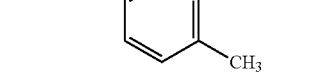

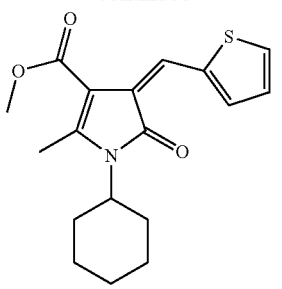
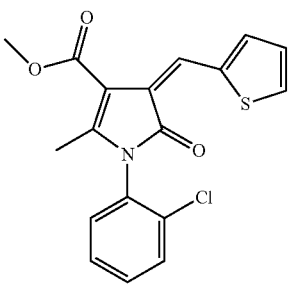
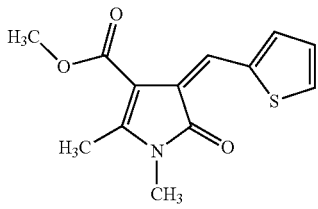
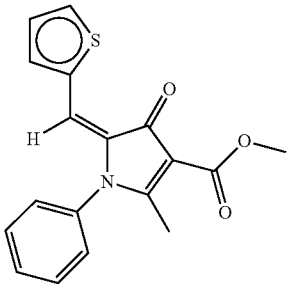
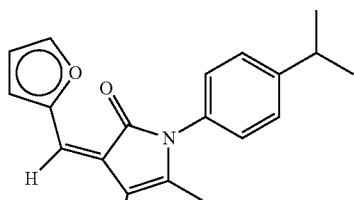
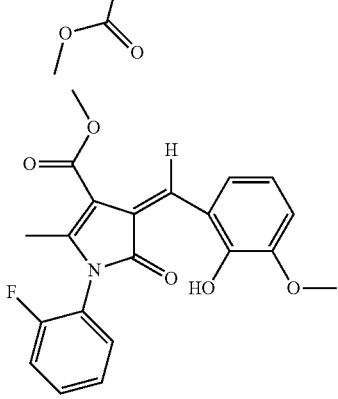

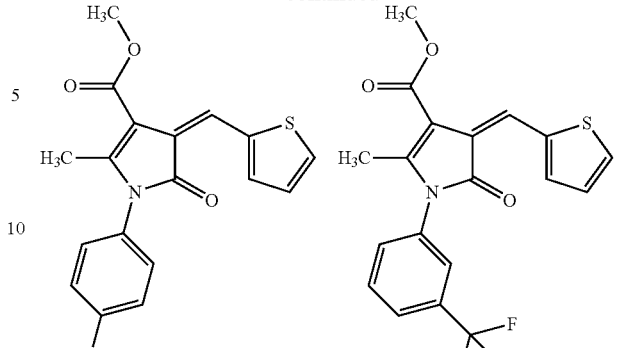

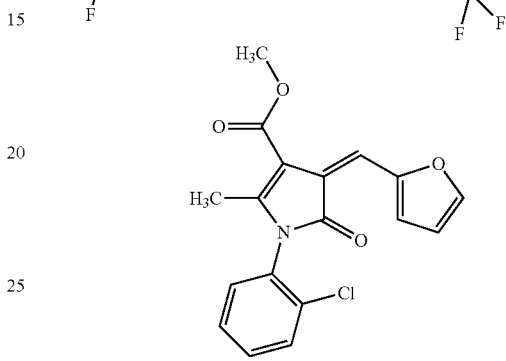

In another related embodiment, PDE7 inhibitors useful in the methods of the invention have the formula:

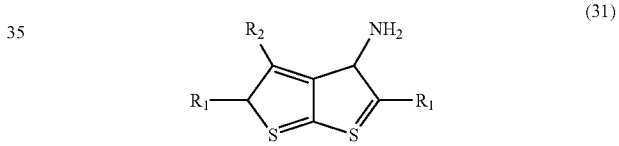

(31)

wherein

R1 is nitrile, or alkylcarboxylate,

R2 is alkyl, aryl, or heteroaryl.

In specific embodiments, R1 is nitrile or methylcarboxylate. In certain embodiments, R2 is a five membered heteroaryl. In more specific embodiments, R2 is furanyl, or thienyl. In other embodiments, R2 is a six membered aryl. In more specific embodiments, R2 is substituted phenyl.

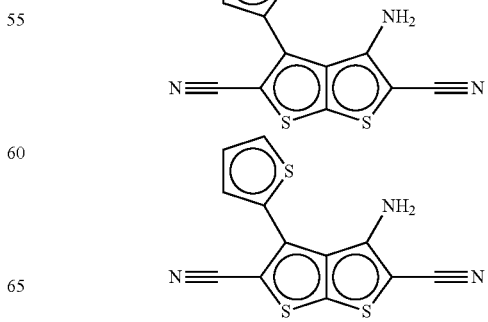

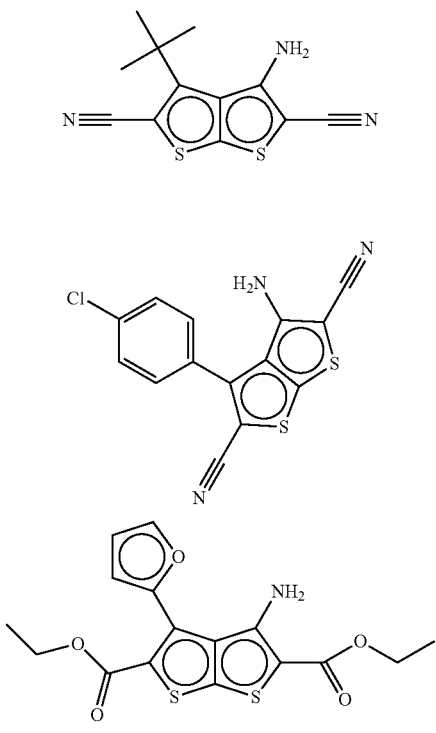

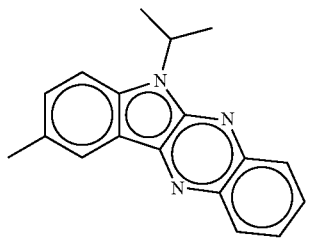

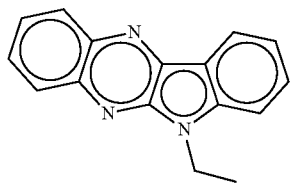

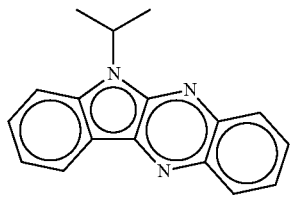

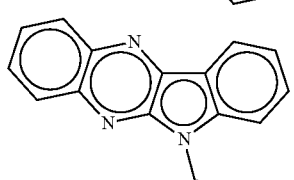

In another related embodiment, PDE7 inhibitors useful in the methods of the invention have the formula:

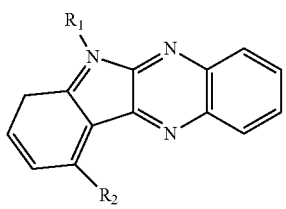

(32)

wherein

R1 is alkyl, alkenyl, or alkylcarboxylic acid,

R2 is halogen.

In certain embodiments R1 is butyl. In other embodiments R1 is terminal alkenyl. In more specific embodiments R1 is allyl, or vinyl. In other embodiments, R1 is $C_{1-4}$alkyl. In specific embodiments R1 is methylcarboxylic acid. In certain embodiments R2 is Cl, or Br. In more specific embodiments, the compounds are selected from:

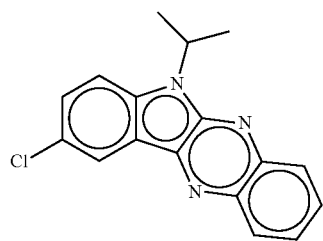

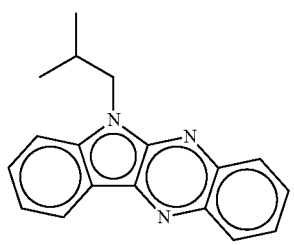

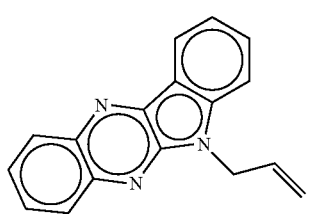

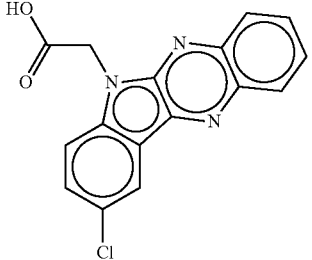

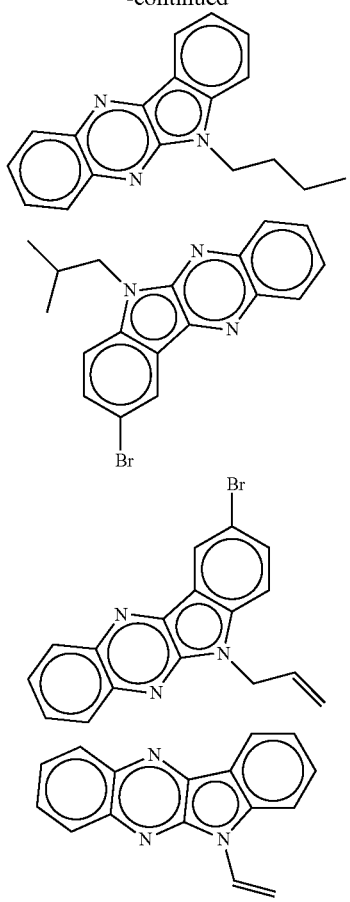

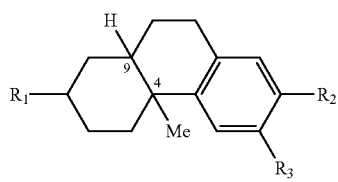

In other related embodiments, PDE7 inhibitors useful in the methods of the invention have the formula:

(33)

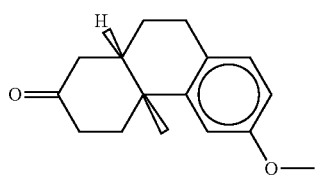

wherein

R1 is CO, or alkylalcohol, R2 is alkyl, R3 is alkoxy, and the C4 and C9 stereocenters are independently (R) or (S).

In certain embodiments R1 is carbonyl, or 2-methylpropan-1-ol. In specific embodiments R2 is methyl. In certain embodiments, R3 is methoxy. In more specific embodiments the compounds are selected from:

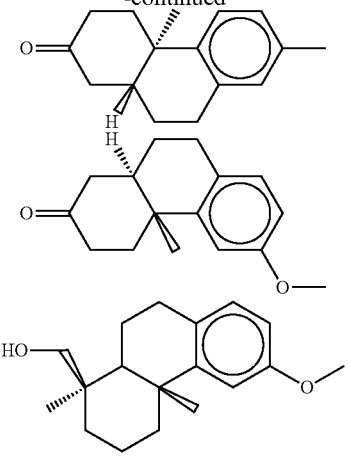

In another related embodiment, PDE7 inhibitors useful in the methods of the invention have the formula:

(34)

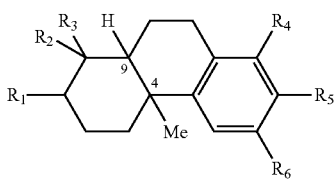

wherein

R1 is hydrogen, hydroxyl, carbonyl, or alkylalcohol,

R2 and R3 are independently selected from hydrogen, alkyl, alkylcarboxylate, or carboxylic acid, R4 is hydrogen, or alkyl, R5 is hydrogen, alkyl, hydroxyl, or acetate, R6 is hydrogen, or alkoxy, and the C4 and C9 stereocenters are independently (R) or (S).

In certain embodiments R1 is 2-methylpropan-1-ol. In specific embodiments R2 is methyl. In certain embodiments, R2 is methylcarboxylate. In specific embodiments R2 and R3 are both methyl. In other embodiments, R2 is methyl, and R3 is methylcarboxylate. In specific embodiments R4 is iso-propyl. In specific embodiments, R5 is methyl. In certain embodiments, R6 is methoxy. In more specific embodiments the compounds are selected from:

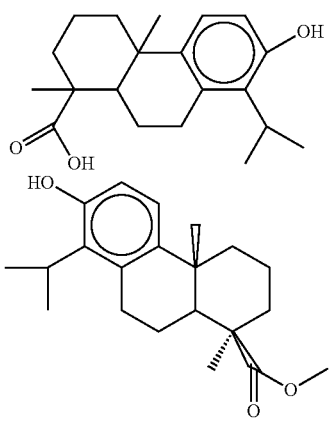

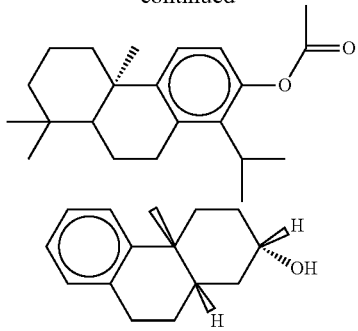

In regards to the above compounds, the terms "alkyl", "alkenyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms. Preferred groups have a total of up to 10 carbon atoms. Cyclic groups can be monocyclic or polycyclic and preferably have from 3 to 10 ring carbon atoms. Exemplary cyclic groups include cyclopropyl, cyclopentyl, cyclohexyl, cyclopropylmethyl, adamantly, norbornane, and norbornee. This is also true of groups that include the prefix "alkyl-", such as alkylcarboxylic acid, alkyl alcohol, alkylcarboxylate, alkylaryl, and the like. Examples of suitable alkylcarboxylic acid groups are methylcarboxylic acid, ethylcarboxylic acid, and the like. Examples of suitable alkylalcohols are methylalcohol, ethylalcohol, isopropylalcohol, 2-methylpropan-1-ol, and the like. Examples of suitable alkylcarboxylates are methylcarboxylate, ethylcarboxylate, and the like. Examples of suitable alkyl aryl groups are benzyl, phenylpropyl, and the like.

The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring hetero atom (e.g., O, S, N). Suitable heteroaryl groups include furyl, thienyl, pyridyl, quinolinyl, isoquinolinyl, indolyl, isoindolyl, thiazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on.

The aryl, and heteroaryl groups can be unsubstituted or substituted by one or more substituents independently selected from the group consisting of alkyl, alkoxy, methylenedioxy, ethylenedioxy, alkylthio, haloalkyl, haloalkoxy, haloalkylthio, halogen, nitro, hydroxy, mercapto, cyano, carboxy, formyl, aryl, aryloxy, arylthio, arylalkoxy, arylalkylthio, heteroaryl, heteroaryloxy, heteroarylalkoxy, heteroarylalkylthio, amino, alkylamino, dialkylamino, heterocyclyl, heterocycloalkyl, alkylcarbonyl, alkenylcarbonyl, alkoxycarbonyl, haloalkylcarbonyl, haloalkoxycarbonyl, alkylthiocarbonyl, arylcarbonyl, heteroarylcarbonyl, aryloxycarbonyl, heteroaryloxycarbonyl, arylthiocarbonyl, heteroarylthiocarbonyl, alkanoyloxy, alkanoylthio, alkanoylamino, arylcarbonyloxy, arylcarbonylthio, alkylaminosulfonyl, alkylsulfonyl, arylsulfonyl, heteroarylsulfonyl, aryldiazinyl, alkylsulfonylamino, arylsulfonylamino, arylalkylsulfonylamino, alkylcarbonylamino, alkenylcarbonylamino, arylcarbonylamino, arylalkylcarbonylamino, arylcarbonylaminoalkyl, heteroarylcarbonylatnino, heteroarylalkycarbonylamino, alkylsulfonylamino, alkenylsulfonylamino, arylsulfonylamino, arylalkylsulfonylamino, heteroarylsulfonylamino, heteroarylalkylsulfonylamino, alkylaminocarbonylamino, alkenylaminocarbonylamino, arylaminocarbonylamino, arylalkylaminocarbonylamino, heteroarylaminocarbonylamino, heteroarylalkylaminocarbonylamino and, in the case of heterocyclyl, oxo. If other groups are described as being "substituted" or "optionally substituted," then those groups can also be substituted by one or more of the above enumerated substituents.

In another embodiment, PDE7 inhibitors useful in the methods of the invention are selected from those compounds generally or specifically disclosed in WO 2008/142550, expressly incorporated herein by reference in its entirety. In one embodiment, PDE7 inhibitors useful in the methods of the invention have the formula:

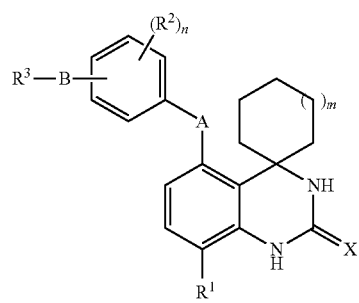

(35)

The substituents for the above compounds are defined as follows:

m is 0, 1 or 2, n is 0, 1, 2 or 3,

X is O, S or N—CN, $R^1$ is halogen or CN,

A is a single bond, $CH_2$, O or S,

B is a single bond, $CH_2$ or $OCH_2$, each $R^2$ is independently halogen, $(C_{1-6})$alkyl (optionally substituted by 1 to 3 fluorine atoms), OH, $(C_{1-6})$alkylthio or CN, $R^3$ is selected from the following groups (i) to (x):

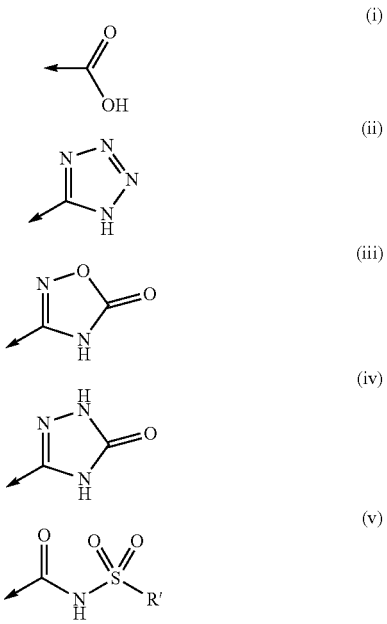

-continued (vi) 

(vii) 

(viii) 

(ix) 

(x) 

R is H or (C$_{1-6}$)alkyl (optionally substituted by 1 to 3 fluorine atoms), R' is (C$_{1-6}$)alkyl (optionally substituted by 1 to 3 fluorine atoms), or a pharmaceutically acceptable salt, solvate, polymorph or prodrug thereof.

In regard to the above compounds, the term "alkyl" denotes a monovalent, straight or branched, saturated hydrocarbon chain containing 1 to 6 carbon atoms Examples of alkyl groups include methyl, ethyl, n-propyl, isopropyl, n-butyl, isobutyl, sec-butyl, tert-butyl, n-pentyl, 2-methylbutyl, 3-methylbutyl, neopentyl, n-hexyl, 2-methylpentyl, 3-methylpentyl, 4-methylpentyl, 2-ethylbutyl and 2,2-dimethylbutyl. Preferred alkyl groups are particularly methyl and ethyl, especially methyl.

Where stated, alkyl groups may be substituted by 1 to 3 fluorine atoms. The substitution may be at any position on the alkyl chain. Preferably, such fluorinated alkyl groups have 1 to 4 carbon atoms, more preferably 1 or 2 carbon atoms. Mono-, di- and trifluoromethyl groups (especially trifluoromethyl), and mono-, di- and trifluoroethyl groups (especially 2,2,2-trifluoroethyl) are especially preferred.

The term "alkoxy" denotes "alkyl-O—", wherein "alkyl" is as defined above, either in its broadest aspect or a preferred aspect. Preferred alkoxy groups are groups, particularly methoxy and ethoxy. The term "alkylthio" denotes "alkyl-S—", wherein "alkyl" is as defined above, either in its broadest aspect or a preferred aspect. Preferred alkylthio groups are (C$_{1-4}$)alkylthio groups, particularly methylthio and ethylthio. The term "halogen" denotes fluoro, chloro, bromo or iodo. Preferred halogen groups are fluoro and chloro.

Preferably, m is 0 or 1, more preferably 1.
Preferably, n is 0 or 1, more preferably 0.
Preferably, X is O or N—CN, more preferably O.
Preferably, R$^1$ is F or Cl, more preferably Cl.
Preferably, A is a single bond or O, more preferably O.
When the group B is OCH$_2$, the oxygen atom is bonded to the benzene ring and the methylene group to the group R$^3$.
Preferably, B is a single bond.
Preferably, R$^2$ is F or Cl, more preferably F.
Preferably, R$^3$ is a group (i), (ii), (iii), (iv), (v) or (vi), more preferably a group (i) or (ii), and especially a group (ii).

In one embodiment, the group —B—R$^3$ is present at the 2-position of the phenyl ring (the position of the group A being the 1-position). In other embodiments, the group —B—R$^3$ is present at the 3-position. In further embodiments, the group —B—R$^3$ is present at the 4-position.

PDE7 inhibitors useful in the methods of the invention include those in which each variable in the above formula is selected from the suitable and/or preferred groups for each variable. Even more preferred PDE7 inhibitors useful in the methods of the invention include those where each variable in the above formula is selected from the more preferred or most preferred groups for each variable.

In a related embodiment, the following PDE7 inhibitors are useful in the methods of the invention:

5-[(8'-chloro-2'-oxo-2',3'-dihydro-1'H-spiro[cyclohexane-1,4'-quinazolin]-5'-yl)]-2-fluorobenzoic acid,
3-(8'-chloro-2-oxo-2',3'-dihydro-1'H-spiro[cyclohexane-1,4'-quinazolin]-5'-ylbenzoic acid,
5-[(8'-chloro-2'-oxo-2',3'-dihydro-1'H-spiro[cyclohexane-1,4'-quinazolin]-4'-yl)]-2-fluorobenzoic acid,
8-chloro-5'-[4-fluoro-3-(2H-tetrazol-5-yl)phenyl]-1'H-spiro[cyclohexane-1,4'-quinazolin]-2'(3'H)-one,
[3-(8'-chloro-2'-oxo-2',3'-dihydro-1'H-spiro[cyclohexane-1,4'-quinazolin]-5'-yl)phenoxy]acetic acid,
2-{(8'-chloro-2'-oxo-2,3'-dihydro-1'H-spiro[cyclohexane-1,4'-quinazolin]-5'-yl)oxy}-3-fluorobenzoic acid,
2-{(8'-chloro-2'-oxo-2',3'-dihydro-1'H-spiro[cyclopentane-1,4'-quinazolin]-5'-oxy}-3-fluorobenzoic acid,
3-chloro-2-{(8'-chloro-2'-oxo-2',3'-dihydro-1'H-spiro[cyclohexane-1,4'-quinazolin]-5'-yl)oxy}benzoic acid,
3-chloro-2-{(8'-fluoro-2'-oxo-2',3'-dihydro-1'H-spiro[cyclohexane-1,4'-quinazolin]-5'-yl)oxy}benzoic acid,
8'-chloro-5'-[2-fluoro-6-(2H-tetrazol-5-yl)phenoxy]-1'H-spiro[cyclohexane-1,4'-quinazolin]-2'(3'H)-one,
8'-chloro-5'-[4-fluoro-2-(1H-tetrazol-5-yl)phenoxy]-1'H-spiro[cyclohexane-1,4'-quinazolin]-2'(3'H)-one,
8'-chloro-5'-[6-fluoro-2-(1H-tetrazol-5-yl)phenoxy]-1'H-spiro[cyclohexane-1,4'-quinazolin]-2'(3'H)-one,
8'-chloro-5'-[4-fluoro-2-(1H-tetrazol-5-yl)phenoxy]-1'H-spiro[cyclopentane-1,4'-quinazolin]-2'(3'H)-one,
8'-chloro-5'-[6-fluoro-2-(1H-tetrazol-5-yl)phenoxy]-1'H-spiro[cyclopentane-1,4'-quinazolin]-2'(3'H)-one,
8'-chloro-5'-[6-chloro-2-(1H-tetrazol-5-yl)phenoxy]-1'H-spiro[cyclopentane-1,4'-quinazolin]-2'(3'H)-one,
8'-chloro-5'-[2-(1H-tetrazol-5-yl)phenoxy]-1'H-spiro[cyclopentane-1,4'-quinazolin]-2'(3'H)-one,
8'-chloro-5'-[2-(1H-tetrazol-5-yl)phenoxy]-1'H-spiro[cyclohexane-1,4'-quinazolin]-2'(3'H)-one,
8'-chloro-5'-[2-fluoro-6-(5-oxo-4,5-dihydro-1,2,4-oxadiazol-3-yl)phenoxy]-1'H-spiro[cyclohexane-1,4'-quinazolin]-2'(3'H)-one,
8'-chloro-5'-[2-fluoro-6-(5-oxo-4,5-dihydro-1H-1,2,4-triazol-3-yl)phenoxy]-1'H-spiro[cyclohexane-1,4'-quinazolin]-2'(3'H)-one,
2-[(8'-chloro-2'-oxo-2',3'-dihydro-1'H-spiro[cyclohexane-1,4'-quinazolin]-5'-yl)oxy]-3-fluoro-N-(methylsulfonyl)benzamide,
N-{2-[(8'-chloro-2'-oxo-2',3'-dihydro-1'H-spiro[cyclohexane-1,4'-quinazolin]-5'-yl)oxy]-3-fluorophenyl}-1,1,1-trifluoromethanesulfonamide,
{2-[(8'-chloro-2'-oxo-2',3'-dihydro-1'H-spiro[cyclohexane-1,4'-quinazolin]-5'-yl)oxy]-3-fluorophenyl}acetic acid,
{2-[(8'-chloro-2'-oxo-2',3'-dihydro-1'H-spiro[cyclohexane-1,4'-quinazolin]-5'-yl)oxy]phenoxy}acetic acid,
{4-[(8'-chloro-2'-oxo-2',3'-dihydro-1'H-spiro[cyclohexane-1,4'-quinazoline-5'-yl)oxy]phenoxy}acetic acid, methyl 2-[(8'-chloro-2'-oxo-2',3'-dihydro-1'H-spiro[cyclohexane-1,4'-quinazolin]-5'-yl)oxy]-3-fluorobenzoate,
and pharmaceutically acceptable salts, solvates and prodrugs thereof.

In another related embodiment, the following PDE7 inhibitors are useful in the methods of the invention:
8'-chloro-5'-[2-fluoro-6-(2H-tetrazol-5-yl)phenoxy]-1'H-spirocyclohexane-1,4'-quinazolin]-2'(3'H)-one,
8'-chloro-5'-[4-fluoro-2-(1H-tetrazol-5-yl)phenoxy]-1'H-spiro[cyclohexane-1,4'-quinazolin]-2'(3'H)-one,
8'-chloro-5'-[6-fluoro-2-(1H-tetrazol-5-yl)phenoxy]-1'H-spiro[cyclohexane-1,4'-quinazolin]-2'(3'H)-one,
8'-chloro-5'-[4-fluoro-2-(1H-tetrazol-5-yl)phenoxy]-1'H-spiro[cyclopentane-1,4'-quinazolin]-2'(3'H)-one,
8'-chloro-5'-[6-fluoro-2-(1H-tetrazol-5-yl)phenoxy]-1'H-spiro[cyclopentane-1,4'-quinazolin]-2'(3'H)-one,
8'-chloro-5'-[6-chloro-2-(1H-tetrazol-5-yl)phenoxy]-1'H-spiro[cyclopentane-1,4'-quinazolin]-2'(3'H)-one,
8'-chloro-5'-[2-(1H-tetrazol-5-yl)phenoxy]-1'H-spiro[cyclopentane-1,4'-quinazolin]-2'(3'H)-one,
8'-chloro-5'-[2-(1H-tetrazol-5-yl)phenoxy]-1'H-spiro[cyclohexane-1,4'-quinazolin]-2'(3'H)-one,
and pharmaceutically acceptable salts, solvates and prodrugs thereof.

The following compounds are most preferred:
8'-chloro-5'-[2-fluoro-6-(2H-tetrazol-5-yl)phenoxy]-1'H-spiro[cyclohexane-1,4'-quinazolin]-2'(3'H)-one,
8'-chloro-5'-[4-fluoro-2-(1H-tetrazol-5-yl)phenoxy]-1'H-spiro[cyclohexane-1,4'-quinazolin]-2'(3'H)-one,
8'-chloro-5'-[6-fluoro-2-(1H-tetrazol-5-yl)phenoxy]-1'H-spiro[cyclopentane-1,4'-quinazolin]-2'(3'H)-one,
8'-chloro-5'-[2-(1H-tetrazol-5-yl)phenoxy]-1'H-spiro[cyclohexane-1,4'-quinazolin]-2'(3'H)-one,
and pharmaceutically acceptable salts, solvates and prodrugs thereof.

The preparation of these compounds is described in WO 2008/142550.

In another embodiment, PDE7 inhibitors useful in the methods of the invention are selected from those compounds generally or specifically disclosed in U.S. Pat. No. 7,498,334, US 2005/0059686 and WO 2003/055882, each expressly incorporated herein by reference in its entirety. In one embodiment, PDE7 inhibitors useful in the methods of the invention have the formula:

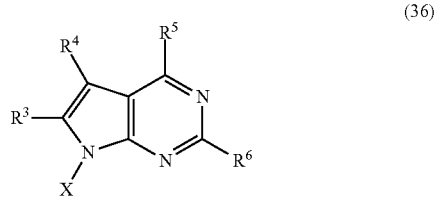

(36)

The substituents for the above compounds are defined as follows:
X is phenyl or Het, each of which is unsubstituted or monosubstituted or polysubstituted by R1 and/or R2, R1 and R2 are each, independently of one another, A, OH, OA, SA, SOA, SO2A, SO2NH2, SO2NHA, SO2AA', CN, NO2, NH2, NHA, NAA', NHCOA, NHCOOA, COOH, COOA, CONH2, CONHA, CONAA' or Hal, R' and R2 together are alternatively —OCH2O— or —OCH2CH2O—, R3 is A, OH, OA, SA, SOA, SO2A, SO2NH2, SO2NHA, SO2AA', CN, NO2, NH2, NHA, NHB, NAA', NHCOA, NHCOOA, NHCOB, NHCOOB, COOH, COOA, COOB, CONH2, CONHA, CONHB, CONAA' or Hal, R4 is branched or unbranched alkyl or alkenyl having up to 10 carbon atoms, which may be substituted by from 1 to 5 F and/or Cl atoms and/or in which one or more CH2 groups may be replaced by O, S, SO, SO2, NH, NA, NHCO, NACO, NHCOO or NACOO, or cycloalkyl or cycloalkenyl having from 3 to 7 carbon atoms, in which one or two CH2 groups may be replaced by O, S, SO, SO2, SO2NH, SO2NA, NH, NHA, NHCONH, NACONH, NACONA, NHCO, NACO, NHCOO or NACOO, R5 is OH, OA, SA, SOA, SO2A, SO2NH2, SO2NHA, SO2AA', CN, NO2, NH2, NHA, NAA', NHCOA, NHCOOA, COOH, COOA, CONH2, CONHA, CONAA' or Hal, R6 is H, OH, OA, SA, SOA, SO2A, SO2NH2, SO2NHA, SO2AA', CN, NO2, NH2, NHA, NAA', NHCOA, NHCOOA, COOH, COOA, CONH2, CONHA, CONAA' or Hal, A and A' are each, independently of one another, branched or unbranched alkyl or alkenyl having up to 10 carbon atoms, which may be substituted by from 1 to 5 F and/or Cl atoms and/or in which one or more CH2 groups may be replaced by O, S, SO, SO2, NH, NR7, NHCO, NR7CO, NHCOO or NR7COO. A and A' together are alternatively alkylene having from 3 to 7 carbon atoms, in which one or two CH2 groups may be replaced by CHR7, CHR7R8, O, S, SO, SO2, NH, NR7, NHCO, NR7CO, NHCOO or NR7COO. B is phenyl or Het, each of which is unsubstituted or monosubstituted or polysubstituted by R1 and/or R2, Het is an aromatic 5- or 6-membered heterocyclic ring having 1-3 N, O and/or S atoms which is unsubstituted or monosubstituted, disubstituted or trisubstituted by A", Hal or CF3, R7 and R8 are each, independently of one another, branched or unbranched alkyl or alkenyl having up to 5 carbon atoms, which may be substituted by from 1 to 5 F and/or Cl atoms and/or in which one or more CH2 groups may be replaced by O, S, SO, SO2 or NH, A" is alkyl having from 1 to 6 carbon atoms, and Hal is F, Cl, Br or I, and pharmaceutically usable derivatives, solvates and stereoisomers thereof, including mixtures thereof in all ratios.

In a related embodiment, PDE7 inhibitors useful in the methods of the invention include compounds of the above formula in which R5 is OH may also be in the form of their tautomers of the formula:

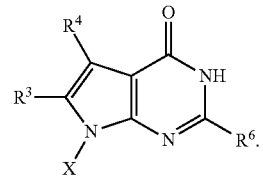

In regard to the above compounds, PDE7 inhibitors useful in methods of the invention include the optically active forms (stereo-isomers), the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, monohydrates, dihydrates or alcoholates.

In regards to the above compounds, the term pharmaceutically usable derivatives is taken to mean, for example, the salts of the above compounds and so-called prodrug compounds. The term prodrug derivatives is taken to mean, for example, the above compounds which have been modified, for example, with alkyl or acyl groups, sugars or oligopeptides and which are rapidly cleaved in the organism and thus release the active compounds. These also include biodegradable polymer derivatives of the above compounds, as described, for example, in *Int. J. Pharm.* 115, 61-67 (1995).

In regard to the above compounds, the meanings of all radicals which occur more than once are in each case independent of one another.

A and A' are preferably alkyl, furthermore preferably alkyl which is substituted by from 1 to 5 fluorine and/or chlorine atoms, furthermore preferably alkenyl.

In the above formulae, alkyl is preferably unbranched and has 1, 2, 3, 4, 5, 6, 7, 8, 9 or 10 carbon atoms, preferably 1, 2, 3, 4, 5 or 6 carbon atoms, and is preferably methyl, ethyl, trifluoromethyl, pentafluoroethyl or propyl, furthermore preferably isopropyl, butyl, isobutyl, sec-butyl or tert-butyl, but also n-pentyl, neopentyl, isopentyl or n-hexyl. Particular preference is given to methyl, ethyl, trifluoromethyl, propyl, isopropyl, butyl, n-pentyl, n-hexyl or n-decyl.

A" is preferably alkyl having 1, 2, 3, 4, 5 or 6 carbon atoms, for example methyl, ethyl or propyl, furthermore preferably isopropyl, butyl, isobutyl, sec-butyl or tert-butyl, but also n-pentyl, neopentyl, isopentyl or n-hexyl. Particular preference is given to methyl, ethyl, propyl, isopropyl or butyl.

Cycloalkyl preferably has 3-7 carbon atoms and is preferably cyclopropyl or cyclobutyl, furthermore preferably cyclopentyl or cyclohexyl, furthermore also cycloheptyl; particular preference is given to cyclopentyl.

Alkenyl is preferably vinyl, allyl, 2- or 3-butenyl, isobutenyl or sec-butenyl; preference is furthermore given to 4-pentenyl, isopentenyl or 5-hexenyl.

Alkylene is preferably unbranched and is preferably methylene or ethylene, furthermore preferably propylene or butylene.

Hal is preferably F, Cl or Br, furthermore also I.

The radicals R1 and R2 may be identical or different and are preferably in the 2- or 4-position of the phenyl ring. They are, for example, independently of one another, A or Hal, or together are methylenedioxy.

However, they are preferably each methyl, ethyl, propyl, methoxy, ethoxy, propoxy, isopropoxy, benzyloxy, but also fluoro-, difluoro- or trifluoro-methoxy, or 1-fluoro-, 2-fluoro-, 1,2-difluoro-, 2,2-difluoro-, 1,2,2-trifluoro- or 2,2,2-trifluoroethoxy, furthermore fluorine or chlorine.

R1 is particularly preferably fluorine, chlorine, methyl, ethyl or propyl.

R2 is particularly preferably fluorine, chlorine, methyl, ethyl or propyl.

X is preferably a phenyl radical which is monosubstituted by R1 or is unsubstituted Het.

X is particularly preferably 2-chlorophenyl, 2-fluorophenyl, 4-methyl-phenyl, 3-chlorophenyl or 4-chlorophenyl.

Het is preferably, for example, unsubstituted 2- or 3-furyl, 2- or 3-thienyl, 1-, 2- or 3-pyrrolyl, 1-, 2-, 4- or 5-imidazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or -5-yl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, or 1,2,3-thia-diazol-4- or -5-yl.

R3 is preferably, for example, COOA" or COOH.

R4 is preferably, for example, unbranched or branched alkyl having 1, 2, 3, 4, 5 or 6 carbon atoms, which may be substituted by 1-5 F or Cl atoms, preferably methyl, ethyl, trifluoromethyl, pentafluoroethyl or propyl, furthermore preferably isopropyl, butyl, isobutyl, sec-butyl or tert-butyl, but also n-pentyl, neopentyl, isopentyl or n-hexyl. Particular preference is given to methyl, ethyl, trifluoromethyl, propyl, isopropyl, butyl, n-pentyl, n-hexyl or n-decyl.

R5 is preferably Cl or OH.

R6 is preferably H.

In regard to the above compounds, at least one of the said radicals has one of the preferred meanings indicated above.

In a related embodiment, PDE7 inhibitors useful in the methods of the invention include the following compounds, wherein X is a phenyl radical which is monosubstituted by R1, or is unsubstituted Het; R1 is A or Hal; R3 is COOA" or COOH; R4 is unbranched or branched alkyl having 1, 2, 3, 4, 5 or 6 carbon atoms, which may be substituted by 1-5 F or Cl atoms; R5 is Cl or OH; and R6 is H;

In other related embodiments, PDE7 inhibitors useful in the methods of the invention include the following compounds, wherein X is a phenyl radical which is monosubstituted by R1, or is unsubstituted Het, R1 is A or Hal, R3 is COOA" or COOH, R4 is unbranched or branched alkyl having 1, 2, 3, 4, 5 or 6 carbon atoms, which may be substituted by 1-5 F or Cl atoms, R5 is Cl or OH, R6 is H, Het is furyl, thienyl, pyrrolyl, imidazolyl, pyridyl or pyrimidinyl, A and A" are each, independently of one another, unbranched or branched alkyl having 1, 2, 3, 4, 5 or 6 carbon atoms, which may be substituted by 1-5 F or Cl atoms, Hal is F, Cl or Br, and pharmaceutically usable derivatives, solvates and stereoisomers thereof, including mixtures thereof in all ratios.

The preparation of the above compounds and also the starting materials for their preparation are described in the literature (for example in the standard works, such as Houben-Weyl, *Methoden der organischen Chemie [Methods of Organic Chemistry]*, Georg-Thieme-Verlag, Stuttgart), to be precise under reaction conditions which are known and suitable for the said reactions. Use can also be made here of variants which are known per se, but are not mentioned here in greater detail.

In another related embodiment, PDE7 inhibitors useful in the methods of the invention include:

ethyl 5-isopropyl-4-oxo-7-p-tolyl-4,7-dihydro-3H-pyrrolo[2,3-d]-pyrimidine-6-carboxylate, ethyl 5-methyl-4-oxo-7-(3-chlorophenyl)-4,7-dihydro-3H-pyrrolo[2,3-d]pyrimidine-6-carboxylate, ethyl 5-methyl-4-oxo-7-(2-chlorophenyl)-4,7-dihydro-3H-pyrrolo[2,3-d]pyrimidine-6-carboxylate, ethyl 5-methyl-4-oxo-7-(2-fluorophenyl)-4,7-dihydro-3H-pyrrolo[2,3-d]pyrimidine-6-carboxylate, ethyl 5-propyl-4-oxo-7-(2-chlorophenyl)-4,7-dihydro-3H-pyrrolo[2,3-d]pyrimidine-6-carboxylate, ethyl 5-methyl-4-oxo-7-(4-chlorophenyl)-4,7-dihydro-3H-pyrrolo[2,3-d]pyrimidine-6-carboxylate, ethyl 5-methyl-4-oxo-7-p-tolyl-4,7-dihydro-3H-pyrrolo[2,3-d]-pyrimidine-6-carboxylate, methyl 5-methyl-4-oxo-7-(2-chlorophenyl)-4,7-dihydro-3H-pyrrolo[2,3-d]pyrimidine-6-carboxylate, methyl 5-methyl-4-oxo-7-phenyl-4,7-dihydro-3H-pyrrolo[2,3-d]-pyrimidine-6-carboxylate, methyl 5-methyl-4-oxo-7-(2-thienyl)-4,7-dihydro-3H-pyrrolo[2,3-d]-pyrimidine-6-carboxylate, and pharmaceutically usable derivatives, solvates and stereoisomers thereof, including mixtures thereof in all ratios.

The preparation of the above compounds is described in U.S. Pat. No. 7,498,334 and WO 2003/055882.

In another embodiment, PDE7 inhibitors useful in the methods of the invention are selected from those compounds generally or specifically disclosed in U.S. Pat. No. 6,884,800 and WO 01/36425, each expressly incorporated herein by reference in its entirety. In one embodiment, PDE7 inhibitors useful in the methods of the invention have the formula:

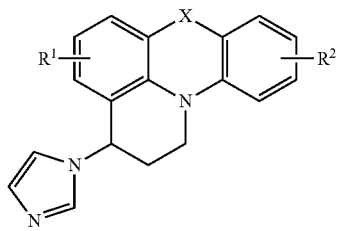

(37)

The substituents for the above compounds are defined as follows:

R1 and R2, independently of one another, each denote A1, OA1, SA1 or Hal, A1 denotes H, A, alkenyl, cycloalkyl or alkylenecycloalkyl, A denotes alkyl having 1-10 carbon atoms, Hal denotes F, Cl, Br or I, and x denotes O, S, SO or SO2, and their physiologically acceptable salts and/or solvates.

In regards to the above compounds, A denotes alkyl having 1-10 carbon atoms and has 1, 2, 3, 4, 5, 6, 7, 8, 9 or 10 carbon atoms and preferably denotes methyl, ethyl or propyl, furthermore preferably isopropyl, butyl, isobutyl, sec-butyl or tert-butyl, but also n-pentyl, neopentyl, isopentyl or hexyl. In these radicals, 1-7 H atoms may also be replaced by F and/or Cl. A therefore also denotes, for example, trifluoromethyl or pentafluoroethyl. Cycloalkyl has 3-9 carbon atoms and preferably denotes, for example, cyclopentyl or cyclohexyl. Alkenyl has 2-10 carbon atoms, is linear or branched and preferably denotes vinyl, propenyl or butenyl. Alkylenecycloalkyl has 4-10 carbon atoms and denotes, for example, methylenecyclopentyl, ethylenecyclopentyl, methylenecyclohexyl or ethylenecyclohexyl. R1 and R2 preferably denote, in each case independently of one another, H, fluorine, chlorine, methyl, ethyl, propyl, methoxy, ethoxy, propoxy, methylthio, cyclopentyl or cyclohexyl.

In a related embodiment, PDE7 inhibitors useful in the methods of the invention include the following compounds, wherein X is S;
X is S, R1 is H;
X is S, R1 is F or Cl;
X is S, R2 is H;
X is S, R2 is F or Cl;
X is S, R1 is H, R2 is F or Cl;
X is S, R1 is F or Cl, R2 is H;
X is S; A1 is H or A, A is alkyl having 1, 2, 3 or 4 carbon atoms;
X is S, R1 and R2, independently of one another, each denote A1 or Hal, A1 is H or A, A is alkyl having 1, 2, 3 or 4 carbon atoms, Hal is F or Cl;

and their physiologically acceptable salts and solvates.

In another related embodiment, PDE7 inhibitors useful in the methods of the invention include the following compounds:

10-Chloro-3-imidazol-1-yl-2,3-dihydro-1H-pyrido[3,2,1-kl]phenothiazine, 4-chloro-3-imidazol-1-yl-2,3-dihydro-1H-pyrido[3,2,1-kl]phenothiazine, 10-methoxy-3-imidazol-1-yl-2,3-dihydro-1H-pyrido[3,2,1-kl]phenothiazine, 10-propoxy-3-imidazol-1-yl-2,3-dihydro-1H-pyrido[3,2,1-kl]phenothiazine, 10-methylthio-3-imidazol-1-yl-2,3-dihydro-1H-pyrido[3,2,1-kl]phenothiazine, 10-fluoro-3-imidazol-1-yl-2,3-dihydro-1H-pyrido[3,2,1-kl]phenothiazine, 4,10-dichloro-3-imidazol-1-yl-2,3-dihydro-1H-pyrido[3,2,1-kl]phenothiazine, 10-trifluoromethyl-3-imidazol-1-yl-2,3-dihydro-1H-pyrido[3,2,1-kl]phenothiazine, 4-cyclopentoxy-3-imidazol-1-yl-2,3-dihydro-1H-pyrido[3,2,1-kl]phenothiazine, 10-chloro-3-imidazol-1-yl-2,3-dihydro-1H-7-oxa-11b-azabenzo[de]-anthracene, and 10-chloro-3-imidazol-1-yl-2,3-dihydro-1H-pyrido[3,2,1-kl]phenothiazine 7,7-dioxide.

The preparation of these compounds is described in U.S. Pat. No. 6,884,800 and WO 01/36425.

In another embodiment, PDE7 inhibitors useful in the methods of the invention are selected from those compounds generally or specifically disclosed in U.S. Pat. No. 6,531,498 and WO 01/32175, each expressly incorporated herein by reference in its entirety. In one embodiment, PDE7 inhibitors useful in the methods of the invention have the formula:

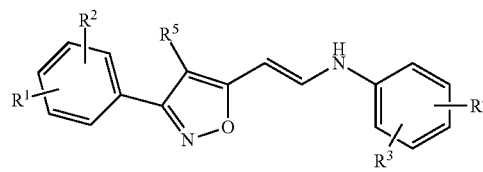

(38)

The substituents of the above compounds are defined as follows:

R1, R2, R3, R4 are each, independently of one another, Hal, OA1, SA1, A, H, COOA1, CN or CONA1A2,
R5 is COOA1, CN or CONA1A2,
A1, A2 are each, independently of one another, H, A, alkenyl, cycloalkyl or alkylenecycloalkyl,
A is alkyl having 1 to 10 C atoms,
Hal is F, Cl, Br or I,
and their physiologically acceptable salts and/or solvates.

In regard to the above compounds, A is alkyl having 1-10 C atoms and has 1, 2, 3, 4, 5, 6, 7, 8, 9 or 10 C atoms and is preferably methyl, ethyl or propyl, also preferably isopropyl, butyl, isobutyl, sec-butyl or tert-butyl, but is also n-pentyl, neopentyl, isopentyl or hexyl. It is also possible for 1-7 H atoms in the radicals to be replaced by F and/or Cl. A is therefore also, for example, trifluoromethyl or pentafluoroethyl.

Cycloalkyl has 3-9 C atoms and is preferably, for example, cyclopentyl or cyclohexyl. Alkenyl has 2-10 C atoms, is linear or branched and is preferably vinyl, propenyl or butenyl.

Alkylenecycloalkyl has 4-10 C atoms and is, for example methylenecyclopentyl, ethylenecyclopentyl, methylenecyclohexyl or ethylenecyclohexyl.

In a related embodiment, PDE7 inhibitors useful in the methods of the invention include the compounds wherein
R1 is H;
R1 and R2 are H;
R1 is H and R2 is F or Cl;
R1, R2 are each, independently of one another, H or Hal;
R1, R2 are each, independently of one another, H or Hal, A1, A2 are each, independently of one another, H or A;
A1, A2 are each, independently of one another, H or A;
R1, R2 are each, independently of one another, H or Hal, A1, A2 are each, independently of one another, H or A, A is alkyl having 1, 2, 3 or 4 C atoms, Hal is F or Cl.

In another related embodiment, PDE7 inhibitors useful in the methods of the invention include the compounds:
5-[2-(2-Fluoro-4-hydroxyphenylamino)vinyl]-4-cyano-3-phenylisoxazole,
5-[2-(2,4-Difluorophenylamino)vinyl]-4-cyano-3-phenylisoxazole, 5-[2-(3-Methylthiophenylamino)vinyl]-4-cyano-3-phenylisoxazole,
5-[2-(2,4-Dimethoxyphenylamino)vinyl]-4-cyano-3-(2-chlorophenyl)isoxazole,
5-(2-Amino-2-phenylvinyl)-4-methylaminocarbonyl-3-phenylisoxazole,
5-(2-Phenylaminovinyl)-4-methoxycarbonyl-3-phenylisoxazole,
5-[2-(4-Carboxyphenylamino)vinyl]-4-cyano-3-phenylisoxazole,
5-[2-(4-Carboxyphenylamino)vinyl]-4-methoxycarbonyl-3-phenylisoxazole,
5-[2-(5-Chloro-2-hydroxyphenylamino)vinyl]-4-cyano-3-phenylisoxazole,
5-[2-(3,4-Dimethylphenylamino)vinyl]-4-cyano-3-(2-chlorophenyl)isoxazole,
5-[2-(4-Chlorophenylamino)vinyl]-4-cyano-3-(2-chlorophenyl)isoxazole,
5-(2-Phenylaminovinyl)-4-cyano-3-(2-chlorophenyl)isoxazole,
5-[2-(4-Methoxyphenylamino)vinyl]-4-cyano-3-(2-chlorophenyl)isoxazole,
5-[2-(4-Carboxyphenylamino)vinyl]-4-cyano-3-(2-chlorophenyl)isoxazole,
5-[2-(2-Fluoro-4-hydroxyphenylamino)vinyl]-4-cyano-3-(2-chlorophenyl)isoxazole,
5-[2-(4-Fluorophenylamino)vinyl]-4-cyano-3-(2-chlorophenyl)isoxazole,
5-[2-(3,5-Dichlorophenylamino)vinyl]-4-cyano-3-(2-chlorophenyl)isoxazole,
5-[2-(3-Chlorophenylamino)vinyl]-4-cyano-3-(2-chlorophenyl)isoxazole,
5-(2-Phenylaminovinyl)-4-cyano-3-(2,6-dichlorophenyl)isoxazole,
5-[2-(4-Chlorophenylamino)vinyl]-4-cyano-3-(2,6-dichlorophenyl)isoxazole,
5-(2-Phenylaminovinyl)-4-methoxycarbonyl-3-(2,6-dichlorophenyl)isoxazole,
5-[2-(4-Chlorophenylamino)vinyl]-4-methoxycarbonyl-3-(2,6-dichlorophenyl)isoxazole,
5-[2-(4-Carboxyphenylamino)vinyl]-4-methoxycarbonyl-3-(2,6-dichlorophenyl)isoxazole,
5-[2-(2,4-Difluorophenylamino)vinyl]-4-cyano-3-(2,6-dichlorophenyl)isoxazole,
5-[2-(2,4-Dichlorophenylamino)vinyl]-4-cyano-3-(2,6-dichlorophenyl)isoxazole,
5-[2-(4-Carboxyphenylamino)vinyl]-4-cyano-3-(2,6-dichlorophenyl)isoxazole,
5-[2-(3,5-Dichlorophenylamino)vinyl]-4-cyano-3-(2,6-dichlorophenyl)isoxazole,
5-[2-(4-Methoxyphenylamino)vinyl]-4-cyano-3-(2,6-dichlorophenyl)isoxazole,
5-[2-(2,4-Dimethoxyphenylamino)vinyl]-4-cyano-3-(2,6-dichlorophenyl)isoxazole,
5-[2-(2-Phenylphenylamino)vinyl]-4-cyano-3-(2,6-dichlorophenyl)isoxazole,
5-[2-(4-Methylphenylamino)vinyl]-4-cyano-3-(2,6-dichlorophenyl)isoxazole,
5-(2-Phenylaminovinyl)-4-cyano-3-(2-chloro-6-fluorophenyl)isoxazole,
5-[2-(4-Carboxyphenylamino)vinyl]-4-cyano-3-(2-chloro-6-fluorophenyl)isoxazole,
5-[2-(4-Chlorophenylamino)vinyl]-4-cyano-3-(2-chloro-6-fluorophenyl)isoxazole,
5-[2-(3-Methoxyphenylamino)vinyl]-4-cyano-3-(2-chloro-6-fluorophenyl)isoxazole,
5-[2-(4-Chlorophenylamino)vinyl]-4-methoxycarbonyl-3-(2-chloro-6-fluorophenyl)isoxazole,
5-(2-Phenylaminovinyl)-4-methoxycarbonyl-3-(2-chloro-6-fluorophenyl)isoxazole,
5-[2-(2,4-Dichlorophenylamino)vinyl]-4-methoxycarbonyl-3-(2-chloro-6-fluorophenyl)isoxazole,
5-(2-Phenylaminovinyl)-4-cyano-3-phenylisoxazole,
5-[2-(3-Trifluoromethoxyphenylamino)vinyl]-4-cyano-3-phenylisoxazole,
5-[2-(4-Methoxyphenylamino)vinyl]-4-cyano-3-phenylisoxazole,
5-[2-(4-Methoxyphenylamino)vinyl]-4-methoxycarbonyl-3-(2-chloro-6-fluorophenyl)isoxazole,
5-[2-(3-Methylthiophenylamino)vinyl]-4-cyano-3-phenylisoxazole,
5-[2-(2,4-Difluorophenylamino)vinyl]-4-cyano-3-phenylisoxazole,
5-[2-(2-Fluoro-4-hydroxyphenylamino)vinyl]-4-cyano-3-phenylisoxazole.

The preparation of these compounds is described in U.S. Pat. No. 6,531,498 and WO 01/32175.

In another embodiment, PDE7 inhibitors useful in the methods of the invention are selected from those compounds generally or specifically disclosed in U.S. Pat. No. 7,491,742 and WO 2001/29049, each expressly incorporated by reference in its entirety. In one embodiment, PDE7 inhibitors useful in the methods of the invention have the formula:

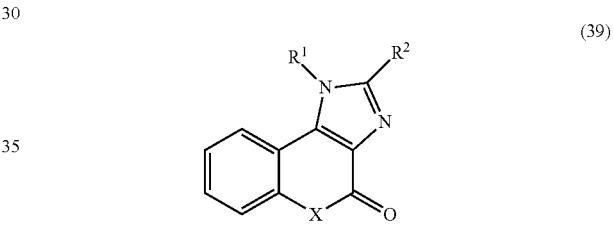

(39)

The substituents of the above compounds are defined as follows:

R1 is H, A, benzyl, indan-5-yl, 1,2,3,4-tetrahydronaphthalen-5-yl, dibenzothien-2-yl, or phenyl which is unsubstituted or mono-, di- or trisubstituted by Hal, A, A-CO—NH, benzyloxy, alkoxy, COOH or COOA, R2 is H or A, X is O or S, Hal is F, Cl, Br or I, A is alkyl with 1 to 6 C atoms, and the physiologically acceptable salts and/or solvates thereof.

In regard to the above compounds, A is alkyl with 1-6 C atoms and has 1, 2, 3, 4, 5 or 6 C atoms and is preferably methyl, ethyl or propyl, also preferably isopropyl, butyl, isobutyl, sec-butyl or tert-butyl, but also n-pentyl, neopentyl, isopentyl or hexyl. A is also cycloalkyl such as, for example, cyclohexyl. Alkoxy is preferably methoxy, ethoxy, propoxy or butoxy. Hal is preferably F or Cl. A-CO—NH is preferably acetamido.

In a related embodiment, PDE7 inhibitors useful in the methods of the invention are selected from the following compounds:

1-Phenyl-[1]benzopyrano[3,4-d]imidazol-4-(1H)-one,
1-Benzyl-[1]benzopyrano[3,4-d]imidazol-4-(1H)-one,
1-Cyclohexyl-[1]benzopyrano[3,4-d]imidazol-4-(1H)-one,
1-Cyclopentyl-[1]benzopyrano[3,4-d]imidazol-4-(1H)-one,
1-Butyl-[1]benzopyrano[3,4-d]imidazol-4-(1H)-one, 1-Isopropyl-[1]benzopyrano[3,4-d]imidazol-4-(1H)-one, 1-Propyl-[1]benzopyrano[3,4-d]imidazol-4-(1H)-one, 1-Ethyl-[1]benzopyrano[3,4-d]imidazol-4-(1H)-one, 1-Methyl-[1]benzopyrano[3,4-d]imidazol-4-(1H)-one, [1]Benzopyrano

[3,4-d]imidazol-4-(1H)-one, 2-Methyl-[1]benzopyrano[3,4-d]imidazol-4-(1H)-one, 1-Phenyl-[1]benzothiopyrano[3,4-d]imidazol-4-(1H)-one, 1-Benzyl-[1]benzothiopyrano[3,4-d]imidazol-4-(1H)-one, 1-Cyclohexyl-[1]benzothiopyrano[3,4-d]imidazol-4-(1H)-one, 1-Cyclopentyl-[1]benzothiopyrano[3,4-d]imidazol-4-(1H)-one, 1-Butyl-[1]benzothiopyrano[3,4-d]imidazol-4-(1H)-one, 1-Isopropyl-[1]benzothiopyrano[3,4-d]imidazol-4-(1H)-one, 1-Propyl-[1]benzothiopyrano[3,4-d]imidazol-4-(1H)-one, 1-Ethyl-[1]benzothiopyrano[3,4-d]imidazol-4-(1H)-one, 1-Methyl-[1]benzothiopyrano[3,4-d]imidazol-4-(1H)-one, [1]Benzothiopyrano[3,4-d]imidazol-4-(1H)-one, 2-Methyl-[1]benzothiopyrano[3,4-d]imidazol-4-(1H)-one, 1-(2-Chlorophenyl-[1]benzopyrano[3,4-d]imidazol-4-(1H)-one, 1-(4-Methyl-phenyl)-[1]benzopyrano[3,4-d]imidazol-4-(1H)-one, 1-(4-Fluorophenyl)-[1]benzopyrano[3,4-d]imidazol-4-(1H)-one, 1-(2,4-Dimethyl-phenyl)-[1]benzopyrano[3,4-d]imidazol-4-(1H)-one, 1-(3-Chlorophenyl)-[1]benzopyrano[3,4-d]imidazol-4-(1H)-one, 1-(2,4-Dichlorophenyl)-[1]benzopyrano[3,4-d]imidazol-4-(1H)-one, 1-(2,5-Dichlorophenyl)-[1]benzopyrano[3,4-d]imidazol-4-(1H)-one, 1-(4-Acetamido-phenyl)-[1]benzopyrano[3,4-d]imidazol-4-(1H)-one, 1-(2-Fluorophenyl)-[1]benzopyrano[3,4-d]imidazol-4-(1H)-one, 1-(3-Fluorophenyl)-[1]benzopyrano[3,4-d]imidazol-4-(1H)-one, 1-(2-Benzyloxy-phenyl)-[1]benzopyrano[3,4-d]imidazol-4-(1H)-one, 1-(2,6-Dimethyl-phenyl)-[1]benzopyrano[3,4-d]imidazol-4-(1H)-one, 1-(Indan-5-yl)-[1]benzopyrano[3,4-d]imidazol-4-(1H)-one, 1-(2-Methoxy-phenyl)-[1]benzopyrano[3,4-d]imidazol-4-(1H)-one, 1-(2,3-Dimethyl-phenyl)-[1]benzopyrano[3,4-d]imidazol-(1H)-4-one, 1-(2,3-Dichlorophenyl)-[1]benzopyrano[3,4-d]imidazol-4-(1H)-one, 1-(3-Chloro-4-methyl-phenyl)-[1]benzopyrano[3,4-d]imidazol-4-(1H)-one, 1-(2,5-Dimethyl-phenyl)-[1]benzopyrano[3,4-d]imidazol-4-(1H)-one, 1-(4-Chlorophenyl)-[1]benzopyrano[3,4-d]imidazol-4-(1H)-one, 1-(1,2,3,4-Tetrahydronaphthalen-5-yl)-[1]benzopyrano-[3,4-d]imidazol-4-(1-H)-one, 1-(Dibenzothien-2-yl)-[1]benzopyrano[3,4-d]imidazol-4-(1H)-one, 1-(3-Methoxy-phenyl)-[1]benzopyrano[3,4-d]imidazol-4-(1H)-one, 1-(4-Carboxy-2-methyl-phenyl)-[1]benzopyrano[3,4-d]imidazol-4-(1H)-one, and their physiologically acceptable salts and/or solvates thereof.

In another embodiment, PDE7 inhibitors useful in the methods of the invention are selected from those compounds generally or specifically disclosed in U.S. Pat. No. 6,737,436 and WO 01/32618, expressly incorporated herein by reference in its entirety. In one embodiment, PDE7 inhibitors useful in the methods of the invention have the formula:

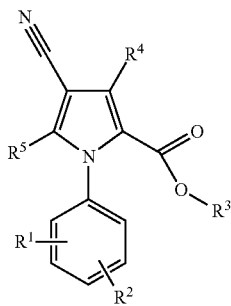

(40)

The substituents for the above compounds are defined as follows:

R1 and R2, independently of one another, each denote H, A, OA, SA or Hal,

R3 denotes H or A,

R4 denotes A or NH2,

R5 denotes H, NH2, NHA or NA2,

A denotes alkyl having 1 to 10 carbon atoms, alkenyl, cycloalkyl or alkylenecycloalkyl, Hal denotes F, Cl, Br or I, and their physiologically acceptable salts and/or solvates.

In regard to the above compounds, A denotes alkyl having 1-10 carbon atoms and has 1, 2, 3, 4, 5, 6, 7, 8, 9 or 10 carbon atoms and preferably denotes methyl, ethyl or propyl, furthermore preferably isopropyl, butyl, isobutyl, sec-butyl or tert-butyl, but also n-pentyl, neopentyl, isopentyl or hexyl. In these radicals, 1-7 H atoms may also be replaced by F and/or Cl. A therefore also denotes, for example, trifluoromethyl or pentafluoroethyl.

A also denotes cycloalkyl having 3-8 carbon atoms and preferably denotes, for example, cyclopentyl or cyclohexyl.

A also denotes alkenyl. Alkenyl has 2-10 carbon atoms, is linear or branched and denotes, for example, vinyl, propenyl or butenyl. A furthermore denotes alkylenecycloalkyl. Alkylenecycloalkyl has 4-10 carbon atoms and preferably denotes, for example, methylenecyclopentyl, ethylenecyclopentyl, methylenecyclohexyl or ethylenecyclohexyl.

R1 and R2 preferably each denote, independently of one another, H, methyl, ethyl, propyl, butyl, isopropyl, tert-butyl, methoxy, ethoxy, propoxy, isopropoxy, butoxy, S-methyl, S-ethyl, F or Cl.

R3 preferably denotes H, methyl or ethyl.

R4 preferably denotes methyl, ethyl, propyl, butyl or NH2.

R5 preferably denotes H, amino, methylamino, ethylamino, dimethylamino or diethylamino.

In a related embodiment, PDE7 inhibitors useful in the methods of the invention include compounds of the above formula wherein R1 and R2 are not both H and wherein when one of R1 or R2 is H, the other cannot be CH3, OCH3 or Cl.

In another related embodiment, PDE7 inhibitors useful in the methods of the invention include compounds wherein R1, R2, R3 and R5 are H and R4 is methyl;

R1 is 4-Cl, R2 is H, R3 is ethyl, R4 is amino and R5 is H;

R1 and R2 are H, R3 is ethyl, R4 is methyl and R5 is amino;

R1 and R2 are H, R3 is ethyl, R4 is amino and R5 is H;

R1 and R2 are H, R3 is ethyl, R4 is H and R5 is amino;

R1 is 3-Cl, R2 is 4-O-methyl, R3 is ethyl, R4 is amino and R5 is H;

R1 is 3-Cl, R2 is 4-O-methyl, R3 is ethyl, R4 is methyl and R5 is amino;

R1 is 4-OCF3, R2 is H, R3 is ethyl, R4 is amino and R5 is H;

R1 is 3-Cl, R2 is 4-O-methyl, R3 is ethyl, R4 is amino and R5 is H;

R1 is 3-Cl, R2 is 4-O-methyl, R3 is ethyl, R4 is methyl and R5 is amino;

R1 is 4-OCF$_3$, R2 is H, R3 is ethyl, and R4 is amino and R5 is H.

In another embodiment, PDE7 inhibitors useful in the methods of the invention are selected from those compounds generally or specifically disclosed in U.S. Pat. No. 6,613,778 and WO 01/34601, expressly incorporated herein by reference in its entirety. In one embodiment, PDE7 inhibitors useful in the methods of the invention have the formula:

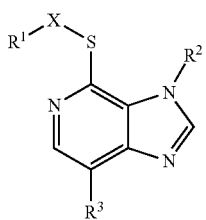

(41)

The substituents for the above compounds are defined as follows:

R1 denotes CONR4R5,
R2 denotes H or A,
R4 and R5, independently of one another, each denote H or A1,
R3 denotes Hal,
Hal denotes F, Cl, Br or I,
A denotes alkyl having 1-4 carbon atoms,
A1 denotes alkyl having 1-10 carbon atoms,
X denotes alkylene having 1-4 carbon atoms, in which an ethylene group may also be replaced by a double or triple bond,
and their physiologically acceptable salts and/or solvates.

In regard to the above compounds, A denotes alkyl having 1-4 carbon atoms and has 1, 2, 3 or 4 carbon atoms and preferably denotes methyl, ethyl or propyl, furthermore preferably isopropyl, butyl, isobutyl, sec-butyl or tert-butyl. 1-7 H atoms in the radicals may also be replaced by F and/or Cl. A therefore also denotes, for example, trifluoromethyl or pentafluoroethyl.

A1 denotes alkyl having 1-10 carbon atoms and has 1, 2, 3, 4, 5, 6, 7, 8, 9 or 10 carbon atoms and preferably denotes methyl, ethyl or propyl, furthermore preferably isopropyl, butyl, isobutyl, sec-butyl or tert-butyl, but also n-pentyl, neopentyl, isopentyl or hexyl. 1-7 H atoms in the radicals may also be replaced by F and/or Cl. A1 therefore also denotes, for example, trifluoromethyl or pentafluoroethyl.

X denotes alkylene having 1-4 carbon atoms, preferably methylene, ethylene, propylene or butylene, in which one ethylene group may also be replaced by a double or triple bond. X therefore also denotes, for example, —CH$_2$—CH=CH—H2- or —C≡C—.

In a related embodiment, PDE7 inhibitors useful in the methods of the invention include the following compounds:
2-(3-Butyl-7-chloro-3H-imidazo[4,5-c]pyridin-4-ylsulfanyl)-N,N-dimethylacetamide

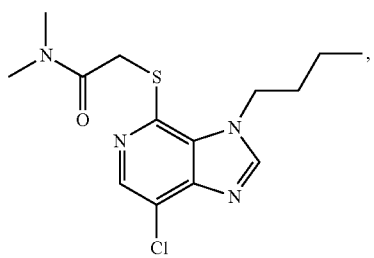 [SMILES: CCCCn1cnc2c(Cl)cnc(SCC(=O)N(C)C)c21]

2-(3-butyl-7-chloro-3H-imidazo[4,5-c]pyridin-4-ylsulfanyl) acetamide,
2-(3-butyl-7-chloro-3H-imidazo[4,5-c]pyridin-4-ylsulfanyl) propionamide,
2-(3-butyl-7-chloro-3H-imidazo[4,5-c]pyridin-4-ylsulfanyl) butyramide,
2-(3-butyl-7-chloro-3H-imidazo[4,5-c]pyridin-4-ylsulfanyl)-N-hexylacetamide,
2-(3-butyl-7-chloro-3H-imidazo[4,5-c]pyridin-4-ylsulfanyl)-N-octylacetamide,
4-(3-butyl-7-chloro-3H-imidazo[4,5-c]pyridin-4-ylsulfanyl)-but-2-enoic acid dimethylamide.

In another related embodiment, PDE7 inhibitors useful in the methods of the invention include the following compounds, wherein
R3 is Cl;
R3 is Cl, and X is alkylene having 1-4 carbon atoms;
R3 is Cl, X is alkylene having 1, 2, 3 or 4 carbon atoms, and A1 is alkyl having 1, 2, 3 or 4 carbon atoms.

The preparation of these compounds is described in U.S. Pat. No. 6,613,778 and WO 01/34601.

In another embodiment, PDE7 inhibitors useful in the methods of the invention are selected from those compounds generally or specifically disclosed in WO 2008/113881 and ES P 200700762, each expressly incorporated herein by reference in its entirety. In one embodiment, PDE7 inhibitors useful in the methods of the invention have the formula:

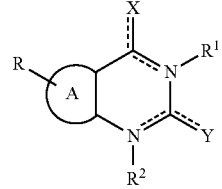

(42)

The substituents for the above compounds are defined as follows:

A is fused carbocyclo or heterocyclo of 5, 6 or 7 members and may be saturated or unsaturated; the dashed lines represent, independently, a single or double bond; X and Y are chosen independently from the group consisting of alkyl, hydrogen, =O, =S, —N (alkyl), —N(aryl), aryl, O-alkyl, O-aryl, alkyl-S and —S-aryl; and R1 and R2 are chosen independently from the group consisting of hydrogen, halogen, alkyl, haloalkyl, aryl, cycloalkyl, (Z)$_n$-aryl, heteroaryl, —OR3; —C(O)OR3, —(Z)$_n$—C(O)OR3 and —S(O), or a pharmaceutically acceptable salt, derivative, prodrug, solvate or stereoisomer of the same.

Exception: when A is unsubstituted benzene, X=O, Y=S, when A is unsubstituted benzene, X=O, Y=O, when A is unsubstituted benzene, X=O, Y=S-Me, when A is unsubstituted thiophene, X=O, Y=S, and when A is unsubstituted benzothiophene, X=O, Y=S.

In related embodiments, the above compounds constitute a useful pharmaceutical composition that includes a therapeutically effective amount of the above compounds, or mixtures of the same, a salt, derivative, prodrug, solvate or pharmaceutically acceptable stereoisomer of the same along with a carrier, adjuvant or pharmaceutically acceptable vehicle, for IV administration to patient.

In other related embodiments, the PDE7 inhibitors useful in the methods of the present invention include the following compound: 4-oxo-2-dioxo-1,2,3,4-tetrahydroquinazoline, and derivatives thereof selected from the following group:

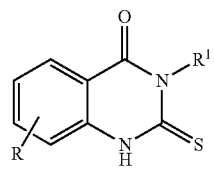

6-Bromo-2,3,4-tetrahydroquinazoline, 6-Bromo-(2,6-difluorophenyl)-4-oxo-2-dioxo-1,2,3,4-tetrahydroquinazoline, 6-Bromo-(2,3,4-trifluorophenyl)-4-oxo-2-dioxo-1,2,3,4-tetrahydroquinazoline, 6-Bromo-(2-bromophenyl)-4-oxo-2-dioxo-1,2,3,4-tetrahydroquinazoline, 3-(2,6-Difluorophenyl)-8-methyl-4-oxo-2-dioxo-1,2,3,4-tetrahydroquinazoline, 3-(2,3,4-Trifluorophenyl)-8-methyl-4-oxo-2-dioxo-1,2,3,4-tetrahydroquinazoline, and 3-(2-Bromophenyl)-8-methyl-4-oxo-2-dioxo-1,2,3,4-tetrahydroquinazoline.

In a further related embodiment, the PDE7 inhibitors useful in the methods of the present invention include the following compound: 2-methylthio-4-oxo-3,4-dihydroquinazoline and derivatives thereof selected from the following group:

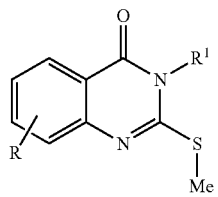

6-Bromo-(2,6-difluorophenyl)-2-methylthio-4-oxo-3,4-dihydroquinazoline, 6-Bromo-(2,3,4-trifluorophenyl)-2-methylthio-4-oxo-3,4-dihydroquinazoline, 6-Bromo-(2-bromophenyl)-2-methylthio-4-oxo-3,4-dihydroquinazoline, 3-Phenyl-8-methyl-2-methylthio-4-oxo-3,4-dihydroquinazoline, 3-(2,6-Difluorophenyl)-8-methyl-2-methylthio-4-oxo-3,4-dihydroquinazoline, 3-(2,3,4-Trifluorophenyl)-8-methyl-2-methylthio-4-oxo-3,4-dihydroquinazoline, and 3-(2-Bromophenyl)-8-methyl-2-methylthio-4-oxo-3,4-dihydroquinazoline.

In another related embodiment, the PDE7 inhibitors useful in the methods of the present invention include the following compound: 2,4-dithioxo-1,2,3,4-tetrahydroquinazoline, and derivatives thereof selected from the following group:

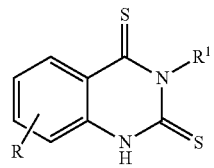

3-Phenyl-2,4-dithioxo-1,2,3,4-tetrahydroquinazoline, 3-(2,6-Difluorophenyl)-2,4-dithioxo-1,2,3,4-tetrahydroquinazoline, and 3-(2,3,4-Trifluorophenyl)-2,4-dithioxo-1,2,3,4-tetrahydroquinazoline.

In another related embodiment, PDE7 inhibitors useful in the methods of the present invention include the following compound: (2-methylthio-4-thioxo-3,4-dihydroquinazoline) and derivatives thereof selected from the following group:

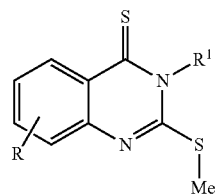

3-Phenyl-2-methylthio-4-thioxo-3,4-dihydroquinazoline, 3-(2,6-Difluorophenyl)-2-methylthio-4-thioxo-3,4-dihydroquinazoline, 3-(2,3,4-Trifluorophenyl)-2-methylthio-4-thioxo-3,4-dihydroquinazoline, and 3-(2-Bromophenyl)-2-methylthio-4-tioxo-3,4-dihydroquinazoline.

The preparation of the above compounds is described in WO 2008/113881.

In a related embodiment, PDE7 inhibitors useful in the methods of the invention are described in ES P 200700762, expressly incorporated by reference herein in its entirety. In one embodiment, PDE7 inhibitors useful in the methods of the invention have the formulas:

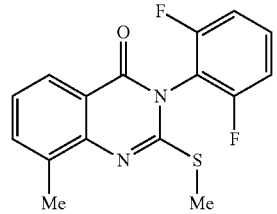

(43A)

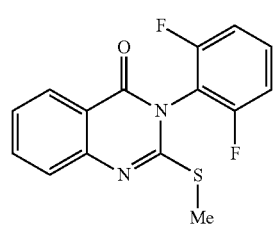

(43B)

In another embodiment, PDE7 inhibitors useful in the methods of the invention are selected from those compounds generally or specifically disclosed in U.S. Pat. No. 7,214,676, and U.S. 2007/0049558, each expressly incorporated herein by reference in its entirety. In one embodiment, PDE7 inhibitors useful in the methods of the invention include the following compounds:

Spiro[cyclohexane-1-4'-(3',4'-dihydro)quinazolin]-2'(1'H)-one, 6'-Methoxyspiro[cyclohexane-1-4'-(3',4'-dihydro)quinazolin]-2'(1'H)-one, Spiro[cycloheptane-1-4'-(3',4'-dihydro)quinazolin]-2'(1'H)-one, 7'-Methoxyspiro[cyclohexane-1-4'-(3',4'-dihydro)quinazolin]-2'(1'H)-one, 6'-Phenylspiro[cycloheptane-1-4'-(3',4'-dihydro)quinazolin]-2'(1'H)-one, 8'-Methoxyspiro[cyclohexane-1-4'-(3',4'-dihydro)quinazolin]-2'(1'H)-one, 8'-Chlorospiro[cyclohexane-1-4'-(3',4'-dihydro)quinazolin]-2'(1'H)-one, 7'-chlorospiro[cyclohexane-1-4'-(3',4'-dihydro)quinazolin]-2'(1'H)-one, 5'-chlorospiro[cyclohexane-1-4'-(3',4'-dihydro)quinazolin]-2'(1'H)-one, 8'-methylspiro[cyclohexane-1-4'-(3',4'-dihydro)quinazolin]-2'(1'H)-one, 6'-chlorospiro[cyclohexane-1-4'-(3',4'-dihydro)quinazolin]-2'(1'H)-one, 8'-bromospiro[cyclohexane-1-4'-(3',4'-dihydro)quinazolin]-2'(1'H)-one, 8'-fluorospiro[cyclohexane-1-4'-(3',4'-dihydro)quinazolin]-2'(1'H)-one, 6'-methylspiro[cyclohexane-1-4'-

(3',4'-dihydro)quinazolin]-2'(1'H)-one, 5',8'-dichlorospiro[cyclohexane-1-4'-(3',4'-dihydro)quinazolin]-2'(1'H)-one, 6',7'-dichlorospiro[cyclohexane-1-4'-(3',4'-dihydro)quinazolin]-2'(1'H)-one, 5',6'-dichlorospiro[cyclohexane-1-4'-(3',4'-dihydro)quinazolin]-2'(1'H)-one, 6'-phenylspiro[cyclohexane-1-4'-(3',4'-dihydro)quinazolin]-2'(1'H)-one, 8'-iodospiro[cyclohexane-1-4'-(3',4'-dihydro)quinazolin]-2'(1'H)-one, 8'-Bromospiro[cyclobutane-1-4'-(3',4'-dihydro)quinazolin]-2'(1'H)-one, 8'-Bromospiro[cycloheptane-1-4'-(3',4'-dihydro)quinazolin]-2'(1'H)-one, 8'-Bromo-4-methylspiro[cyclohexane-1-4'-(3',4'-dihydro)quinazolin]-2'(1'H)-one, 8'-Bromospiro[bicyclo[3,2,1]octane-2-4'-(3',4'-dihydro)quinazolin]-2'(1'H)-one, 6',8'-dichlorospiro[cyclohexane-1-4'-(3',4'-dihydro)quinazolin]-2'(1'H)-one, 8'-chloro-6'-iodospiro[cyclohexane-1-4'-(3',4'-dihydro)quinazolin]-2'(1'H)-one, 8'-chloro-6'-methoxyspiro[cyclohexane-1-4'-(3',4'-dihydro)quinazolin]-2'(1'H)-one, 8'-chloro-6'-phenylspiro[cycloheptane-1-4'-(3',4'-dihydro)quinazolin]-2'(1'H)-one, 8'-chloro-6'-phenylspiro[cyclohexane-1-4'-(3',4'-dihydro)quinazolin]-2'(1'H)-one, 8'-chloro-6'-methylspiro[cyclohexane-1-4'-(3',4'-dihydro)quinazolin]-2'(1'H)-one, 8'-chloro-6'-(3-pyridyl)spiro[cyclohexane-1-4'-(3',4'-dihydro)quinazolin]-2'(1'H)-one, 8'-chloro-6'-(4-pyridyl)spiro[cyclohexane-1-4'-(3',4'-dihydro)quinazolin]-2'(1'H)-one, 6'-(4-carboxyphenyl)-8'-chlorospiro[cyclohexane-1-4'-(3',4'-dihydro)quinazolin]-2'(1'H)-one, 6'-(3-carboxyphenyl)-8'-chlorospiro(cyclohexane-1-4'-(3',4'-dihydro)-quinazolin]-2'(1'H)-one, 8'-chloro-6'-(1H-indol-5yl)spiro[cyclohexane-1-4'-(3',4'-dihydro)quinazolin]-2'(1'H)-one, 8'-chloro-6'-(2-pyridyl)spiro[cyclohexane-1-4'-(3',4'-dihydro)quinazolin]-2'(1'H)-one, 8'-chloro-6'-(3-dimethylamino-prop-1-ynyl)spiro[cyclohexane-1-4'-(3',4'-dihydro)-quinazolin]-2'(1'H)-one, 8'-chloro-6'-(3-methylamino-prop-1-ynyl)spiro[cyclohexane-1-4'-(3',4'-dihydro)quinazolin]-2'(1'H)-one, 8'-chloro-6'-[4-(4-methyl-piperazine-1-carbonyl)phenyl]spiro[cyclohexane-1-4'-(3',4'-dihydro)quinazolin]-2'(1'H)-one, 8'-chloro-6'-[4-(3-N-dimethylamino-propylcarboxamide)phenyl]-spiro-[cyclohexane-1-4'-(3',4'-dihydro)quinazolin]-2'(1'H)-one, 8'-chloro-6'-[4-(2-N-dimethylamino-ethylcarboxamide)phenyl]-spiro-[cyclohexane-1-4'-(3',4'-dihydro)quinazolin]-2'(1'H)-one, 8'-chloro-6'-[3-(3-N-dimethylamino-propylcarboxamide)phenyl]-spiro-[cyclohexane-1-4'-(3',4'-dihydro)quinazolin]-2'(1'H)-one, 8'-chloro-6'-[3-(4-methyl-piperazine-1-carbonyl)-phenyl]spiro-[cyclohexane-1-4'-(3',4'-dihydro)quinazolin]-2'(1'H)-one, 8'-chloro-6'-[3-(2-N-dimethylamino-ethylcarboxamide)phenyl]-spiro-[cyclohexane-1-4'-(3',4'-dihydro)quinazolin]-2'(1'H)-one, 8'-Chlorospiro[cyclohexane-1-4'-(3',4'-dihydro)quinazolin]-2'(1'H)-thione, 8'-Chloro-2'-cyanoiminospiro[cyclohexane-1-4'-(3',4'-dihydro)quinazoline, 8'-chloro-6'-[4-(4-pyrimidin-2-yl-piperazine-1-carbonyl)phenyl]spiro[-cyclohexane-1-4'-(3',4'-dihydro)quinazolin]-2'(1'H)-one, 8'-chloro-6'-[4-(4-(2-morpholin-4-yl-ethyl)-piperazine-1-carbonyl)-phenyl]spiro[-cyclohexane-1-4'-(3',4'-dihydro)quinazolin]-2'(1'H)-one, 8'-chloro-6'-[4-(4-(2-morpholin-4-yl-2-oxo-ethyl)-piperazine-1-carbonyl)-phenyl]spiro[-cyclohexane-1-4'-(3',4'-dihydro)quinazolin]-2'(1'H)-one, 8'-chloro-6'-[4-(4-(2-hydroxy-ethoxy)-ethyl)-piperazine-1-carbonyl)-phenyl]spiro[-cyclohexane-1-4'-(3',4'-dihydro)quinazolin]-2'(1'H)-one, Spiro[cyclohexane-1-9'-(8',9'-dihydro)-pyrazolo[4',3'-f]quinazolin]-7'(6'H)-one, 8'-Chloro-5'-methoxyspiro[cyclohexane-1-4'-(3',4'-dihydro)quinazolin]-2'(1'H)-one, 5',8'-difluorospiro[cyclohexane-1-4'-(3',4'-dihydro)quinazolin]-2'(1'H)-one, 8'-Chloro-5'-methylspiro[cyclohexane-1-4'-(3',4'-dihydro)quinazolin]-2'(1'H)-one, 8'-Chloro-6'-(morpholin-4-yl)methylspiro[cyclohexane-1-4'-(3',4'-dihydro)quinazolin]-2'(1'H)-one, 8'-Chloro-5'-hydroxyspiro[cyclohexane-1-4'-(3',4'-dihydro)quinazolin]-2'(1'H)-one, 8'-Chloro-5'-hydroxy-6'-iodo-spiro[cyclohexane-1-4'-(3',4'-dihydro)quinazolin]-2'(1'H)-one, 8'-Chloro-6'-iodo-5'-methoxy-spiro[cyclohexane-1-4'-(3',4'-dihydro)quinazolin]-2'(1'H)-one, 8'-Chloro-6'-cyano-5'-methoxy-spiro[cyclohexane-1-4'-(3',4'-dihydro)quinazolin]-2'(1'H)-one, 8'-Chloro-5'-[2-(4-morpholino)ethoxy]spiro[cyclohexane-1-4'-(3',4'-dihydro)quinazolin]-2'(1'H)-one, 8'-Chloro-5'-[2-dimethylaminoethoxy]spiro[cyclohexane-1-4'-(3',4'-dihydro)quinazolin]-2'(1'H)-one, 8'-Chloro-5'-(2-aminoethoxy)-spiro[cyclohexane-1-4'-(3',4'-dihydro)quinazolin]-2'(1'H)-one, 8'-Chloro-5'-[2-(methylamino)ethoxy]-spiro[cyclohexane-1-4'-(3',4'-dihydro)quinazolin]-2'(1'H)-one, 8'-Chloro-5'-[2-(2-aminoethoxy)ethoxy]spiro[cyclohexane-1-4'-(3',4'-dihydro)quinazolin]-2'(1'H)-one, 8'-Chloro-5'-[3-dimethylaminopropoxy]spiro[cyclohexane-1-4'-(3',4'-dihydro)quinazolin]-2'(1'H)-one, 8'-Chloro-5'-ethoxycarbonylmethoxyspiro[cyclohexane-1-4'-(3',4'-dihydro)quinazolin]-2'(1'H)-one, 5'-carboxymethoxy-8'-chloro-spiro[cyclohexane-1-4'-(3',4'-dihydro)quinazolin]-2'(1'H)-one, 5'-carboxypropoxy-8'-chloro-spiro[cyclohexane-1-4'-(3',4'-dihydro)quinazolin]-2'(1'H)-one, 8'-chloro-5'-(3-sulphopropoxy)-spiro[cyclohexane-1-4'-(3',4'-dihydro)quinazolin]-2'(1'H)-one, 8'-Chloro-5'-[2-(tetrahydro-pyran-2-yloxy)-ethoxy]-spiro[cyclohexane-1-4'-(3',4'-dihydro)quinazolin]-2'(1'H)-one, 8'-Chloro-5'-(2-hydroxy-ethoxy)-Spiro[cyclohexane-1-4'-(3',4'-dihydro)quinazolin]-2'(1'H)-one, 8'-Chloro-5'-(5-ethoxycarbonyl-furan-2-ylmethoxy)-spiro[cyclohexane-1-4'-(3',4'-dihydro)quinazolin]-2'(1'H)-one, 8'-Chloro-5'-(5-carboxy-furan-2-ylmethoxy)-spiro[cyclohexane-1-4'-(3',4'-dihydro)quinazolin]-2'(1'H)-one, 8'-Chloro-5'-cyanomethoxyspiro[cyclohexane-1-4'-(3',4'-dihydro)quinazolin]-2'(1'H)-one, 8'-Chloro-5'-(1H-tetrazol-5-ylmethoxy)-spiro[cyclohexane-1-4'-(3',4'-dihydro)quinazolin]-2'(1'H)-one, 8'-Chloro-5'-(5-hydroxy-[1,2,4]oxadiazol-3-ylmethoxy)-spiro[cyclohexane-1-4'-(3',4'-dihydro)quinazolin]-2'(1'H)-one, 8'-Chloro-6'-iodo-5'-[2-dimethylamino-ethoxy]spiro[cyclohexane-1-4'-(3',4'-dihydro)quinazolin]-2'(1'H)-one, 6'-(4-carboxyphenyl)-8'-chloro-5'-methoxyspiro[cyclohexane-1-4'-(3',4'-dihydro)quinazolin]-2'(1'H)-one, 6'-(3-carboxyphenyl)-8'-chloro-5'-methoxyspiro[cyclohexane-1-4'-(3',4'-dihydro)quinazolin]-2'(1'H)-one, 8'-chloro-6'-[2-(4-methyl-piperazine-1-carbonyl)phenyl]spiro[cyclohexane-1-4'-(3',4'-dihydro)quinazolin]-2'(1'H)-one, 8'-chloro-6'-[2-methyl-4-(4-methyl-piperazine-1-carbonyl)phenyl]spiro[cyclohexane-1-4'-(3',4'-dihydro)quinazolin]-2'(1'H)-one, 8'-chloro-6'-[4-(piperazine-1-carbonyl)phenyl]spiro[cyclohexane-1-4'-(3',4'-dihydro)quinazolin]-2'(1'H)-one, 8'-chloro-6'-[4-carbamoyl-phenyl]spiro[cyclohexane-1-4'-(3',4'-dihydro)quinazolin]-2'(1'H)-one, 8'-chloro-6'-[4-((1-methyl-piperidin-4-yl)-piperazine-1-carbonyl)phenyl]spiro[cyclohexane-1-4'-(3',4'-dihydro)quinazolin]-2'(1'H)-one, 8'-chloro-5'-methoxy-6-[4-(4-methyl-piperazine-1-carbonyl)phenyl]spiro[cyclohexane-1-4'-(3',4'-dihydro)quinazolin]-2'(1'H)-one, 8'-Trifluoromethylspiro[cyclohexane-1-4'-(3',4'-dihydro)quinazolin]-2'(1'H)-one, 8'-Chloro-6'-cyanomethylspiro[cyclohexane-1-4'-(3',4'-dihydro)quinazolin]-2'(1'H)-one, 8'-Chloro-5'-(3-dimethylamino-2-hydroxy-propoxy)-spiro[cyclohexane-1-4'-(3',4'-dihydro)quinazolin]-2'(1'H)-one, 8'-Chloro-5'-(3-methylamino-2-hydroxy-propoxy)-spiro[cyclohexane-1-4'-(3',4'-dihydro)quinazolin]-2'(1'H)-one, 8'-Chloro-5'-[2-(ethoxycarbonylmethyl-amino)-ethoxy]-spiro[cyclohexane-1-4'-(3',4'-dihydro)quinazolin]-2'(1'H)-one, 8'-Chloro-5'-[2-(carboxymethyl-amino)-ethoxy]-spiro[cyclohexane-1-4'-(3', 4'-dihydro)quinazolin]-2'(1'H)-one hydrochloride, 8'-Chloro-5'-(2-methanesulfonylamino-2-oxo-ethoxy)-spiro[cyclohexane-1-4'-(3',4'-dihydro)quinazolin]-2'(1'H)-one, 8'-Chloro-5'-(2-[(5-methyl-isoxazol-3-ylmethyl)-amino]ethoxy)-spiro[cyclohexane-1-4'-(3',4'-dihydro)quinazolin]-2'(1'H)-one.

Preparation of these compounds is described in U.S. Pat. No. 7,087,614, U.S. 2007/0049558 and WO 2002/074754.

In another embodiment, PDE7 inhibitors and dual PDE4/7 inhibitors useful in the methods of the invention are selected from those compounds generally or specifically disclosed in U.S. Pat. No. 7,087,614, US 2003/0162802 and WO 2002/102313, each expressly incorporated herein by reference in its entirety. In one embodiment, PDE7 inhibitors useful in the methods of the invention have the formula:

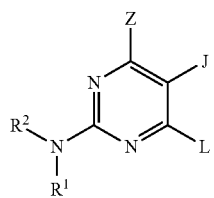

(16)

The PDE7 inhibitors useful in the methods of the invention include enantiomers, diastereomers, tautomers, and pharmaceutically acceptable salts, prodrugs, and solvates of the compounds of the above formula.

The substituents for the above compounds are defined as follows:

R1 is H or alkyl;

R2 is (a) heteroaryl, or heterocyclo, either of which may be optionally substituted with one to three groups T1, T2, T3; (b) aryl substituted with one to three groups T1, T2, T3 provided that at least one of T1, T2, T3 is other than H; or (c) aryl fused to a heteroaryl or heterocyclo ring wherein the combined ring system may be optionally substituted with one to three groups T1, T2, T3;

Z is (a) —OR4, —C(O)R4, —C(O)OR4, —SR4, —NR3R4, —C(O)NR3R4, —NR3SO2R4c, halogen, nitro, haloalkyl; or (b) alkyl, aryl, heteroaryl, heterocyclo, or cycloalkyl any of which may be optionally substituted with one to three groups T1a, T2a T3a;

J is (a) hydrogen, halo, —OR4a, or (b) alkyl, alkenyl, or alkynyl any of which may be optionally substituted with one to three groups T1b, T2b or T3b;

L is (a) hydrogen, —OR4b, —C(O)R4b, —C(O)OR4b, —SR4b, —NR5R6, —C(O)NR5R6, —NR5SO2R4d, halogen, haloalkyl, nitro, or (b) alkyl, aryl, heteroaryl, heterocyclo, or cycloalkyl any of which may be optionally substituted with one to three groups T1c, T2c or T3c;

R3 and R4 are independently H, alkyl, alkenyl, aryl, (aryl)alkyl, heteroaryl, (heteroaryl)alkyl, cycloalkyl, (cycloalkyl)alkyl, heterocylo or (heterocyclo)alkyl any of which may be optionally substituted with one to three groups T1a, T2a or T3a;

or R3 and R4 together with the nitrogen atom to which they are attached may combine to form a 4 to 8 membered heterocyclo ring optionally substituted with one to three groups T1a, T2a or T3a;

R4a is hydrogen, alkyl, alkenyl, aryl, heteroaryl, (aryl)alkyl, (heteroaryl)alkyl, heterocylo, (heterocyclo)alkyl, cycloalkyl or (cycloalkyl)alkyl any of which may be optionally substituted with one to three groups T1b, T2b or T3b;

R4b is hydrogen, alkyl, alkenyl, aryl, heteroaryl, (aryl)alkyl, (heteroaryl)alkyl, heterocylo, (heterocyclo)alkyl, cycloalkyl or (cycloalkyl)alkyl any of which may be optionally substituted with one to three groups T1c, T2c or T3c;

R4c and R4d are independently alkyl, alkenyl, aryl, (aryl)alkyl, heteroaryl, (heteroaryl)alkyl, cycloalkyl, (cycloalkyl)alkyl, heterocylo or (heterocyclo)alkyl any of which may be optionally substituted with one to three groups T1a, T2a or T3a;

R5 and R6 are independently H, alkyl, alkenyl, aryl, (aryl)alkyl, heteroaryl, (heteroaryl)alkyl, cycloalkyl, (cycloalkyl)alkyl, heterocylo or (heterocyclo)alkyl any of which may be optionally independently substituted where valance allows with one to three groups T1c, T2c or T3c;

or R5 and R6 together with the nitrogen atom to which they are attached may combine to form a 4 to 8-membered heterocyclo ring optionally substituted with one to three groups T1c, T2c or T3c;

T1-1c T2-2c, and T3-3c are each independently (1) hydrogen or T6, where T6 is (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; (ii) a group (i) which is itself substituted by one or more of the same or different groups (i); or (iii) a group (i) or (ii) which is independently substituted by one or more (preferably 1 to 3) of the following groups (2) to (13) of the definition of T1-1c, T2-2c and T3-3c (2) —OH or —OT6, (3) —SH or —ST6, (4) —C(O)tH, —C(O)tT6, or —O—C(O)T6, where t is 1 or 2; (5) —SO3H, —S(O)T6, or S(O)tN(T9)T6, (6) halo, (7) cyano, (8) nitro, (9) -T4-NT7T8, (10) -T4-N(T9)-T5-NT7T8, (11) -T4-N(T10)-T5-T6, (12) -T4-N(T10)-T5-H, (13) oxo, T4 and T5 are each independently (1) a single bond, (2)-T11-S(O)t-T12-, (3) -T11-C(O)-T12-, (4) -T11-C(S)-T12-, (5) -T11-O-T12-, (6) -T11-S-T12-, (7) -T11-O—C(O)-T12-, (8) -T11-C(O)—O-T12-, (9) -T11-C(=NT9a)-T12-, or (10) -T11-C(O)—C(O)-T12, T7, T8, T9, T9a and T10 (1) are each independently hydrogen or a group provided in the definition of T6, or (2) T7 and T8 may together be alkylene or alkenylene, completing a 3- to 8-membered saturated or unsaturated ring together with the atoms to which they are attached, which ring is unsubstituted or substituted with one or more groups listed in the description of T1-1c, T2-2c and T3-3c, or (3) T7 or T8, together with T9, may be alkylene or alkenylene completing a 3- to 8-membered saturated or unsaturated ring together with the nitrogen atoms to which they are attached, which ring is unsubstituted or substituted with one or more groups listed in the description of T1-1c, T2-2c and T3-3c, or (4) T7 and T8 or T9 and T10 together with the nitrogen atom to which they are attached may combine to form a group-N=CT13T14 where T13 and T14 are each independently H or a group provided in the definition of T6;

and T11 and T12 are each independently (1) a single bond, (2) alkylene, (3) alkenylene, or (4) alkynylene.

In a related embodiment, PDE7 inhibitors useful in the methods of the present invention include the above compounds, wherein:

Z is (a) halogen, alkoxy, haloalkyl, —NR3R4, —C(O)OR4, —C(O)NR3R4; (b) aryl or heteroaryl either of which may be optionally substituted with one or more T1a, T2a, T3a (especially cyano, optionally substituted alkyl, (hydroxy)alkyl, —OH, —OT6, —ST6, —SOtT6, —COtH, —COtT6, -T4NT7T8, or -T4N(T10)-T5-T6); (c) optionally substituted alkyl (especially substituted with one or more —OH, —COtH, —COtT6, -T4-NT7T8, -T4-N(T10)-T5-H, or -T4-N(T10)-T5-T6);

J is (a) H, or (b) alkyl or alkenyl either of which may be optionally substituted (especially with one or more —OH, —OT6, —COtH, or —COtT6);

L is (a) H; (b) halogen, alkoxy, haloalkyl, —NR5R6, —C(O)OR4b, —C(O)NR5R6; (c) aryl or heteroaryl either of which may be optionally substituted with one or more T1c, T2c, T3c (especially cyano, optionally substituted alkyl, (hydroxy)alkyl, —OH, —OT6, —ST6, —SOtT6, —COtH, —COtT6, -T4NT7T8, or -T4N(T10)-T5-T6); or (d) optionally substituted alkyl (especially substituted with one or more —OH, —COtH, —COtT6, -T4-NT7T8, -T4-N(T10)-T5-H, or; -T4-N(T10)-T5-T6);

R1 is H or alkyl;

R2 is (a) heteroaryl (more preferably thiazolyl or oxazolyl) optionally substituted with one to three groups T1, T2, T3, preferably including H, alkyl, haloalkyl, halo, heteroaryl, cyano, C(O)tT6, OT6, -T4NT7T8; (b) aryl substituted with one to three groups T1, T2, T3 (preferably including heteroaryl (preferably, imidazolyl, oxazolyl, or thiazolyl any of which may be further optionally substituted), cyano, C(O)tT6, S(O)tN(T9)T6, halo alkyl, and haloalkyl); or (c) aryl fused to a heterocyclo ring (e.g., 2,3-dihydro-1H-indole bound through the aryl ring, quinolyl bound through the aryl ring (especially quinol-6-yl), quinazolinyl bound through the aryl ring (especially quinazolin-7-yl), cinnolinyl bound through the aryl ring (especially cinnolin-6-yl), isoqinolinyl bound through the aryl ring (especially isoquinol-6-yl), and phthalazinyl bound through the aryl ring (especially phthalazin-6-yl)) wherein the combined ring system may be optionally substituted with one to three groups T1, T2, T3 (especially halo, OH, OT6, alkyl, —COtH, —COtT6, or —C(O)NT7T8);

R3 is H or optionally substituted alkyl (especially substituted with one or more —OH, or —OT6);

R4 is (a) hydrogen; (b) (aryl)alkyl where the aryl group is optionally independently substituted with one or more groups T1a, T2a, T3a (especially optionally substituted alkyl, halo, cyano, nitro, (hydroxy)alkyl, —OH, —OT6, —ST6, —COtH, —COtT6, —SO3H, —SOtT6, —SOtN(T9)(T6), -T4NT7T8, -T4-N(T10)-T5-T6, heterocyclo, or heteroaryl); (c) (heteroaryl)alkyl where the heteroaryl group is optionally independently substituted with one or more groups T1a, T2a, T3a (especially optionally substituted alkyl, halo, cyano, nitro, (hydroxy)alkyl, —OH, —OT6, —ST6, —COtH, —COtT6, —SO3H, —SOtT6, —SOtN(T9)(T6), -T4NT7T8, -T4-N(T10)-T5-T6, heterocyclo, or heteroaryl); (d) (heterocyclo)alkyl where the heterocyclo group is optionally independently substituted with one or more groups T1a, T2a, T3a (especially optionally substituted alkyl, halo, cyano, nitro, oxo, (hydroxy)alkyl, —OH, —OT6, —ST6, —COtH, —COtT6, —SO$_3$H, —SOtT6, —SOtN(T9)(T6), -T4NT7T8, -T4-N(T10)-T5-T6, heterocyclo, or heteroaryl); (e) alkyl optionally independently substituted with one or more groups T1a, T2a, T3a (especially —OH, —OT6, —COtH, —COtT6, -T4NTT8 or -T4-N(T10)-T5-T6); (f) heterocyclo optionally independently substituted with one or more groups T1a, T2a, T3a (especially optionally substituted alkyl, optionally substituted aryl, optionally substituted heteroaryl, optionally substituted aralkyl, optionally substituted heterocyclo, cyano, —OH, —OT6, —COtH, —COtT6, oxo, hydroxy (alkyl), (alkoxy)alkyl, -T4-N(T10)-T5-T6, or -T4-NT2T8);

or R3 and R4 together with the nitrogen atom to which they are attached combine to form a 4 to 8-membered heterocyclo ring (especially pyrrolidinyl, piperadinyl, piperazinyl, morpholinyl, diazapanyl or 1,4-dioxa-8-azaspiro[4.5]decan-8-yl) optionally substituted with one to three groups T1a, T2a, T3a (especially optionally substituted alkyl, optionally substituted aryl, optionally substituted heteroaryl, optionally substituted aralkyl, optionally substituted heterocyclo, cyano, —OH, —OT6, —COtH, —COtT6, oxo, hydroxy(alkyl), (alkoxy)alkyl, -T4-N(T10)-T5-T6, or -T4-NT7T8);

R5 is hydrogen or alkyl;

R6 is (a) hydrogen; (b) (aryl)alkyl where the aryl group is optionally independently substituted with one or more groups T1c, T2c, T3c (especially optionally substituted alkyl, halo, cyano, nitro, (hydroxy)alkyl, —OH, —OT6, —ST6, —COtH, —COtT6, —SO3H, —SOtT6, —SOtN(T9)(T6), -T4-N(T10)-T5-T6, heterocyclo, or heteroaryl); (c) (heteroaryl)alkyl where the heteroaryl group is optionally independently substituted with one or more groups T1c, T2c, T3c (especially optionally substituted alkyl, halo, cyano, nitro, (hydroxy)alkyl, —OH, —OT6, —ST6, —COtH, —COtT6, —SO3H, —SOtT6, —SOtN(T9)(T6), -T4-N(T10)-T5-T6, heterocyclo, or heteroaryl); (d) (heterocyclo)alkyl where the heterocyclo group is optionally independently substituted with one or more groups T1c, T2c, T3c (especially optionally substituted alkyl, halo, cyano, nitro, oxo, (hydroxy)alkyl, —OH, —OT6, —ST6, —COtH, —COtT6, —SO3H, —SOtT6, —SOtN(T9)(T6), -T4-N(T10)-T5-T6, heterocyclo, or heteroaryl); (e) alkyl optionally independently substituted with one or more groups T1c, T2c, T3c (especially —OH, —OT6, —COtH, —COtT6, -T4NT7T8 or -T4-N(T10)-T5-T6); (f) heterocyclo optionally independently substituted with one or more groups T1c, T2c, T3c (especially optionally substituted alkyl, optionally substituted aryl, optionally substituted heteroaryl, optionally substituted aralkyl, optionally substituted heterocyclo, cyano, —OH, —OT6, —COtH, —COtT6, oxo, hydroxy(alkyl), (alkoxy)alkyl, -T4-N(T10)-T5-T6, or -T4-NT7T8);

or R5 and R6 together with the nitrogen atom to which they are attached combine to form a 4 to 8-membered heterocyclo ring (especially pyrrolidinyl, piperadinyl, piperazinyl, morpholinyl, diazapanyl or 1,4-dioxa-8-azaspiro[4.5]decan-8-yl) optionally substituted with one to three groups T1c, T2c, T3c (especially optionally substituted alkyl, optionally substituted aryl, optionally substituted heteroaryl, optionally substituted aralkyl, optionally substituted heterocyclo, cyano, —OH, —OT6, —COtH, —COtT6, oxo, hydroxy(alkyl), (alkoxy)alkyl, -T4-N(T10)-T5-T6, or -T4-NT7T8).

In another related embodiment, PDE7 inhibitors useful in the methods of the present invention include the above compounds, wherein:

Z is (a) halogen, alkoxy, haloalkyl, —NR3R4, —C(O)OR4, —C(O)NR3R4; (b) aryl or heteroaryl either of which may be optionally substituted with one or more T1a, T2a, T3a selected from cyano, optionally substituted alkyl, (hydroxy)alkyl, —OH, —OT6, —ST6, —SOtT6, —COtH, —COtT6, -T4NT7T8, or -T4N(T10)-T5-T6, where T4 is a bond or —C(O)—; T5 is —C(O)—, or —C(O)O—; T6 is alkyl or haloalkyl; T7 and T8 are independently H; alkyl optionally substituted with cycloalkyl, heteroaryl, hydroxy or —NT7T8 cycloalkyl; or aryl optionally substituted with halogen; or T7 and T8 together with the nitrogen atom to which they are attached combine to form a heterocyclo ring optionally substituted with (hydroxy)alkyl, COtH or COtT6, T10 is hydrogen; (c) alkyl optionally substituted with one or more —OH, —COtH, —COtT6, -T4-NT7T8, -T4-N(T10)-T5-H, or -T4-N(T10)-T5-T6 where T4 is —C(O)—; T5 is -alkylene-O—; T6 is alkyl; T7 and T8 are independently H, alkyl, cycloalkyl, aryl, (aryl)alkyl (optionally substituted as described in the definition of R4), or heterocyclo (optionally substituted as described in the definition of R3 and R4 combining to form a heterocyclo ring); and T10 is H;

J is (a) H, or (b) alkyl or alkenyl either of which may be optionally substituted with one or more —OH, —OT6, —COtH, or —COtT6, where T6 is alkyl;

L is (a) H; (b) halogen, alkoxy, haloalkyl, —NR5R6, —C(O)OR4b, —C(O)NR5R6; (c) aryl or heteroaryl either of which may be optionally substituted with one or more T1c, T2c, T3c selected from cyano, optionally substituted alkyl (especially substituted with COtH or COtT6), (hydroxy)alkyl, —OH, —OT6, —ST6, —SOtT6, —COtH, —COtT6, -T4NT7T8, or -T4N(T10)-T5-T6, where T4 is a bond or —C(O)—; T5 is —C(O)—, or —C(O)O—; T6 is alkyl or haloalkyl; T7 and T8 are independently H; alkyl optionally substituted with cycloalkyl, heteroaryl, hydroxy or —NT7T8; cycloalkyl; or aryl optionally substituted with halogen; or T7 and T8 together with the nitrogen atom to which they are attached combine to form a heterocyclo ring optionally substituted with (hydroxy)alkyl, COtH or COtT6; T10 is hydrogen; (d) alkyl optionally substituted with one or more —OH, —COtH, —COtT6, -T4-NT7T8, -T4-N(T10)-T5-H, or -T4-N(T10)-T5-T6 where T4 is —C(O)—; T5 is -alkylene-O—; T6 is alkyl; T7 and T8 are independently H, alkyl, cycloalkyl, aryl, (aryl)alkyl (optionally substituted as described in the definition of R4), or heterocyclo (optionally substituted as described in the definition of R3 and R4 combining to form a heterocyclo ring); and T10 is H;

R1 is H or alkyl;

R2 is (a) heteroaryl (more preferably thiazolyl or oxazolyl) optionally substituted with one to three groups T1, T2, T3, preferably including H, alkyl, haloalkyl, halo, heteroaryl, cyano, C(O)tT6, OT6, -T4NT7T8; (b) aryl substituted with one to three groups T1, T2, T3 (preferably including heteroaryl (preferably, imidazolyl, oxazolyl, or thiazolyl any of which may be further optionally substituted), cyano, C(O)tT6, S(O)tN(T9)T6, halo alkyl, and haloalkyl); or (c) aryl fused to a heterocyclo ring (e.g., 2,3-dihydro-1H-indole bound through the aryl ring) wherein the combined ring system may be optionally substituted with one to three groups T1, T2, T3 (especially halo, —OH, —OT6, alkyl, —COtH, —COtT6, or —C(O)NT7T8);

R3 is H or optionally substituted alkyl (especially substituted with one or more —OH, or —OT6);

R4 is (a) hydrogen; (b) (aryl)alkyl where the aryl group is optionally independently substituted with one or more groups T1a, T2a, T3a selected from optionally substituted alkyl, halo, cyano, nitro, (hydroxy)alkyl, —OH, —OT6, —ST6, —COtH, —COtT6, —SO3H, —SOtT6, —SOtN(T9)(T6), -T4NT7T8, -T4N(T10)-T5-T6, heterocyclo, or heteroaryl) where T4 is a bond, —SO$_2$—, or —C(O)—; T5 is —SO2-, or -alkylene-O—; T6 is alkyl, or cycloalkyl; T7 and T8 are independently H or alkyl; and T9 and T10 are hydrogen; (c) (heteroaryl)alkyl where the heteroaryl group is optionally independently substituted with one or more groups T1a, T2a, T3a selected from optionally substituted alkyl, halo, cyano, nitro, oxo, (hydroxy)alkyl, —OH, —OT6, —ST6, —COtH, —COtT6, —SO3H, —SOtT6, —SOtN(T9)(T6), -T4NT7T8, -T4-N(T10)-T5-T6, heterocyclo, or heteroaryl) where T4 is a bond, —SO2-, or —C(O)—; T5 is —SO2-, or -alkylene-O—; T6 is alkyl, or cycloalkyl; T7 and T8 are independently H or alkyl; and T9 and T10 are hydrogen; (d) (heterocyclo)alkyl where the heterocyclo group is optionally independently substituted with one or more groups T1a, T2a, T3a selected from optionally substituted alkyl, halo, cyano, nitro, (hydroxy)alkyl, —OH, —OT6, —ST6, —COtH, —COtT6, —SO3H, —SOtT6, -T4NT7T8, -T4-N(T10)-T5-T6, heterocyclo, or heteroaryl) where T4 is a bond, —SO2-, or —C(O)—; T5 is —SO2-, or -alkylene-O—; T6 is alkyl, or cycloalkyl; T7 and T8 are independently H or alkyl; and T9 and T10 are hydrogen; (e) alkyl optionally independently substituted with one or more groups T1a, T2a T3a selected from —OH, —OT6, —COtH, —COtT6, -T4NT7T8 or -T4-N(T10)-T5-T6) where T4 is a bond; T5 is —C(O)—; T6 is alkyl; T7 and T8 are independently H or alkyl; and T10 is hydrogen; heterocyclo optionally independently substituted with one or more groups T1a, T2a, T3a selected from optionally substituted alkyl (especially substituted with -T4NT7T8), optionally substituted aryl (especially substituted with halogen or haloalkyl), cyano, —OH, —OT6, —COtH, —COtT6, oxo, hydroxy(alkyl), (alkoxy)alkyl, -T4-N(T10)-T5-T6, or -T4-NT7T8) where T4 is a bond or —C(O)—; T5 is —C(O)—, —SO2-, or -alkylene-C(O)O—; T6 is alkyl, alkoxy, or heteroaryl; T7 and T8 are independently H, alkyl, or cycloalkyl; or T7 and T8 together with the nitrogen atom to which they are attached combine to form an optionally substituted heterocyclo ring;

or R3 and R4 together with the nitrogen atom to which they are attached combine to form a heterocyclo ring selected from pyrrolidinyl, piperadinyl, piperazinyl, morpholinyl, diazapanyl or 1,4-dioxa-8-azaspiro[4.5]decan-8-yl), any of which are optionally independently substituted with one to three groups T1a, T2a, T3a selected from optionally substituted alkyl (especially substituted with -T4NT7T8), optionally substituted aryl (especially substituted with halogen or haloalkyl), cyano, —OH, —OT6, —COtH, —COtT6, oxo, hydroxy(alkyl), (alkoxy)alkyl, -T4-N(T10)-T5-T6, or -T4-NT7T8) where T4 is a bond or —C(O)—; T5 is —C(O)—, —SO2-, or -alkylene-C(O)O—; T6 is alkyl, alkoxy, or heteroaryl; T7 and T8 are independently H, alkyl, or cycloalkyl; or T7 and T8 together with the nitrogen atom to which they are attached combine to form an optionally substituted heterocyclo ring;

R5 is hydrogen or alkyl;

R6 is (a) hydrogen; (b) (aryl)alkyl where the aryl group is optionally independently substituted with one or more groups T1c, T2c, T3c selected from optionally substituted alkyl, halo, cyano, nitro, (hydroxy)alkyl, —OH, —OT6, —ST6, —COtH, —COtT6, —SO3H, —SOtT6, —SOtN(T9)(T6), -TNT7T8, -T4-N(T10)-T5-T6, heterocyclo, or heteroaryl) where T4 is a bond, —SO2-, or —C(O)—; T5 is —SO2-, or -alkylene-O—; T6 is alkyl, or cycloalkyl; T7 and T8 are independently H or alkyl; and T9 and T10 are hydrogen; (c) (heteroaryl)alkyl where the heteroaryl group is optionally independently substituted with one or more groups T1c, T2c, T3c selected from optionally substituted alkyl, halo, cyano, nitro, oxo, (hydroxy)alkyl, —OH, —OT6, —ST6, —COtH, —COtT6, —SO3H, —SOtT6, —SOtN(T9)(T6), -T4NT7T8, -T4-N(T10)-T5-T6, heterocyclo, or heteroaryl) where T4 is a bond, —SO2-, or —C(O)—; T5 is —SO2-, or -alkylene-O—; T6 is alkyl, or cycloalkyl; T7 and T8 are independently H or alkyl; and T9 and T10 are hydrogen; (d) (heterocyclo)alkyl where the heterocyclo group is optionally independently substituted with one or more groups T1c, T2c, T3c selected from optionally substituted alkyl, halo, cyano, nitro, (hydroxy)alkyl, —OH, —OT6, —ST6, —COtH, —COtT6, —SO3H, —SOtT6, -T4NT7T8, -T4-N(T10)-T5-T6, heterocyclo, or heteroaryl) where T4 is a bond, —SO2-, or —C(O)—; T5 is —SO2-, or -alkylene-O—; T6 is alkyl, or cycloalkyl; T7 and T8 are independently H or alkyl; and T9 and T10 are hydrogen; (e) alkyl optionally independently substituted with one or more groups T1c, T2c, T3c selected from —OH, —OT6, —OCtH, —COtT6, -T4NT7T8 or -T4-N(T10)-T5-T6) where T4 is a bond; T5 is —C(O)—; T6 is alkyl; T7 and T8 are independently H or alkyl; and T10 is hydrogen; heterocyclo optionally independently substituted with one or more groups T1c, T2c, T3c selected from optionally substituted alkyl (especially substituted with -T4NT7T8), optionally substituted aryl (especially substituted with halogen or haloalkyl), cyano, —OH, —OT6, —COtH, —COtT6, oxo, hydroxy(alkyl), (alkoxy)alkyl, -T4-N(T10)-T5-T6, or -T4-NT7T8, where T4 is a bond or —C(O)—; T5 is —C(O)—, —SO2-, or -alkylene-C(O)O—; T6 is alkyl, alkoxy, or heteroaryl; T7 and T8 are independently H, alkyl, or cycloalkyl; or T7 and T8 together with the nitrogen atom to which they are attached combine to form an optionally substituted heterocyclo ring;

or R5 and R6 together with the nitrogen atom to which they are attached combine to form a heterocyclo ring selected from pyrrolidinyl, piperadinyl, piperazinyl, morpholinyl, diazapanyl or 1,4-dioxa-8-azaspiro[4.5]decan-8-yl), any of which are optionally independently substituted with one to three groups T1a, T2a, T3a selected from optionally substituted alkyl (especially substituted with -T4NT7T8), optionally substituted aryl (especially substituted with halogen or haloalkyl), cyano, —OH, —OT6, —COtH, —COtT6, oxo, hydroxy(alkyl), (alkoxy)alkyl, -T4-N(T10)-T5-T6, or -T4-NT7T8 where T4 is a bond or —C(O)—; 5 is —C(O)—, —SO2-, or -alkylene-C(O)O—; T6 is alkyl, alkoxy, or heteroaryl; T7 and T8 are independently H, alkyl, or cycloalkyl; or T7 and T8 together with the nitrogen atom to which they are attached combine to form a an optionally substituted heterocyclo ring.

In a further related embodiment, PDE7 inhibitors useful in the methods of the present invention include the following compounds:

2-[[4-[[[4-(Aminosulfonyl)phenyl]methy]amino]-6-(4-methyl-1-piperazinyl)-2-pyrimidinyl]amino]-4-methyl-5-thiazolecarboxylic acid ethyl ester; 2-[[4-[[(3,4-Dimethoxyphenyl)methyl]amino]-6-(1-piperazinyl)-2-pyrimidinyl]amino]-4-methyl-5-thiazolecarboxylic acid ethyl ester trifluoroacetate salt; 2-[[4-[[[4-(Aminosulfonyl)phenyl]methyl]amino]-6-(1-piperazinyl)-2-pyrimidinyl]amino]-4-methyl-5-thiazolecarboxylic acid ethyl ester; 4-Methyl-2-[[4-[[[4-(methylsulfonyl)phenyl]methyl]amino]-6-(1-piperazinyl)-2-pyrimidinyl]amino]-5-thiazolecarboxylic acid ethyl ester; 2-[[4-[[(4-Methoxyphenyl)methyl]amino]-6-(1-piperazinyl)-2-pyrimidinyl]amino]-4-methyl-5-thiazolecarboxylic acid ethyl ester; 2-[[4-[[(3-Methoxyphenyl)methyl]amino]-6-(1-piperazinyl)-2-pyrimidinyl]amino]-4-methyl-5-thiazolecarboxylic acid ethyl ester; 2-[[4-[[(2-Methoxyphenyl)methyl]amino]-6-(1-piperazinyl)-2-pyrimidinyl]amino]-4-methyl-5-thiazolecarboxylic acid ethyl ester; 4-Methyl-2-[[4-(1-piperazinyl)-6-[[(3,4,5-trimethoxyphenyl)methyl]amino]-2-pyrimidinyl]amino]-5-thiazolecarboxylic acid ethyl ester; 2-[[4-[[(2-Ethoxyphenyl)methyl]amino]-6-(1-piperazinyl)-2-pyrimidinyl]amino]-4-methyl-5-thiazolecarboxylic acid ethyl ester; 2-[[4-[[(2,5-Dimethoxyphenyl)methyl]amino]-6-(1-piperazinyl)-2-pyrimidinyl]amino]-4-methyl-5-thiazolecarboxylic acid ethyl ester; 2-[[4-[[(3,5-Dimethoxyphenyl)methyl]amino]-6-(1-piperazinyl)-2-pyrimidinyl]amino]-4-methyl-5-thiazolecarboxylic acid ethyl ester; 2-[[4-[[(2,6-Dimethylphenyl)methyl]amino]-6-(1-piperazinyl)-2-pyrimidinyl]amino]-4-methyl-5-thiazolecarboxylic acid ethyl ester; 2-[[4-[[[4-(Methoxycarbonyl)phenyl]methyl]amino]-6-(1-piperazinyl)-2-pyrimidinyl]amino]-4-methyl-5-thiazolecarboxylic acid ethyl ester; 2-[[4-[[(3-Bromophenyl)methyl]amino]-6-(1-piperazinyl)-2-pyrimidinyl)amino]-4-methyl-5-thiazolecarboxylic acid ethyl ester; 2-[[4-[(1,3-Benzodioxol-5-ylmethyl)amino]-6-(1-piperazinyl)-2-pyrimidinyl]amino]-4-methyl-5-thiazolecarboxylic acid ethyl ester; 4-Methyl-2-[[4-[methyl(3-pyridinylmethyl)amino]-6-(1-piperazinyl)-2-pyrimidinyl]amino]-5-thiazolecarboxylic acid ethyl ester; 4-Methyl-2-[[4-(1-piperazinyl)-6-[[[4-(1,2,3-thiadiazol-4-yl)phenyl]methyl]amino]-2-pyrimidinyl]amino]-5-thiazolecarboxylic acid ethyl ester; 2-[[4-[[[3-(Cyclopentyloxy)-4-methoxyphenyl]methyl]amino]-6-(1-piperazinyl)-2-pyrimidinyl]amino]-4-methyl-5-thiazolecarboxylic acid ethyl ester; 4-Methyl-2-[[4-[(phenylmethyl)amino]-6-(1-piperazinyl)-2-pyrimidinyl]amino]-5-thiazolecarboxylic acid ethyl ester; 4-Methyl-2-[[4-(4-methyl-1-piperazinyl)-6-[[(3,4,5-trimethoxyphenyl)methyl]amino]-2-pyrimidinyl]amino]-5-thiazolecarboxylic acid ethyl ester; 2-[[4-(4-Hydroxy-1-piperidinyl)-6-[[[4-(methylsulfonyl)phenyl]methyl]amino]-2-pyrimidinyl]amino]-4-methyl-5-thiazolecarboxylic acid ethyl ester; 4-Methyl-2-[[4-[[2-(1-methylethoxy)ethyl]amino]-6-[[[4-(methylsulfonyl)phenyl]methyl]amino]-2-pyrimidinyl]amino]-5-thiazolecarboxylic acid ethyl ester; 2-[[4-[3-(Aminocarbonyl)-1-piperidinyl]-6-[[[4-(methylsulfonyl)phenyl]methyl]amino]-2-pyrimidinyl]amino]-4-methyl-5-thiazolecarboxylic acid ethyl ester; 2-[[4-[[(2-(1H-imidazol-4-yl)ethyl]amino]-6-[[[4-(methylsulfonyl)phenyl]methyl]amino]-2-pyrimidinyl]amino]-4-methyl-5-thiazolecarboxylic acid ethyl ester; 4-Methyl-2-[[4-[[[4-(methylsulfonyl)phenyl]methyl]amino]-6-[[3-(4-morpholinyl)propyl]amino]-2-pyrimidinyl]amino]-5-thiazolecarboxylic acid ethyl ester; 2-[[4-[(2-Methoxy-1-methylethyl)amino]-6-[[[4-(methylsulfonyl)phenyl]methyl]amino]-2-pyrimidinyl]amino]-4-methyl-5-thiazolecarboxylic acid ethyl ester; 4-Methyl-2-[[4-[[[4-(methylsulfonyl)phenyl]methyl]amino]-6-[[(tetrahydro-2-furanyl)methyl]amino]-2-pyrimidinyl]amino]-5-thiazolecarboxylic acid ethyl ester; 2-[[4-[4-(2-Hydroxyethyl)-1-piperazinyl]-6-[[[4-(methylsulfonyl)phenyl]methyl]amino]-2-pyrimidinyl]amino]-4-methyl-5-thiazole carboxylic acid ethyl ester; 2-[[4-[2-(Aminocarbonyl)-1-pyrrolidinyl]-6-[[[4-(methylsulfonyl)phenyl]methyl]amino]-2-pyrimidinyl]amino]-4-methyl-5-thiazolecarboxylic acid ethyl ester; 4-Methyl-2-[[4-[methyl(3-pyridinylmethyl)amino]-6-[[[4-(methylsulfonyl)phenyl]methyl]amino]-2-pyrimidinyl]amino]-5-thiazolecarboxylic acid ethyl ester; 2-[[4-[4-(Hydroxymethyl)-1-piperidinyl]-6-[[[4-(methylsulfonyl)phenyl]methyl]amino]-2-pyrimidinyl]amino]-4-methyl-5-thiazolecarboxylic acid ethyl ester; 2-[[4-[[2-(Diethylamino)ethyl]methylamino]-6-[[[4-(methylsulfonyl)phenyl]methyl]amino]-2-pyrimidinyl]amino]-4-methyl-5-thiazole carboxylic acid ethyl ester; 4-Methyl-2-[[4-[[[4-(methylsulfonyl)phenyl]methyl]amino]-6-[[3-(2-oxo-1-pyrrolidinyl)propyl]amino]-2-pyrimidinyl]amino]-5-thiazolecarboxylic acid ethyl ester; 2-[[4-[3-(Hydroxymethyl)-1-piperidinyl]-6-[[[4-(methylsulfonyl)phenyl]methyl]amino]-2-pyrimidinyl]amino]-4-methyl-5-thiazolecarboxylic acid ethyl ester; 4-Methyl-2-[[4-(4-methyl-1-piperazinyl)-6-[[[(4-(methylsulfonyl)phenyl]methyl]amino]-2-pyrimidinyl]amino]-5-thiazolecarboxylic acid ethyl ester; 2-[[4-[[2-[(Acetylamino)ethyl]amino]-6-[[[(4-(methylsulfonyl)phenyl]methyl]amino]-2-pyrimidinyl]amino]-4-methyl-5-thiazolecarboxylic acid ethyl ester; 2-[[4-(4-Ethyl-1-piperazinyl)-6-[[[4-(methylsulfonyl)phenyl]methyl]amino]-2-pyrimidinyl]amino]-4-methyl-5-thiazolecarboxylic acid ethyl ester; 2-[[4-(4-Acetyl-1-piperazinyl)-6-[[[4-(methylsulfonyl)phenyl]methyl]amino]-2-pyrimidinyl]amino]-4-methyl-5-thiazolecarboxylic acid ethyl ester; 2-[[4-[[2-(Dimethylamino)ethyl]amino]-[[[4-(methylsulfonyl)phenyl]methyl]amino]-2-pyrimidinyl]amino]-4-methyl-5-thiazolecarboxylic acid ethyl ester; 2-[[4-3-(Aminocarbonyl)-1-piperazinyl]-6-[[[4-(methylsulfonyl)phenyl]methyl]amino]-2-pyrimidinyl]amino]-4-methyl-5-thiazolecarboxylic acid ethyl ester; 2-[[4-(3-Hydroxy-1-pyrrolidinyl)-6-[[[4-(methylsulfonyl)phenyl]methyl]amino]-2-pyrimidinyl]amino]-4-methyl-5- thiazolecarboxylic acid ethyl ester; 2-[[4-[(4-Hydroxybutyl) amino]-6-[[[4-(methylsulfonyl)phenyl]methyl]amino]-2-pyrimidinyl]amino]-4-methyl-5-thiazolecarboxylic acid ethyl ester; 2-[[4-[(2,3-Dihydroxypropyl)amino]-6-[[[4-(methylsulfonyl)phenyl]methyl]amino]-2-pyrimidinyl] amino]-4-methyl-5-thiazolecarboxylic acid ethyl ester; 2-[[4-[(4-Amino-1-piperidinyl)-64 [[4-(methylsulfonyl)phenyl]methyl]amino]-2-pyrimidinyl]amino]-4-methyl-5-thiazolecarboxylic acid ethyl ester; 2-[[4-[4-Hydroxy-3-(hydroxymethyl)-1-piperidinyl]-6-[[[4-(methylsulfonyl) phenyl]methyl]amino]-2-pyrimidinyl]amino]-4-methyl-5-thiazolecarboxylic acid ethyl ester; 2-[[4-(4-Dimethylamino-1-piperidinyl)-6-[[[4-(methylsulfonyl)phenyl]methyl] amino]-2-pyrimidinyl]amino]-4-methyl-5-thiazolecarboxylic acid ethyl ester; 2-[[4-[[[4-(Aminosulfonyl)phenyl]methyl]amino]-6-(methylamino)-2-pyrimidinyl]amino]-4-methyl-5-thiazolecarboxylic acid, ethyl ester; 2-[4,6-Bis-(4-methyl-piperazin-1-yl)-pyrimidin-2-ylamino]-4-methyl-thiazole-5-carboxylic acid ethyl ester; 2-[4-(4-Hydroxy-piperidin-1-yl)-6-(4-methyl-piperazin-1-yl)-pyrimidin-2-ylamino]-4-methyl-thiazole-5-carboxylic acid ethyl ester; 2-[4(3-Hydroxymethyl-piperidin-1-yl)-6-(4-methyl-piperazin-1-yl)-pyrimidin-2-ylamino]-4-methyl-thiazole-5-carboxylic acid ethyl ester; 4-Methyl-2-[4-(4-methyl-piperazin-1-yl)-6-morpholin-4-yl-pyrimidin-2-ylamino]-thiazole-5-carboxylic acid ethyl ester; 2-[4-(4-Amino-piperidin-1-yl)-6-(4-methyl-piperazin-1-yl)-pyrimidin-2-ylamino]-4-methyl-thiazole-5-carboxylic acid ethyl ester; 2-[4,6-Bis-(4-hydroxy-piperidin-1-yl)-pyrimidin-2-ylamino]-4-methyl-thiazole-5-carboxylic acid ethyl ester; 2-[4-(4-oxo-piperidin-1-yl)-6-(4-methyl-piperazin-1-yl)-pyrimidin-2-ylamino]-4-methyl-thiazole-5-carboxylic acid ethyl ester; 2-[4-(4-methyl-4-hydroxy-piperidin-1-yl)-6-(4-methyl-piperazin-1-yl)-pyrimidin-2-ylamino]-4-methyl-thiazole-5-carboxylic acid ethyl ester; 2-[-(4-hydroxy-piperidin-1-yl)-6-(4-dimethylmethyl-piperazin-1-yl)-pyrimidin-2-ylamino]-4-methyl-thiazole-5-carboxylic acid ethyl ester; 2-[4-(4-hydroxymethyl-piperidin-1-yl)-6-(4-dimethylmethyl-piperazin-1-yl)-pyrimidin-2-ylamino]-4-methyl-thiazole-5-carboxylic acid ethyl ester; 2-[4-(3-hydroxymethyl-piperidin-1-yl)-6-(4-dimethylmethyl-piperazin-1-yl)-pyrimidin-2-ylamino]-4-methyl-thiazole-5-carboxylic acid ethyl ester; 2-[4-(4-hydroxymethyl-piperidin-1-yl)-6-(4-hydroxy-piperazin-1-yl)-pyrimidin-2-ylamino]-4-methyl-thiazole-5-carboxylic acid ethyl ester; 4-Methyl-2-[4-(4-hydroxy-piperazin-1-yl)-6-morpholin-4-yl-pyrimidin-2-ylamino]-thiazole-5-carboxylic acid ethyl ester; 2-[[(4-[[[4-(Methylsulfonyl)phenyl]methyl]amino]-6-chloro-2-pyrimidinyl]amino]-4-methyl-5-thiazolecarboxylic acid, ethyl ester; 2-[[4-[[[4-(Aminosulfonyl)phenyl]methyl]amino]-6-chloro-2-pyrimidinyl]amino]-4-methyl-5-thiazolecarboxylic acid, ethyl ester; 2-[4-[4-(Dimethylamino)-1-piperidinyl]-6-[[(3,4,5-trimethoxyphenyl)methyl]amino]-2-pyrimidinyl]amino]-4-methyl-5-thiazolecarboxylic acid, ethyl ester; 2-[[4-[1-piperizinyl]-6-methyl-6-[[(3,4,5-trimethoxyphenyl)methyl] amino]-2-pyrimidinyl]amino]-4-methyl-5-thiazolecarboxylic acid, ethyl ester; 2-[[4-(4-Amino-1-piperidinyl)-6-[[[4-(methylsulfonyl)phenyl]methyl]amino]-2-pyrimidinyl]amino]-4-methyl-5-thiazolecarboxylic acid, ethyl ester; 2-[[4-[4-hydroxy-1-piperidinyl]-6-methyl-6-[[(3,4,5-trimethoxyphenyl)methyl]amino]-2-pyrimidinyl] amino]-4-methyl-5-thiazolecarboxylic acid, ethyl ester; 2-[[4-[4-(Hydroxymethyl)-1-piperidinyl]-6-methyl-6-[[(3,4, 5-trimethoxyphenyl)methyl]amino]-2-pyrimidinyl]amino]-4-methyl-5-thiazolecarboxylic acid, ethyl ester; 2-[4-(4-Hydroxypiperidin-1-yl)-6-(3-oxo-piperazin-1-yl)-pyrimidin-2-ylamino]-4-methyl-thiazole-5-carboxylic acid ethyl ester; 2-[[4-[3-(Aminocarbonyl)-1-piperizinyl]-6-methyl-6-[[(3,4,5-trimethoxyphenyl)methyl]amino]-2-pyrimidinyl]amino]-4-methyl-5-thiazolecarboxylic acid, ethyl ester; 2-[[4-[1-morpholinyl]-6-methyl-6-[[(3,4,5-trimethoxyphenyl) methyl]amino]-2-pyrimidinyl]amino]-4-methyl-5-thiazolecarboxylic acid, ethyl ester; 2-[[4-[3-Oxo-1-piperizinyl]-6-[[(1,1-dioxido-3-oxo-1,2-benzisothiazol-2-(3H)-yl)methyl]amino]-2-pyrimidinyl]amino]-4-methyl-5-thiazolecarboxylic acid, ethyl ester; 2-[[4-[3-Oxo-1-piperizinyl]-6-[[(4-(ethylsulfonylamino)phenyl)methyl] amino]-2-pyrimidinyl]amino]-4-methyl-5-thiazolecarboxylic acid, ethyl ester; 2-[[4-[3-Oxo-1-piperizinyl]-6-[[(4-(hydroxysulfonyl)phenyl)methyl] amino]-2-pyrimidinyl]amino]-4-methyl-5-thiazolecarboxylic acid, ethyl ester; 2-[4-(4-Hydroxypiperidin-1-yl)-6-(4-methyl-3-oxo-piperazin-1-yl)-pyrimidin-2-ylamino]-4-methyl-thiazole-5-carboxylic acid ethyl ester; 2-[4-(4(Dimethylamino)-piperizin-1-yl)-6-(4-[((1-pyrrolidinyl)carbonylmethyl)piperazin-1-yl)-pyrimidin-2-ylamino]-4-methyl-thiazole-5-carboxylic acid ethyl ester; 2-[[4-[3-(Aminocarbonyl)-1-piperazinyl]-6-[[(3,4,5-trimethoxyphenyl)methyl]amino]-2-pyrimidinyl]amino]-4-methyl-5-thiazolecarboxylic acid, ethyl ester; 2-[[4-(4-Amino-1-piperidinyl)-6-[[(3,4,5-trimethoxyphenyl)methyl] amino]-2-pyrimidinyl]amino]-4-methyl-5-thiazolecarboxylic acid, ethyl ester; 2-[[4-[4-(Hydroxymethyl)-1-piperidinyl]-6-[4-[tetrazol-5-yl]-4-hydroxypiperidin-1-yl]2-pyrimidinyl]amino]-4-methyl-5-thiazolecarboxylic acid, ethyl ester; 2-[[4-[4-methyl-1-piperazinyl]-6-[N-methyl-N-[(3,4,5-trimethoxyphenyl) methyl]amino]-2-pyrimidinyl]amino]-4-methyl-5-thiazolecarboxylic acid, ethyl ester; 2-[[4-[4-Hydroxy-1-piperidinyl]-6-[[(4-(hydroxysulfonyl)phenyl)methyl] amino]-2-pyrimidinyl]amino]-4-methyl-5-thiazolecarboxylic acid, ethyl ester; 2-[[4-[[(4-Cyanophenyl) methyl]amino]-6-(1-piperazinyl)-2-pyrimidinyl]amino]-4-methyl-5-thiazolecarboxylic acid, ethyl ester; trifluoroacetate (1:1); 2-[[4-[[[4-(Aminosulfonyl)phenyl] methyl]amino]-6-(4-morpholinyl)-2-pyrimidinyl]amino]-4-methyl-5-thiazole carboxylic acid, ethyl ester; 2-[[4-[4-Hydroxy-1-piperidinyl]-6-[(1-oxa-3,8-diazaspiro[4.5]decan-2, 4,dion-8-yl]-2-pyrimidinyl]amino]-4-methyl-5-thiazolecarboxylic acid, ethyl ester; 2-[4-(2-(Dimethylamino)ethyl)-piperazin-1-yl)-6-(4-methylpiperazin-1-yl)-pyrimidin-2-ylamino]-4-methyl-thiazole-5-carboxylic acid ethyl ester; 2-[[4-(4-Hydroxy-1-piperidinyl)-6-[methyl(3-pyridinylmethyl)amino]-2-pyrimidinyl]amino]-4-methyl-5-thiazolecarboxylic acid, ethyl ester; 2-[[4-[4-Hydroxy-3-hydroxymethylpiperidin-1-yl]-6-[[(3,4,5-trimethoxyphenyl)methyl]amino]-2-pyrimidinyl]amino]-4-methyl-5-thiazolecarboxylic acid, ethyl ester; 2-[[4-(3,4-Dihydro-6,7-dihydroxy-2(1H)-isoquinolinyl)-6-(4-methyl-1-piperazinyl)-2-pyrimidinyl]amino]-4-methyl-5-thiazolecarboxylic acid, ethyl ester, trifluoroacetate 1:1); 2-[[4-[4-[(Methoxyacetyl)amino]-1-piperidinyl]-6-[[4-(methylsulfonyl)phenyl]methyl]amino]-2-pyrimidinyl]amino]-4-methyl-5-thiazolecarboxylic acid, ethyl ester; 2-[[4-[[(3,4-Dimethoxyphenyl)methyl]amino]-6-[4-(dimethylamino)-1-piperidinyl]-2-pyrimidinyl]amino]-4-methyl-thiazolecarboxylic acid, ethyl ester; 2-[[4-[4-(Hydroxyethyl) piperidin-1-yl]-6-[4-(dimethylamino)-1-piperidinyl]-2-pyrimidinyl]amino]-4-methyl-5-thiazolecarboxylic acid, ethyl ester; 2-[[4-[4-(Dimethylamino)-1-piperidinyl]-6-[methyl(3-pyridinylmethyl)amino]-2-pyrimidinyl]amino]-4-methyl-5-thiazolecarboxylic acid, ethyl ester; 2-[[4-[4-(Hydroxy)piperidin-1-yl]-6-[4-(methoxycarbonyl)-1- piperidinyl]-2-pyrimidinyl]amino]-4-methyl-5-thiazolecarboxylic acid, ethyl ester; 2-[[4-[4-(Hydroxy)piperidin-1-yl]-6-[4-(methyl)-4-(hydroxy)-1-piperidinyl]-2-pyrimidinyl]amino]-4-methyl-5-thiazolecarboxylic acid, ethyl ester; 2-[4-(3-oxopiperazin-1-yl)-6-(4-methylpiperazin-1-yl)-pyrimidin-2-ylamino]-4-methyl-thiazole-5-carboxylic acid ethyl ester; 2-[[4-[[(4-Cyanophenyl)methyl]amino]-6-[4-dimethylamino)-1-piperidinyl]-2-pyrimidinyl]amino]-4-methyl-5-thiazolecarboxylic acid, ethyl ester; 4-Methyl-2-[[4-[[(3-nitrophenyl)methyl]amino]-6-(1-piperazinyl)-2-pyrimidinyl]amino]-5-thiazolecarboxylic acid, ethyl ester, trifluoroacetate (1:1); 2-[[4-(4-Hydroxy-1-piperidinyl]-6-[[(3,4,5-trimethoxyphenyl)methyl]amino]-2-pyrimidinyl]amino]-4-methyl-5-thiazolecarboxylic acid, ethyl ester; 2-[4-(Dimethylamino)-piperazin-1-yl)-6-(4-methylpiperazin-1-yl)-pyrimidin-2-2-ylamino]-4-methyl-thiazole-5-carboxylic acid ethyl ester; 2-[4-(Dimethylamino)-piperidin-1-yl]-6-(3-(aminocarbonyl)-1-piperazinyl)-pyrimidin-2-ylamino]-4-methyl-thiazole-5-carboxylic acid ethyl ester; 2-[4-(2-Hydroxyethyl)-piperazin-1-yl)-6-(4-methyl-1-piperazinyl)-pyrimidin-2-ylamino]-4-methyl-thiazole-5-carboxylic acid ethyl ester; 2-[[4-[4-(Aminocarbonyl)-1-piperidinyl]-6-[[[4-(methylsulfonyl)phenyl]methyl]amino]-2-pyrimidinyl]amino]-4-methyl-5-thiazolecarboxylic acid, ethyl ester; 2-[[4-[4-(Hydroxymethyl)-1-piperidinyl]-6-[N-methyl-N-(3-pyridinylmethyl)amino]-2-pyrimidinyl]amino]-4-methyl-5-thiazolecarboxylic acid, ethyl ester; 2-[[4-[4-Methylpiperazin-1-yl]-6-[[(3,4-dimethoxyphenyl)methyl]amino]-2-pyrimidinyl]amino]-4-methyl-5-thiazolecarboxylic acid, ethyl ester; 2-[[4-[piperazin-1-yl]-6-[[(4-carboxyphenyl)methyl]amino]-2-pyrimidinyl]amino]-4-methyl-5-thiazolecarboxylic acid, ethyl ester; 2-[4-[3-Hydroxymethylpiperidin-1-yl]-6-[[N-[(3,4,5-trimethoxyphenyl)methyl]]-N-(methyl)amino]-2-pyrimidinyl]amino]-4-methyl-5-thiazolecarboxylic acid, ethyl ester; 2-[4-(4-Hydroxypiperidin-1-yl)-6-(4-carboxypiperidin-1-yl)-pyrimidin-2-ylamino]-4-methyl-thiazole-5-carboxylic acid ethyl ester; 2-[[4-[piperazin-1-yl]-6-[[(3,4-dimethoxyphenyl)methyl]amino]-2-pyrimidinyl]amino]-4-methyl-5-thiazolecarboxylic acid, ethyl ester; 2-[[4-(4-Formyl-1-piperazinyl)-6-[[[4-(methylsulfonyl)phenyl]methyl]amino]-2-pyrimidinyl]amino]-4-methyl-5-thiazolecarboxylic acid, ethyl ester; 2-[4-(4-Hydroxypiperidin-1-yl)-6-(4-(hydroxy)-4-(4-chlorophenyl)piperidin-1-yl)-pyrimidin-2-ylamino]-4-methyl-thiazole-5-carboxylic acid ethyl ester; 4-Methyl-2-[[4-[4-dimethylamino-1-piperidinyl]-6-[[(tetrahydro-2-furanyl)methyl]amino]-2-pyrimidinyl]amino]-5-thiazolecarboxylic acid ethyl ester; 2-[[4-[Piperazin-1-yl]-6-[[N-methyl-N-(5-tetrazolylmethyl]amino]-2-pyrimidinyl]amino]-4-methyl-5-thiazolecarboxylic acid, ethyl ester; 2-[[4-[4-Morpholinyl]-6-[4-[tetrazol-5-yl]-4-hydroxypiperidin-1-yl]-2-pyrimidinyl]amino]-4-methyl-5-thiazolecarboxylic acid, ethyl ester; 2-[[4-[4-Hydroxy-1-piperidinyl]-6-[[(1,1-dioxido-3-oxo-1,2-benzisothiazol-2-(3H)-yl]methyl]amino]-2-pyrimidinyl]amino]-4-methyl-5-thiazolecarboxylic acid, ethyl ester; 2-[4-(4-Hydroxypiperidin-1-yl)-6-(4-(1-methyl-1-hydroxyethyl)piperidin-1-yl)-pyrimidin-2-ylamino]-4-methyl-thiazole-5-carboxylic acid ethyl ester; 2-[[4-[3-(Aminocarbonyl)-1-piperidinyl]-6-[[N-methyl-N-(3-pyridinylmethyl)]amino]-2-pyrimidinyl]amino]-4-methyl-5-thiazolecarboxylic acid, ethyl ester; 2-[[4-[4-Hydroxymethyl-1-piperidinyl]-6-[[(4-(ethylsulfonylamino)phenyl)methyl]amino]-2-pyrimidinyl]amino]-4-methyl-5-thiazolecarboxylic acid, ethyl ester; 2-[[4-[4-Hydroxy-1-piperidinyl]-6-[4-[tetrazol-5-yl]-4-hydroxypiperidin-1-yl]2-pyrimidinyl]amino]-4-methyl-5-thiazolecarboxylic acid, ethyl ester; 2-[[4-[4-tertButyloxycarbonylamino-1-piperidinyl]-6-[[N-[(3,4,5-trimethoxyphenyl)methyl]]-N-(methyl)amino]-2-pyrimidinyl]amino]-4-methyl-5-thiazolecarboxylic acid, ethyl ester; 2-[[4-[[(4-Cyanophenyl)methyl]amino]-6-(4-methyl-1-piperazinyl)-2-pyrimidinyl]amino]-4-methyl-5-thiazolecarboxylic acid, ethyl ester, trifluoroacetate (1:1); 2-[[4-[4-[[(2-Ethoxy-2-oxoethyl)amino]carbonyl]-1-piperazinyl]-6-[methyl(3-pyridinylmethy)amino]-2-pyrimidinyl]amino]-4-methyl-5-thiazolecarboxylic acid, ethyl ester, trifluoroacetate (1:1); 2-[4-(4-Hydroxypiperidin-1-yl)-6-(3-hydroxypiperidin-1-yl)-pyrimidin-2-ylamino]-4-methyl-thiazole-5-carboxylic acid ethyl ester; 2-[4-(4-Hydroxypiperidin-1-yl)-6-(4-hydroxy-4-phenyl-1-piperidinyl)-pyrimidin-2-ylamino]-4-methyl-thiazole-5-carboxylic acid ethyl ester; 4-Methyl-2-[[4-[4-morpholinyl]-6-[[tetrahydro-2-furanyl)methyl]amino]-2-pyrimidinyl]amino]-5-thiazolecarboxylic acid ethyl ester; 2-[[4-[(Tetrahydro-2-furanyl)methyl]amino]-6-[[N-[(3,4,5-trimethoxyphenyl)methyl]]-N-(methyl)amino]-2-pyrimidinyl]amino]-4-methyl-5-thiazolecarboxylic acid, ethyl ester; 2-[[4-[4-Morpholinyl]-6-[[(4-(hydroxysulfonyl)phenyl)methyl]amino]-2-pyrimidinyl]amino]-4-methyl-5-thiazolecarboxylic acid, ethyl ester; 2-[Bis-4,6-(4-Cyano-1-piperidinyl)-pyrimidin-2-ylamino]-4-methyl-thiazole-5-carboxylic acid ethyl ester; 2-[[4-[4-(Cyclopentylaminocarbonyl)-1-piperazinyl]-6-[N-methyl-N-(3-pyridinylmethyl)amino]-2-pyrimidinyl]amino]-4-methyl-5-thiazolecarboxylic acid, ethyl ester; 2-[4-(2-Methoxyethyl)-piperazin-1-yl)-6-(4-methyl-1-piperzinyl)-pyrimidin-2-ylamino]-4-methyl-thiazole-5-carboxylic acid ethyl ester; 2-[4-(4-Hydroxypiperidin-1-yl)-6-(3-carboxypiperidin-1-yl)-pyrimidin-2-ylamino]-4-methyl-thiazole-5-carboxylic acid ethyl ester; 2-[[4-[4-Methylpiperazin-1-yl]-6-[3-(acetylamino)-1-pyrrolidinyl]-2-pyrimidinyl]amino]-4-methyl-5-thiazolecarboxylic acid, ethyl ester; 2-[[4-[3-(Aminocarbonyl)-1-piperazinyl]-6-[[N-methyl-N-(3-pyridinylmethyl)]amino]-2-pyrimidinyl]amino]-4-methyl-5-thiazolecarboxylic acid, ethyl ester; 2-[[4-[2-Methyl-3-oxol-piperizinyl]-6-[4-methyl-1-piperazinyl]-2-pyrimidinyl]amino]-4-methyl-5-thiazolecarboxylic acid, ethyl ester; 2-[[4-[3-(Aminocarbonyl)-1-piperazinyl]-6-(4-methyl-1-piperazinyl)-2-pyrimidinyl]amino]-4-methyl-5-thiazolecarboxylic acid, ethyl ester; 2-[[4-[3-(Aminocarbonyl)-1-piperidinyl]-6-(4-dimethylamino-1-piperidinyl)-2-pyrimidinyl]amino]-4-methyl-5-thiazolecarboxylic acid, ethyl ester; 2-[[4-[1-piperazinyl]-6-[[N-methyl-N-(2-furylmethyl)]amino]-2-pyrimidinyl]amino]-4-methyl-5-thiazolecarboxylic acid, ethyl ester; 2-[[4-[[(4-Methoxycarbonylphenyl)methyl]amino]-6-(4-dimethyl-1-piperidinyl)-2-pyrimidinyl]amino]-4-methyl-5-thiazolecarboxylic acid, ethyl ester, trifluoroacetate (1:1); 2-[[4-[3-Oxo-1-piperazinyl]-6-[[(4-(methylsulfonylamino)phenyl)methyl]amino]-2-pyrimidinyl]amino]-4-methyl-5-thiazolecarboxylic acid, ethyl ester; 2-[[4-[3-Oxo-1-piperazinyl]-6-[[(4-(propylsulfonylamino)phenyl)methyl]amino]-2-pyrimidinyl]amino]-4-methyl-5-thiazolecarboxylic acid, ethyl ester; 2-[[4-[3-(Aminocarbonyl)-1-piperidinyl]-6-[[(3,4,5-trimethoxyphenyl)methyl]amino]-2-pyrimidinyl]amino]-4-methyl-5-thiazolecarboxylic acid, ethyl ester; 2-[Bis-4,6-(4-Hydroxy-4-methyl-1-piperidinyl)-pyrimidin-2-ylamino]-4-methyl-thiazole-5-carboxylic acid ethyl ester; 4-Methyl-2-[[4-[4-dimethylamino-1-piperidinyl]-6-[[(2-oxo-1-pyrrolidinyl)propyl]amino]-2-pyrimidinyl]amino]-5-thiazolecarboxylic acid ethyl ester; 2-[[4-[3-oxo-1-piperazinyl]-6-[[(4-(iso-propylsulfonylamino)phenyl)methyl]amino]-2-pyrimidinyl]amino]-4-methyl-5-thiazolecarboxylic acid, ethyl ester; 2-[4-(4-Hydroxypiperidin-1-yl)-6-(3-hydroxymethyl-1- piperidinyl)-pyrimidin-2-ylamino]-4-methyl-thiazole-5-carboxylic acid ethyl ester; 4-Methyl-2-[[4-[4-hydroxy-1-piperidinyl]-6-[[(2-(4-morpholinyl)ethyl]amino]-2-pyrimidinyl]amino]-5-thiazolecarboxylic acid ethyl ester; 2-[[4-[[[4-(Ethylaminosulfonyl)phenyl]methyl]amino]-6-methoxy-2-pyrimidinyl]amino]-4-methyl-5-thiazolecarboxylic acid, methyl ester, trifluoroacetate (1:1); 2-[[4-[4-Morpholinyl]-6-[(1-oxa-3,8-diazaspiro[4.5]decan-2,4, dion-8-yl]-2-pyrimidinyl]amino]-4-methyl-5-thiazolecarboxylic acid, ethyl ester; 2-[[4-[4-Hydroxy-1-piperidinyl]-6-[[(4-(ethylsulfonylamino)phenyl)methyl]amino]-2-pyrimidinyl]amino]-4-methyl-5-thiazolecarboxylic acid, ethyl ester; 2-[[4-[tertButyloxycarbonyl-1-piperazinyl]-6-[[(3,4,5-trimethoxyphenyl)methyl]amino]-2-pyrimidinyl]amino]-4-methyl-5-thiazolecarboxylic acid, ethyl ester; 2-[[4-[3-(Aminocarbonyl)-1-piperidinyl]-6-[[(3,4-dimethoxyphenyl)methyl]amino]-2-pyrimidinyl]amino]-4-methyl-5-thiazolecarboxylic acid, ethyl ester; 2-[[4-[4-ethoxycarbonyl-1-piperazinyl]-6-[[N-methyl-N-(5-tetrazolylmethyl]amino]-2-pyrimidinyl]amino]-4-methyl-5-thiazolecarboxylic acid, ethyl ester; 2-[[4-[3-oxo-1-piperizinyl]-6-[[(4-(cyclopropylsulfonylamino)phenyl)methyl]amino]-2-pyrimidinyl]amino]-4-methyl-5-thiazolecarboxylic acid, ethyl ester; 2-[[4-[4-Hydroxymethyl-1-piperidinyl]-6-[[(4-(methylsulfonylamino)phenyl)methyl]amino]-2-pyrimidinyl]amino]-4-methyl-5-thiazolecarboxylic acid, ethyl ester; 2-[4-(4-Dimethylamino-1-piperazinyl)-6-(4-tert-butyloxycarbonylamino-1-piperidinyl)-pyrimidin-2-ylamino]-4-methyl-thiazole-5-carboxylic acid ethyl ester; 2-[4-(4-Hydroxypiperidin-1-yl)-6-(4-methoxymethyl-1-piperidinyl)-pyrimidin-2-ylamino]-4-methyl-thiazole-5-carboxylic acid ethyl ester; 2-[4-(4-Hydroxypiperidin-1-yl)-6-(4-hydroxyethyl-1-piperidinyl)-pyrimidin-2-ylamino]-4-methyl-thiazole-5-carboxylic acid ethyl ester; 2-[4-(4-Hydroxypiperidin-1-yl)-6-(4-(hydroxy)-4-(3-trifluoromethylphenyl)piperidin-1-yl)-pyrimidin-2-ylamino]-4-methyl-thiazole-5-carboxylic acid ethyl ester; 2-[[4-[4-morpholinyl]-6-[4-[1-methyl-1-hydroxyethyl]-1-piperidinyl]-2-pyrimidinyl]amino]-4-methyl-5-thiazolecarboxylic acid, ethyl ester; 2-[[4-(3-oxo-1-piperizinyl]-6-[[3-pyridyl]oxy]-2-pyrimidinyl]amino]-4-methyl-5-thiazolecarboxylic acid, ethyl ester; 2-[[4-[4-Methyl-1-piperazinyl]-6-[(1,4-dioxaspiro[4.5]decan-8-yl]-2-pyrimidinyl]amino]-4-methyl-5-thiazolecarboxylic acid, ethyl ester; 2-[[4-[4-Morpholinyl]-6-[[(4-(methylsulfonylamino)phenyl)methyl]amino]-2-pyrimidinyl]amino]-4-methyl-5-thiazolecarboxylic acid, ethyl ester; 2-[[4-[3-oxo-1-piperazinyl]-6-[(1-oxa-3,8-diazospiro[4.5]decan-2,4, dion-8-yl]-2-pyrimidinyl]amino]-4-methyl-5-thiazolecarboxylic acid, ethyl ester; 2-[[4-[4-Hydroxy-1-piperidinyl]-6-[[(4-(carboxy)phenyl)methyl]amino]-2-pyrimidinyl]amino]-4-methyl-5-thiazolecarboxylic acid, ethyl ester; 2-[4-(4-Hydroxypiperidin-1-yl)-6-(4-(hydroxy)-4-(4-bromophenyl)piperidin-1-yl)-pyrimidin-2-ylamino]-4-methyl-thiazole-5-carboxylic acid ethyl ester; 2-[[4-[4-Morholinyl]-6-[[(4-ethylsulfonylamino)phenyl)methyl]amino]-2-pyrimidinyl]amino]-4-methyl-5-thiazolecarboxylic acid, ethyl ester; 2-[[4-[3-(Aminocarbonyl)-1-piperazinyl]-6-[[(3,4-dimethoxyphenyl)methyl]amino]-2-pyrimidinyl]amino]-4-methyl-5-thiazolecarboxylic acid, ethyl ester; 2-[[4-[4-Formyl-1-piperazinyl]-6-[[(3-(5-(1H)tetrazolyl)phenyl)methyl]amino]-2-pyrimidinyl]amino]-4-methyl-5-thiazolecarboxylic acid, ethyl ester; 2-[[4-[4-(Hydroxymethyl)-1-Piperidinyl]-6-[[N-methyl-N-(5-tetrazolylmethyl]amino]-2-pyrimidinyl]amino]-4-methyl-5-thiazolecarboxylic acid, ethyl ester; 2-[[4-[4-Methyl-1-piperazinyl]-6-[[(2,5-dimethyl)phenyl)methyl]amino]-2-pyrimidinyl]amino]-4-methyl-5-thiazolecarboxylic acid, ethyl ester; 2-[[4-[3-(2-oxo-1-pyrrolidinyl)propyl]amino]-6-[N-methyl-N-(3-pyridinylmethyl)amino]-2-pyrimidinyl] amino]-4-methyl-5-thiazolecarboxylic acid, ethyl ester; 2-[[4-[(1-Morpholinyl)]-6-[[N-methyl-N-(5-tetrazolylmethyl]amino]-2-pyrimidinyl]amino]-4-methyl-5-thiazolecarboxylic acid, ethyl ester; 2-[[4-[4-methyl-1-piperazinyl]-6-[4-[methylsulfonylamino]-1-piperidinyl]-2-pyrimidinyl] amino]-4-methyl-5-thiazolecarboxylic acid, ethyl ester; 2-[[4-[4-hydroxy-1-piperidinyl]-6-[[(2,5-dimethyl)phenyl)methyl]amino]-2-pyrimidinyl]amino]-4-methyl-5-thiazolecarboxylic acid, ethyl ester; 4-Methyl-2-[[4-(4-morpholinyl)-6-[[(3,4,5-trimethoxyphenyl)methyl]amino]-2-pyrimidinyl]amino]-5-thiazolecarboxylic acid, ethyl ester; 2-[4-(4-Hydroxypiperidin-1-yl)-6-(3-hydroxy-1-piperidinyl)-pyrimidin-2-ylamino]-4-methyl-thiazole-5-carboxylic acid ethyl ester; 4-Methyl-2-[[4-(4-methyl-1-piperazinyl)-6-[methyl(3-pyridinylmethyl)amino]-2-pyrimidinyl]amino]-5-thiazolecarboxylic acid, ethyl ester; 2-[[4-[3-Oxo-1-piperazinyl]-6-[[(2-(5-(1H)tetrazolyl)phenyl)methyl]amino]-2-pyrimidinyl]amino]-4-methyl-4-thiazolecarboxylic acid, ethyl ester; 2-[[4-[(2-Furanylmethyl)amino]-6-(1-piperazinyl)-2-pyrimidinyl]amino]-4-methyl-5-thiazolecarboxylic acid, ethyl ester, trifluoroacetate (1:1); 2-[[4-[[(3,4-Dimethoxyphenyl)methyl]amino]-6-(4-morpholinyl)-2-pyrimidinyl]amino]-4-methyl-5-thiazolecarboxylic acid, ethyl ester; 4-Methyl-2-[[4-[methyl(3-pyridinylmethyl)amino]-6-[[(tetrahydro-2-furanyl)methyl]amino]-2-pyrimidinyl] amino]-5-thiazolecarboxylic acid, ethyl ester; 2-[[4-[(4-hydroxy-1-piperidinyl)]-6-[[N-methyl-N-(5-tetrazolylmethyl]amino]-2-pyrimidinyl]amino]-4-methyl-5-thiazolecarboxylic acid, ethyl ester; 2-[4-(4-Hydroxypiperidin-1-yl)-6-[(4-(hydroxy)-4-(phenylmethyl) piperidin-1-yl)]-pyrimidin-2-ylamino]-4-methyl-thiazole-5-carboxylic acid ethyl ester; 2-[4-(4-Dimethylamino-1-piperazinyl)-6-[[2-(1-morpholinyl)ethyl]amino]pyrimidin-2-ylamino]-4-methyl-thiazole-5-carboxylic acid ethyl ester; 2-[[4-[4-hydroxy-1-piperidinyl]-6-[[(3-pyridinylmethyl)]oxy]-2-pyrimidinyl]amino]-4-methyl-5-thiazolecarboxylic acid, ethyl ester; 2-[[4-[3-(Aminocarbonyl)-1-piperidinyl]-6-[[(2,6-dimethylphenyl)methyl]amino]-2-pyrimidinyl] amino]-4-methyl-5-thiazolecarboxylic acid, ethyl ester; 2-[[4-[4-hydroxy-1-piperidinyl]-6-[[(4-(methylsulfonylamino)phenyl)methyl]amino]-2-pyrimidinyl]amino]-4-methyl-5-thiazolecarboxylic acid, ethyl ester; 2-[[4-[4-hydroxy-1-piperidinyl]-6-[[(4-(propylsulfonylamino)phenyl)methyl]amino]-2-pyrimidinyl]amino]-4-methyl-5-thiazolecarboxylic acid, ethyl ester; 2-[[4-[3-(Aminocarbonyl)-1-piperidinyl]-6-(4-methyl-1-piperazinyl)-2-pyrimidinyl]amino]-4-methyl-5-thiazolecarboxylic acid, ethyl ester; 2-[[4-(3,4-Dihydro-6,7-dimethoxy-2(1H)-isoquinolinyl)-6-(4-methyl-1-piperazinyl)-2-pyrimidinyl]amino]-4-methyl-5-thiazolecarboxylic acid, ethyl ester; 2-[[4-[4-Formyl-1-piperazinyl]-6-[[N-methyl-N-(5-tetrazolylmethyl]amino]-2-pyrimidinyl]amino]-4-methyl-5-thiazolecarboxylic acid, ethyl ester; 2-[[4-[[(4-Carboxyphenyl)methyl]amino]-6-[4-(hydroxymethyl)-1-piperidinyl]-2-pyrimidinyl]amino]-4-methyl-5-thiazolecarboxylic acid, ethyl ester; 2-[[4-[[(4-Carboxyphenyl)methyl]amino]-6-(4-methyl-1-piperazinyl)-2-pyrimidinyl]amino]-4-methyl-5-thiazolecarboxylic acid, ethyl ester, monohydrochloride; 4-Methyl-2-[[4-(4-methyl-1-piperazinyl)-6-[[(tetrahydro-2-furanyl)methyl]amino]-2-pyrimidinyl]amino]-5-thiazolecarboxylic acid, ethyl ester; 2-[[4-[[(4-Carboxyphenyl)methyl]amino]-6-[3-(hydroxymethyl)-1-piperidinyl]-2-pyrimidinyl]amino]-4-methyl-5- thiazole carboxylic acid, ethyl ester; 2-[[4-[[[4-[[(2-Methoxyethyl)amino]carbonyl]phenyl]methyl]amino]-6-(4-methyl-1-piperazinyl)-2-pyrimidinyl]amino]-4-methyl-5-thiazolecarboxylic acid, ethyl ester, trifluoroacetate (1:1); 2-[4,6-Bis-(1-morpholinyl)-pyrimidin-2-ylamino]-4-methyl-thiazole-5-carboxylic acid ethyl ester; 2-[[4-[3-(Aminocarbonyl)-1-piperazinyl]-6-[[N-methyl-N-(5-tetrazolylmethyl]amino]-2-pyrimidinyl]amino]-4-methyl-5-thiazolecarboxylic acid ethyl ester; 4-Methyl-2-[[4-[-methyl(3-pyridinylmethyl)amino]-6-[4-morpholinyl]-2-pyridinylmethyl]amino]-5-thiazolecarboxylic acid, ethyl ester; 2-[[4-[3-(Aminocarbonyl)-1-piperazinyl]-6-[[[4-(methoxycarbonyl)phenyl]methyl]amino]-2-pyrimidinyl]amino]-4-methyl-5-thiazolecarboxylic acid, ethyl ester; 2-[[4-Chloro-6-[(1-oxa-3,8-diazaspiro[4.5]decan-2,4-dion-8-yl]-2-pyrimidinyl]amino]-4-methyl-5-thiazolecarboxylic acid, ethyl ester; 2-[[4-[4-(Hydroxymethyl)-1-piperidinyl]-6-[[(3,4,5-trimethoxyphenyl)methyl]amino]-2-pyrimidinyl]amino]-4-methyl-5-thiazolecarboxylic acid, ethyl ester; 2-[[4-[3-(Hydroxymethyl)-1-Piperidinyl]-6-[[N-methyl-N-(5-tetrazolylmethyl]amino]-2-pyrimidinyl]amino]-4-methyl-5-thiazolecarboxylic acid, ethyl ester; 2-[[4-[3-(Hydroxymethyl)-1-pyrrolidinyl]-6-[[N-methyl-N-(5-tetrazolylmethyl]amino]-2-pyrimidinyl]amino]-4-methyl-5-thiazolecarboxylic acid, ethyl ester; 4-Methyl-2-[[4-[methyl(phenylmethyl)amino]-6-(4-methyl-1-piperazinyl)-2-pyrimidinyl]amino]-5-thiazolecarboxylic acid, ethyl ester; 2-[[4-(Dimethylamino)-6-[[[4-(methylsulfonyl)phenyl]methyl]amino]-2-pyrimidinyl]amino]-4-methyl-5-thiazolecarboxylic acid, ethyl ester; 2-[[4-[4-Hydroxy-1-piperidinyl]-6-[[(3-(5-(1H)tetrazolyl)phenyl)methyl]amino]-2-pyrimidinyl]amino]-4-methyl-5-thiazolecarboxylic acid, ethyl ester; 2-[[4-[4-hydroxymethyl-1-piperidinyl]-6-[[(4-(propylsulfonylamino)phenyl)methyl]amino]-2-pyrimidinyl]amino]-4-methyl-5-thiazolecarboxylic acid, ethyl ester; 2-[[4-[4-hydroxymethyl-1-piperidinyl]-6-[[(4-(cyclopropylsulfonylamino)phenyl)methyl]amino]-2-pyrimidinyl]amino]-4-methyl-5-thiazolecarboxylic acid, ethyl ester; 2-[[4-[3-(Hydroxymethyl)-1-piperidinyl]-6-[[(3,4,5-trimethoxyphenyl)methyl]amino]-2-pyrimidinyl]amino]-4-methyl-5-thiazolecarboxylic acid, ethyl ester; 2-[[4-[4-tetrahydropyranyl]oxy-6-[[N-[(3,4,5-trimethoxyphenyl)methyl]]-N-(methyl)amino]-2-pyrimidinyl]amino]-4-methyl-5-thiazolecarboxylic acid, ethyl ester; 2-[[4-[4-Methyl-1-piperazinyl]-6-[(4-methoxyphenyl)oxy]-2-pyrimidinyl]amino]-4-methyl-5-thiazolecarboxylic acid, ethyl ester; 4-Methyl-2-[4-(4-methyl-piperazin-1-yl)-6-[[[4-(aminosulfonyl)phenyl]methyl]amino]pyrimidin-2-ylamino]-thiazole-5-carboxylic acid ethyl ester; 2-[4-Isopropyl-6-(4-sulfamoyl-benzylamino)-pyrimidin-2-ylamino]-4-methyl-thiazole-5-carboxylic acid ethyl ester; 4-Methyl-2-[4-(4-sulfamoyl-benzylamino)-6-methyl-pyrimidin-2-ylamino]-thiazole-5-carboxylic acid ethyl ester; 4-Methyl-2-[4-(4-sulfamoyl-benzylamino)-6-hydroxymethyl-pyrimidin-2-ylamino]-thiazole-5-carboxylic acid ethyl ester; 4-Methyl-2-[4-(4-methyl-piperazin-1-yl)-6-[4-(1H-tetrazol-5-yl)-benzylamino]-pyrimidin-2-ylamino]-thiazole-5-carboxylic acid ethyl ester; 2-[4-(4-Hydroxy-piperidin-1-yl)-6-[4-(1H-tetrazol-5-yl)-benzylamino]-pyrimidin-2-ylamino]-4-methyl-thiazole-5-carboxylic acid ethyl ester; 4-Methyl-2-[4-[(tetrahydro-furan-2-ylmethyl)-amino]-6-[4-(1H-tetrazol-5-yl)-benzylamino]-pyrimidin-2-ylamino]-thiazole-5-carboxylic acid ethyl ester; 4-Methyl-2-[4-morpholin-4-yl-6-[4-(1H-tetrazol-5-yl)-benzylamino]-pyrimidin-2-ylamino]-thiazole-5-carboxylic acid ethyl ester; 2-[4-(3-Carbamoyl-piperidin-1-yl)-6-[4-(1H-tetrazol-5-yl)-benzylamino]-pyrimidin-2-ylamino])-4-methyl-thiazole-5-carboxylic acid ethyl ester; 2-[4-(4-Hydroxymethylpiperidin-1-yl)-6-[4-(1H-tetrazol-5-yl)-benzylamino]-pyrimidin-2-ylamino]-4-methyl-thiazole-5-carboxylic acid ethyl ester; 2-[4-(2-Hydroxymethyl-1-pyrrolidinyl)-6-[4-(1H-tetrazol-5-yl)-benzylamino]-pyrimidin-2-ylamino]-4-methyl-thiazole-5-carboxylic acid ethyl ester; 2-[4-(3-N,N-Diethylcarbamoyl-1-piperidinyl)-6-[4-(1H-tetrazol-5-yl)-benzylamino]-pyrimidin-2-ylamino]-4-methyl-thiazole-5-carboxylic acid ethyl ester; 2-[4-(3-Hydroxy-1-pyrrolidinyl)-6-[4-(1H-tetrazol-5-yl)-benzylamino]-pyrimidin-2-ylamino]-4-methyl-thiazole-5-carboxylic acid ethyl ester; 4-Methyl-2-[[[2-[4-morpholin-4-yl]ethyl]amino-6-[4-(1H-tetrazol-5-yl)-benzylamino]pyrimidin-2-ylamino]-thiazole-5-carboxylic acid ethyl ester; 4-Methyl-2-[[[4-hydroxyl]butyl]amino-6-[4-(1H-tetrazol-5-yl)-benzylamino]-pyrimidin-2-ylamino]-thiazole-5-carboxylic acid ethyl ester; 2-[4-(4-Formyl-1-piperazinyl)-6-[4-(1H-tetrazol-5-yl)-benzylamino]-pyrimidin-2-ylamino]-4-methyl-thiazole-5-carboxylic acid ethyl ester; 2-[[4-[[(4-Chlorophenyl)methyl]amino]-6-(5-oxazolyl)-2-pyrimidinyl]amino]-4-methyl-5-thiazolecarboxylic acid ethyl ester; 2-[[4-[[(4-Aminosylfonylphenyl)methyl]amino]-6-(5-oxazolyl)-2-pyrimidinyl]amino]-4-methyl-5-thiazolecarboxylic acid ethyl ester; 2-[[4-Morpholino-6-(5-oxazolyl)-2-pyrimidinyl]amino]-4-methyl-5-thiazolecarboxylic acid ethyl ester; 2-[[4-[[(3,4-Dimethoxyphenyl)methyl]amino]-6-(5-oxazolyl)-2-pyrimidinyl]amino]-4-methyl-5-thiazolecarboxylic acid ethyl ester; 2-[[4-(1,4-Dioxa-8-aza-spiro[4.5]dec-8-yl)-6-(5-oxazoly)-2-pyrimidinyl]amino]-4-methyl-5-thiazolecarboxylic acid ethyl ester; 2-[[4-[4-Hydroxy-4-phenyl-piperidinyl]-6-(5-oxazolyl)-2-pyrimidinyl]amino]-4-methyl-5-thiazolecarboxylic acid ethyl ester; 2-[[4-[[(4-Methylsulfonylphenyl)methyl]amino]-6-(5-oxazolyl)-2-pyrimidinyl]amino]-4-methyl-5-thiazolecarboxylic acid ethyl ester; 2-[[4-[4-Hydroxy-piperidinyl]-6-(5-oxazolyl)-2-pyrimidinyl]amino]-4-methyl-5-thiazolecarboxylic acid ethyl ester; 2-[[4-[4-Ethoxycarbonyl-piperidinyl]-6-(5-oxazolyl)-2-pyrimidinyl]amino]-4-methyl-5-thiazolecarboxylic acid ethyl ester; 2-[[4-Piperidinyl-6-(5-oxazolyl)-2-pyrimidinyl]amino]-4-methyl-5-thiazolecarboxylic acid ethyl ester; 2-[[4-[N-Methylpiperazinyl-6-(5-oxazolyl)-2-pyrimidinyl]amino]-4-methyl-5-thiazolecarboxylic acid ethyl ester; 2-[[4-[N-(2-Furylcarbonyl)piperazinyl-6-(5-oxazolyl)-2-pyrimidinyl]amino]-4-methyl-5-thiazolecarboxylic acid ethyl ester; 2-[[4-[N-Acetyl-[1,4-d]azepyl]-6-(5-oxazolyl)-2-pyrimidinyl]amino]-4-methyl-5-thiazolecarboxylic acid ethyl ester; 2-[[4-[N-Methyl-N—(N-methyl-4-piperidinyl)-amino]-6-(5-oxazolyl)-2-pyrimidinyl]amino]-4-methyl-5-thiazolecarboxylic acid ethyl ester; 2-[[4-[N-Methyl-[1,4]-diazepyl]-6-(5-oxazolyl)-2-pyrimidinyl]amino]-4-methyl-5-thiazole carboxylic acid ethyl ester; 2-[[4-N,N-Dimethoxyethylamino-6-(5-oxazolyl)-2-pyrimidinyl]amino]-4-methyl-5-thiazolecarboxylic acid ethyl ester; 2-[[4-[(1',4)-Bipiperidinyl]-6-(5-oxazolyl)-2-pyrimidinyl]amino]-4-methyl-5-thiazolecarboxylic acid ethyl ester; 2-[4-(4-Hydroxy-piperidin-1-yl)-6-(3,4,5-trimethoxy-phenyl)-pyrimidin-2-ylamino]-4-methylthiazole-5-carboxylic acid ethyl ester; 2-[(4-(4-Hydroxy-piperidin-1-yl)-6-[4-(1H-tetrazol-5-yl)-phenyl]-pyrimidin-2-ylamino]-4-methylthiazole-5-carboxylic acid ethyl ester; 2-[4-(4-Hydroxy-piperidin-1-yl)-6-pyridin-3-yl-pyrimidin-2-ylamino]-4-methylthiazole-5-carboxylic acid ethyl ester; 2-[4-(4-Methanesulfonyl-benzylamino)-6-pyridin-3-yl-pyrimidin-2-ylamino]-4-methylthiazole-5-carboxylic acid ethyl ester; 2-[4-(4-Hydroxy-piperidin-1-yl)-6-pyrimidin-4-yl-pyrimidin-2- ylamino]-4-methylthiazole-5-carboxylic acid ethyl ester; 2-[4-(4-Cyano-phenyl)-6-(4-hydroxy-piperidin-1-yl)-pyrimidin-2-ylamino]-4-methylthiazole-5-carboxylic acid ethyl ester; 2-[4-(4-Acetyl-phenyl)-6-(4-hydroxy-piperidin-1-yl)-pyrimidin-2-ylamino]-4-methylthiazole-5-carboxylic acid ethyl ester; 2-[4-(4-Hydroxymethyl-phenyl)-6-(4-hydroxy-piperidin-1-yl)-pyrimidin-2-ylamino]-4-methylthiazole-5-carboxylic acid ethyl ester; 2-[4-(4-Hydroxy-phenyl)-6-(4-hydroxy-piperidin-1-yl)-pyrimidin-2-ylamino]-4-methylthiazole-5-carboxylic acid ethyl ester; 2-[4-(4-Methanesulfonyl-benzylamino)-6-(3,4,5-trimethoxy-phenyl)-pyrimidin-2-ylamino]-4-methylthiazole-5-carboxylic acid ethyl ester; 2-[4-(4-Methanesulflnylphenyl)-6-(4-hydroxypiperidin-1-yl)-pyrimidin-2-ylamino]-4-methylthiazole-5-carboxylic acid ethyl ester; 2-[4-(4-(Amino)phenyl)-6-(4-hydroxy-piperidin-1-yl)-pyrimidin-2-ylamino]-4-methylthiazole-5-carboxylic acid ethyl ester; 2-[4-(4-Carboxymethyl-phenyl)-6-(4-hydroxy-piperidin-1-yl)-pyrimidin-2-ylamino]-4-methylthiazole-5-carboxylic acid ethyl ester; 2-[4-(4-(Trifluoromethylcarbonylamino)phenyl)-6-(4-hydroxy-piperidin-1-yl)-pyrimidin-2-ylamino]-4-methylthiazole-5-carboxylic acid ethyl ester; 2-[4-(4-(Ethoxycarbonylmethyl)phenyl)-6-(4-hydroxy-piperidin-1-yl)-pyrimidin-2-ylamino]-4-methylthiazole-5-carboxylic acid ethyl ester; 2-[4-(1,2,3,6-Tetrahydropyridin-4-yl)-6-(4-hydroxy-piperidin-1-yl)-pyrimidin-2-ylamino]-4-methylthiazole-5-carboxylic acid ethyl ester; 2-[4-(3-(cyano)phenyl)-6-(4-hydroxy-piperidin-1-yl)-pyrimidin-2-ylamino]-4-methylthiazole-5-carboxylic acid ethyl ester; 2-[4-(4-(Methoxycarbonyl)phenyl)-6-(4-hydroxy-piperidin-1-yl)-pyrimidin-2-ylamino]-4-methylthiazole-5-carboxylic acid ethyl ester; 2-[4-(2-(Methoxy)-5-pyridinyl)-6-(4-hydroxy-piperidin-1-yl)-pyrimidin-2-ylamino]-4-methylthiazole-5-carboxylic acid ethyl ester; 2-[4-(4-tertButyloxycarbonyl-1,2,3,6-Tetrahydropyridin-4-yl)-6-(4-hydroxy-piperidin-1-yl)-pyrimidin-2-ylamino]-4-methylthiazole-5-carboxylic acid ethyl ester; 2-[4-(1,4-Dioxaspiro[4.5]dec-7-en-8-yl)-6-(4-hydroxy-piperidin-1-yl)-pyrimidin-2-ylamino]-4-methylthiazole-5-carboxylic acid ethyl ester; 2-[4-(4-Methyl-1-piperazin-yl)-6-(3,4,5-trimethoxy-phenyl)-pyrimidin-2-ylamino]-4-methylthiazole-5-carboxylic acid ethyl ester; 2-[4-(4-Morpholinyl)-6-(3,4,5-trimethoxy-phenyl)-pyrimidin-2-ylamino]-4-methylthiazole-5-carboxylic acid ethyl ester; 2-[4-(4-Morpholinyl)-6-(3-pyridinyl)-pyrimidin-2-ylamino]-4-methylthiazole-5-carboxylic acid ethyl ester; 2-[4-(Piperadin-4-yl)-6-(4-hydroxy-piperidin-1-yl)-pyrimidin-2-ylamino]-4-methylthiazole-5-carboxylic acid ethyl ester; 2-[[4-[4-Hydroxy-piperidinyl]-6-(3,5-dimethyl-4-isoxazolyl)-2-pyrimidinyl]amino]-4-methyl-5-thiazolecarboxylic acid ethyl ester; 2-[4-(4-tert-Butoxycarbonylamino-phenyl)-6-(4-hydroxy-piperidin-1-yl)-pyrimidin-2-ylamino]-4-methyl-5-thiazolecarboxylic acid ethyl ester; 2-[4-(4-Cyano-phenyl)-6-(4-methanesulfonyl-benzylamino)-pyrimidin-2-ylamino]-4-methyl-5-thiazolecarboxylic acid ethyl ester; 2-[4-(4-Methanesulfonylphenyl)-6-(4-hydroxypiperidin-1-yl)-pyrimidin-2-ylamino]-4-methylthiazole-5-carboxylic acid ethyl ester; 2-[4-(4-Methanesulfanylphenyl)-6-(4-hydroxypiperidin-1-yl)-pyrimidin-2-ylamino]-4-methylthiazole-5-carboxylic acid ethyl ester; 2-[4-(4-Carboxy-phenyl)-6-(4-hydroxy-piperidin-1-yl)-pyrimidin-2-ylamino]-4-methyl-thiazole-5-carboxylic acid ethyl ester; 2-[4-(4-Carboxy-phenyl)-6-(3-oxo-piperazin-1-yl)-pyrimidin-2-ylamino]-4-methylthiazole-5-carboxylic acid ethyl ester; 2-[4-(4-Carboxy-phenyl)-6-(4-methyl-piperazin-1-yl)-pyrimidin-2-ylamino]-4-methylthiazole-5-carboxylic acid ethyl ester; 2-[4-(4-Carboxy-phenyl)-6-morpholin-4-yl-pyrimidin-2-ylamino]-4-methylthiazole-5-carboxylic acid ethyl ester; 2-[4-(4-Carboxy-phenyl)-6-(4-methyl-[1,4]diazepan-1-yl)-pyrimidin-2-ylamino]-4-methylthiazole-5-carboxylic acid ethyl ester; 2-[4-(4-Carboxy-phenyl)-6-(3-R-hydroxy-piperidin-1-yl)-pyrimidin-2-ylamino]-4-methylthiazole-5-carboxylic acid ethyl ester; 2-[4-(4-Carboxy-phenyl)-6-(3-hydroxymethyl-piperidin-1-yl)-pyrimidin-2-ylamino]-4-methylthiazole-5-carboxylic acid ethyl ester; 2-[4-(4-Acetyl-[1,4]diazepan-1-yl)-6-(4-carboxy-phenyl)-pyrimidin-2-ylamino]-4-methylthiazole-5-carboxylic acid ethyl ester; 2-[4-(4-Carboxy-phenyl)-6-[N-methyl-N-(1-N-methyl-piperidin-4-yl)-amino]-pyrimidin-2-ylamino]-4-methylthiazole-5-carboxylic acid ethyl ester; 2-[4-(4-Carboxy-phenyl)-6-piperazin-1-yl-pyrimidin-2-ylamino]-4-methylthiazole-5-carboxylic acid ethyl ester; 2-[4-(4-Carboxy-phenyl)-6-(4-sulfamoyl-benzylamino)-pyrimidin-2-ylamino]-4-methylthiazole-5-carboxylic acid ethyl ester; 2-[[4-[[5-Allyl[4-(aminosulfonyl)phenyl]methyl]amino]-6-chloro-2-pyrimidinyl]amino]-4-methyl-5-thiazolecarboxylic acid, ethyl ester; 2-[[4-[[[4-(Aminosulfonyl)phenyl]methyl]amino]-5-methyl-6-(1-piperazinyl)-2-pyrimidinyl]amino]-4-methyl-5-thiazolecarboxylic acid, ethyl ester, trifluoroacetate (1:3); 2-[[4-[[[4-(Aminosulfonyl)phenyl]methyl]amino]-5-methyl-6-(4-morpholinyl)-2-pyrimidinyl]amino]-4-methyl-5-thiazolecarboxylic acid, ethyl ester; 2-[[4-[[5-Allyl[4-(aminosulfonyl)phenyl]methyl]amino]-6-(4-methylpiperazinyl)-2-pyrimidinyl]amino]-4-methyl-5-thiazolecarboxylic acid, ethyl ester; 2-[[4-[[5-[2-[2-Methylprop-3-en]]-4-[4-(aminosulfonyl)phenyl]methyl]amino]-6-(4-methylpiperazinyl)-2-pyrimidinyl]amino]-4-methyl-5-thiazolecarboxylic acid, ethyl ester; 2-[[4-[[[(3,4,5-(Trimethoxy)phenyl]methyl]amino]-5-methyl-6-(1-piperazinyl)-2-pyrimidinyl]amino]-4-methyl-5-thiazolecarboxylic acid, ethyl ester, trifluoroacetate; 2-[[4-[[5-[2,3-propandiol][4-(aminosulfonyl)phenyl]methyl]amino]-6-(4-methylpiperazinyl)-2-pyrimidinyl]amino]-4-methyl-5-thiazolecarboxylic acid, ethyl ester; 2-[[4-[[[3,4,5-(Trimethoxy)phenyl]methyl]amino]-5-methyl-6-(4-methyl-1-piperazinyl)-2-pyrimidinyl]amino]-4-methyl-5-thiazolecarboxylic acid, ethyl ester, trifluoroacetate; 2-[[4-[[5-[2-[2-Methylprop-3-en]]-4-[4-(aminosulfonyl)phenyl]methyl]amino]-6-chloro-2-pyrimidinyl]amino]-4-methyl-5-thiazolecarboxylic acid, ethyl ester; 2-[[4-[[[4-(Aminosulfonyl)phenyl]methyl]amino]-5-methyl-6-(4-tertbutyloxycarbonyl-1-piperazinyl)-2-pyrimidinyl]amino]-4-methyl-5-thiazolecarboxylic acid, ethyl ester; 2-[[4-[N-[[3,4,5-(Trimethoxy)phenyl]methyl]-N-methylamino]-5-methyl-6-(4-methyl-1-piperazinyl)-2-pyrimidinyl]amino]-4-methyl-5-thiazolecarboxylic acid, ethyl ester; 2-[4,6-Bis-(4-hydroxy-piperidin-1-yl)-5-methylpyrimidin-2-ylamino]-4-methyl-thiazole-5-carboxylic acid ethyl ester; 2-[4,6-Bis-(3-oxo-piperazin-1-yl)-5-[ethoxycarbonylmethyl]pyrimidin-2-ylamino]-4-methyl-thiazole-5-carboxylic acid ethyl ester; 2-[4,6-Bis-(4-hydroxy-piperidin-1-yl)-5-methoxypyrimidin-2-ylamino]-4-methyl-thiazole-5-carboxylic acid ethyl ester; 2-[[4-[N-[[3,4,5-(Trimethoxy)phenyl]methyl]-N-methylamino]-5-methoxy-6-(4-methyl-1-piperazinyl)-2-pyrimidinyl]amino]-4-methyl-5-thiazolecarboxylic acid, ethyl ester; 2-[[4-[[3-pyridyl]methyloxy]-5-(2-propenyl-6-(4-morpholinyl)-2-pyrimidinyl]amino]-4-methyl-5-thiazolecarboxylic acid, ethyl ester; 2-[(4-Ethoxycarbonylmethyl-6-morpholin-4-yl-pyrimidin-2-yl)-amino]-4-methyl-5-thiazolecarboxylic acid ethyl ester; 2-[(4-Ethoxycarbonylmethyl-6-[3-oxo-1-piperazinyl]-pyrimidin-2-yl)-amino]-4-methyl-5-thiazolecarboxylic acid ethyl ester; 2-[(4-Carboxymethyl-6-morpholin-4-yl-pyrimidin-2-yl)-amino]-4-methyl-5-thiazolecarboxylic acid; 2-[4-Morpholin-4-yl-6-[(3,4,5-trimethoxy-phenylcarbamoyl)-methyl]-pyrimidin-2-ylamino]-4-methyl-5-thiazolecarboxylic acid ethyl ester; 2-[[4-[2-oxo-2-(3-oxo-piperazin-1-yl)-ethyl]-6-(4-sulfamoyl-benzylamino)-2-pyrimidinyl]amino]-4-methyl-5-thiazolecarboxylic acid ethyl ester; 2-[[4-(4-sulfamoyl-benzylamino)-6-[(4-sulfamoyl-benzylcarbamoyl)-methyl]-2-pyrimidinyl]amino]-4-methyl-5-thiazolecarboxylic acid ethyl ester; 2-[4-[2-(1,4-Dioxa-8-aza-spiro[4.5]dec-8-yl)-2-oxo-ethyl]-6-(4-sulfamoyl-benzylamino)-2-pyrimidinyl]amino]-4-methyl-5-thiazolecarboxylic acid ethyl ester; 2-[[4-[[(4-Chlorophenyl)-methyl-carbamoyl]-methyl]-6-(4-sulfamoyl-benzylamino)2-pyrimidinyl]amino]-4-methyl-5-thiazolecarboxylic acid ethyl ester; 2-[[4-[2-(4-Hydroxy-piperidin-1-yl)-2-oxo-ethyl]-6-(4-sulfamoyl-benzylamino)-2-pyrimidinyl]amino]-4-methyl-5-thiazolecarboxylic acid ethyl ester; 2-[[4-[2-(4-Ethoxycarbonyl-piperidin-1-yl)-2-oxo-ethyl]-6-(4-sulfamoyl-benzylamino)-2-pyrimidinyl]amino]-4-methyl-5-thiazolecarboxylic acid ethyl ester; 2-[[4-(2-oxo-2-piperidin-1-yl-ethyl)-6-(4-sulfamoyl-benzylamino)$_2$-pyrimidinyl]amino]-4-methyl-5-thiazolecarboxylic acid ethyl ester; 2-[[4-[2-[4-(Furan-2-carbonyl)-piperazin-1-yl]-2-oxo-ethyl]-6-(4-sulfamoyl-benzylamino)2-pyrimidinyl]amino]-4-methyl-5-thiazolecarboxylic acid ethyl ester; 2-[[4-[(Cyclohexyl-methyl-carbamoyl)-methyl]-6-(4-sulfamoyl-benzylamino)2-pyrimidinyl]amino]-4-methyl-5-thiazolecarboxylic acid ethyl ester; 2-[[4-[2-(4-Acetyl-[1,4]diazepan-1-yl)-2-oxo-ethyl]-6-(4-sulfamoyl-benzylamino)-2-pyrimidinyl]amino]-4-methyl-5-thiazolecarboxylic acid ethyl ester; 2-[[4-[[Methyl-(1-methyl-piperidin-4-yl)-carbamoyl]-methyl]-6-(4-sulfamoyl-benzylamino)-2-pyrimidinyl]amino]-4-methyl-5-thiazolecarboxylic acid ethyl ester; 2-[[4-[2-(4-methyl-[1,4]diazepan-1-yl)-2-oxo-ethyl]-6-(4-sulfamoyl-benzylamino)-2-pyrimidinyl]amino]-4-methyl-5-thiazolecarboxylic acid ethyl ester; 2-[[4-[[Bis-(2-methoxy-ethyl)-carbamoyl]-methyl]-6-(4-sulfamoyl-benzylamino)-2-pyrimidinyl]amino]-4-methyl-5-thiazolecarboxylic acid ethyl ester; 2-[[4-(2-[1,4']Bipiperidinyl-1'-yl-2-oxo-ethyl)-6-(4-sulfamoyl-benzylamino)-2-pyrimidinyl]amino]-4-methyl-5-thiazolecarboxylic acid ethyl ester; 2-[[4-[2-(4-Hydroxy-4-phenyl-piperidin-1-yl)-2-oxo-ethyl]-6-(4-sulfamoyl-benzylamino)-2-pyrimidinyl]amino]-4-methyl-5-thiazolecarboxylic acid ethyl ester; 2-[[4-Ethoxycarbonyl-6-(4-sulfamoyl-benzylamino)-2-pyrimidinyl]amino]-4-methyl-5-thiazolecarboxylic acid ethyl ester; 2-[[4-Carboxyl-6-(4-sulfamoyl-benzylamino)-2-pyrimidinyl]amino]-4-methyl-5-thiazolecarboxylic acid ethyl ester; 2-[[4-(Carboxymethyl-carbamoyl)-6-(4-sulfamoyl-benzylamino)-2-pyrimidinyl]amino]-4-methyl-5-thiazolecarboxylic acid ethyl ester; 2-[4-(4-Hydroxy-piperidin-1-yl)-6-(4-methylsulfanyl-benzyl)-pyrimidin-2-ylamino]-4-methyl-5-thiazolecarboxylic acid ethyl ester; 2-[4-(4-Hydroxy-piperidin-1-yl)-6-(4-methanesulfinyl-benzyl)-pyrimidin-2-ylamino]-4-methyl-5-thiazolecarboxylic acid ethyl ester; 2-[[4-(4-Hydroxy-piperidin-1-yl)-6-(4-methanesulfonyl-benzyl)-2-pyrimidinyl]amino]-4-methyl-5-thiazole carboxylic acid ethyl ester; 2-[[4-[4-methyl-1-piperazinyl]-6-[N-methyl-N-[(3,4,5-trimethoxyphenyl)methyl]amino]-2-pyrimidinyl]amino]-4-trifluoromethyl-5-thiazolecarboxylic acid, ethyl ester; 2-[[4-[4-Methylpiperazin-1-yl]-6-(N-methyl-N-[[(3,4,5-trimethoxyphenyl)methyl]amino]-2-pyrimidinyl]amino]-4-methyl-5-cyanothiazole; 2-[[4-[4-Methylpiperazin-1-yl]-6-methyl-6-[[(3,4,5-trimethoxyphenyl)methyl]amino]-2-pyrimidinyl]amino]-4-methyl-5-thiazolecarboxylic acid, 2-methoxyethyl ester; 2-[[4-[4-Hydroxy-piperidin-1-yl]-6-[N-methyl[[N-[(3,4,5-trimethoxyphenyl)methyl][-N-methyl]amino]-2-pyrimidinyl]amino]-4-methyl-5-thiazolecarboxylic acid, butyl ester; 2-[[4-[1-morpholinyl]-6-[[2-[1-morpholinyl]ethyl]amino]-2-pyrimidinyl]amino]-4-methyl-5-thiazolecarboxylic acid, butyl ester; 2-[[4-[4-methyl-1-piperazinyl]-6-[[N-[(3,4,5-trimethoxyphenyl)methyl]]-N-(methyl)amino]-2-pyrimidinyl]amino]-4-isopropyl-5-thiazolecarboxylic acid, ethyl ester; 2-[[4-[4-methyl-1-piperazinyl]-6-[[N-[(3,4,5-trimethoxyphenyl)methyl]]-N-(methyl)amino]-2-pyrimidinyl]amino]-4-methyl-5-thiazolecarboxylic acid, methyl amide; 2-[4-[4-(2-Diisopropylamino-ethylcarbamoyl)-phenyl]-6-(4-hydroxy-piperidin-1-yl)-pyrimidin-2-ylamino]-4-methyl-5-thiazolecarboxylic acid ethyl ester; 2-[4-[4-(3-Dimethylamino-propylcarbamoyl)-phenyl]-6-(4-hydroxy-piperidin-1-yl)-pyrimidin-2-ylamino]-4-methyl-5-thiazolecarboxylic acid ethyl ester; 2-[4-[4-(Cyclohexylmethylcarbamoyl)-phenyl]-6-(4-hydroxy-piperidin-1-yl)-pyrimidin-2-ylamino]-4-methyl-5-thiazolecarboxylic acid ethyl ester; 2-[4-[4-(Pyridin-4-ylmethylcarbamoyl)-phenyl]-6-(4-hydroxy-piperidin-1-yl)-pyrimidin-2-ylamino]-4-methyl-5-thiazolecarboxylic acid ethyl ester; 2-[4-[4-(Isobutylcarbomoyl)-phenyl]-6-(4-hydroxy-piperidin-1-yl)-pyrimidin-2-ylamino]-4-methyl-5-thiazole carboxylic acid ethyl ester; 2-[4-[4-(N-Cyclohexyl-N-methylcarbamoyl)-phenyl]-6-(4-hydroxy-piperidin-1-yl)-pyrimidin-2-ylamino]-4-methyl-5-thiazolecarboxylic acid ethyl ester; 2-[4-[4-(N-Cyclopropylmethyl-N-propylcarbamoyl)-phenyl]-6-(4-hydroxy-piperidin-1-yl)-pyrimidin-2-ylamino]-4-methyl-5-thiazolecarboxylic acid ethyl ester; 2-[4-[4-(4-Ethoxycarbonylpyperidine-1-carbamoyl)-phenyl]-6-(4-hydroxy-piperidin-1-yl)-pyrimidin-2-ylamino]-4-methyl-5-thiazolecarboxylic acid ethyl ester; 2-[4-[4-(3-Hydroxymethyl-piperidine-1-carbonyl)-phenyl]-6-(4-hydroxy-piperidin-1-yl)-pyrimidin-2-ylamino]-4-methyl-5-thiazolecarboxylic acid ethyl ester; 2-[4-[-(N-2-Hydroxyethyl-N-ethylcarbamoyl)-phenyl]-6-(4-hydroxy-piperidin-1-yl)-pyrimidin-2-ylamino]-4-methyl-5-thiazolecarboxylic acid ethyl ester; 2-[4-[4-(Thiomorpholine-1-carbonyl)-phenyl]-6-(4-hydroxy-piperidin-1-yl)-pyrimidin-2-ylamino]-4-methyl-5-thiazolecarboxylic acid ethyl ester; 2-[4-[4-(Morpholine-1-carbonyl)-phenyl]-6-(4-hydroxy-piperidin-1-yl)-pyrimidin-2-ylamino]-4-methyl-5-thiazole carboxylic acid ethyl ester; and 2-[4-[4-(4-Chloro-phenylcarbamoyl)-phenyl]-6-(4-hydroxy-piperidin-1-yl)-pyrimidin-2-ylamino]-4-methyl-5-thiazolecarboxylic acid ethyl ester; or a stereoisomer, a pharmaceutically acceptable salt, or a hydrate thereof.

In another related embodiment, PDE7 inhibitors useful in the methods of the present invention include the following compounds:

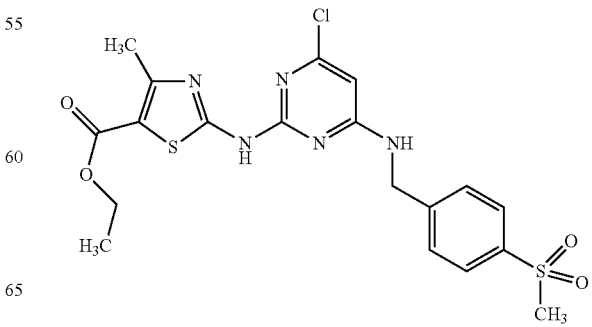

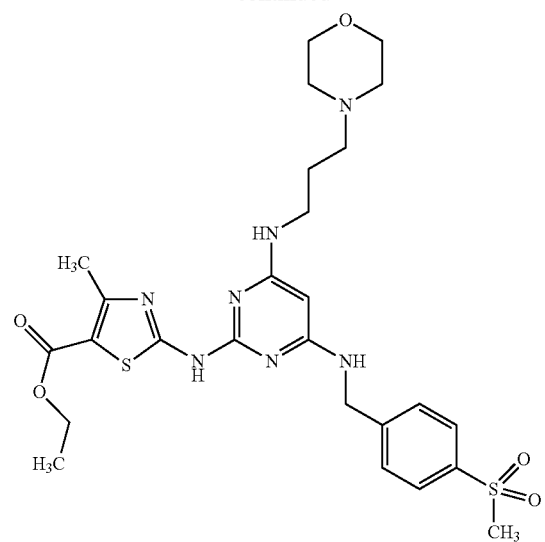
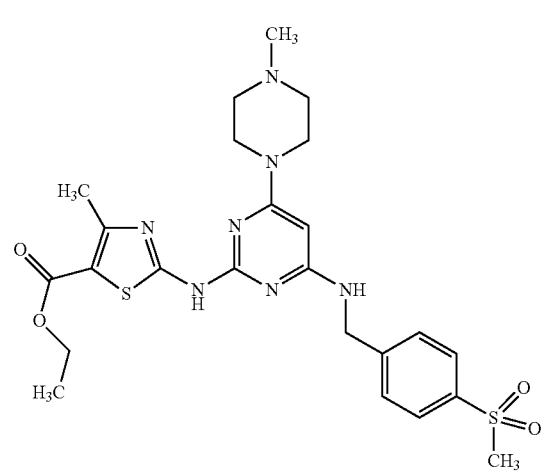
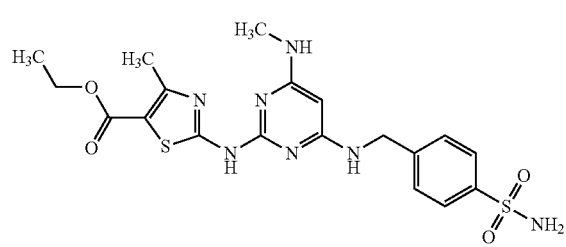
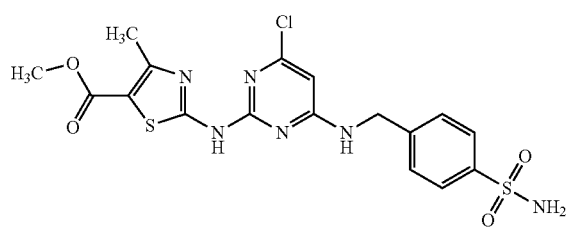
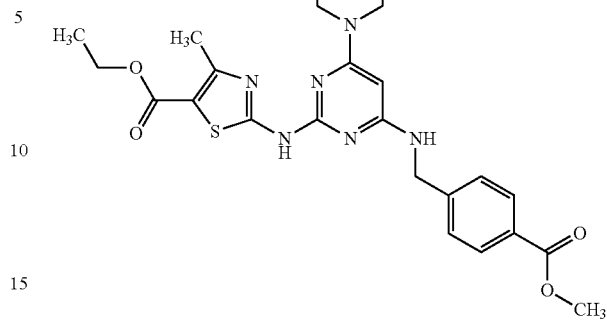
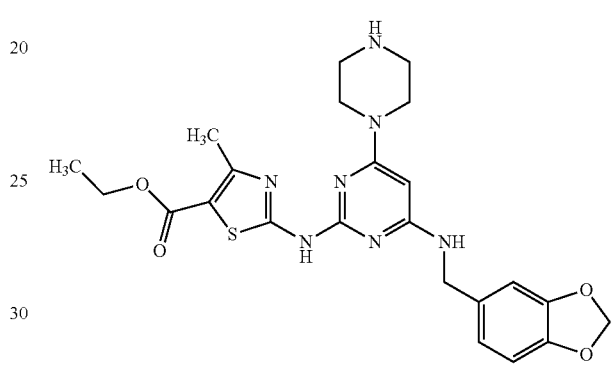
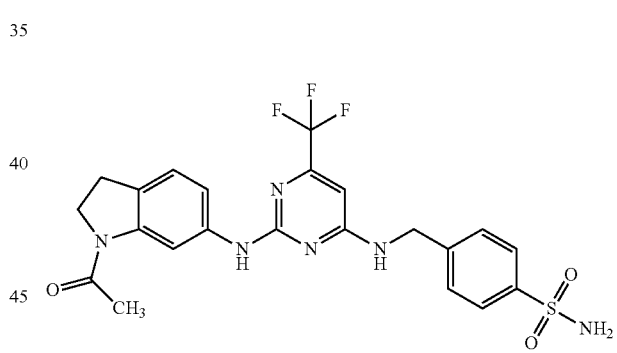
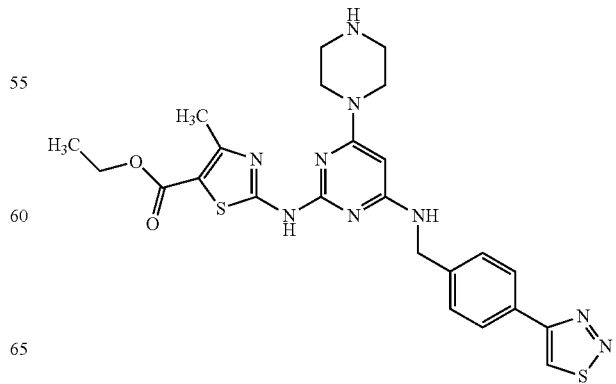

123
-continued
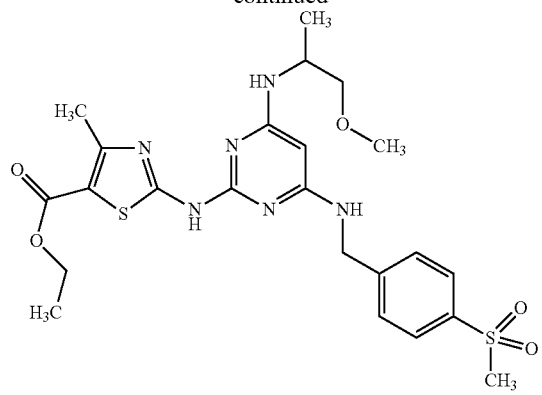
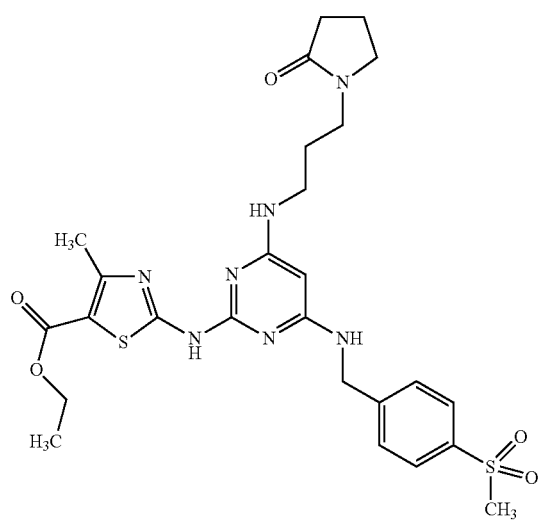
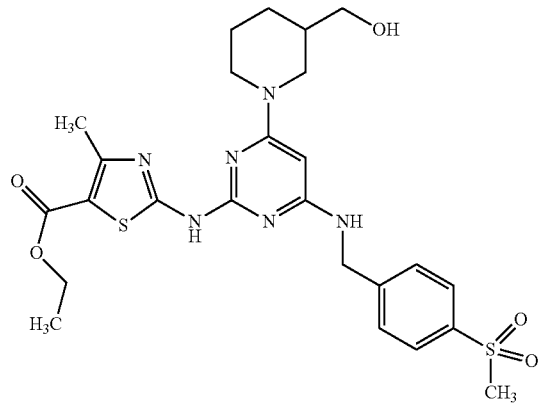
124
-continued
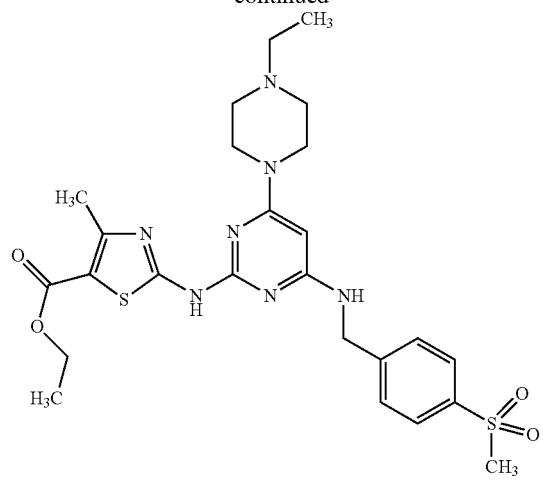

125
-continued
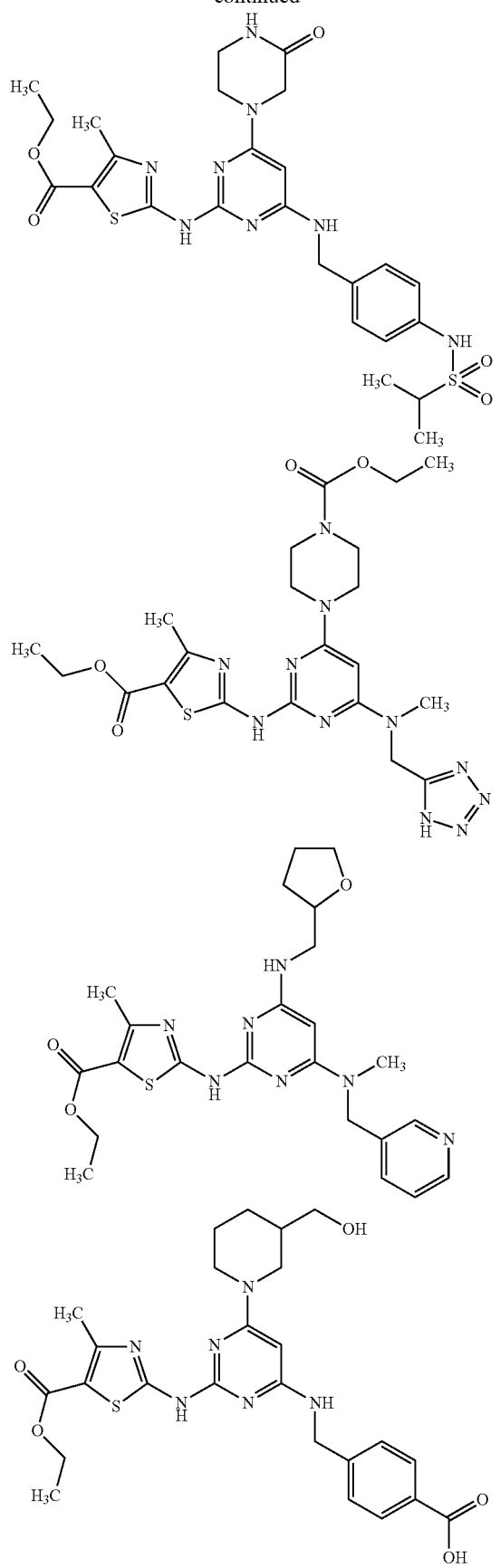
126
-continued
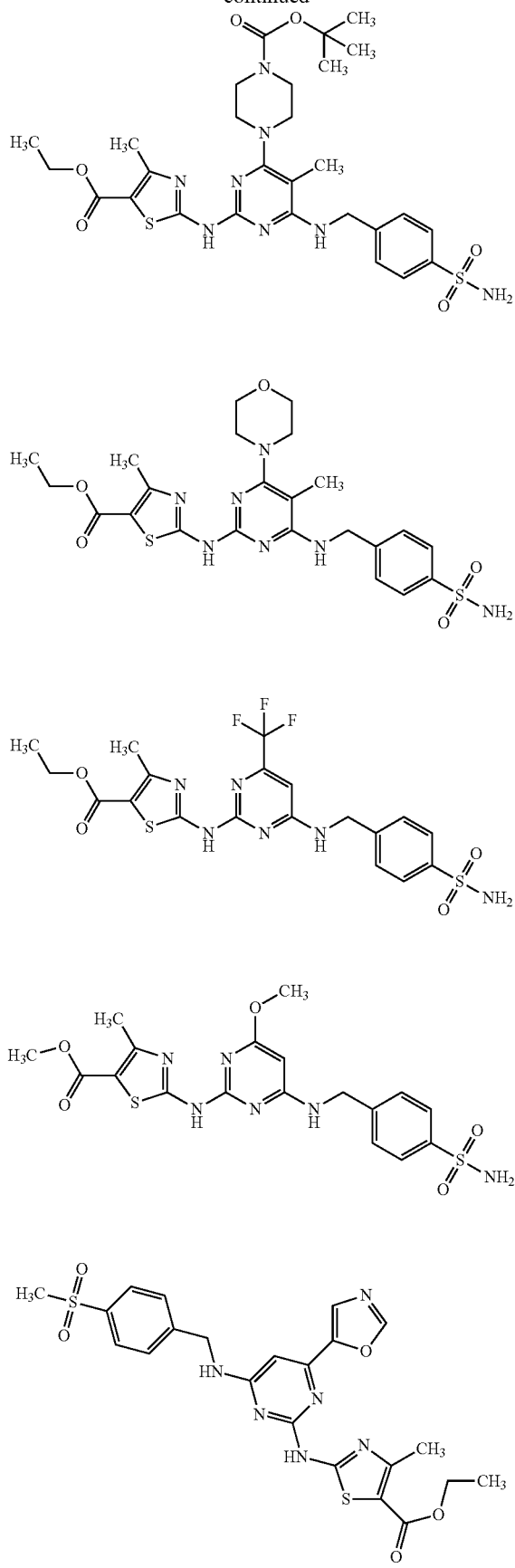

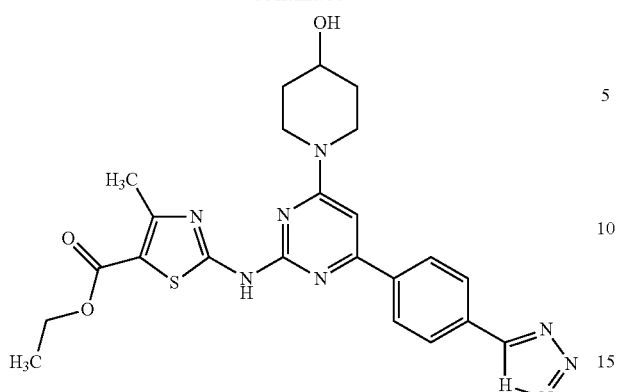

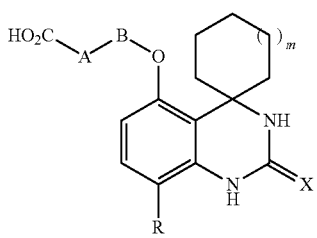

or a stereoisomer, a pharmaceutically acceptable salt, or a hydrate thereof.

The preparation of these compounds is described in U.S. Pat. No. 7,087,614, U.S. 20030162802, and WO 2002/102313.

In another embodiment, PDE7 inhibitors useful in the methods of the invention are selected from those compounds generally or specifically disclosed in US 2007/0129388 and WO 2007/063391, each expressly incorporated by reference herein in its entirety. In one embodiment, PDE7 inhibitors useful in the methods of the invention have the formula:

(44)

The substituents for the above compounds are defined as follows:

m is 0, 1 or 2; X is O, S or N—CN; R is F, Cl or CN; A is a $C_{3-6}$ cycloalkylene group optionally substituted with a $C_{1-4}$ alkyl group; and B is a single bond or a $C_{1-2}$ alkylene group; or a pharmaceutically acceptable salt, solvate, polymorph or prodrug thereof.

In regard to the above compounds, the term "alkylene" denotes a divalent saturated hydrocarbon chain having 1 or 2 carbon atoms. Examples of alkylene groups include methylene, ethylene and methylmethylene, of which methylene is preferred.

The term "cycloalkylene" denotes a divalent saturated carbocyclic ring having 3 to 6 carbon atoms. Examples of cycloalkylene groups include cyclopropylene (e.g., 1,1-cyclopropylene and cis- and trans-1,2-cyclopropylene), cyclobutylene (e.g., 1,1-cyclobutylene, cis and trans-1,2-cyclobutylene, and cis and trans-1,3-cyclobutylene), cyclopentylene (e.g., 1,1-cyclopentylene, cis and trans-1,2-cyclopentylene, and cis- and trans-1,3-cyclopentylene) and cyclohexylene (e.g., 1,1-cyclohexylene, cis- and trans-1,2-cyclohexylene, cis- and trans-1,3-cyclohexylene) and cis- and trans-1,4-cyclohexylene). Preferred examples include cyclobutylene and cyclohexylene, more preferably cyclobutylene, even more preferably 1,3-cyclobutylene, and most preferably trans-1,3-cyclobutylene.

The term "alkyl" denotes a monovalent, straight or branched, saturated hydrocarbon chain containing 1 to 4 carbon atoms. Examples of alkyl groups include methyl, ethyl, n-propyl, isopropyl, n-butyl, isobutyl, sec-butyl and tert-butyl. Preferred examples include methyl and ethyl, especially methyl.

The cycloalkylene group is optionally substituted with a $C_{1-4}$ alkyl group. Preferably, the alkyl substituent, if present, is a methyl or ethyl group, more preferably a methyl group. The alkyl substituent, if present, may be present at any position on the ring, but is preferably present at the 1-position (i.e., the same position as the carboxylic acid group).

Preferably, m is 1 or 2, more preferably 1.
Preferably, X is O or N—CN, more preferably O.
Preferably, R is F or Cl, more preferably Cl.
Preferably, A is a cyclobutylene or cyclohexylene group optionally substituted with a methyl group. More preferably, A is a cyclobutylene group. Even more preferably, A is a 1,3-cyclobutylene group, especially a trans-1,3-cyclobutylene group.

Preferably, B is a single bond or a methylene group. More preferably, B is a single bond.

In another embodiment, a PDE7 inhibitor useful in the methods of the invention is selected from the following compounds:
cis-3-[(8'-Chloro-2'-oxo-2',3'-dihydro-1'H-spiro[cyclohexane-1,4'-quinazo-lin]-5'-yl)oxy]cyclobutanecarboxylic acid; trans-3-[(8'-Chloro-2'-oxo-2',3'-dihydro-1'H-spiro[cyclohexane-1,4'-quina-zolin]-5'-yl)oxy]cyclobutanecarboxylic acid; 3-[(8'-fluoro-2'-oxo-2',3'-dihydro-1'H-spiro[cyclohexane-1,4'-quinazolin]-5'-yl)oxymethyl]cyclobutanecarboxylic acid; trans-3-[(8'-cyano-2'-oxo-2',3'-dihydro-1'H-spiro[cyclohexane-1,4'-quinaz-olin]-5'-yl)oxy]cyclobutanecarboxylic acid; 1-[(8'-fluoro-2'-oxo-2',3'-dihydro-1'H-spiro[cyclohexane-1,4'-quinazolin]-5'-yl)oxymethyl]cyclobutanecarboxylic acid; trans-3-[(8'-chloro-2'-oxo-2',3'-dihydro-1'H-spiro[cycloheptyl-1,4'-quinazolin]-5'-yl)oxy]cyclobutanecarboxylic acid; and trans-3-[(8'-chloro-2'-oxo-2',3'-dihydro-1'H-spiro[cyclopentyl-1,4'-quinazolin]-5'-yl)oxy]cyclobutanecarboxylic acid; or a pharmaceutically acceptable salt, solvate, polymorph or prodrug thereof.

The preparation of the above compounds is described in US 2007/0129388 and WO 2007/063391.

In another embodiment, PDE7 inhibitors useful in the methods of the invention include the compound ASB16165 (1-Cyclohexyl-N-[6-(4-hydroxy-1-piperidinyl)-3-pyridinyl]-3-methyl-1H-thieno[2,3-c]pyrazole-5-carboxamide monohydrate) described in Kadoshima-Yamaoka, K. et al., "ASB16165, a novel inhibitor for phosphodiesterase 7A (PDE7A), suppresses IL-12-induced IFN-g production by mouse activated T lymphocytes," Immunology Letters 122: 193-197, 2009, expressly incorporated by reference herein. In one embodiment, a PDE7 inhibitor useful in the methods of the invention has the formula:

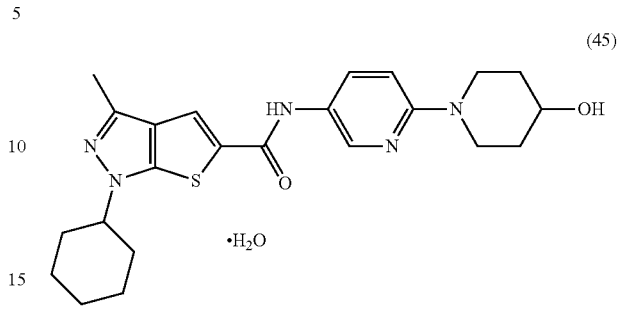

(45)

Methods for preparing the above compound are described in WO 2006/004040.

In another embodiment, PDE7 inhibitors useful in the methods of the invention include the compound YM-393059 ((±)-N-(4,6-dimethylpyrimidin-2-yl)-4-[2-(4-methoxy-3-methylphenyl)-5-(4-methylpiperazin-1-yl)-4,5,6,7-tetrahydro-1H-indol-1-yl]benzenesulfonamide difumarate) described in Yamamoto, S. et al., "The effects of a novel phosphodiesterase 7A and –4 dual inhibitor, YM-393059, on T-cell-related cytokine production in vitro and in vivo." *European Journal of Pharmacology* 541:106-114, 2006, expressly incorporated by reference herein in its entirety. In one embodiment, PDE7 inhibitors useful in the methods of the invention have the formula:

(46)

In another embodiment, PDE7 inhibitors useful in the methods of the invention are selected from those compounds generally or specifically disclosed in Martinez et al., "Benzyl derivatives of 2,1,3-benzo- and benzothieno 3,2-aathiadiazine 2,2-dioxides: first phosphodiesterase 7 inhibitors," *J. Med. Chem.* 43:683-689, 2000, which is expressly incorporated herein by reference in its entirety. In one embodiment, PDE7 inhibitors useful in the methods of the invention include the following compounds:
1-[(4-Methoxyphenyl)carbonylmethyl]benzothieno-[3,2-a]-1,2,6-thiadiazin-493H)-one 2,2-dioxide; and 1-[(3,4-dichlorophenyl)-methyl]-2,1,3-b enzothiadiazin-4(3H)-one 2,2 dioxide.

The preparation of the above compounds is described in *J. Med. Chem.* 43:683-689, 2000.

In another embodiment, PDE7 inhibitors useful in the methods of the invention are selected from those compounds generally or specifically disclosed in Castro, A. et al., "CODES, a novel procedure for ligand-based virtual screening: PDE7 inhibitors as an application example," *J. Med. Chem.* 43:1349-1359, 2008, which is expressly incorporated herein by reference in its entirety. In one embodiment, PDE7 inhibitors useful in the methods of the invention include the following compounds:

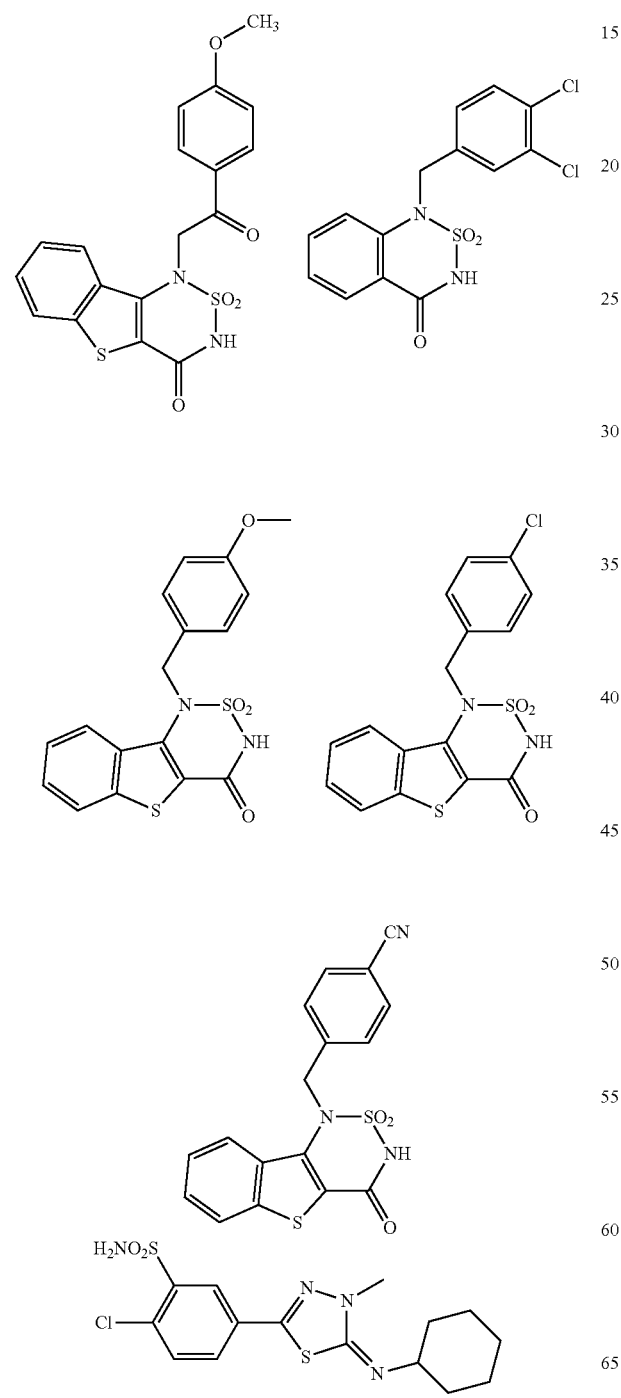

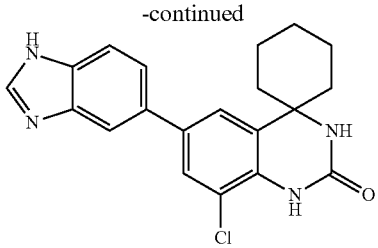

In another embodiment, PDE7 inhibitors useful in the methods of the invention have the formulas:

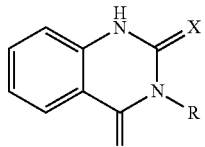
(47)

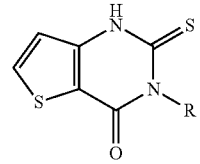
(48)

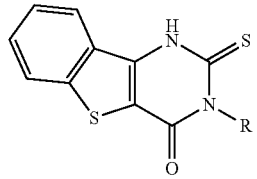
(49)

The substituents for the above compounds are defined as follows:
X=O or S,
R=H, Ph, 4-OMePh, 2,6-diFPh, 2,3,4-triFPh, 2-BrPh, Bn, Naphthyl, or Me.

In another embodiment, PDE7 inhibitors useful in the methods of the invention include the following compounds:
5.2.4. 3-(2,3,4-Trifluorophenyl)-2-thioxo-(1H)-quinazolin-4-one;
5.3.2. 3-Phenyl-2-thioxo-(1H)-thieno[3,2-d]pyrimidin-4-one;
5.3.3. 3-(2,6-Difluorophenyl)-2-thioxo-(1H)-thieno[3,2-d]pyrimidin-4-one; and
5.4.2. 3-(2,6-Difluorophenyl-2-thioxo-(1H)-benzo[4,5]-thieno[3,2-d]-pyrimidin-4-one.

The preparation of the above compounds is described in *J. Med. Chem.* 43:1349-1359, 2008.

In another embodiment, PDE7 inhibitors useful in the methods of the invention include BMS-586353, as described in Yang, G. et al., "Phosphodiesterase 7A-deficient mice have functional T cells," *J. Immunol.* 171:6414-6420, 2003, which is expressly incorporated herein by reference in its entirety.

In another embodiment, PDE7 inhibitors useful in the methods of the invention are selected from those compounds generally or specifically disclosed in Pitts, W. J. et al., "Identification of purine inhibitors of phosphodiesterase 7 (PDE7)," *Bioorg. Med. Chem. Lett.* 14:2955-2958, 2004, and Kempson, J. et al., "Fused pyrimidine based inhibitors of phosphodiesterase 7 (PDE7): synthesis and initial structure-activity relationships," *Bioorg. Med. Chem. Lett.* 15:1829-1833, 2005, each expressly incorporated herein by reference in its entirety. In one embodiment, PDE7 inhibitors useful in the methods of the invention have the formula:

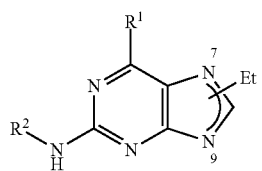
(50)

The substituents for the above compounds are defined as follows:

R1 is

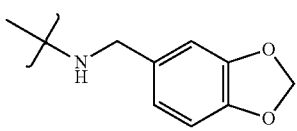

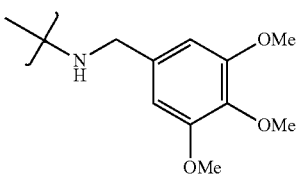

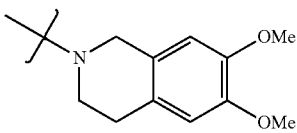

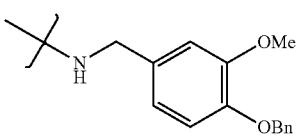

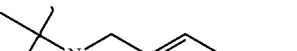

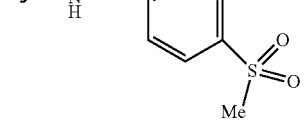

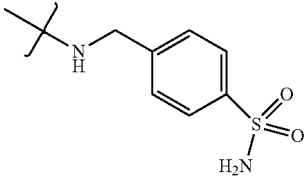

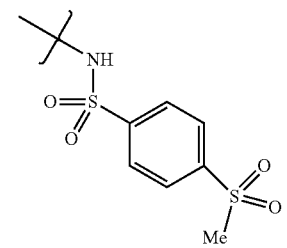

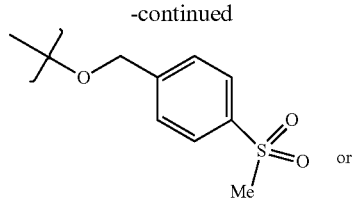 or

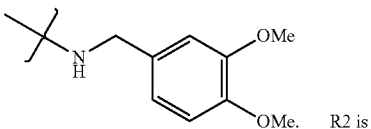 R2 is

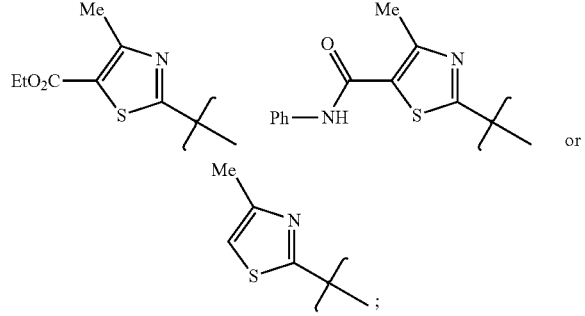

wherein the ethyl group may be attached to the 7 or 9 position.

In a related embodiment, PDE7 inhibitors useful in the methods of the invention have the formulas:

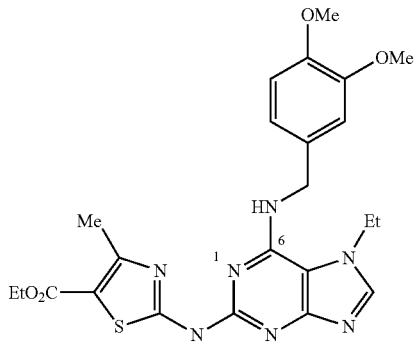

In another related embodiment, PDE7 inhibitors useful in the methods of the invention have the formula:

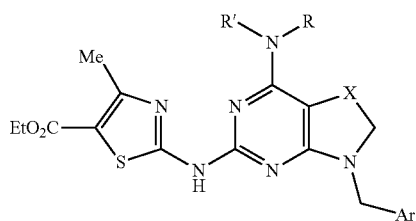

where X=CH2, CH2CH2 or OCH2;
Ar is

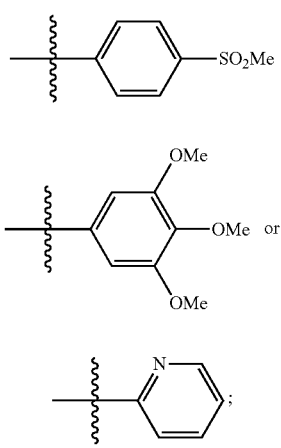

and NRR' is

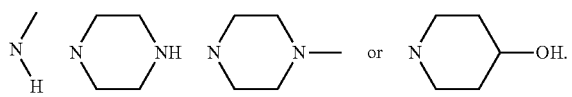

In another embodiment, PDE7 inhibitors useful in the methods of the invention are selected from those compounds generally or specifically disclosed in Kang, N. S. et al., "Docking and 3-D QSAR studies of dual PDE4-PDE7 inhibitors," *Molecular Simulation* 33:1109-1117, 2007, expressly incorporated by reference herein in its entirety. In one embodiment, PDE7 inhibitors useful in the methods of the invention include the following compounds:

(51)

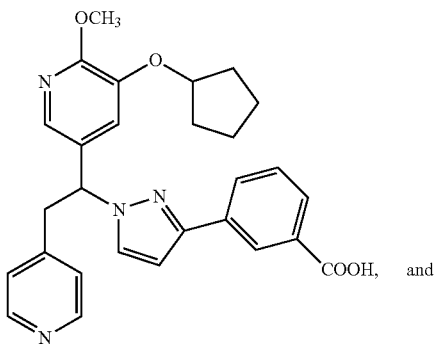

(52)

(53)

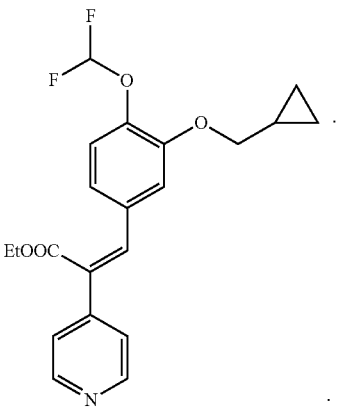

Methods for preparing the above compounds are described in *Molecular Simulation* 33:1109-1117, 2007.

Polypeptide or Peptide Inhibitors

In some embodiments, the PDE7 inhibitory agent comprises isolated PDE7 polypeptide or peptide inhibitors, including isolated natural peptide inhibitors and synthetic peptide inhibitors that inhibit PDE7 activity. As used herein, the term "isolated PDE7 polypeptide or peptide inhibitors" refers to polypeptides or peptides that inhibit PDE7 dependent cleavage of cAMP by binding to PDE7, competing with PDE7 for binding to a substrate, and/or directly interacting with PDE7 to inhibit PDE7-dependent cleavage of cAMP, that are substantially pure and are essentially free of other substances with which they may be found in nature to an extent practical and appropriate for their intended use.

Peptide inhibitors have been used successfully in vivo to interfere with protein-protein interactions and catalytic sites. For example, peptide inhibitors to adhesion molecules structurally related to LFA-1 have recently been approved for clinical use in coagulopathies (Ohman, E. M., et al., *European Heart J.* 16:50-55, 1995). Short linear peptides (<30 amino acids) have been described that prevent or interfere with integrin-dependent adhesion (Murayama, O., et al., *J. Biochem.* 120:445-51, 1996). Longer peptides, ranging in length from 25 to 200 amino acid residues, have also been used successfully to block integrin-dependent adhesion (Zhang, L., et al., *J. Biol. Chem.* 271(47):29953-57, 1996). In general, longer peptide inhibitors have higher affinities and/or slower off-rates than short peptides and may therefore be more potent inhibitors. Cyclic peptide inhibitors have also been shown to be effective inhibitors of integrins in vivo for the treatment of human inflammatory disease (Jackson, D. Y., et al., *J. Med. Chem.* 40:3359-68, 1997). One method of producing cyclic peptides involves the synthesis of peptides in which the terminal amino acids of the peptide are cysteines, thereby allowing the peptide to exist in a cyclic form by disulfide bonding between the terminal amino acids, which has been shown to improve affinity and half-life in vivo for the treatment of hematopoietic neoplasms (e.g., U.S. Pat. No. 6,649,592 to Larson).

Synthetic PDE7 Peptide Inhibitors

PDE7 inhibitory peptides useful in the methods of the invention are exemplified by amino acid sequences that mimic the target regions important for PDE7 enzyme activity, such as the catalytic domain of PDE7. PDE7A and PDE7B have an identity of 70% in the catalytic domain. (Hetman, J. M., et al., *PNAS* 97(1):472-476, 2000.) The catalytic domain of PDE7A1 is from amino acid residue 185 to 456 of SEQ ID NO:2. The catalytic domain of PDE7A2 is from amino acid residue 211 to 424 of SEQ ID NO:4. The catalytic domain of PDEB is from amino acid residue 172 to 420 of SEQ ID NO:6. The inhibitory peptides useful in the practice of the methods of the invention range in size from about 5 amino acids to about 250 amino acids. One may also use molecular modeling and rational molecular design to generate and screen for peptides that mimic the molecular structure of the PDE7 catalytic regions and inhibit the enzyme activity of PDE7. The molecular structures used for modeling include the CDR regions of anti-PDE7 monoclonal antibodies. Methods for identifying peptides that bind to a particular target are well known in the art. For example, molecular imprinting may be used for the de novo construction of macromolecular structures such as peptides that bind to a particular molecule. See, for example, Shea, K. J., "Molecular Imprinting of Synthetic Network Polymers: The De Novo Synthesis of Macromolecular Binding and Catalytic Sties," *TRIP* 2(5), 1994.

As an illustrative example, one method of preparing mimics of PDE7 binding peptides is as follows. Functional monomers of a binding region of an anti-PDE7 antibody that exhibits PDE7 inhibition (the template) are polymerized. The template is then removed, followed by polymerization of a second class of monomers in the void left by the template, to provide a new molecule that exhibits one or more desired properties that are similar to the template. In addition to preparing peptides in this manner, other PDE7 binding molecules that are PDE7 inhibitory agents, such as polysaccharides, nucleosides, drugs, nucleoproteins, lipoproteins, carbohydrates, glycoproteins, steroids, lipids, and other biologically active materials, can also be prepared. This method is useful for designing a wide variety of biological mimics that are more stable than their natural counterparts because they are typically prepared by free radical polymerization of functional monomers, resulting in a compound with a nonbiodegradable backbone.

The PDE7 inhibitory peptides can be prepared using techniques well known in the art, such as the solid-phase synthetic technique initially described by Merrifield in *J. Amer. Chem. Soc.* 85:2149-2154, 1963. Automated synthesis may be achieved, for example, using Applied Biosystems 431A Peptide Synthesizer (Foster City, Calif.) in accordance with the instructions provided by the manufacturer. Other techniques may be found, for example, in Bodanszky, M., et al., *Peptide Synthesis*, second edition, John Wiley & Sons, 1976, as well as in other reference works known to those skilled in the art. The peptides can also be prepared using standard genetic engineering techniques known to those skilled in the art.

A candidate PDE7 inhibitory peptide may be tested for the ability to function as a PDE7 inhibitory agent in one of several assays, including, for example, a PDE7 phosphodiesterase assay as described in Example 1.

Expression Inhibitors of PDE7

In some embodiments of the methods of the invention, the PDE7 inhibitory agent is a PDE7 expression inhibitor capable of inhibiting PDE7-dependent cAMP cleavage (PDE7A, PDE7B, or both). In the practice of this embodiment of the invention, representative PDE7 expression inhibitors include PDE7 antisense nucleic acid molecules (such as antisense mRNA, antisense DNA, or antisense oligonucleotides), PDE7 ribozymes, and PDE7 RNAi molecules.

Anti-sense RNA and DNA molecules act to directly block the translation of PDE7 mRNA by hybridizing to PDE7 mRNA and preventing translation of PDE7 protein. An antisense nucleic acid molecule may be constructed in a number of different ways provided that it is capable of interfering with the expression of PDE7. For example, an antisense nucleic acid molecule can be constructed by inverting the coding region (or a portion thereof) of PDE7A1 cDNA (SEQ ID NO:1), PDE7A2 cDNA (SEQ ID NO:3) or PDE7B cDNA (SEQ ID NO:5) relative to its normal orientation for transcription to allow for the transcription of its complement. Methods for designing and administering antisense oligonucleotides are well known in the art and are described, e.g., in Mautino et al., *Hum Gene Ther* 13:1027-37, 2002; and Pachori et al., *Hypertension* 39:969-75, 2002, each of which is hereby incorporated by reference.

The antisense nucleic acid molecule is usually substantially identical to at least a portion of the target gene or genes. The nucleic acid, however, need not be perfectly identical to inhibit expression. Generally, higher homology can be used to compensate for the use of a shorter antisense nucleic acid molecule. The minimal percent identity is typically greater than about 65%, but a higher percent identity may exert a more effective repression of expression of the endogenous sequence. Substantially greater percent identity of more than about 80% typically is preferred, though about 95% to absolute identity is typically most preferred.

The antisense nucleic acid molecule need not have the same intron or exon pattern as the target gene, and non-coding segments of the target gene may be equally effective in achieving antisense suppression of target gene expression as coding segments. A DNA sequence of at least about 8 or so nucleotides may be used as the antisense nucleic acid molecule, although a longer sequence is preferable. In the present invention, a representative example of a useful inhibitory agent of PDE7 is an antisense PDE7 nucleic acid molecule that is at least ninety percent identical to the complement of a portion of the PDE7A1 cDNA consisting of the nucleic acid sequence set forth in SEQ ID NO:1. Another representative example of a useful inhibitory agent of PDE7 is an antisense PDE7 nucleic acid molecule which is at least ninety percent identical to the complement of a portion of the PDE7A2 cDNA consisting of the nucleic acid sequence set forth in SEQ ID NO:3. Another representative example of a useful inhibitory agent of PDE7 is an antisense PDE7 nucleic acid molecule which is at least ninety percent identical to the complement of a portion of the PDE7B cDNA consisting of the nucleic acid sequence set forth in SEQ ID NO:5.

The targeting of antisense oligonucleotides to bind PDE7 mRNA is another mechanism that may be used to reduce the level of PDE7 protein synthesis. For example, the synthesis of polygalacturonase and the muscarine type 2 acetylcholine receptor is inhibited by antisense oligonucleotides directed to their respective mRNA sequences (U.S. Pat. No. 5,739,119 to Cheng, and U.S. Pat. No. 5,759,829 to Shewmaker). Furthermore, examples of antisense inhibition have been demonstrated with the nuclear protein cyclin, the multiple drug resistance gene (MDG1), ICAM-1, E-selectin, STK-1, striatal GABA$_A$ receptor and human EGF (see, e.g., U.S. Pat. No. 5,801,154 to Baracchini; U.S. Pat. No. 5,789,573 to Baker; U.S. Pat. No. 5,718,709 to Considine; and U.S. Pat. No. 5,610,288 to Reubenstein).

A system has been described that allows one of ordinary skill to determine which oligonucleotides are useful in the invention, which involves probing for suitable sites in the target mRNA using Rnase H cleavage as an indicator for accessibility of sequences within the transcripts. Scherr, M., et al., *Nucleic Acids Res.* 26:5079-5085, 1998; Lloyd, et al., *Nucleic Acids Res.* 29:3665-3673, 2001. A mixture of antisense oligonucleotides that are complementary to certain regions of the PDE7 transcript is added to cell extracts expressing PDE7 and hybridized in order to create an RNAseH vulnerable site. This method can be combined with computer-assisted sequence selection that can predict optimal sequence selection for antisense compositions based upon their relative ability to form dimers, hairpins, or other secondary structures that would reduce or prohibit specific binding to the target mRNA in a host cell. These secondary structure analysis and target site selection considerations may be performed using the OLIGO primer analysis software (Rychlik, I., 1997) and the BLASTN 2.0.5 algorithm software (Altschul, S. F., et al., *Nucl. Acids Res.* 25:3389-3402, 1997). The antisense compounds directed towards the target sequence preferably comprise from about 8 to about 50 nucleotides in length. Antisense oligonucleotides comprising from about 9 to about 35 or so nucleotides are particularly preferred. The inventors contemplate all oligonucleotide compositions in the range of 9 to 35 nucleotides (i.e., those of 9, 10, 11, 12, 13, 14, 15, 16, 17, 18, 19, 20, 21, 22, 23, 24, 25, 26, 27, 28, 29, 30, 31, 32, 33, 34, or 35 or so bases in length) are highly preferred for the practice of antisense oligonucleotide-based methods of the invention. Highly preferred target regions of the PDE7 mRNA are those that are at or near the AUG translation initiation codon, and those sequences that are substantially complementary to 5' regions of the mRNA, e.g., between the 0 and +10 regions of the PDE7 gene nucleotide sequence (SEQ ID NO:1, SEQ ID NO:3, SEQ ID NO:5).

The term "oligonucleotide" as used herein refers to an oligomer or polymer of ribonucleic acid (RNA) or deoxyribonucleic acid (DNA) or mimetics thereof. This term also covers those oligonucleobases composed of naturally occurring nucleotides, sugars and covalent internucleoside (backbone) linkages as well as oligonucleotides having non-naturally occurring modifications. These modifications allow one to introduce certain desirable properties that are not offered through naturally occurring oligonucleotides, such as reduced toxic properties, increased stability against nuclease degradation and enhanced cellular uptake. In illustrative embodiments, the antisense compounds of the invention differ from native DNA by the modification of the phosphodiester backbone to extend the life of the antisense oligonucleotide in which the phosphate substituents are replaced by phosphorothioates. Likewise, one or both ends of the oligonucleotide may be substituted by one or more acridine derivatives that intercalate between adjacent basepairs within a strand of nucleic acid.

Another alternative to antisense is the use of "RNA interference" (RNAi). Double-stranded RNAs (dsRNAs) can provoke gene silencing in mammals in vivo. The natural function of RNAi and co-suppression appears to be protection of the genome against invasion by mobile genetic elements such as retrotransposons and viruses that produce aberrant RNA or dsRNA in the host cell when they become active (see, e.g., Jensen, J., et al., *Nat. Genet.* 21:209-12, 1999). The double-stranded RNA molecule may be prepared by synthesizing two RNA strands capable of forming a double-stranded RNA molecule, each having a length from about 19 to 25 (e.g., 19-23 nucleotides). For example, a dsRNA molecule useful in the methods of the invention may comprise the RNA corresponding to a portion of at least one of SEQ ID NO:1, SEQ ID NO:3, SEQ ID NO:5 and its complement. Preferably, at least one strand of RNA has a 3' overhang from 1-5 nucleotides. The synthesized RNA strands are combined under conditions that form a double-stranded molecule. The RNA sequence may comprise at least an 8 nucleotide portion of SEQ ID NO:1, SEQ ID NO:3 or SEQ ID NO:5 with a total length of 25 nucleotides or less. The design of siRNA sequences for a given target is within the ordinary skill of one in the art. Commercial services are available that design siRNA sequence and guarantee at least 70% knockdown of expression (Qiagen, Valencia, Calif.). Exemplary PDE7 shRNAs and siRNAs are commercially available from Sigma-Aldrich Company (product # SHDNA_-NM_002603; SASI_Hs01_00183420 to SASI_Hs01_00010490).

The dsRNA may be administered as a pharmaceutical composition and carried out by known methods, wherein a nucleic acid is introduced into a desired target cell. Commonly used gene transfer methods include calcium phosphate, DEAE-dextran, electroporation, microinjection and viral methods. Such methods are taught in Ausubel et al., *Current Protocols in Molecular Biology*, John Wiley & Sons, Inc., 1993. Therapeutic nucleic acid molecules may be modified to cross the blood-brain barrier. For example, it has been demonstrated that a phosphorothiolate antisense oligonucleotide directed towards the Abeta midregion of amyloid precursor protein (APP) given by i.c.v. administration can reverse the learning and memory deficits in an Alzheimer mouse model. Banks W. A. et al., *Journal of Pharm. and Exp. Therapeutics,* 297(3): 1113-1121, 2001.

Ribozymes:

In some embodiments, a PDE7 inhibitory agent is a ribozyme that specifically cleaves the mRNA of a target PDE7, such as PDE7A, PDE7B or both. Ribozymes that target PDE7 may be utilized as PDE7 inhibitory agents to decrease the amount and/or biological activity of PDE7. Ribozymes are catalytic RNA molecules that can cleave nucleic acid molecules having a sequence that is completely or partially homologous to the sequence of the ribozyme. It is possible to design ribozyme transgenes that encode RNA ribozymes that specifically pair with a target RNA and cleave the phosphodiester backbone at a specific location, thereby functionally inactivating the target RNA. In carrying out this cleavage, the ribozyme is not itself altered, and is thus capable of recycling and cleaving other molecules. The inclusion of ribozyme sequences within antisense RNAs confers RNA-cleaving activity upon them, thereby increasing the activity of the antisense constructs.

Ribozymes useful in the practice of the invention typically comprise a hybridizing region of at least about nine nucleotides, which is complementary in nucleotide sequence to at least part of the target PDE7 mRNA, and a catalytic region that is adapted to cleave the target PDE7 mRNA (see generally, European patent No. 0 321 201; WO 88/04300; Haseloff, J., et al., *Nature* 334:585-591, 1988; Fedor, M. J., et al., *Proc. Natl. Acad. Sci. USA* 87:1668-1672, 1990; Cech, T. R., et al., *Ann. Rev. Biochem.* 55:599-629, 1986).

Ribozymes can either be targeted directly to cells in the form of RNA oligonucleotides incorporating ribozyme sequences, or introduced into the cell as an expression vector encoding the desired ribozymal RNA. Ribozymes may be used and applied in much the same way as described for antisense polynucleotides.

Anti-sense RNA and DNA, ribozymes and RNAi molecules useful in the methods of the invention may be prepared by any method known in the art for the synthesis of DNA and RNA molecules. These include techniques for chemically synthesizing oligodeoxyribonucleotides and oligoribonucleotides well known in the art, such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well known modifications of the DNA molecules may be introduced as a means of increasing stability and half-life. Useful modifications include, but are not limited to, the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

IV. Screening Methods for PDE7 Inhibitors Useful to Treat a Movement Abnormality Associated with the Pathology of a Neurological Movement Disorder In another aspect, methods are provided for identifying an agent that inhibits PDE7 activity useful for treating a movement abnormality associated with the pathology of a neurological movement disorder in a mammalian subject in need thereof. The methods of this aspect of the invention comprise: (a) determining the $IC_{50}$ for inhibiting PDE7 activity for a plurality of each of a plurality of agents; (b) selecting agents from the plurality of agents having an $IC_{50}$ for inhibition of PDE7 activity of less than about 1 µM; (c) determining the $IC_{50}$ for inhibiting PDE4 activity of the agents having an $IC_{50}$ for inhibiting PDE7 activity of less than about 1 µM; (d) identifying agents useful for treating a movement disorder by selecting compounds having an $IC_{50}$ for inhibiting PDE4 activity greater than 10 times the $IC_{50}$ for inhibiting PDE7; and (e) evaluating the activity of the identified compounds in a neurological movement disorder model assay, wherein an agent that has an $IC_{50}$ for PDE7 inhibition of less than about 1 µM, and an $IC_{50}$ for inhibiting PDE4 activity greater than 10 times the $IC_{50}$ for inhibiting PDE7, and is determined to be effective to treat at least one movement abnormality in a model assay is indicative of a PDE7 inhibitory agent useful for treating a movement abnormality associated with the pathology of a neurological movement disorder in a mammalian subject.

Representative agents that may be used in the practice of the methods of this aspect of the invention include molecules that bind to PDE7 and inhibit the enzyme activity of PDE7 (such as small molecule inhibitors or blocking peptides that bind to PDE7 and reduce enzymatic activity), and molecules that decrease the expression of PDE7 at the transcriptional and/or translational level (such as PDE7 antisense nucleic acid molecules, PDE7 specific RNAi molecules and PDE7 ribozymes), thereby preventing PDE7 from cleaving cAMP.

V. General Composition Description and Definitions

In one aspect, the invention provides a method of treating a movement abnormality associated with the pathology of a neurological movement disorder comprising administering to a patient in need thereof an amount of a PDE7 inhibitory agent effective to inhibit the enzymatic activity of PDE7, wherein such inhibition of PDE7 enzymatic activity is the principal therapeutic mode of action of the PDE7 inhibitor in the treatment of the movement abnormality. In some embodiments of the method, the neurological movement disorder is treatable with a dopamine receptor agonist or a precursor of a dopamine receptor agonist. In some embodiments of the method, the neurological movement disorder is selected from the group consisting of Parkinson's disease, Post-Encephalitic Parkinsonism, Dopamine-Responsive Dystonia, Shy-Drager Syndrome, Periodic Limb Movement Disorder (PLMD), Periodic Limb Movements in Sleep (PLMS), and Restless Leg(s) Syndrome (RLS).

In other embodiments, the neurological movement disorder is selected from the group consisting of Tourrette's syndrome, Huntington's disease (i.e., Huntington's chorea), and drug-induced Parkinsonism.

For each of the PDE7 inhibitory chemical compounds useful in the method of the present invention, all possible stereoisomers and geometric isomers are included. The compounds include not only racemic compounds, but also the optically active isomers. When a PDE7 inhibitory agent is desired as a single enantiomer, it can be obtained either by resolution of the final product or by stereospecific synthesis from either isomerically pure starting material or use of a chiral auxiliary reagent, for example, see Ma, Z., et al., *Tetrahedron: Asymmetry* 8(6):883-888, 1997. Resolution of the final product, an intermediate, or a starting material can be achieved by any suitable method known in the art. Additionally, in situations where tautomers of the compounds are possible, the present invention is intended to include all tautomeric forms of the compounds.

The PDE7 inhibitory agents that contain acidic moieties can form pharmaceutically acceptable salts with suitable cations. Suitable pharmaceutically acceptable cations include alkali metal (e.g., sodium or potassium) and alkaline earth metal (e.g., calcium or magnesium) cations. The pharmaceutically acceptable salts of the PDE7 inhibitory agents, which contain a basic center, are acid addition salts formed with pharmaceutically acceptable acids. Examples include the hydrochloride, hydro bromide, sulfate or bisulfate, phosphate or hydrogen phosphate, acetate, benzoate, succinate, fumarate, maleate, lactate, citrate, tartarate, gluconate, methanefulgonate, benzenesulphonate, and p-toluenesulphonate salts. In light of the foregoing, any reference to compounds useful in the method of the invention appearing herein is intended to include PDE7 inhibitory agents, as well as pharmaceutically acceptable salts and solvates thereof.

The compounds of the present invention can be therapeutically administered as the neat chemical, but it is preferable to administer the PDE7 inhibitory agents as a pharmaceutical composition or formulation. Accordingly, the present invention further provides for pharmaceutical compositions or formulations comprising a PDE7 inhibitory agent, or pharmaceutically acceptable salts thereof, together with one or more pharmaceutically acceptable carriers and, optionally, other therapeutic and/or prophylactic ingredients. Suitable carriers are compatible with the other ingredients of the formulation and not deleterious to the recipient thereof. Compounds of the present invention may also be carried in a delivery system to provide for sustained release or enhanced uptake or activity of the compound, such as a liposomal or hydrogel system for injection, a micropartical, nanopartical, or micelle system for oral or parenteral delivery, or a staged capsule system for oral delivery.

In particular, a selective PDE7 inhibitory agent useful in the method of the present invention is useful alone or in combination with one or more additional therapeutic agent, for example: a dopamine receptor agonist, a precursor of a dopamine receptor agonist, another dopaminergic agent, or combinations of the foregoing. Examples of dopamine receptor agonists and precursors include for example levodopa (also referred to as "L-dopa"), carbidopa, bromocriptine, pergolide, pramipexole, ropinirole cabergoline, apomorphine and lisuride. Other agents useful in combination with a selective PDE7 inhibitory agent include anticholinergic medications, such as biperidenHCl, benztropine mesylate, procyclidine and trihexyphenidyl; monoamine oxidase B inhibitors, such as Eldepryl™, Atapryl™ and Carbex™ and the NMDA antagonist amantadine (Symmetrel™)

In one embodiment, a selective PDE7 inhibitory agent is useful in combination with one or more additional therapeutic agents or precursors of therapeutic agents that activate the dopamine D1 receptor and/or increase the concentration of dopamine in the nigrostriatal nerve terminals and/or the nigrostriatal synaptic cleft. Such agents include L-dopa, non-selective dopamine receptor agonists such as apomorphine, bromocryptine, and pergolide; and D1 selective agents such as ABT-431, A86929, and SKF38393.

In one embodiment, the invention provides a method of treating a movement abnormality associated with the pathology of Parkinson's disease comprising administering to a patient in need thereof an amount of a PDE7 inhibitory agent effective to inhibit the enzymatic activity of PDE7, wherein such inhibition of PDE7 is the principal therapeutic mode of action of the PDE7 inhibitor in the treatment of the movement abnormality. As demonstrated in Examples 5-7 herein, selective PDE7 inhibitors are useful in the treatment of a movement abnormality associated with the pathology of Parkinson's disease. In the context of Parkinson's disease, treatment includes symptomatic therapy to lessen, alleviate, mask, or prevent the symptoms of at least one movement abnormality selected from the group consisting of tremor at rest, rigidity, bradykinesia, or deficiency of postural reflexes.

Compounds and pharmaceutical compositions suitable for use in the present invention include those wherein the active ingredient is administered in an effective amount to achieve its intended purpose. More specifically, a "therapeutically active amount" means an amount effective to prevent development of symptoms in, or to alleviate the existing symptoms of, the subject being treated. Determination of the effective amounts is well within the capability of those skilled in the art, especially in light of the detailed disclosure provided herein. It is further appreciated that the amount of a compound of the invention required for use in treatment varies with the nature of the condition being treated, and with the age and condition of the patient, and is ultimately determined by the attendant physician. Generally, however, doses employed for adult human treatment typically are in the range of 0.001 mg/kg to about 100 mg/kg per day.

A "therapeutically effective dose" refers to that amount of the compound that results in achieving the desired effect to treat or ameliorate a movement abnormality associated with the pathology of a neurological movement disorder. Toxicity and therapeutic efficacy of such compounds can be determined by standard pharmaceutical procedure in cell cultures or experimental animals, e.g., for determining the LD50 (the dose lethal to 50% of the population) and the ED50 (the dose therapeutically effective in 50% of the population).

In one embodiment, a therapeutically effective dose is an amount of PDE7 inhibitory agent sufficient to inhibit PDE7 enzyme activity in a neuronal cell. In another embodiment of the methods of the invention, a therapeutically effective dose is an amount of PDE7 inhibitory agent sufficient to inhibit PDE7 enzyme activity in striatal neurons. The determination of an effective dose of a PDE7 inhibitory agent sufficient to cross a cellular membrane and inhibit PDE7 enzyme activity within a cell may be determined using a cellular assay for PDE7 inhibition, such as described by Smith S. J. et al., Molecular Pharmacology 66(6): 1679-1689 (2004), hereby incorporated by reference. The determination of an effective dose of a PDE7 inhibitory agent sufficient to inhibit PDE7 enzyme activity in the striatum may be determined using an assay for measuring the effect of a PDE inhibitory agent on cAMP levels in the striatum, as described in Siuciak J. A. et al., Neuropharmacology 51: 386-396 (2006), hereby incorporated by reference.

The dose ratio between toxic and therapeutic effects is the therapeutic index, which is expressed as the ratio between LD50 and ED50. Compounds which exhibit high therapeutic indices are preferred. The data obtained from such analysis can be used in formulating a dosage range for use in humans. The dosage of such compounds preferably lies within a range of circulating concentrations that include the ED50 range depending upon the dosage form employed, and the route of administration utilized.

Toxicity and therapeutic efficacy of PDE7 inhibitory agents can be determined by standard pharmaceutical procedures employing experimental animal models, such as the murine MPTP model described in Examples 5-7. Using such animal models, the NOAEL (no observed adverse effect level) and the MED (the minimally effective dose) can be determined using standard methods. The dose ratio between NOAEL and MED effects is the therapeutic ratio, which is expressed as the ratio NOAEL/MED. PDE7 inhibitory agents that exhibit large therapeutic ratios or indices are most preferred. The data obtained from the cell culture assays and animal studies can be used in formulating a range of dosages for use in humans. The dosage of the PDE7 inhibitory agent preferably lies within a range of circulating concentrations that include the MED with little or no toxicity. The dosage may vary within this range depending upon the dosage form employed and the route of administration utilized.

For any compound formulation, the therapeutically effective dose can be estimated using animal models. For example, a dose may be formulated in an animal model to achieve a circulating plasma concentration or brain tissue range that includes the MED. Quantitative levels of the PDE7 inhibitory agent in plasma or brain may also be measured, for example, as described in Example 4 herein.

The exact formulation, route of administration, and dosage can be chosen by the individual physician in view of the patient's condition. Dosage amount and interval can be adjusted individually to provide plasma levels of the active moiety which are sufficient to maintain the therapeutic effects.

The desired dose can be conveniently administered in a single dose, or as multiple doses administered at appropriate intervals, for example as two, three, four, or more sub-doses per day. In practice, the physician determines the actual dosing regimen that is most suitable for an individual patient, and the dosage varies with the age, weight, and response of the particular patient. The dosages described above are exemplary of the average case, but there can be individual instances in which higher or lower dosages are merited, and such are within the scope of the present invention.

Formulations of the present invention can be administered in a standard manner for the treatment of the indicated diseases, such as orally, parenterally, transmucosal (e.g., sublingually or via buccal administration), topically, transdermally, rectally, via inhalation (e.g., nasal or deep lung inhalation). Parenteral administration includes, but is not limited to intravenous, intra-arterial, intraperitoneal, subcutaneous, intramuscular, intrathecal, and intraarticular. Parenteral administration also can be accomplished using a high pressure technique, such as a POWDERJECT™ system.

In another aspect, this invention provides pharmaceutical compositions comprising a PDE7 inhibitory agent for treating neurological movement disorders such as Parkinson's disease, Post-Encephalitic Parkinsonism, Dopamine-Responsive Dystonia, Shy-Drager Syndrome, Periodic Limb Movement Disorder (PLMD), Periodic Limb Movements in Sleep (PLMS), Tourette's syndrome, or Restless Leg(s) Syndrome (RLS).

For buccal or oral administration, the pharmaceutical composition can be in the form of tablets or lozenges formulated in conventional manner. For example, tablets and capsules for oral administration can contain conventional excipients such as binding agents (for example, syrup, acacia, gelatin, sorbitol, tragacanth, mucilage of starch, or polyvinylpyrrolidone), fillers (for example, lactose, sugar, microcrystalline, cellulose, maize-starch, calcium phosphate, or sorbitol), lubricants (for example, magnesium, stearate, stearic acid, talc, polyethylene glycol, or silica), disintegrants (for example, potato starch or sodium starch glycollate), or wetting agents (for example, sodium lauryl sulfate). The tablets can be coated according to methods well known in the art.

Alternatively, the compounds of the present invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, such as suspending agents, such as sorbitol syrup, methyl cellulose, glucose/sugar syrup, gelatin, hydroxyethylcellulose, hydroxypropylmethylcellulose, carboxymethyl cellulose, aluminum stearate gel, and hydrogenated edible fats; emulsifying agents, such as lecithin, sorbitan monooleate, or acacia; nonaqueous vehicles (which can include edible oils), such as almond oil, fractionated coconut oil, oily esters, propylene glycol, and ethyl alcohol; and preservatives, such as methyl or propyl p-hydroxybenzoate and sorbic acid.

Such preparations also can be formulated as suppositories, e.g., containing conventional suppository bases, such as cocoa butter or other glycerides. Compositions for inhalation typically can be provided in the form of a solution, suspension or emulsion that can be administered as a dry powder or in the form of an aerosol using a conventional propellant, such as dichlorodifluoromethane or trichlorofluoromethane. Typically topical and transdermal formulations comprise conventional aqueous or nonaqueous vehicles, such as eye drops, creams, ointments, lotions, pastes, or in the form of medicated plaster, patch, or membrane.

Additionally, compositions of the present invention can be formulated for parenteral administration by injection or continuous infusion. Formulations for injection can be in the form of suspensions, solutions, or emulsions in oily or aqueous vehicles, and can contain formulation agents, such as suspending, stabilizing, and/or dispersing agents. Alternatively, the active ingredient can be in powder form for constitution with a suitable vehicle (e.g., sterile, hydrogen-free water) before use.

A composition in accordance with the present invention also can be formulated as a depot preparation. Such long acting formulations can be administered by implantation (for example, subcutaneously or intramuscularly) or by intramuscular injection. Accordingly, the compounds of the invention can be formulated with suitable polymeric or hydrophobic materials (e.g., an emulsion in an acceptable oil), ion exchange resins, or as sparingly soluble derivatives (e.g., a sparing soluble salt).

Thus, the invention provides in a further aspect a pharmaceutical composition comprising a PDE7 inhibitor, together with pharmaceutically acceptable diluents or carrier therefor. The present invention further provides a process of preparing a pharmaceutical composition comprising a PDE7 inhibitor, which process comprises mixing a PDE7 inhibitor, together with a pharmaceutically acceptable diluent or carrier therefor.

Blood-Brain Barrier:

In some embodiments, the PDE7 inhibitory agent is administered so as to either pass through, or by-pass the blood-brain barrier. Preferably the inhibitory agent, compound or composition administered in the method of treatment can cross through the blood-brain barrier in sufficient quantities and at a sufficient rate so as to allow the treatment of the movement disorder. Methods for allowing agents to pass through the blood-brain barrier are known in the art, and include minimizing the size of the agent, providing hydrophobic factors which facilitate passage, and conjugation to a carrier molecule that has substantial permeability across the blood brain barrier.

In some embodiments, an effective amount of a PDE7 inhibitory agent is an amount that achieves a concentration within brain tissue at or above the $IC_{50}$ for activity of a given PDE7 inhibitory agent. In some embodiments, the PDE7 inhibitory agent is administered in a manner and dosage that gives a peak concentration of about 1, 1.5, 2, 2.5, 5, 10, 20 or more times the $IC_{50}$ concentration for inhibiting the greater of PDE7A or PDE7B.

In some instances, a PDE7 inhibitory agent or combination of agents is administered by a surgical procedure implanting a catheter coupled to a pump device. The pump device can be implanted or be extracorporally positioned. Administration of a PDE7 inhibitory agent can be in intermittent pulses or as a continuous infusion. Devices for injection to discrete areas of the brain are known in the art. In certain embodiments, the PDE7 inhibitory agent or a composition comprising a PDE7 inhibitory agent is administered locally to the ventricle of the brain, substantia nigra, striatum, locus ceruleus, nucleus basalis Meynert, pedunculopontine nucleus, cerebral cortex, and/or spinal cord by injection.

EXAMPLES

Example 1

This Example describes an assay for measuring the potency of PDE7 inhibitors and demonstrates the potency of PDE7 inhibition of several representative PDE7 inhibitory agents useful in the methods of the invention.

Methods:

The compounds listed in TABLE 1 were tested for inhibitory activity in a PDE7 phosphodiesterase assay performed using recombinant human PDE7A and 7B enzymes expressed in a baculoviral system. The recombinant human PDE7A enzyme was purchased from BPS Bioscience (Catalog #60070), Genbank Accession No. NM_002603 (amino acid 121-end) with an N-terminal GST tag, MW=66 kDa, expressed in a Baculovirus infected Sf9 cell expression system, with a specific activity of 302 pmol/min/μg. The recombinant human PDE7B enzyme was purchased from BPS Bioscience (Catalog #60071), Genbank Accession No.

NM_018945 (amino acid 107-end), with an N-terminal GST tag, MW=66 kDa, expressed in a Baculovirus infected Sf9 cell expression system, with a specific activity of 53 pmol/min/μg.

TABLE 1

PDE7 Inhibitory Compounds

| ID Number | Compound Reference Number | MW |
|---|---|---|
| OM69 | 1 | 353.42 |
| OM056 | 2 | 353.42 |
| OM955 | 3 | 310.78 |
| OM956 | 4 | 330.45 |

PDE7 Activity Assay:

The assay method used was a scintillation proximity assay (SPA) (obtained from GE Healthcare, Product Code TRKQ7100), with [$^3$H]-cGMP as the substrate (SPA manual, Amersham Biosciences). Purified human PDE7A and PDE7B (obtained from BPS Bioscience, San Diego, Calif.) were diluted and stored in a solution containing 25 mM Tris-Cl (pH 8.0), 100 mM NaCl, 0.05% Tween 20, 50% glycerol, and 3 mM DTT. PDE7 assays were carried out in the following reaction mixture (final concentrations): 50 mM Tris-Cl (pH 8.0), 8.3 mM MgCl$_2$, 1.7 mM EGTA, 0.5 mg/ml BSA, 5% DMSO (except for OM056 which was in 2.5% DMSO) and 2 ng PDE7A or 0.2 ng PDE7B recombinant protein in a final volume of 0.1 mL.

For determination of IC$_{50}$ values against PDE7A or PDE7B, assays were run in duplicate on a single plate at eight concentrations of inhibitor, with a known PDE7 inhibitor (BRL50481) as a positive control. The inhibitor concentrations ranged from 0.61 nM to 10,000 nM, except in the case of OM056, for which the range was 0.24 nM to 4,000 nM. Reactions were initiated by addition of enzyme, incubated for 20 minutes at 30° C., and then terminated by the addition of 50 μl of SPA beads containing Zn$^{2+}$.

The mixture was shaken, allowed to settle for 3 hours, then the production of [$^3$H]-5'AMP from the substrate was quantitated by scintillation counting in a Wallac® plate counter. The results in net cpm values were fitted to a four parameter logistic model using Excel Solver®.

Results:

The results of the PDE7 phosphodiesterase enzyme inhibition assay are summarized below in TABLE 2, and shown in FIGS. 3A to 6B.

TABLE 2

IC$_{50}$ Values for Representative PDE7 Inhibitory Compounds With Respect to PDE7A and PDE7B Inhibition

| Compound ID | Compound Number | PDE7A IC50 | PDE7B IC50 | 7A/7B Ratio |
|---|---|---|---|---|
| OM69 | 1 | 1.30 nM | 4.8 nM* | 3.69 |
| OM056 | 2 | 5.67 nM | 9.27 nM | 1.63 |
| OM955 | 3 | 51.8 nM | 106 nM | 2.05 |
| OM956 | 4 | 140 nM | 144 nM | 1.03 |

*OM69 was previously assayed by the inventors for inhibition of the activity of PDE7A and PDE7B. It is noted with regard to the IC$_{50}$ value for PDE7B inhibition with OM69 that in the initial assay, using a different assay methodology, the IC$_{50}$ value was determined to be 96.9 nM. In that initial assay, the background signal (counts per minute) was high relative to the maximal signal and the Hill coefficient was low, findings that call into question the reliability of the initial assay results.

Figure 3A:
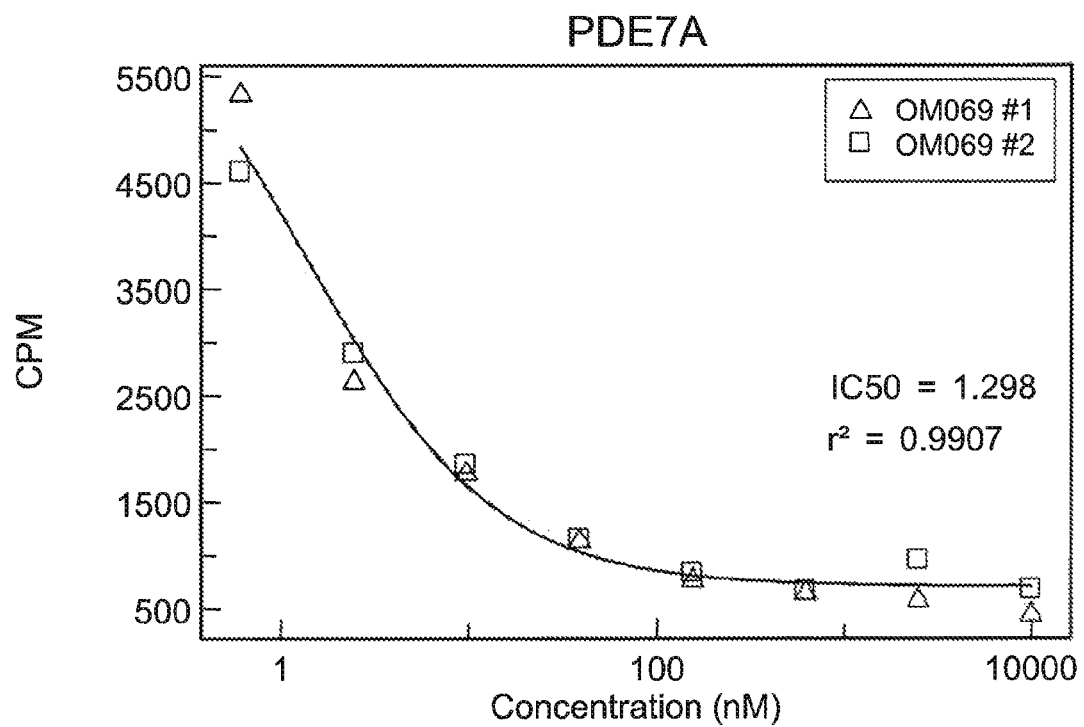
FIG. 3A is a graph illustrating the PDE7A inhibitory activity ($IC_{50}$), expressed as counts per minute ("CPM"), of a representative PDE7 inhibitory agent (OM69) useful in the methods of the invention.
Figure 3B:
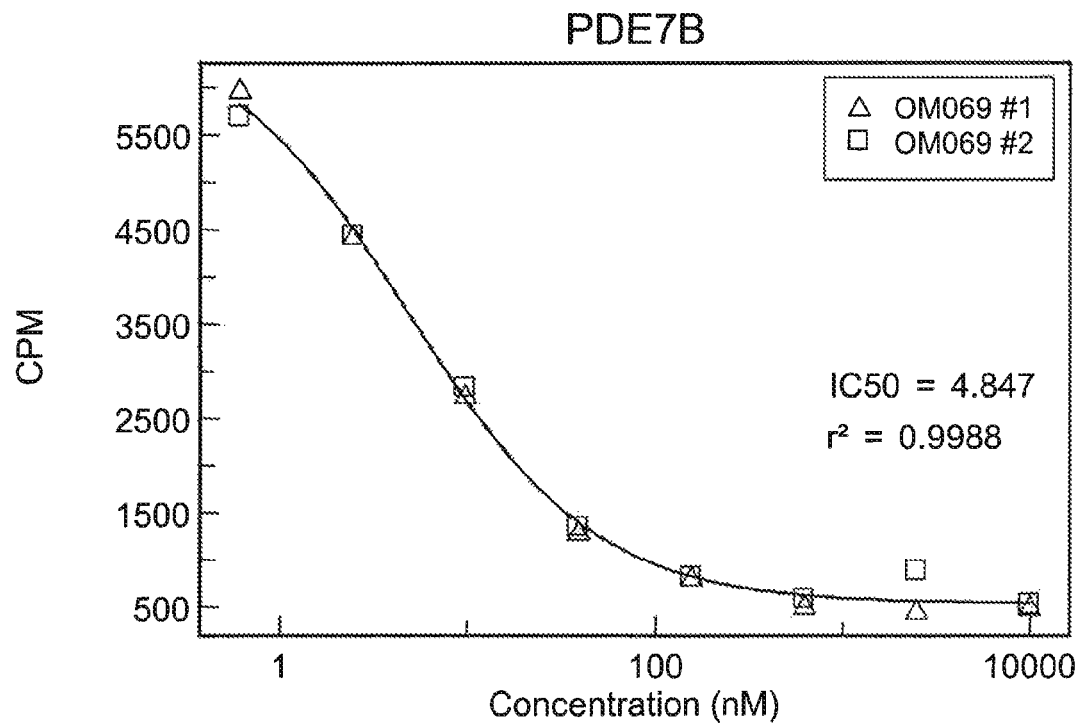
FIG. 3B is a graph illustrating the PDE7B inhibitory activity ($IC_{50}$), expressed as CPM, of a representative PDE7 inhibitory agent (OM69) useful in the methods of the invention.
Figure 4A:
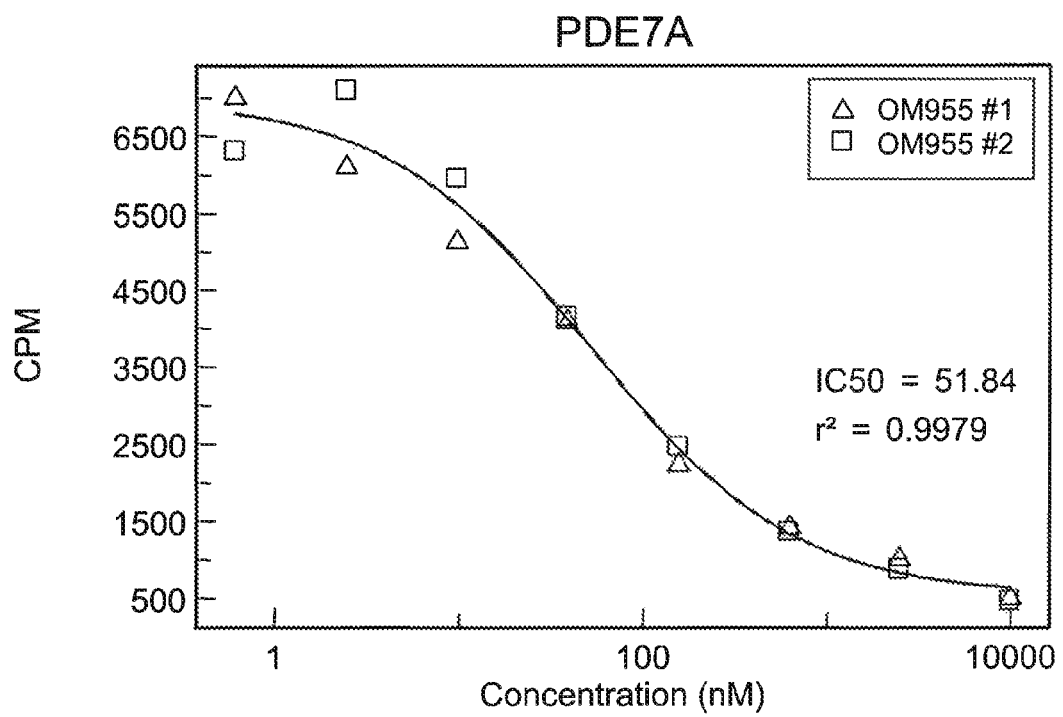
FIG. 4A is a graph illustrating the PDE7A inhibitory activity ($IC_{50}$), expressed as CPM, of a representative PDE7 inhibitory agent (OM955) useful in the methods of the invention.
Figure 4B:
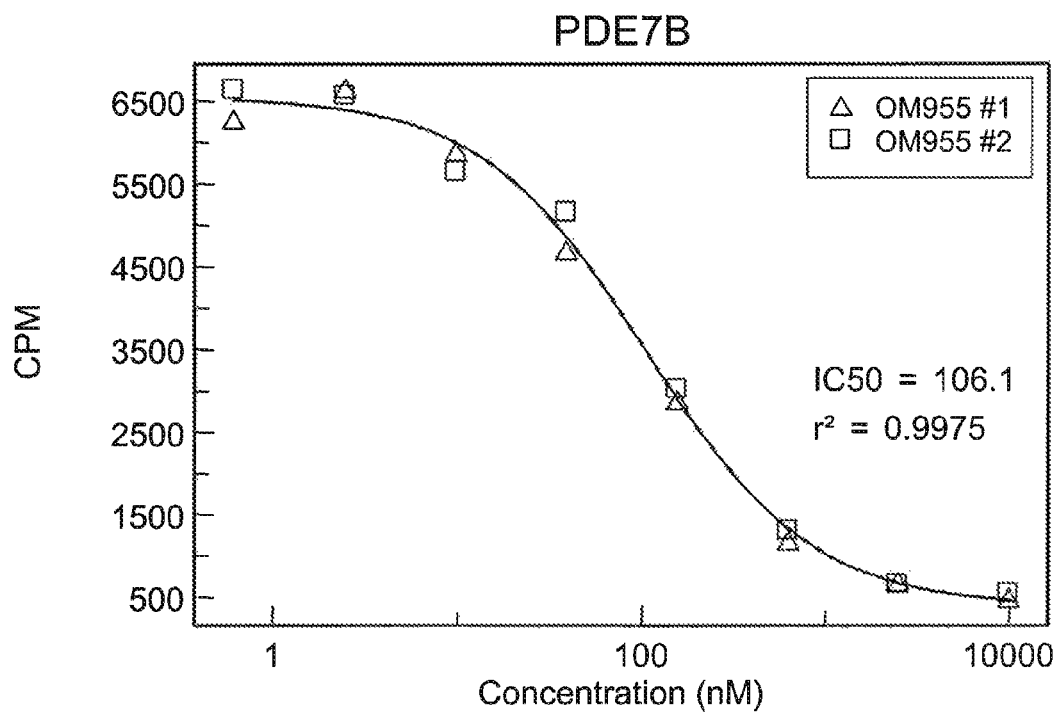
FIG. 4B is a graph illustrating the PDE7B inhibitory activity ($IC_{50}$), expressed as CPM, of a representative PDE7 inhibitory agent (OM955) useful in the methods of the invention.
Figure 5A:
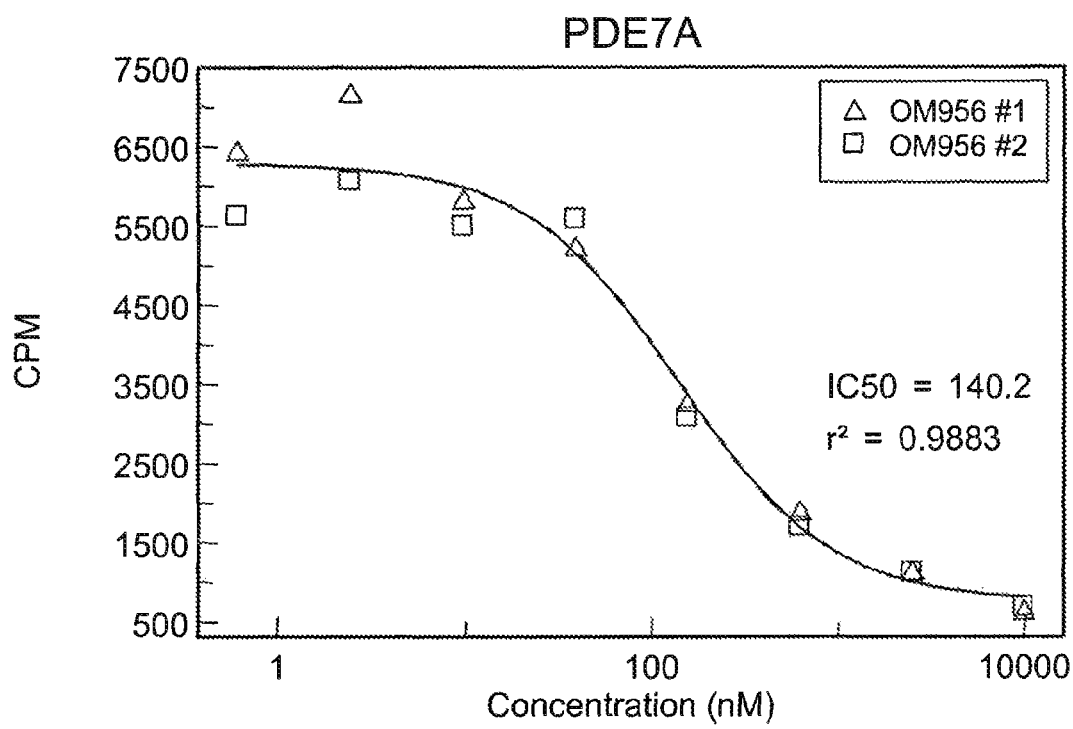
FIG. 5A is a graph illustrating the PDE7A inhibitory activity ($IC_{50}$), expressed as CPM, of a representative PDE7 inhibitory agent (OM956) useful in the methods of the invention.
Figure 5B:
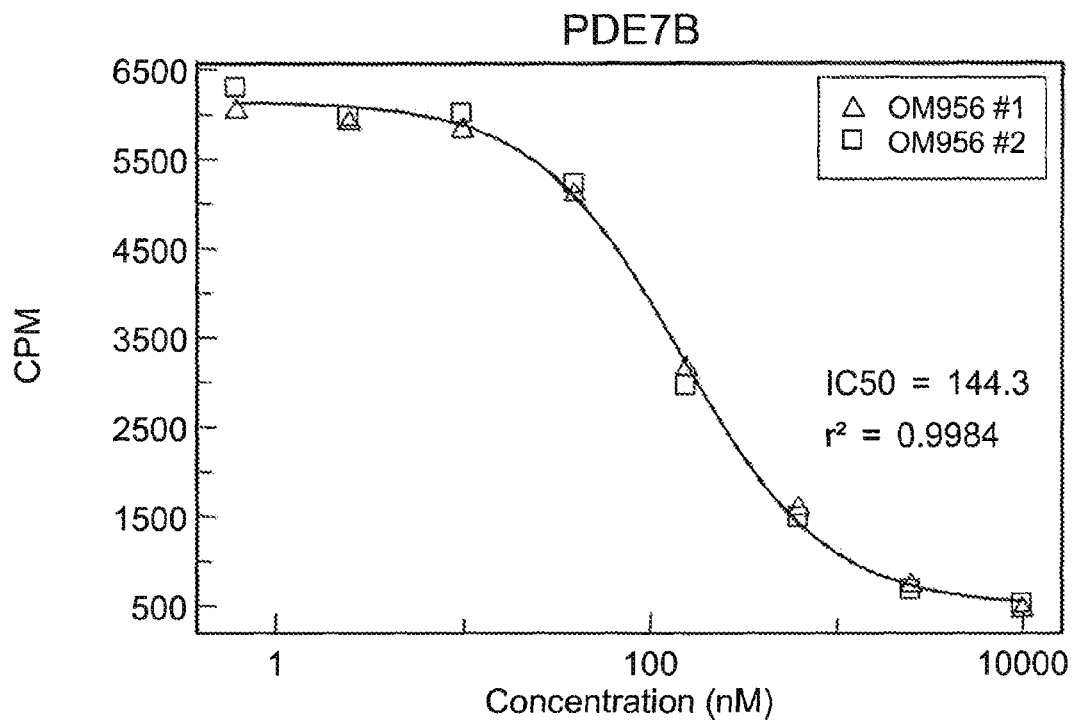
FIG. 5B is a graph illustrating the PDE7B inhibitory activity ($IC_{50}$), expressed as CPM, of a representative PDE7 inhibitory agent (OM956) useful in the methods of the invention.
Figure 6A:
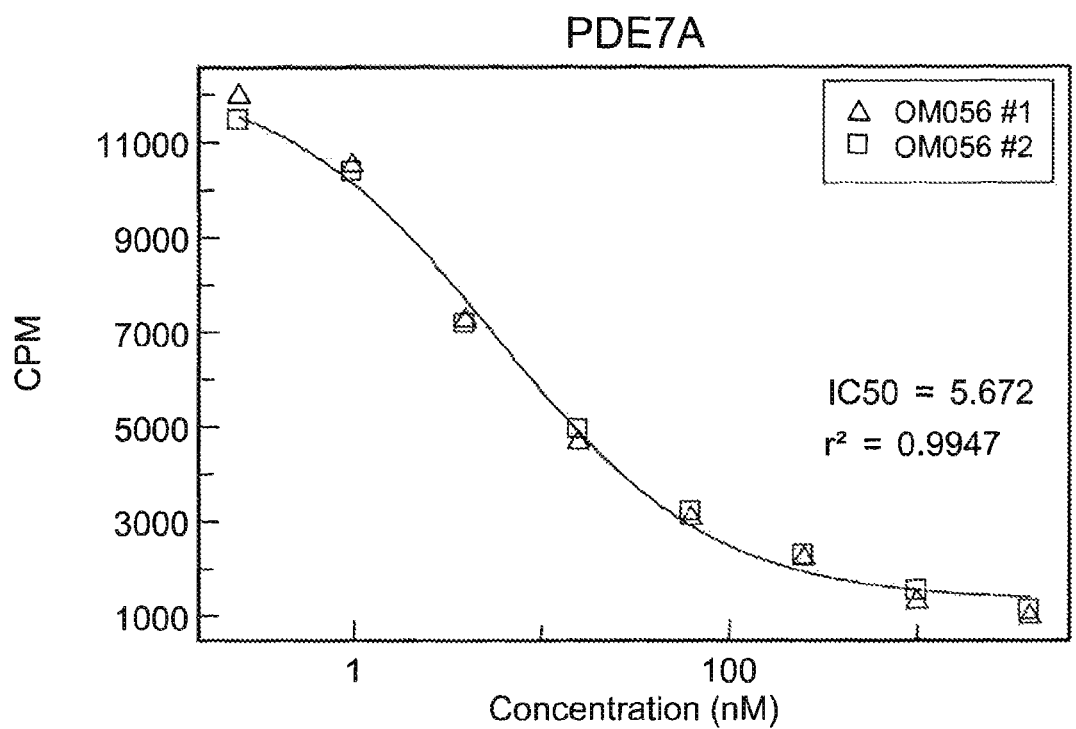
FIG. 6A is a graph illustrating the PDE7A inhibitory activity ($IC_{50}$), expressed as CPM, of a representative PDE7 inhibitory agent (OM056) useful in the methods of the invention.
Figure 6B:
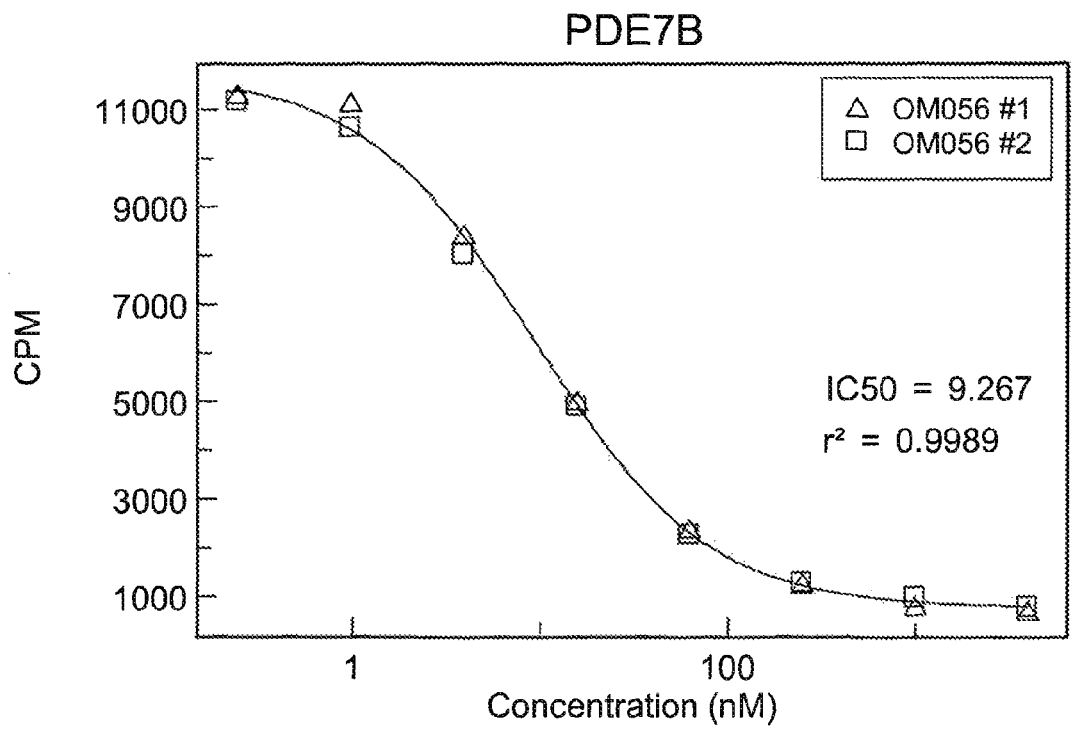
FIG. 6B is a graph illustrating the PDE7B inhibitory activity ($IC_{50}$), expressed as CPM, of a representative PDE7 inhibitory agent (OM056) useful in the methods of the invention.

The assay results shown above in TABLE 2, indicating an IC$_{50}$ value for PDE7B inhibition with OM69 of 4.8 nM is believed to be a more accurate value because, as shown in FIG. 3B, the r$^2$ value for the fit to a 4-parameter logistic dose-response model is 0.9988, as would be expected for a simple competitive inhibitor. The IC50 value for PDE7A inhibition with OM69 in the initial assay work was 3.5 nM, not inconsistent with the value for PDE7A inhibition of 1.30 nM set forth in Table 2.

FIGS. 3A, 4A, 5A, and 6A are graphs illustrating the PDE7A inhibitory activity (IC$_{50}$), expressed as counts per minute ("CPM") versus the concentration of the representative PDE7 inhibitory agents OM69, OM955, OM956, and OM056, respectively, over a concentration range of 0.61 nM to 10,000 nM (for OM69, OM955 and OM956), or a concentration range of 0.24 nM to 4,000 nM (for OM056).

FIGS. 3B, 4B, 5B, and 6B are graphs illustrating the PDE7B inhibitory activity (IC$_{50}$), expressed as counts per minute ("CPM") versus the concentration of the representative PDE7 inhibitory agents OM69, OM955, OM956, and OM056, respectively, over a concentration range of 0.61 nM to 10,000 nM (for OM69, OM955 and OM956), or a concentration range of 0.24 nM to 4,000 nM (for OM056).

These results indicate that OM69 and OM056 inhibit both PDE7A and PDE7B with high potency, while OM955 and OM956 inhibit both these enzymes with moderate potency. The OM69, OM056, OM955 and OM956 compounds display little or no selectivity between PDE7A and PDE7B.

Example 2

This Example describes a set of assays for measuring the selectivity of PDE7 inhibitors, and demonstrates that OM69 (compound 1), OM056 (compound 2), OM955 (compound 3), and OM956 (compound 4) each selectively inhibit PDE7 as compared to all other phosphodiesterase enzymes tested. These assays included a representative of every PDE family with the exception of PDE6.

Methods:

Phosphodiesterase activity was measured by a scintillation proximity assay (SPA, GE Healthcare: Product Code TRKQ7100) with [$^3$H]-cAMP as the substrate for PDEs 3A, 4A, 8A, or with [$^3$H]-cGMP as the substrate for PDEs 1B, 2A, 5A, 9A, 10A and 11A. Purified human PDE1B, PDE2A, PDE3A, PDE4A, PDE5A, PDE8A, PDE9A and PDE11A4 were obtained from BPS Bioscience, San Diego, Calif. Purified murine PDE10A was also obtained from BPS Biosciences. It is noted that murine PDE10A exhibits kinetic and inhibitory behavior that is indistinguishable from human PDE10. Therefore, the results obtained using murine PDE10A are believed to be representative of human PDE10.

The purified PDE enzymes were each diluted and stored in a solution containing 25 mM Tris-Cl (pH 8.0), 100 mM NaCl, 0.05% Tween 20, 50% glycerol, and 3 mM DTT. PDE assays were carried out in the following assay cocktail (final concentrations): 50 mM Tris-Cl (pH 8.0), 8.3 mM MgCl$_2$, 1.7 mM EGTA, 0.5 mg/ml BSA, 2.5% DMSO and between 0.2 ng and 6 ng of the PDE protein (depending on the enzyme activity) in a final volume of 0.1 mL.

Assays were performed in duplicate at four concentrations (10 μM, 1.25 μM, 0.156 μM, and 0.019 μM) of the PDE7 inhibitors OM69 (compound 1), OM056 (compound 2), OM955 (compound 3) and OM956 (compound 4). Reactions were initiated by addition of enzyme, incubated for 20 minutes at 30° C. and then terminated by the addition of 50 μl of SPA beads containing Zn$^{2+}$.

The mixture was shaken, and allowed to settle for 3 hours. Then the production of [$^3$H]-AMP or [$^3$H]-GMP from the substrate was quantitated by scintillation counting in a Wallac® plate counter. The results in net cpm values were fitted to a four parameter logistic model using Excel Solver®. For calculation of selectivity ratios, the $IC_{50}$ values obtained with each enzyme were divided by the $IC_{50}$ values obtained with PDE7A in Example 1.

Results:

TABLE 3 shows the results of selectivity assays with the four PDE7 inhibitory compounds assayed against the panel of PDEs tested. The values in TABLE 3 are shown in units of fold selectivity for PDE7A versus the other PDEs, and were determined by dividing the $IC_{50}$ value against the indicated PDE by the $IC_{50}$ value against PDE7A in Example 1. Thus, for example, the value of 342-fold for OM955 with PDE1B means that OM955 is 342-fold less potent as an inhibitor of PDE1B as compared to PDE7A. The numbers shown in parenthesis are $IC_{50}$ values against PDE7A of the various compounds from Example 1. The fold selectivity values provided in TABLE 3 as "greater than" reflect situations in which the highest concentration of compound inhibited the enzyme target only slightly (i.e., less than 50%), and higher concentrations could not be used because the compound became insoluble in the assay mixture. As a result, only a minimum estimate of selectivity could be generated.

TABLE 3

PDE7A Selectivity of Representative PDE7 Inhibitory Compounds

| Target | OM69 (Compound 1) Fold Selectivity | OM056 (Compound 2) Fold Selectivity | OM955 (Compound 3) Fold Selectivity | OM956 (Compound 4) Fold Selectivity |
|---|---|---|---|---|
| PDE1B | 29,608 | >1750 | 342 | >71 |
| PDE2A | 11,100 | 5670 | 209 | 546 |
| PDE3A | 8170 | >1750 | >192 | >71 |
| PDE4A | 6500 | 942 | 113 | >71 |
| PDE5A | 4630 | 3300 | 355 | >71 |
| PDE7A | 1 (1.30 nM) | 1 (5.67 nM) | 1 (51.8 nM) | 1 (140 nM) |
| PDE7B | 3.7 | 1.6 | 2.0 | 1.0 |
| PDE8A | >7700 | >1750 | >192 | >71 |
| PDE9A | >7700 | >1750 | >192 | >71 |
| PDE10A | 1050 | 428 | 379 | 106 |
| PDE11A | 7070 | 2600 | >192 | >71 |

Discussion of Results:

As shown above in TABLE 3, the representative PDE7 inhibitory agents OM69, OM056, OM955, and OM956 are all selective for PDE7A and PDE7B as compared to PDE1B, PDE2A, PDE3A, PDE4A, PDE5A, PDE8A, PDE9A, PDE10A, and PDE11A.

As shown in TABLE 3, OM69 (compound 1) is a potent inhibitor of both PDE7A ($IC_{50}$=1.3 nM) and PDE7B ($IC_{50}$=4.8 nM), displays a greater than 1000-fold selectivity for inhibition of the PDE7A enzyme as compared to the other PDEs, and a 250-fold selectivity for inhibition of the PDE7B enzyme as compared to the other PDEs.

As further shown in TABLE 3, OM056 (compound 2) is a potent inhibitor of both PDE7A ($IC_{50}$=5.7 nM) and PDE7B ($IC_{50}$=9.27), displays a greater than 400-fold selectivity for inhibition of the PDE7A enzyme as compared to the other PDES, and a greater than 200-fold selectivity for inhibition of the PDE7B enzyme as compared to the other PDEs.

As further shown in TABLE 3, OM955 (compound 3) is a moderately potent inhibitor of both PDE7A ($IC_{50}$=51.8 nM) and PDE7B ($IC_{50}$=106 nM), and displays a greater than 100-fold selectivity for inhibition of the PDE7A enzyme as compared to the other PDEs, and a greater than 50-fold selectivity for inhibition of the PDE7B enzyme as compared to the other PDEs.

As also shown in TABLE 3, OM956 (compound 4) is a moderately potent inhibitor of both PDE7A ($IC_{50}$=140 nM) and PDE7B ($IC_{50}$=144 nM), and displays a greater than 71-fold selectivity for inhibition of the PDE7A and PDE7B enzymes as compared to the other PDEs.

These results, taken together with the results described in Examples 4-7, demonstrate that inhibition of PDE7 activity is necessary and sufficient for the improvement in movement abnormalities observed after administration of these compounds in the MPTP mouse model. Moreover, the use of selective inhibitors of PDE7 rather than non-selective PDE inhibitors provides the advantage of less toxicity, because they will not significantly inhibit PDEs known to cause unwanted effects, such as PDE3 and PDE4.

Example 3

This Example describes a method for evaluating the metabolic stability of PDE7 inhibitors and the ability of PDE7 inhibitors to partition into mouse brain in vivo.

Animal Testing Protocol

Mouse Strain:

Adult male C57BL/6J; retired breeders, aged between 7-9 months (Jackson Laboratory, Bar Harbor, Me., USA), singly housed.

Compound Administration:

Each PDE7 inhibitor (OM69 (compound 1), OM056 (compound 2), OM955 (compound 3), and OM956 (compound 4)) was dissolved in a vehicle consisting of DMSO, 0.03 M phosphoric acid and Tween 80 (5:95:0.2) and injected via the intraperitoneal route at a dose of 1.0 mg/kg for OM69, 10.0 mg/kg for OM56 and 30.0 mg/kg for OM955 and OM956.

Collection of Blood and Brain Samples:

Just prior to the harvesting of tissues, mice were anesthetized with avertin. Samples of whole brain or plasma were collected from three animals per time point at 15 minutes, 30 minutes, 60 minutes, 120 minutes, and 240 minutes after injection. Blood samples were collected by retro-orbital bleeding. Plasma was prepared and red cells were removed by centrifugation. The mice were perfused with saline to remove contaminating blood. The brains were removed and rapidly frozen in liquid nitrogen for subsequent analysis. The plasma and brain samples were stored at =80° C. or on dry ice and the concentration of compound was determined by LC/MS/MS analysis as follows:

Whole brain tissue was homogenized using a Mini-Beaddeater-8™ (BioSpec Products, Bartlesville, Okla.). Plasma or homogenized brain samples were precipitated with acetonitrile and filtered in 96-well format using Captiva® 0.20 micron filtration plates (Varian Corp, Lake Forest, Calif.). Filtrates were evaporated under nitrogen to dryness at 50° C. and were then reconstituted for LC-MS analysis.

Quantitative measurements for inhibitory compound in plasma and brain samples were obtained using a Thermo Ultra triple quadrupole mass spectrometer (Thermo Fisher Scientific, San Jose, Calif.), utilizing electrospray ionization in the multiple reaction monitoring mode of data acquisition. Sample extracts were injected onto a 2.1×30 mm packed Xterra C18-MS high pressure liquid chromatography (HPLC) column (Waters Corp, Milford, Mass.). The mobile phase eluting the compound from the HPLC column was applied using a Thermo Surveyor MS Plus HPLC quaternary pumping system (Thermo Fisher Scientific, San Jose, Calif.) and a HTC PAL autoinjector (LEAP Technologies, Chapel Hill, N.C.).

Figure 7:
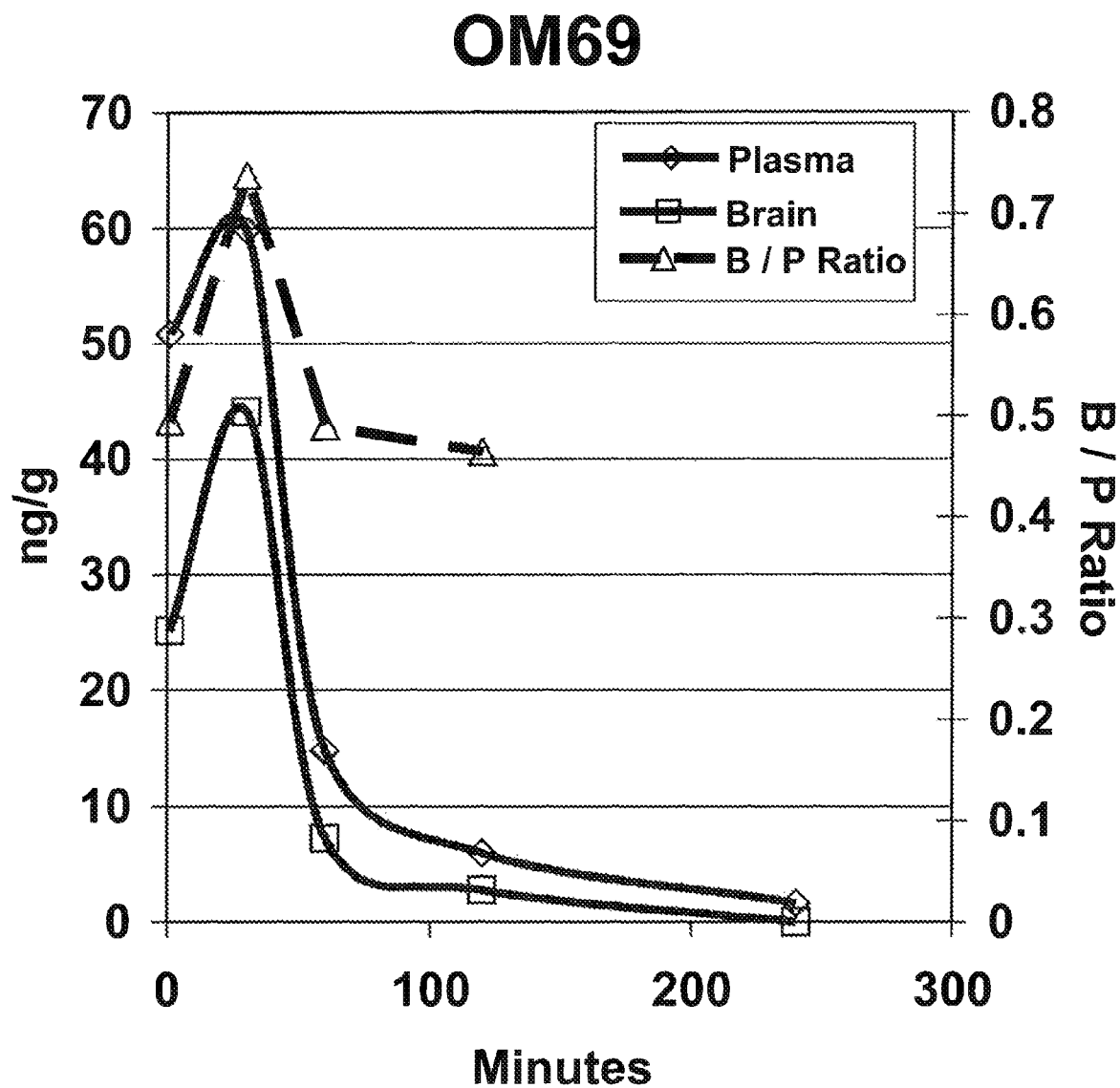
FIG. 7 is a graph comparing the concentration (ng/g) in plasma and brain tissue over time of a representative PDE7 inhibitor (OM69) useful in the method of the invention.

Results:

The data on tissue concentration of OM69 (compound 1), OM056 (compound 2), OM955 (compound 3) and OM956 (compound 4) were collected from 3 mice per time point and averaged. FIG. 7 graphically illustrates the plasma concentration, the brain concentration, and the brain/plasma ratio of compound OM69 (compound 1) over a 240 minute time course. As shown in FIG. 7, within the first 15 minutes of exposure, OM69 was detected in plasma (51 ng/g) and brain tissue (25 ng/g). Peak levels were seen at 30 minutes post IP injection (plasma 59 ng/g and brain 44 ng/g) after which both plasma and brain levels dropped rapidly. At all time points, when both brain and plasma levels were greater than the lower limit of quantitation in the LC/MS/MS assay (2 ng/g), brain to plasma ratios were 45-75%.

Using the approach described for compound OM69, a ratio was calculated of the total exposure in brain (area under the curve: AUC) divided by the total exposure in plasma for each compound tested. The results are shown below in TABLE 4. Ratio values greater than "1" indicate that the compound was concentrated in the brain. Values that are shown as ">1" indicate that the compound levels were already high in the brain by the time the first measurement was taken. As a result, the ratio of 1 represents a minimum estimate in these cases.

TABLE 4

Brain/Plasma Ratio of PDE7 Inhibitory Compounds

| Compound | Ratio of Total Brain Exposure/Total Plasma Exposure |
|---|---|
| OM69 (compound 1) | 0.78 |
| OM056 (compound 2) | 1.8 |
| OM955 (compound 3) | >1 |
| OM956 (compound 4) | >1 |

Discussion of Results:

The data shown in FIG. 7 suggests that OM69 (compound 1) reaches concentrations in the brain of 44 ng/g, which converts to 124 nM at 30 minutes after injection of a 1 mg/kg dose. Assuming linearity of uptake and uniform brain distribution, doses of 0.1 mg/kg to a mouse would be expected to yield maximal concentrations of 12.4 nM, which is sufficient to achieve PDE7 inhibition in the brain based on the $IC_{50}$ values of 1.3 nM and 4.8 nM reported in Example 1. The analogous calculations for the three other compounds tested in the MPTP model (as described in Examples 5 to 7), yield the following results for maximal brain concentrations at doses and time points where efficacy was observed: OM955: 292 nM at 0.5 mg/kg; OM956: 5260 nM at 0.5 mg/kg; and OM056: 358 nM at 0.5 mg/kg. In each case, it is noted that these levels are at least 2-fold in excess of the greater of the $IC_{50}$ values of the compounds to inhibit PDE7A or PDE7B.

Example 4

This Example demonstrates that the representative PDE7 inhibitor OM69 (compound 1) does not interact significantly with known Parkinson's disease targets.

Methods:

A representative PDE7 inhibitor, OM69 (compound 1) was tested against a panel of known Parkinson's disease targets to determine whether there was evidence of interaction with any of the tested targets.

Assays:

1. Catechol-O-Methyltransferase (COMT) Enzyme Assay

Catechol-O-Methyltransferase (COMT) was assayed as described in Zurcher, G., et al., *J. Neurochem* 38:191-195, 1982, with the following modifications. The source of COMT was isolated from pig liver. The substrate was 3 mM Catechol+S-Adenosyl-L-[methyl-$^3$H]methionine. The vehicle control was 1% DMSO. Compound OM69 was tested at 10 µM in incubation buffer (100 mM Potassium Phosphate, 10 mM $MgCl_2$, 3 mM DTT containing 12 U/ml ADA, pH 7.4). The reaction was pre-incubated for 15 minutes at 37° C., COMT enzyme was added, and the reaction was incubated for 60 minutes at 37° C. [$^3$H]-Guaiacol was counted and quantitated. The positive control reference compound 3,5-Dinitrocatechol was run in this assay, with a historical $IC_{50}$ value of 0.31 µM.

2. Monoamine Oxidase MAO-B Enzyme Assay

Monoamine Oxidase MAO-B was assayed as described in Urban, P., et al., *FEBS Lett* 286(1-2):142-146, 1991, with the following modifications. Human recombinant MAO-B was isolated from insect Hi5 cells. The substrate was 50 µM Kynuramine. The vehicle control was 1% DMSO. Compound OM69 was tested at 10 µM in incubation buffer (100 mM potassium phosphate, pH 7.4) in Experiment 1. In Experiment 2, compound OM69 was tested at 10 µM and 1 µM. The reaction was pre-incubated for 15 minutes at 37° C., MAO-B enzyme was added, and the reaction was incubated for 60 minutes at 37° C. Spectrofluorimetric quantitation of 4-hydroxyquinoline was carried out. The positive control reference compound R(-)-Deprenyl was run in this assay, with a historical $IC_{50}$ value of 5.3 nM.

3. Tyrosine Hydroxylase Enzyme Assay

Tyrosine Hydroxylase was assayed as described in Roskoski, R., Jr., et al., *J. Biochem* 218:363-370 (1993) with the following modifications. Tyrosine Hydroxylase was isolated from Wistar rat brain. The substrate was 100 µM L-[3,5-$^3$H]Tyrosine+L-Tyrosine. The vehicle control was 1% DMSO. Compound OM69 was tested at 10 µM in incubation buffer (125 mM MES, pH 6.0, 0.5 mg/ml Catalase, 12.5 mM DTT, 0.5 mM (6R)-5,6,7,8-Tetrahydrobiopterin). The reaction was pre-incubated for 15 minutes at 37° C. Tyrosine Hydroxylase enzyme was added, and the reaction was incubated for 20 minutes at 37° C. [$^3$H]—$H_2O$ was quantitated. The positive control reference compound α-Methyl-L-P-Tyrosine was run in this assay, with a historical $IC_{50}$ value of 20 µM.

4. Dopamine $D_1$ Radioligand Binding Assay

A Dopamine $D_1$ radioligand binding assay was carried out as described in Dearry, A., et al., *Nature* 347:72-76, 1990, with the following modifications. Human recombinant Dopamine D1 receptor was expressed in CHO cells. The ligand used in the assay was 1.4 nM [$^3$H] SCH-23390. The non-specific ligand was 10 µM (+)-butaclamol. The vehicle control was 1% DMSO. Compound OM69 was tested at 10 µM in incubation buffer (50 mM Tris-HCL, pH 7.4, 1.4 mM Ascorbic Acid, 0.001% BSA, 150 mM NaCl). The reaction was incubated for 2 hours at 37° C. Radioligand binding was quantitated. The positive control reference compound R(+)-SCH-23390 was run in this assay, with a historical $IC_{50}$ value of 1.4 nM.

5. Dopamine $D_{2L}$ Radioligand Binding Assay

A Dopamine $D_{2L}$ radioligand binding assay was carried out as described in Grandy, D. K., et al., *PNAS* 86:9762-9766, 1989, with the following modifications. Human recombinant Dopamine $D_{2L}$ receptor was expressed in CHO cells. The ligand used in the assay was 0.16 nM [$^3$H]-spiperone. The non-specific ligand was 10 µM Haloperidol. The vehicle control was 1% DMSO. Compound OM69 was tested at 10 µM in incubation buffer (50 mM Tris-HCL, pH 7.4, 1.4 mM Ascorbic Acid, 0.001% BSA, 150 mM NaCl). The reaction was incubated for 2 hours at 25° C. Radioligand binding was quantitated. The positive control reference compound spiperone was run in this assay, with a historical $IC_{50}$ value of 0.26 nM.

6. Dopamine $D_3$ Radioligand Binding Assay

A Dopamine $D_3$ radioligand binding assay was carried out as described in Sokoloff, P., et al., Nature 347:146-151, 1990, with the following modifications. Human recombinant Dopamine $D_3$ receptor was expressed in CHO cells. The ligand used in the assay was 0.7 nM [$^3$H]-spiperone. The non-specific ligand was 25 µM S(-)Sulpiride. The vehicle control was 1% DMSO. Compound OM69 was tested at 10 µM in incubation buffer (50 mM Tris-HCL, pH 7.4, 1.4 mM Ascorbic Acid, 0.001% BSA, 150 mM NaCl). The reaction was incubated for 2 hours at 37° C. Radioligand binding was quantitated. The positive control reference compound spiperone was run in this assay, with a historical $IC_{50}$ value of 0.36 nM.

7. Dopamine $D_{42}$ Radioligand Binding Assay

A Dopamine $D_{42}$ radioligand binding assay was carried out as described in Van tol, H. H. M., et al., Nature 350:610-614, 1991, with the following modifications. Human recombinant Dopamine $D_{42}$ receptor was expressed in CHO-K1 cells. The ligand used in the assay was 0.5 nM [$^3$H]-spiperone. The non-specific ligand was 10 µM Halperidol. The vehicle control was 1% DMSO. Compound OM69 was tested at 10 µM in incubation buffer (50 mM Tris-HCL, pH 7.4, 1.4 mM Ascorbic Acid, 0.001% BSA, 150 mM NaCl). The reaction was incubated for 2 hours at 25° C. Radioligand binding was quantitated. The positive control reference compound spiperone was run in this assay, with a historical $IC_{50}$ value of 0.5 nM.

8. Dopamine $D_5$ Radioligand Binding Assay

A Dopamine $D_5$ radioligand binding assay was carried out as described in Sunahara, R. K., et al., Nature 350:614-619, 1991, with the following modifications. Human recombinant Dopamine $D_5$ receptor was expressed in CHO cells. The ligand used in the assay was 2 nM [$^3$H]-SCH-23390. The non-specific ligand was 10 µM Flupentixol. The vehicle control was 1% DMSO. Compound OM69 was tested at 10 µM in incubation buffer (50 mM Tris-HCL, pH 7.4, 1.4 mM Ascorbic Acid, 0.001% BSA, 150 mM NaCl). The reaction was incubated for 2 hours at 37° C. Radioligand binding was quantitated. The positive control reference compound R(+)-SCH23390 was run in this assay, with a historical $IC_{50}$ value of 1.5 nM.

9. Gabapentin Radioligand Binding Assay

A Gabapentin radioligand binding assay was carried out as described in Gee, N. S., et al., J. Biol. Chem. 271(10):5768-5776, 1996, with the following modifications. Gabapentin was obtained from Wistar Rat brain cortex. The ligand used in the assay was 0.02 µM [$^3$H] Gabapentin. The non-specific ligand was 100 µM Gabapentin. The vehicle control was 1% DMSO. Compound OM69 was tested at 10 µM in incubation buffer (10 mM HEPES, pH 7.4). The reaction was incubated for 30 minutes at 25° C. Radioligand binding was quantitated. The positive control reference compound Gabapentin was run in this assay, with a historical $IC_{50}$ value of 0.04 µM.

10. Dopamine Transporter (DAT) Radioligand Binding Assay

A Dopamine Transporter (DAT) radioligand binding assay was carried out as described in Giros, B., et al., Trends Pharmacol Sci 14:43-49, 1993, with the following modifications. Human recombinant DAT was expressed in CHO-K1 cells. The ligand used in the assay was 0.15 nM [$^{125}$I]-RTI-55. The non-specific ligand was 10 µM Nomifensine. The vehicle control was 1% DMSO. Compound OM69 was tested at 10 µM in incubation buffer (50 mM Tris-HCL, pH 7.4, 100 mM NaCl, 1 µM Leupeptin, 10 µM PMSF). The reaction was incubated for 3 hours at 4° C. Radioligand binding was quantitated. The positive control reference compound GBR-12909 was run in this assay, with a historical $IC_{50}$ value of 1.7 nM.

11. Adenosine $A_{2A}$ Receptor Radioligand Binding Assay

An Adenosine $A_{2A}$ receptor radioligand binding assay was carried out as described in Varani, K., et al., Br. J. Pharmacol. 117:1693-1701, 1996, with the following modifications. Human recombinant $A_{2A}$ receptor was expressed in HEK-293 cells. The ligand used in the assay was 0.05 µM [$^3$H]CGS-21680. The non-specific ligand was 50 µM NECA. The vehicle control was 1% DMSO. Compound OM69 was tested at 10 µM in incubation buffer (50 mM Tris-HCL, pH 7.4, 10 mM $MgCl_2$, 1 mM EDTA, 2 U/mL Adenosine Deaminase). The reaction was incubated for 90 minutes at 25° C. Radioligand binding was quantitated. The positive control reference compound CGS-21680 was run in this assay, with a historical $IC_{50}$ value of 0.13 µM.

Results:

The results of the assays described above are summarized below in TABLE 5. The amount of OM69 used in the assay is indicated in parentheses in the column labeled "OM69." The results are presented in terms of percent inhibition of ligand binding to, or enzymatic activity of, the target. Positive controls were included in each assay as indicated, as a check on the assay's performance.

TABLE 5

Level of Inhibition of Known Parkinson's Disease Targets With Representative PDE7 Inhibitory Agent OM69 (Compound 1)

| Target | OM69 (compound 1) | Positive Control Expected $IC_{50}$ | Positive Control Observed $IC_{50}$ |
|---|---|---|---|
| Catechol-O-Methyltransferase (COMT) | 19.0% (10.0 µM) | 0.31 µM | 0.606 µM |
| Monoamine Oxidase MAO-B (Exp #1) | 49.0% (10.0 µM) | 5.3 nM | 6.69 nM |
| Monoamine Oxidase MAO-B (Exp #2) | 67.0% (10.0 µM) | 5.3 nM | 9.96 nM |
| Monoamine Oxidase MAO-B (Exp #2) | 27.0% (1.0 µM) | 5.3 nM | 9.96 nM |
| Tyrosine Hydroxylase | 4.0% (10.0 µM) | 20 µM | 20.2 µM |
| Dopamine $D_1$ | -5.0% (10.0 µM) | 1.4 nM | 1.83 nM |
| Dopamine $D_{2L}$ | 4.0% (10.0 µM) | 0.26 nM | 0.277 nM |
| Dopamine $D_3$ | -13.0% (10.0 µM) | 0.36 nM | 0.774 nM |
| Dopamine $D_{4.2}$ | -16.0% (10.0 µM) | 0.5 nM | 0.441 nM |
| Dopamine $D_5$ | 4.0% (10.0 µM) | 1.5 nM | 2.31 nM |
| Gabapentin | 15.0% (10.0 µM) | 0.04 µM | 0.0796 µM |
| Dopamine Transporter (DAT) | 18.0% (10.0 µM) | 1.7 nM | 0.975 nM |
| Adenosine $A_{2A}$ Receptor | 41.0% (10.0 µM) | 0.13 µM | 0.0924 µM |

Discussion of Results:

The results shown in TABLE 5 demonstrate that, even at a concentration that is 2000-fold greater than its $IC_{50}$ for PDE7B, the representative PDE7 inhibitor OM69 does not substantially inhibit COMT, tyrosine hydroxylase, the dopamine transporter, the gabapentin receptor, or any of the dopamine receptor subtypes.

With regard to the Adenosine $A_{2A}$ receptor result, although the results in TABLE 5 show that OM69 inhibited binding to $A_{2A}$ receptors by 41% at a concentration of 10 µM, it is believed that $A_{2A}$ is not a target of OM69 for at least the following reasons. As shown in Example 3, OM69 reaches levels in the mouse brain of 30 to 60 ng/g after a dose of 1 mg/kg. Assuming linear pharmacokinetics, then a dose of 0.1 mg/kg, which is highly effective in the mouse MPTP model, as demonstrated in Examples 5 and 6, would produce levels in the brain of 3 to 6 ng/g, which is equivalent to 3 to 6 ng/ml or 8.5 to 17 nM. At this concentration, using a conservative value of $IC_{50}$ for OM69 of 10 µM, the percent occupation of $A_{2A}$ receptors would be only about 0.17%. Therefore, the conclusion is that $A_{2A}$ is not a target for OM69.

With regard to the MAO-B assay, a percentage inhibition of 27% at a concentration of 1 µM would indicate an $IC_{50}$ value of approximately 2.7 µM. Therefore, if OM69 were present in the brain at a concentration of 17 nM (as discussed in the previous paragraph), it would inhibit MAO-B by less than 0.7%. Therefore, the conclusion is that MAO-B is not a target for OM69.

Example 5

Pharmacological Evaluation of a Representative PDE7 Inhibitory Compound in the MPTP Model of Parkinson's Disease In this Example, representative PDE7 inhibitory agent, OM69 (compound 1), was evaluated in an initial study in the mouse MPTP model of Parkinson's disease.

Animal Testing Protocol

Mouse Strain:

Adult male C57BL/6J; retired breeders, aged between 7-9 months (Jackson Laboratory, Bar Harbor, Me., USA), singly housed.

Handling:

Animals were handled daily for 2 weeks prior to injection in order to make them amenable to behavioral testing. All mice were maintained on a standard 12-h light/dark cycle and given ad libitum access to lab chow and water.

MPTP Administration:

Mice received 2 subcutaneous injections of methylphenyltetrahydropyridine ("MPTP") at a dose of 15 mg/kg (free base) with a 10-12 hour interval between injections. Control mice (sham lesion groups) were administered saline instead of MPTP.

Administration of PDE7 Inhibitory Compound:

Seven days after MPTP or saline administration, OM69 was administered to mice. For each dose, a 100× stock of OM69 compound was prepared in 100% DMSO and subsequently diluted 100× into phosphate buffered saline (PBS). Then 100 µL of this 1× solution was administered via intraperitoneal (IP) injection.

It was previously determined from pharmacokinetic studies that OM69 is washed out of mice within 12 hours, so dosing of various test compounds on consecutive days was used to maximize the information that could be obtained from each group of lesioned animals.

Stride Length:

Prior to injection with MPTP or saline, animals were pre-trained to walk across a clean sheet of paper into their home cage without stopping. For assessment of stride length, animals had their forepaws placed in black ink and the length of forepaw steps during normal walking (in a straight line only) was measured. The animals were immediately put back into their home cage upon completion of the task. Stride length was determined by measuring the distance between each step on the same side of the body, measuring from the middle toe of the first step to the heel of the second step. An average of at least four clear steps was calculated.

Experimental Protocol

Retired breeder male mice (12-15 per group, ~48-60 animals total) were treated with either saline or 2×15 mg/kg MPTP (12 saline; 36 MPTP) to induce a Parkinsonian state (neurochemical loss of dopamine with corresponding behavioral deficits). A flow chart schematically illustrating the protocol is shown in FIG. 8.

Figure 8:
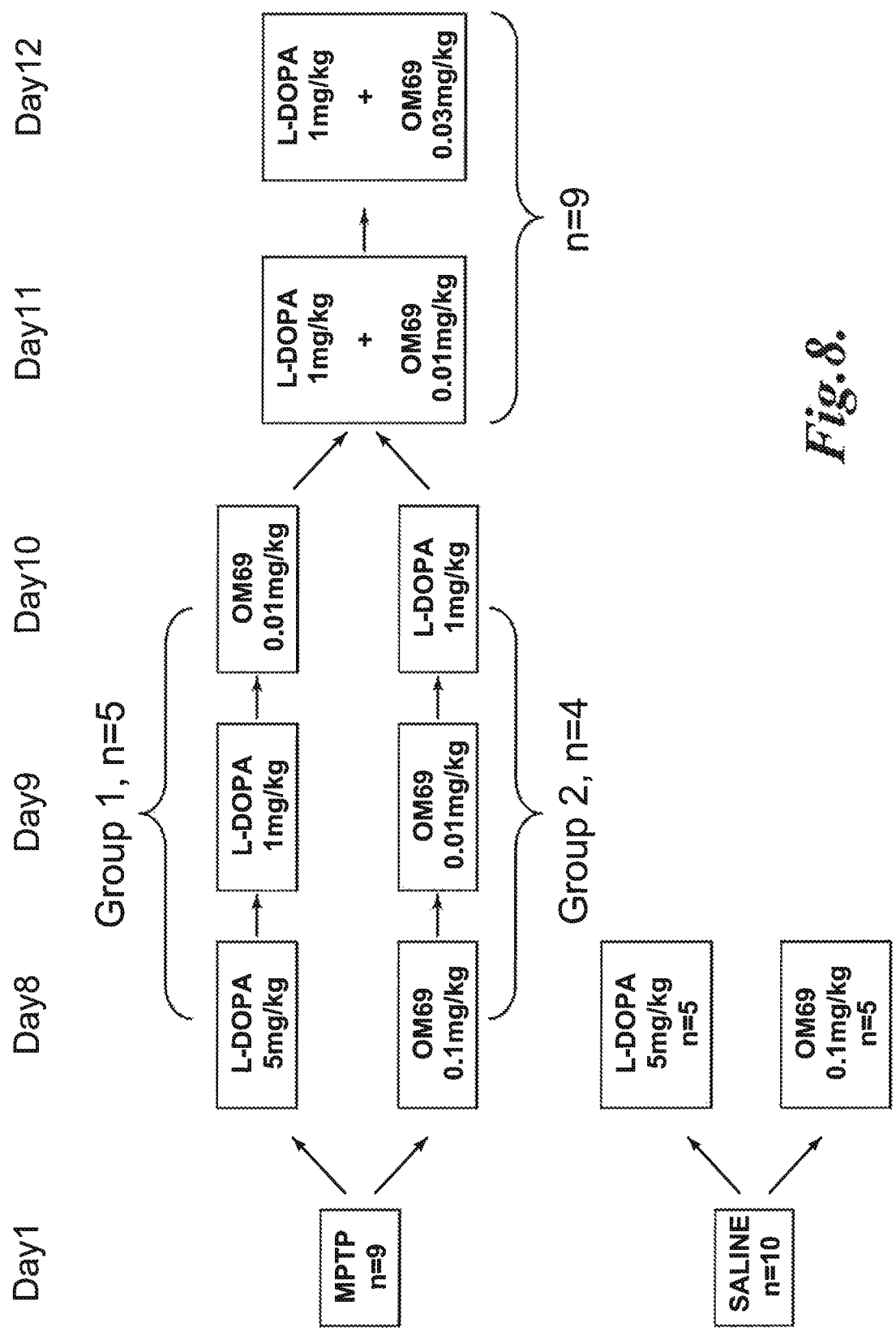
FIG. 8 is a flow diagram illustrating an experiment carried out in a methylphenyltetrahydropyridine ("MPTP") mouse model of Parkinson's disease to initially evaluate a representative PDE7 inhibitory agent (OM69) useful in the methods of the invention, administered alone or in combination with L-dopa, as compared to the effect of L-dopa alone, as described in Example 5.

As shown in FIG. 8, on day one baseline stride length was measured and then mice were treated with either MPTP (n=9) or with saline as a control (n=10). On day eight stride length was measured again, and the control value for stride length was derived from the stride length of saline-treated animals. Following this measurement the first treatments with L-dopa (5 mg/kg) or OM69 (0.1 mg/kg) were administered on day eight, as shown in FIG. 8. Stride length was then measured for each animal 20 minutes after dosing. Neither L-dopa (5 mg/kg) nor OM69 (0.1 mg/kg) altered the stride length of saline-treated mice. Dosing with the treatments shown in FIG. 8 was carried out on successive days, with stride length measured 20 minutes after each dosing. As mentioned above, it was previously determined from pharmacokinetic studies that OM69 is washed out of the mice within 12 hours after dosing, so the stride length test carried out 20 minutes after dosing was believed to be measuring the effect of only the compounds administered on the day of treatment.

As shown in FIG. 8, on day eight Group 1 animals were treated with L-dopa (5 mg/kg) and Group 2 animals were treated with OM69 (0.1 mg/kg). On day nine Group 1 animals were treated with L-dopa (1 mg/kg), and Group 2 animals were treated with OM69 (0.01 mg/kg). On day ten the treatment groups were crossed over, and Group 1 animals were treated with OM69 (0.01 mg/kg), and Group 2 animals were treated with L-dopa (1 mg/kg).

As further shown in FIG. 8, for the combination studies, all the mice in Group 1 and Group 2 were combined. On day 11 following MPTP administration, all the animals in Group 1 and Group 2 (n=9) were treated with the combination of L-dopa (1 mg/kg) and OM69 (0.01 mg/kg), with the stride length test carried out 20 minutes after dosing. On day 12 following MPTP administration, all the animals in Group 1 and Group 2 (n=9) were treated with the combination of L-dopa (1 mg/kg) and OM69 (0.03 mg/kg) with the stride length test carried out 20 minutes after dosing. In these combination studies carried out on day 11 and day 12, the average stride length data from two of the nine animals was not scorable because these two animals either ran rather than walking at a normal speed, or they kept starting and stopping rather than walking continuously. Therefore, these two animals were excluded, and only the remaining seven animals (n=7) were scored for the combination studies.

Stride Length Increase

The MPTP model used in this Example is a generally accepted mouse model of PD that is viewed by those of skill in the art as being predictive for PD in humans (Tillerson, J. L., et al., *Exp. Neurol.* 178(1):80-90, 2002; Tillerson, J. L., et al., *J. Neurosci Methods* 123(2):189-200, 2003).

To assess and compare the effects of OM69 and L-dopa at these doses, data from mice with equivalent dosing was pooled. Thus, the average stride length for animals treated with L-dopa (1 mg/kg) was determined using measurements obtained from all nine animals. Similarly, the average stride length for animals treated with OM69 (0.01 mg/kg) was determined using measurements obtained from all nine animals. The results of the MPTP study described in this Example are provided in FIGS. 9-11.

Figure 9:
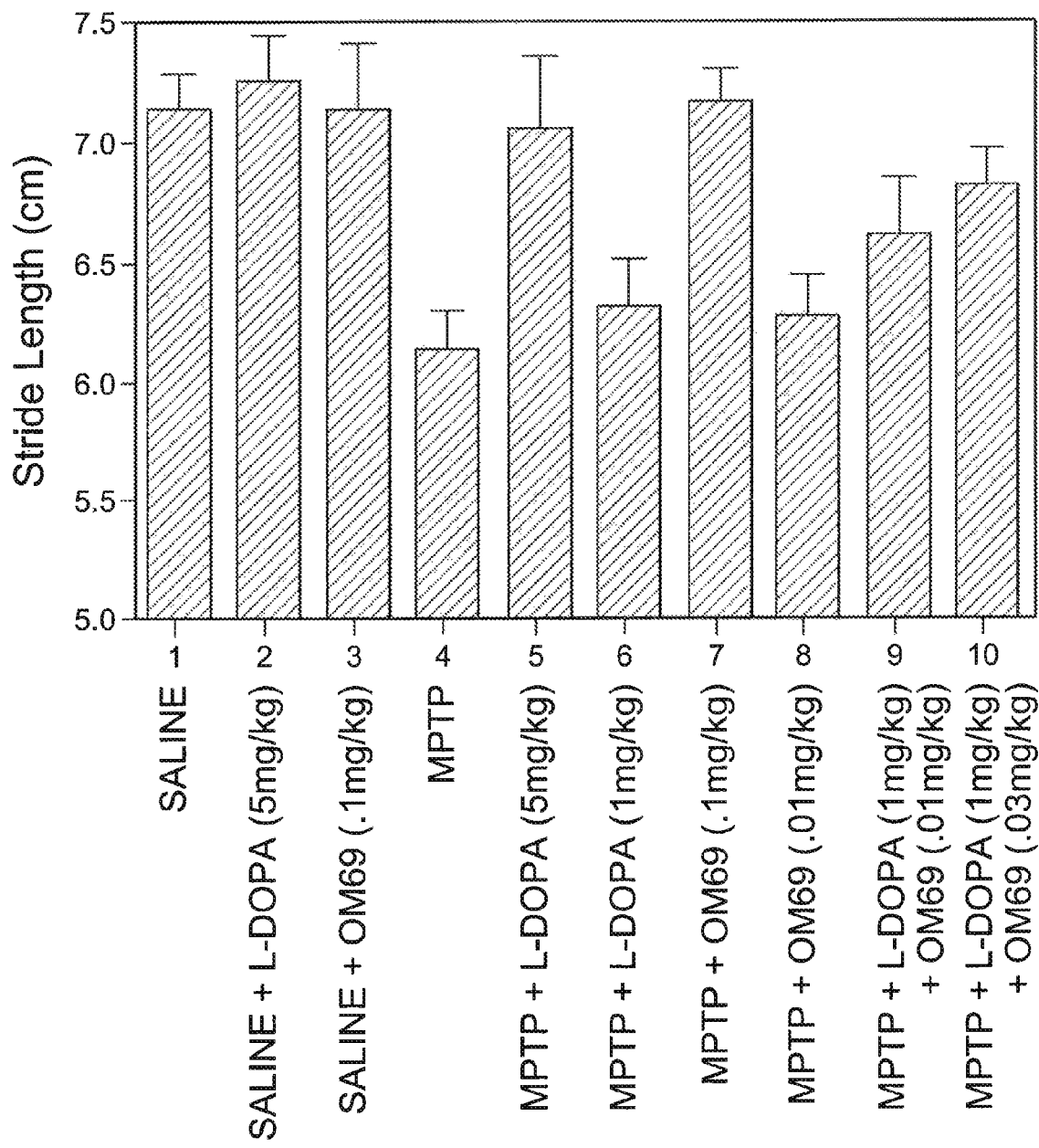
FIG. 9 is a bar graph illustrating the testing of inked paw stride length in the MPTP mouse model following the protocol illustrated in FIG. 8, demonstrating that a representative PDE7 inhibitory agent (OM69) useful in the method of the invention increases stride length in MPTP-treated mice, when administered alone or in combination with L-dopa, and compares the effectiveness of this inhibitor to L-dopa alone and to a saline control, as described in Example 5.
Figure 10:
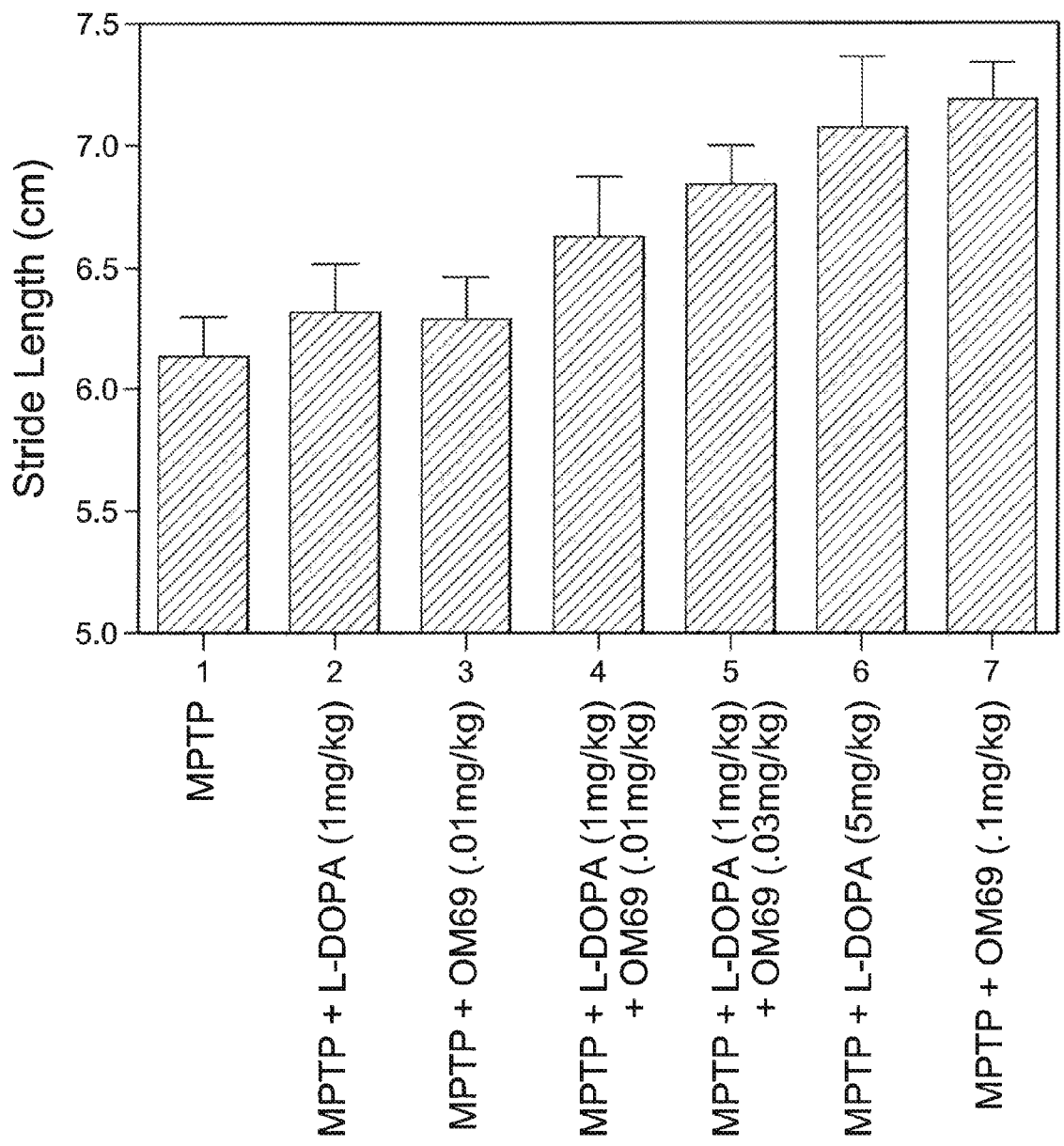
FIG. 10 is a bar graph illustrating a subset of the data shown in FIG. 9, comparing the effect on stride length in the MPTP mouse model of various dosages of a representative PDE7 inhibitory agent (OM69 (compound 1)) useful in the method of the invention, various dosages of L-dopa, and combinations of OM69 and L-dopa, as described in Example 5.
Figure 11:
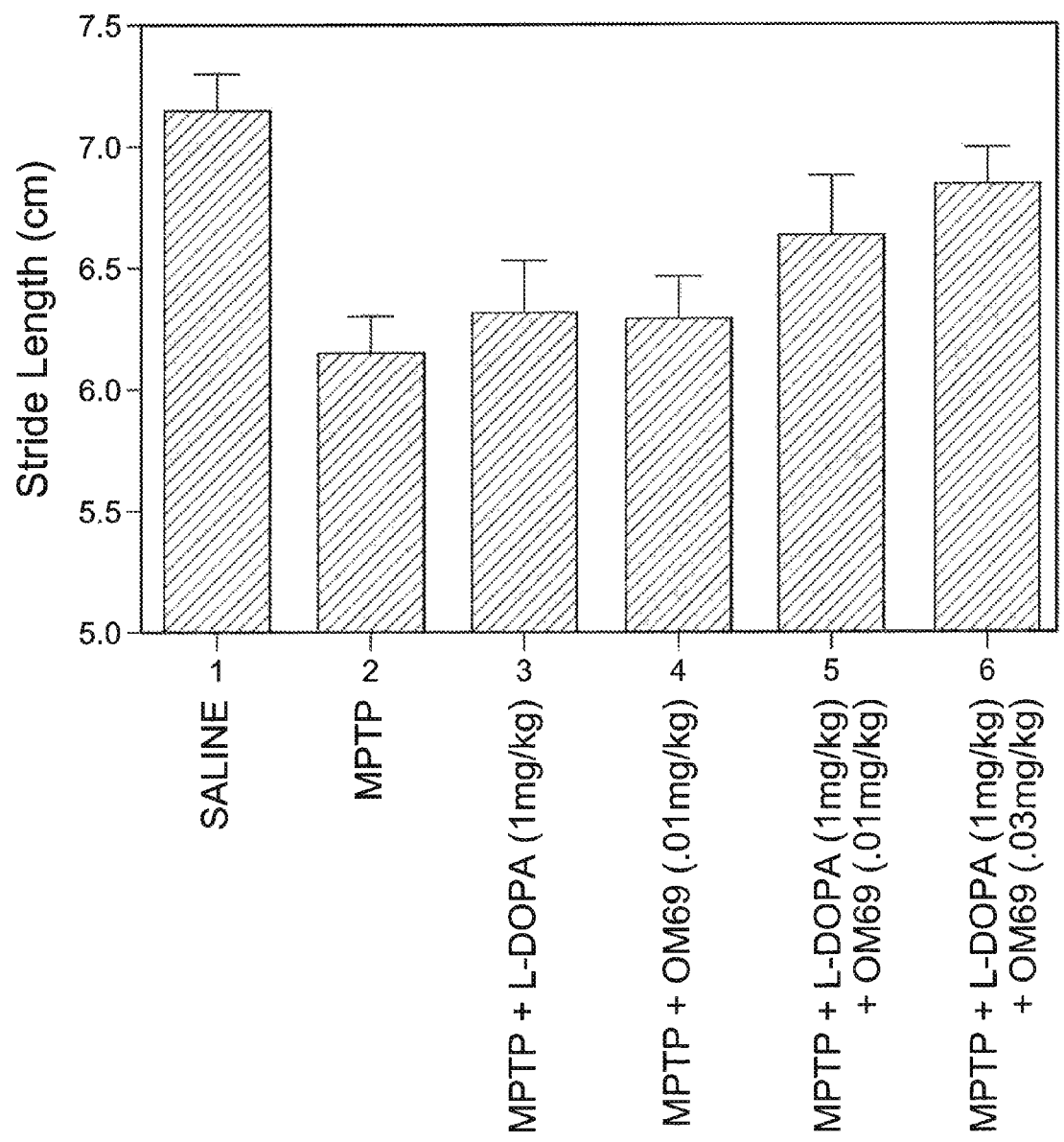
FIG. 11 is a bar graph illustrating a subset of the data shown in FIG. 9, comparing the effect on stride length in the MPTP mouse model of a representative PDE7 inhibitor (OM69) useful in the method of the invention, L-dopa, and combinations thereof, as compared to saline control (i.e., non-MPTP-treated) mice, as described in Example 5.

FIGS. 9-11 are bar graphs illustrating the results of the testing of inked paw stride length. They demonstrate that representative PDE7 inhibitor OM69 (compound 1) increases stride length in MPTP lesioned mice and does so at significantly lower doses as compared to L-dopa.

As shown in FIGS. 9 and 11, treatment of mice with MPTP decreases their stride length as measured from tracks left by inked mouse paws, in comparison with saline controls. See FIG. 9 (#1 versus #4) and FIG. 11 (#1 versus #2).

As shown in FIGS. 9 and 10, treatment of MPTP-treated mice with L-dopa increases their stride length in a dose-dependent manner. See FIG. 9 (#4 versus #5 and #6) and FIG. 10 (#1 versus #2 and #6).

It was unexpectedly determined that representative PDE7 inhibitor OM69 (compound 1), when administered IP at 0.1 mg/kg, has the same effect to increase stride length in the MPTP-treated mice as a 50-fold higher dose of L-dopa (5 mg/kg). As shown in FIG. 9, at the above noted concentrations, both L-dopa (#5) and OM69 (#7) fully restore the stride length to that seen without MPTP treatment (#1). These results demonstrate the surprising finding that OM69 (compound 1), a representative PDE7 inhibitor useful in the method of the invention, is effective to increase stride length in MPTP mice at a significantly lower dose as compared to L-dopa.

As shown in FIGS. 9-11, at lower doses of L-dopa (1 mg/kg) (see FIG. 9, #6; FIG. 10, #2) or OM69 (0.01 mg/kg) (see FIG. 9 #8; FIG. 10, #3) there was only a small effect observed on the stride length of MPTP-treated mice. However, when these lower doses of OM69 and L-dopa were administered in combination, the increase in stride length trended toward a greater effect than the sum of the increases seen from either drug alone. See FIG. 9, #9, and FIG. 10 #4. These results demonstrate that the administration of representative PDE7 inhibitor OM69 (compound 1) is effective to increase stride length in MPTP lesioned mice at a significantly lower dose as compared to L-dopa, and is therefore useful in the methods of the invention directed to the treatment of a movement abnormality associated with the pathology of a movement disorder such as Parkinson's disease.

Example 6

Pharmacological Evaluation of a Representative PDE7 Inhibitory Compound in the MPTP Model of Parkinson's Disease: Confirmatory Study In this Example, a representative PDE7 inhibitor, OM69 (compound 1), was evaluated in the mouse MPTP model of Parkinson's disease. This study was designed to confirm the findings in Example 5 and to provide statistical proof of the effects of OM69.

Animal Testing Protocol.
Mouse Strain:
Adult male C57BL/6J; retired breeders, aged between 7-9 months (Jackson Laboratory, Bar Harbor, Me., USA), singly housed.
Handling:
Animals handled daily for 2 weeks prior to injection, in order to make them amenable to behavioral testing. All mice were maintained on a standard 12-h light/dark cycle, and given ad libitum access to lab chow and water.

MPTP Administration:
MPTP Mice received 2 subcutaneous injections of methylphenyltetrahydropyridine ("MPTP") at a dose of 15 mg/kg (free base) with a 10-12 hour interval between injections. Control mice (sham lesion groups) were administered saline instead of MPTP.

OM69 (Compound 1) Administration:
Seven days after MPTP/saline administration, OM69 was administered to mice. For each dose, a 100× stock of OM69 was prepared in 100% DMSO and subsequently diluted 100× into phosphate buffered saline (PBS). Then 100 μL of this 1× solution was administered intraperitoneally (IP).

Stride Length:
Prior to injection with MPTP or saline, animals were pre-trained to walk across a clean sheet of paper into their home cage without stopping. For assessment of stride length, animals had their forepaws placed in black ink and the length of forepaw steps during normal walking (in a straight line only) was measured. The animals were immediately put back into their home cage upon completion of the task. Stride length was determined by measuring the distance between each step on the same side of the body, measuring from the middle toe of the first step to the heel of the second step. An average of at least four clear steps was calculated.

Statistical Analysis
Data was analyzed using Prism 4.0 software. Groups were analyzed by one way ANOVA and Student-Newman-Keuls post hoc test when appropriate. Significance was considered reached at $p<0.05$. Treatment groups in the stride length graph that are statistically different are indicated by the letters in Table 6. Groups that share a letter are not statistically different; groups that do not share a letter are significantly different from each other.

Figure 12:
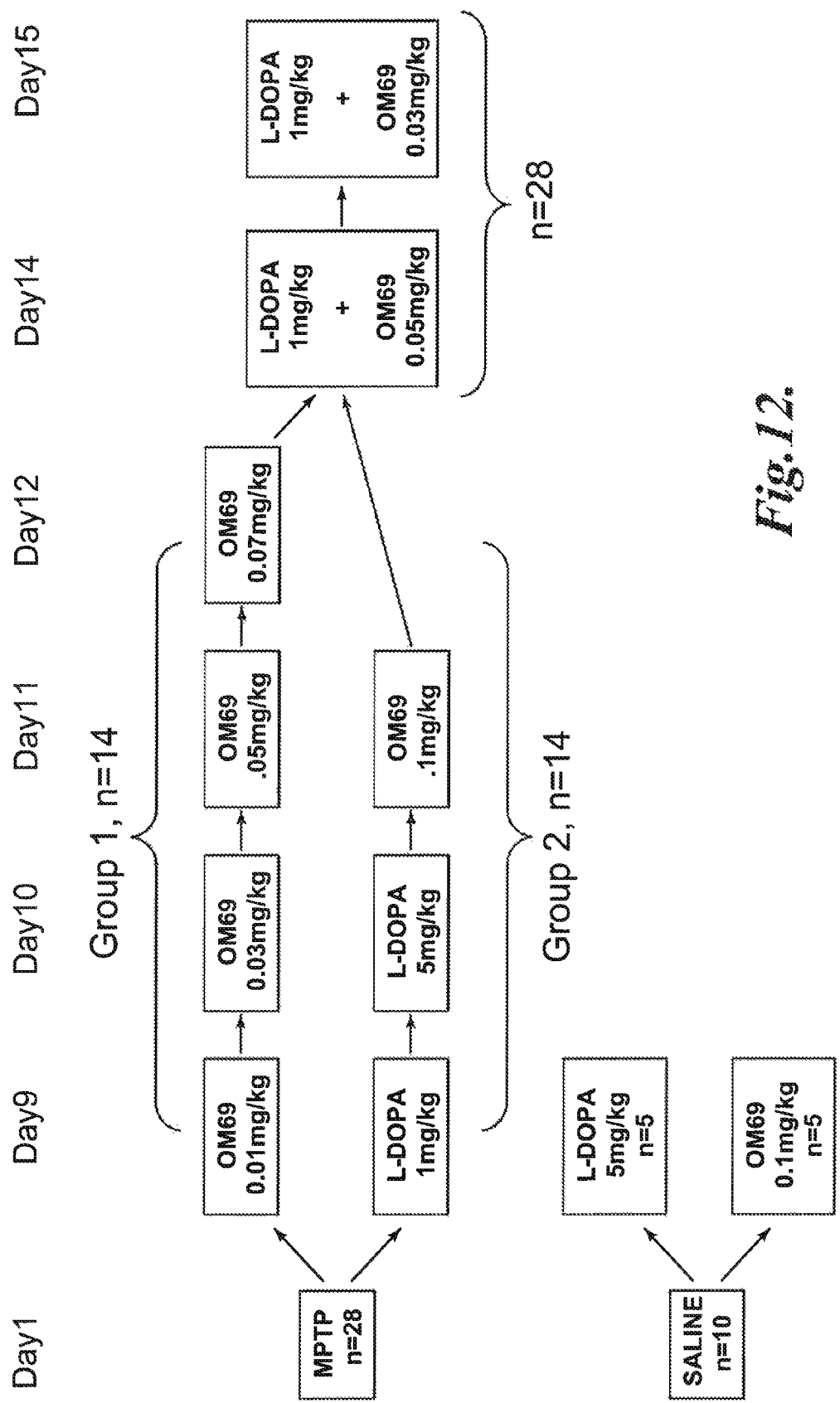
FIG. 12 is a flow diagram illustrating an experiment carried out in the MPTP mouse model of Parkinson's disease to confirm that the representative PDE7 inhibitor (OM69) increases stride length in MPTP-treated mice, as described in Example 6.

Experimental Protocol:
Retired breeder male mice (28 animals total) were treated with 2×15 mg/kg MPTP (12 saline; 36 MPTP) to induce a Parkinsonian state (neurochemical loss of dopamine with corresponding behavioral deficits). A flow chart schematically illustrating the protocol is shown in FIG. 12. On day 1 baseline stride length was measured and then all mice were treated with MPTP or saline. On day 8 stride length was measured again, and then the MPTP-treated animals were divided randomly into two groups of fourteen. As described in Example 5, dosing with the successive treatments indicated in FIG. 12 occurred on consecutive days, and in each case stride length was measured 20 minutes after dosing. The "n" values inside the boxes in the flow chart indicate the number of animals for which useful data was obtained on that day (occasionally, a few animals failed to perform the stepping task).

On Day 9, Group 1 animals were treated with OM69 (0.01 mg/kg) and Group 2 were treated with L-dopa (1 mg/kg). On Day 10, Group 1 animals were treated with OM69 (0.03 mg/kg) and Group 2 were treated with L-dopa (5 mg/kg). On Day 11, Group 1 animals were treated with OM69 (0.05 mg/kg) and Group 2 were treated with OM69 (0.1 mg/kg). On Day 12, Group 1 was treated with OM69 (0.07 mg/kg).

Next, for combination studies, the two groups were combined. On Day 14, all the animals were treated with both L-dopa (1 mg/kg) and OM69 (0.01 mg/kg). On Day 15, all the animals were treated with L-dopa (1 mg/kg) in combination with a higher dose of OM69 (0.03 mg/kg).

Figure 18:
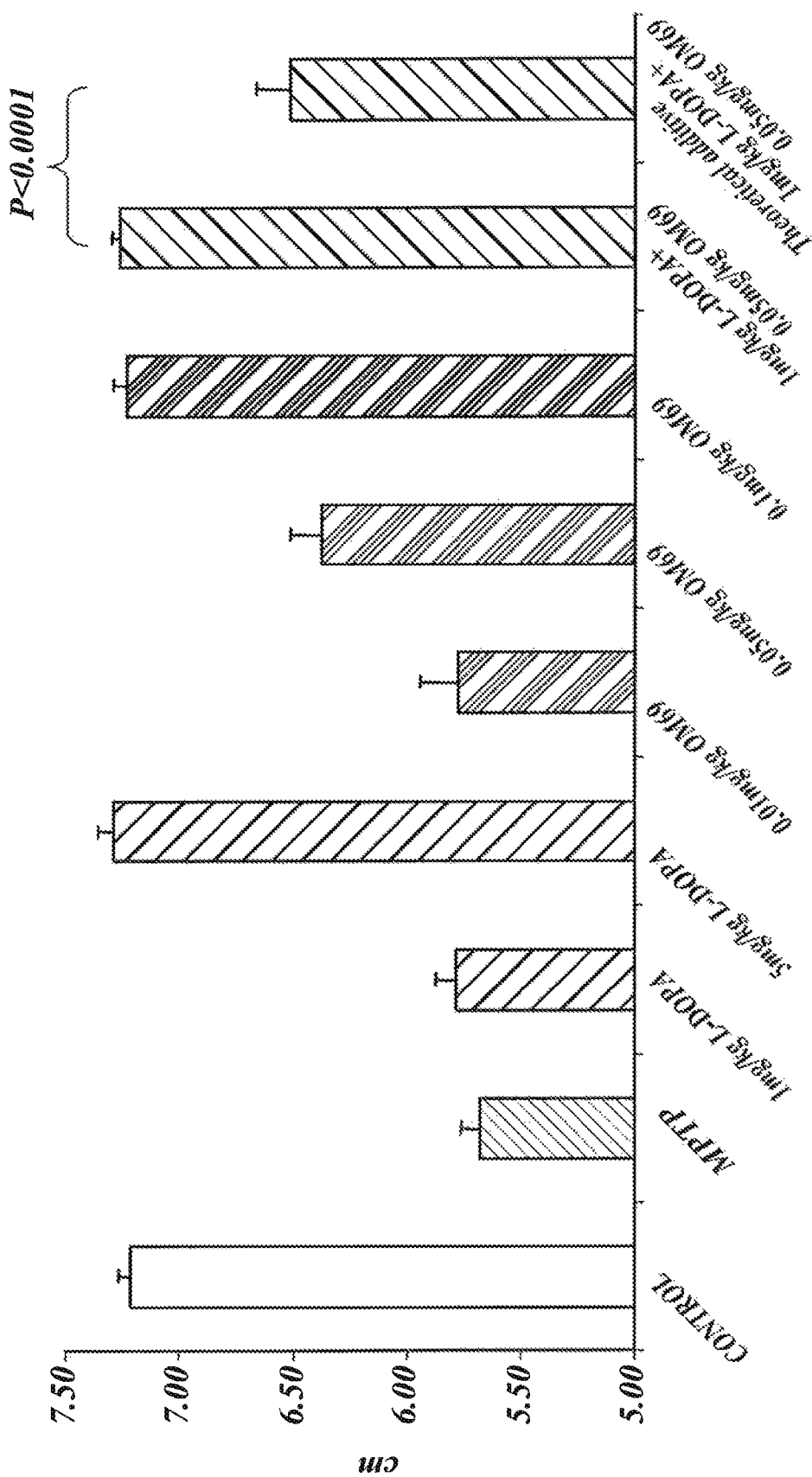
FIG. 18 is a bar graph illustrating the testing of inked paw stride length in the MPTP mouse model, demonstrating that the representative PDE7 inhibitory agent OM69 (compound 1) increases stride length in MPTP-treated mice in a dose-dependent manner, and further demonstrating that the combination of OM69 and L-dopa provides a greater than additive (i.e., synergistic) increase in stride length in MPTP-treated mice, as described in Example 6.

Results:
The results of these studies are summarized below in TABLE 6, in which the stride length of the MPTP-treated mice treated with L-dopa at two different dosages, OM69 (compound 1) at five different dosages, and the combination of L-dopa and OM69 are compared to the untreated control mice and the MPTP-treated mice receiving no drug. FIG. 18 illustrates a subset of this data.

TABLE 6

Stride Length in MPTP-lesioned Mice

| Treatment | Stride length (cm) MEAN ± SEM | Number of animals successfully performing task | Letter Designation |
|---|---|---|---|
| No treatment | 7.21 ± 0.06 | 28 | A |
| MPTP | 5.68 ± 0.09 | 25 | B |
| 1 mg/kg L-DOPA | 5.78 ± 0.09 | 13 | B |
| 5 mg/kg L-DOPA | 7.29 ± 0.07 | 14 | A |
| 0.01 mg/kg OM69 | 5.77 ± 0.17 | 11 | B |
| 0.03 mg/kg OM69 | 5.93 ± 0.14 | 14 | B |
| 0.05 mg/kg OM69 | 6.38 ± 0.14 | 13 | C |
| 0.07 mg/kg OM69 | 6.65 ± 0.18 | 13 | C |
| 0.1 mg/kg OM69 | 7.23 ± 0.07 | 14 | A |
| 1 mg/kg L-DOPA + 0.03 mg/kg OM69 | 6.81 ± 0.07 | 26 | C |
| 1 mg/kg L-DOPA + 0.05 mg/kg OM69 | 7.26 ± 0.04 | 25 | A |

Discussion of Results:

Comparison of OM69 to L-Dopa:

Referring to TABLE 6, in this experiment, MPTP caused a significant decrease in stride length (letter "B" vs. "A"). Treatment with 1 mg/kg L-dopa did not result in a significant increase in stride length, but treatment with 5 mg/kg L-dopa returned stride length to control (unlesioned) values ("A" vs. "A"). Treatment with low doses of OM69 (0.01 mg/kg or 0.03 mg/kg) also did not increase stride length, but treatment with intermediate doses resulted in a statistically significant ($p<0.05$) increase in stride length ("C" vs. "B"). Treatment with a higher dose (0.1 mg/kg) of OM69 also resulted in a statistically significant ($p<0.05$) increase in stride length and, furthermore, returned stride length to control (unlesioned) values ("A" vs. "A"). These results demonstrate that the PDE7 inhibitory compound OM69 is as effective as L-dopa in restoring stride length in MPTP-treated mice and, moreover, is approximately 50-fold more potent than L-dopa.

OM69 and L-Dopa Administered in Combination:

Two dose combinations of OM69 with L-dopa were also tested in this experiment. The first combination (1 mg/kg L-dopa plus 0.03 mg/kg OM69) caused a statistically significant ($p<0.05$) increase in stride length of 1.13 cm, which was greater than the sum of the non-significant increases with those agents alone at those doses (0.35 cm). The second combination (1 mg/kg L-dopa plus 0.05 mg/kg OM69) also resulted in a statistically significant ($p<0.05$) increase in stride length and, furthermore, returned stride length to control (unlesioned) values ("A" vs. "A"). The magnitude of this increase (1.58 cm) was statistically significantly greater ($p<0.0001$) than the sum of the increase with 0.05 mg/kg OM69 plus the non-significant increase with 1 mg/kg L-dopa (0.8 cm), as represented by the theoretical additive bar on the right hand side of the chart in FIG. 18. These results strongly suggest that the PDE7 inhibitory compound OM69 and L-dopa interact in a greater-than-additive manner to correct the stride length of MPTP-treated mice.

Example 7

Pharmacological Evaluation of a Panel of Representative PDE7 Inhibitory Compounds in the MPTP Model of Parkinson's Disease In this Example, a panel of representative PDE7 inhibitory agents were evaluated in the mouse MPTP model of Parkinson's disease in order to test the hypothesis that inhibition of PDE7 will improve Parkinsonian symptoms in this model regardless of the particular chemical structure of the inhibitor used, and that therefore, inhibition of PDE7 is sufficient for the observed improvement in stride length.

Animal Testing Protocol.

Mouse Strain:

Adult male C57BL/6J; retired breeders, aged between 7-9 months Charles River Laboratories, Wilmington, Mass.), singly housed. Three groups of 35 mice were tested in series one week apart.

Handling:

Animals were handled daily for 2 weeks prior to injection, in order to make them amenable to behavioral testing. All mice were maintained on a standard 12-h light/dark cycle, and given ad libitum access to lab chow and water.

MPTP Administration:

Mice received 2 subcutaneous injections of methylphenyltetrahydropyridine ("MPTP") at a dose of 15 mg/kg (free base) with a 10-12 hour interval between injections. Control mice (sham lesion groups) were administered saline instead of MPTP.

Stride Length:

Prior to injection with MPTP or saline, animals were pre-trained to walk across a clean sheet of paper into their home cage without stopping. For assessment of stride length, animals had their forepaws placed in black ink and the length of forepaw steps during normal walking (in a straight line only) was measured. The animals were immediately put back into their home cage upon completion of the task. Stride length was determined by measuring the distance between each step on the same side of the body, measuring from the middle toe of the first step to the heel of the second step. An average of at least four clear steps was calculated. The schedule for this experiment was as follows:

Week 0—Training to striding task: (at least 4 sessions)
Day 1—collect baseline stride
Day 2a—collect $2^{nd}$ baseline stride
Day 2b—MPTP injections
Day 7—collect and screen for stride deficit
Day 8a—collect $2^{nd}$ deficit strides
Day 8b—begin compound trials
Day 9 onward.—different doses of compound were administered on successive days.

Figure 13A:
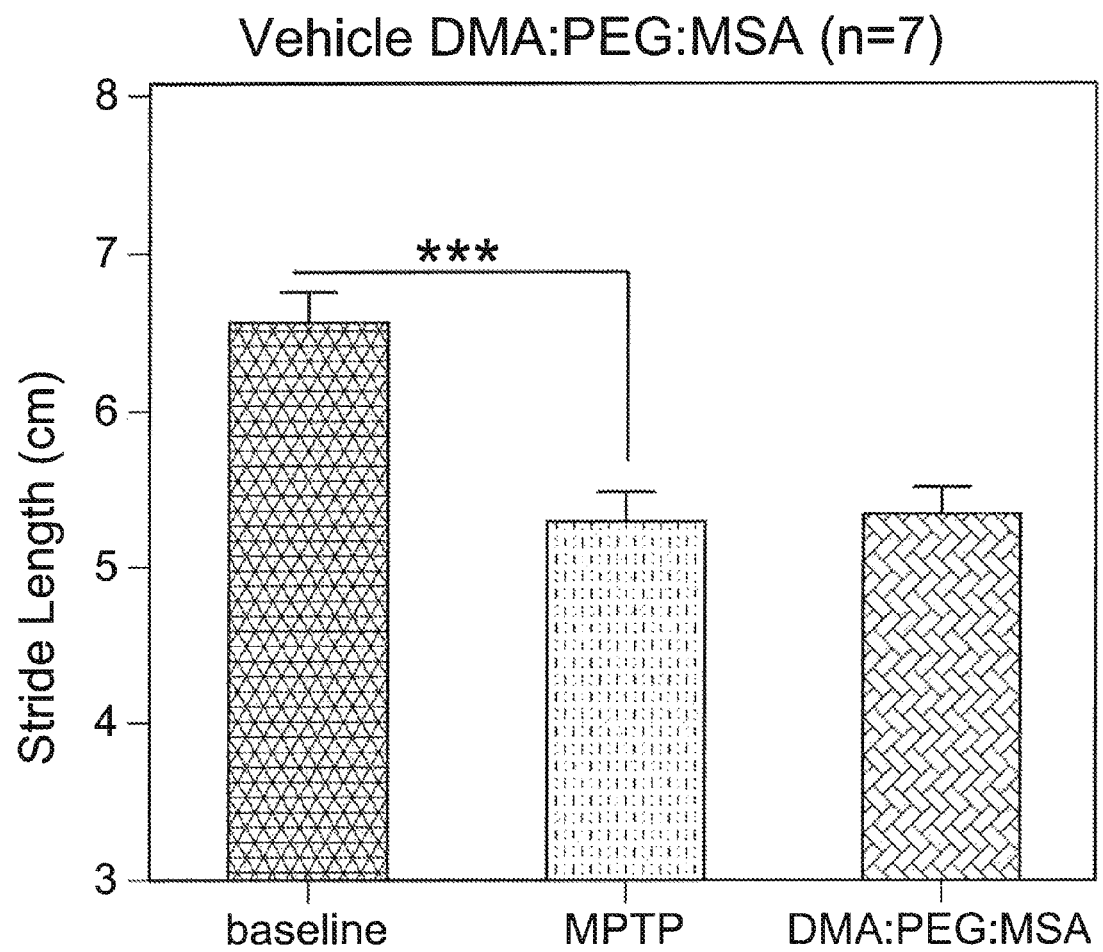
FIG. 13A is a bar graph illustrating that the vehicle control dimethylacetamide:polyethylene glycol:methane sulfonic acid (DMA:PEG:MSA) did not alter stride length in MPTP-treated mice when administered alone, as described in Example 7.
Figure 13B:
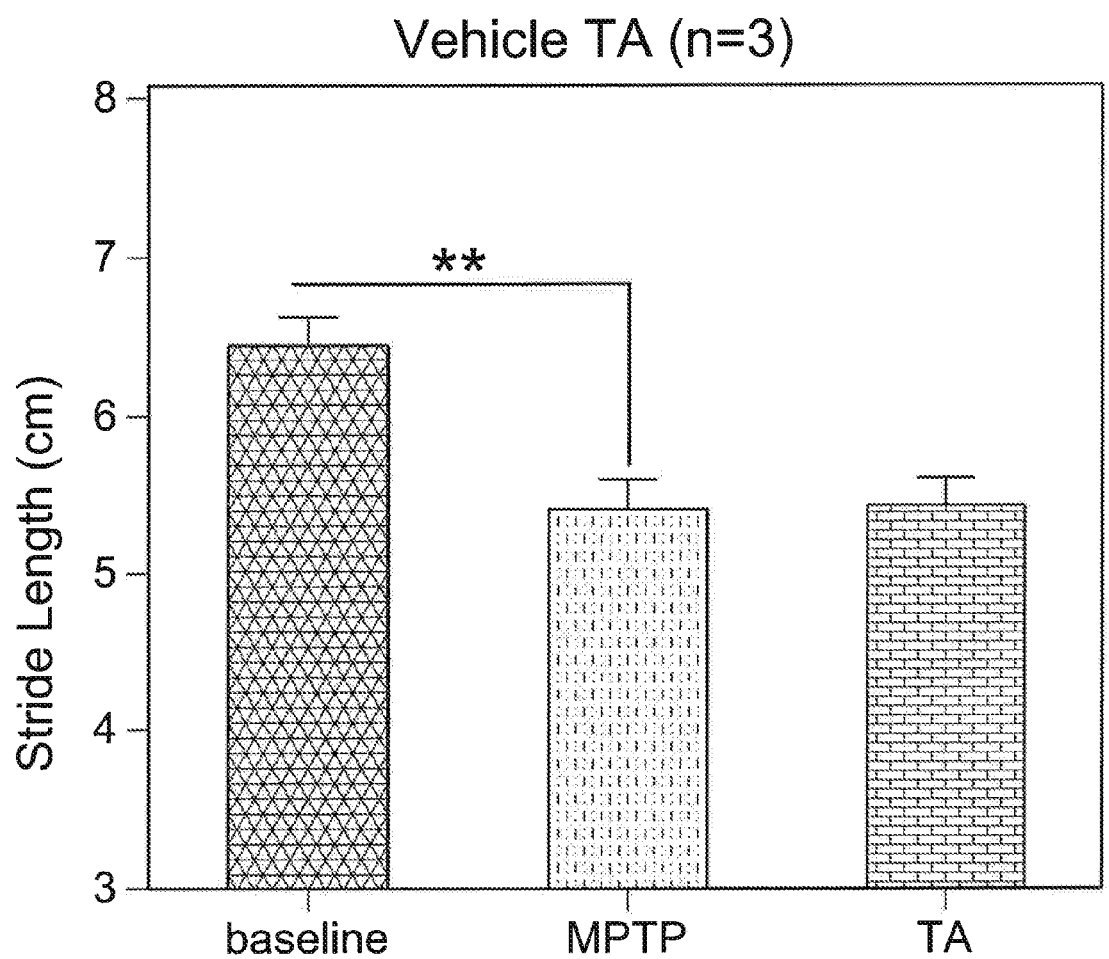
FIG. 13B is a bar graph illustrating that the vehicle control Tartaric Acid (TA) did not alter stride length in MPTP-treated mice when administered alone, as described in Example 7.

Compound Administration:

Because of the wide variation in aqueous solubility among these compounds, a number of different formulations were required. L-dopa was administered in 100 µl of phosphate buffered saline. For animals treated with L-dopa, the dopa decarboxylase inhibitor benserazide (100 µL of a 12.5 mg/kg solution) was administered 15 minutes prior to treatment with L-dopa in order to minimize the destruction of L-dopa in the peripheral blood. OM955 (compound 3) and OM056 (compound 2) were administered in 200 µl of dimethyl acetamide:polyethylene glycol 400:0.03M methane sulfonic acid (DMA:PEG:MSA-10%:40%:50%). OM956 (compound 4) was administered in 200 µl of 0.03 M Tartaric acid (TA). FIGS. 13A and 13B show that neither of these vehicles, when administered by themselves, alter stride length in MPTP-treated mice. Therefore, the treatment effects observed are due solely to the PDE7 inhibitory compounds themselves. For each compound tested, preliminary experiments were performed to identify the most effective dose in the MPTP model. In some cases, it was observed that doses higher than the optimal dose did not yield significant increases in stride length. This phenomenon of "overshoot" has also been observed with L-dopa in MPTP-treated mice in which lower doses ameliorate hypoactivity while higher doses induce dyskinesias or uncontrolled movements (Lundblad M. et al., *Exp Neurol.* 194(1):66-75 (2005); Pearce R. K. et al., *Mov Disord.* 10(6):731-40 (1995); Fredriksson, A. et al, *Pharmacol-Toxicol.* 67(4): 295-301 (1990)).

Experimental Protocol:

Retired breeder male mice were treated with either saline or 2×15 mg/kg MPTP to induce a Parkinsonian state (neurochemical loss of dopamine with corresponding behavioral deficits). On day one baseline stride length was measured and then mice were treated with either MPTP or with saline as a control. On day eight stride length was measured again, and the control value for stride length was derived from the stride length of saline-treated animals. The animals were then divided randomly into treatment groups. Compound OM955 (compound 3) was tested at 0.1 mg/kg, at 0.5 mg/kg, and at 0.1 mg/kg in combination with 1 mg/kg L-dopa. Compound OM956 (compound 4) was tested at 0.1 mg/kg and 0.5 mg/kg. Compound OM056 (compound 2) was tested at 0.05 mg/kg, 0.1 mg/kg, 0.5 mg/kg, and 1 mg/kg.

Figure 14:
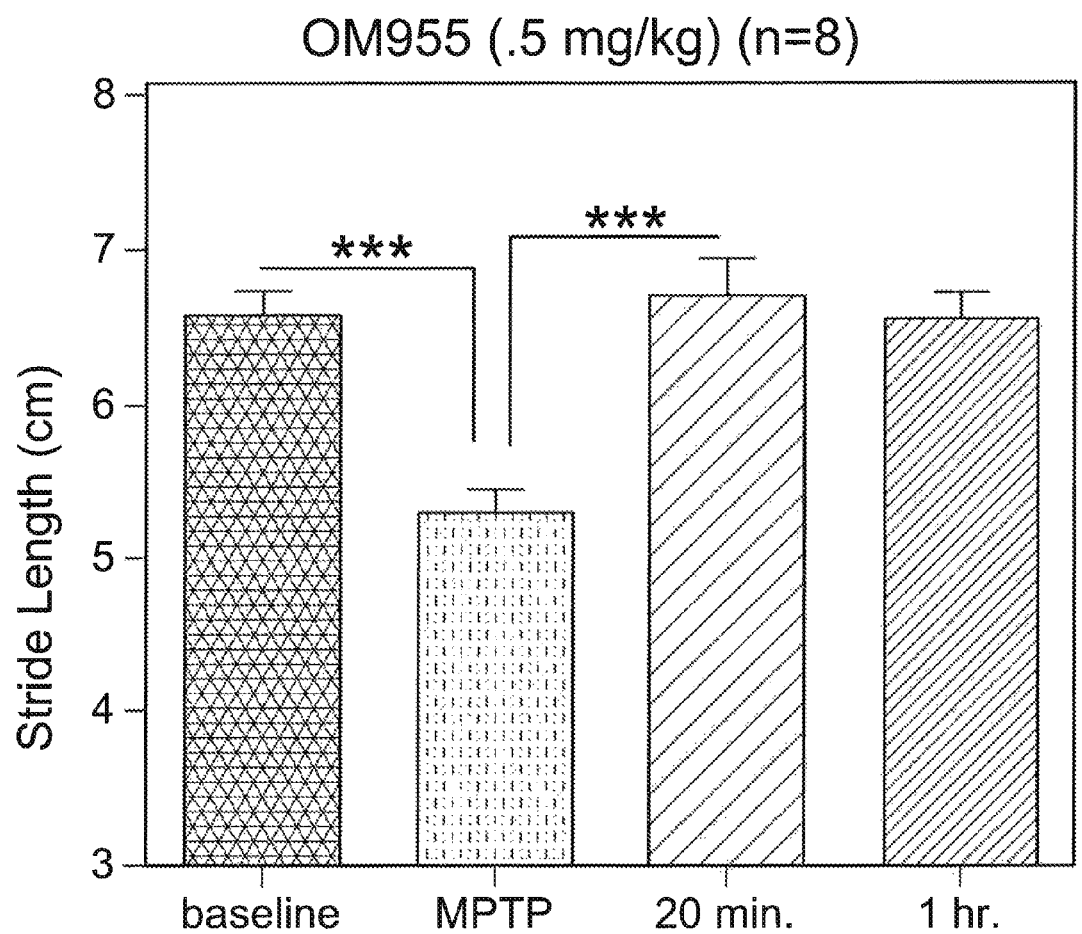
FIG. 14 is a bar graph illustrating the testing of inked paw stride length in the MPTP mouse model demonstrating that the representative PDE7 inhibitory agent OM955 (compound 2) increases stride length in MPTP mice, with full recovery of baseline stride length at 20 minutes after a dose of 0.5 mg/kg, as described in Example 7.
Figure 15A:
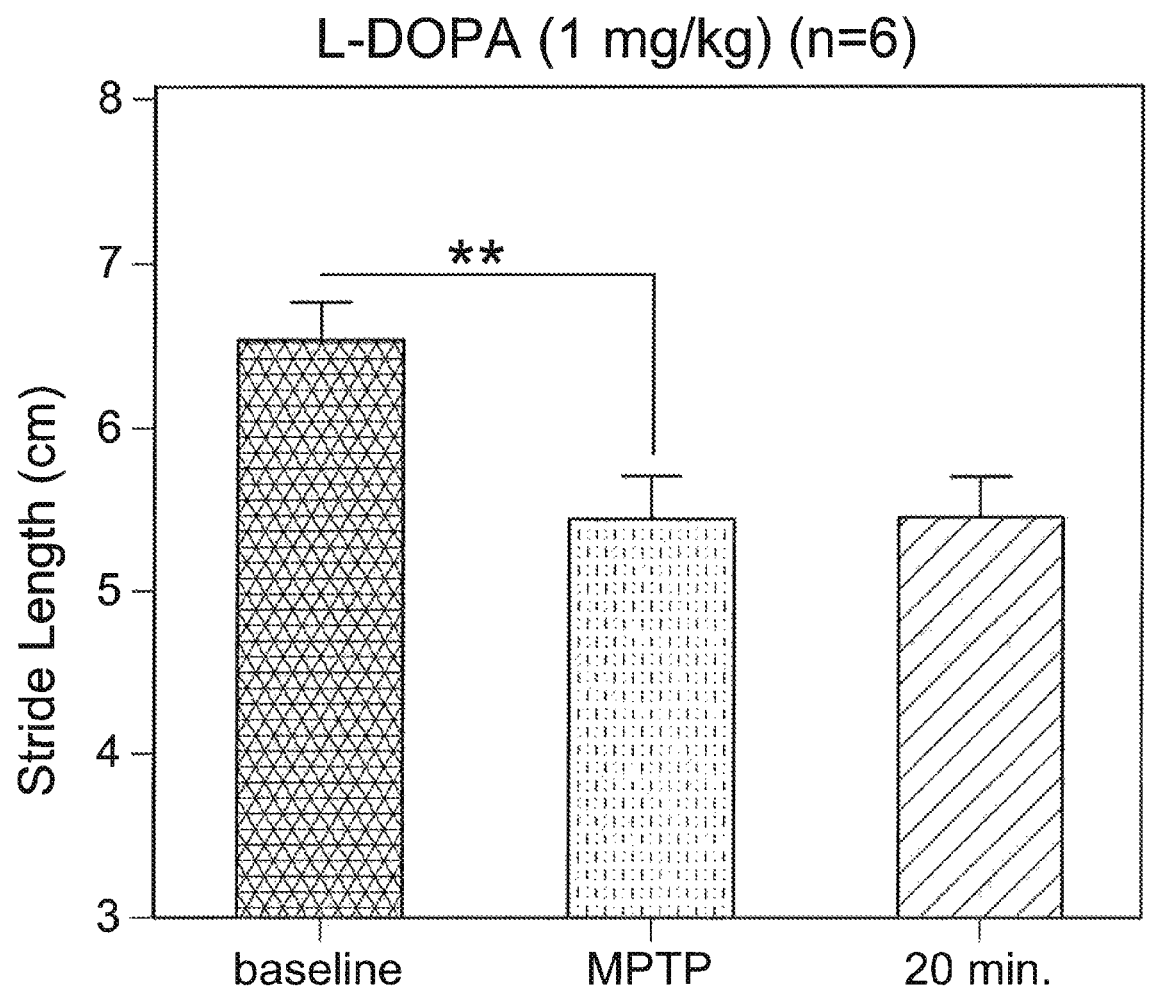
FIG. 15A is a bar graph illustrating the testing of inked paw stride length in the MPTP mouse model demonstrating that 1 mg/kg of L-dopa does not increase stride length in MPTP mice to a significant level at 20 minutes after administration, as described in Example 7.
Figure 15B:
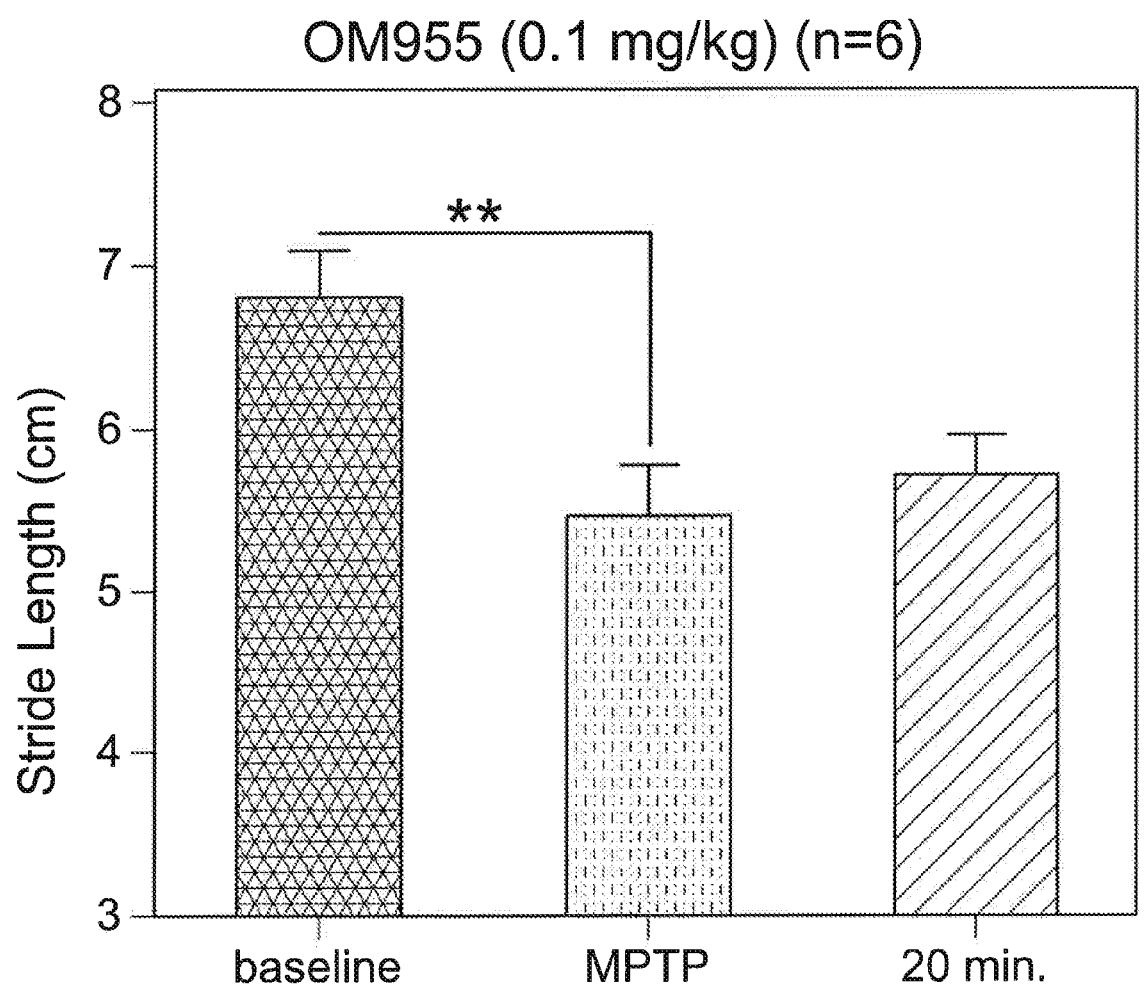
FIG. 15B is a bar graph illustrating the testing of inked paw stride length in the MPTP mouse model, demonstrating that 0.1 mg/kg of OM955 (compound 2) does not increase stride length in MPTP mice to a significant level at 20 minutes after administration, as described in Example 7.
Figure 15C:
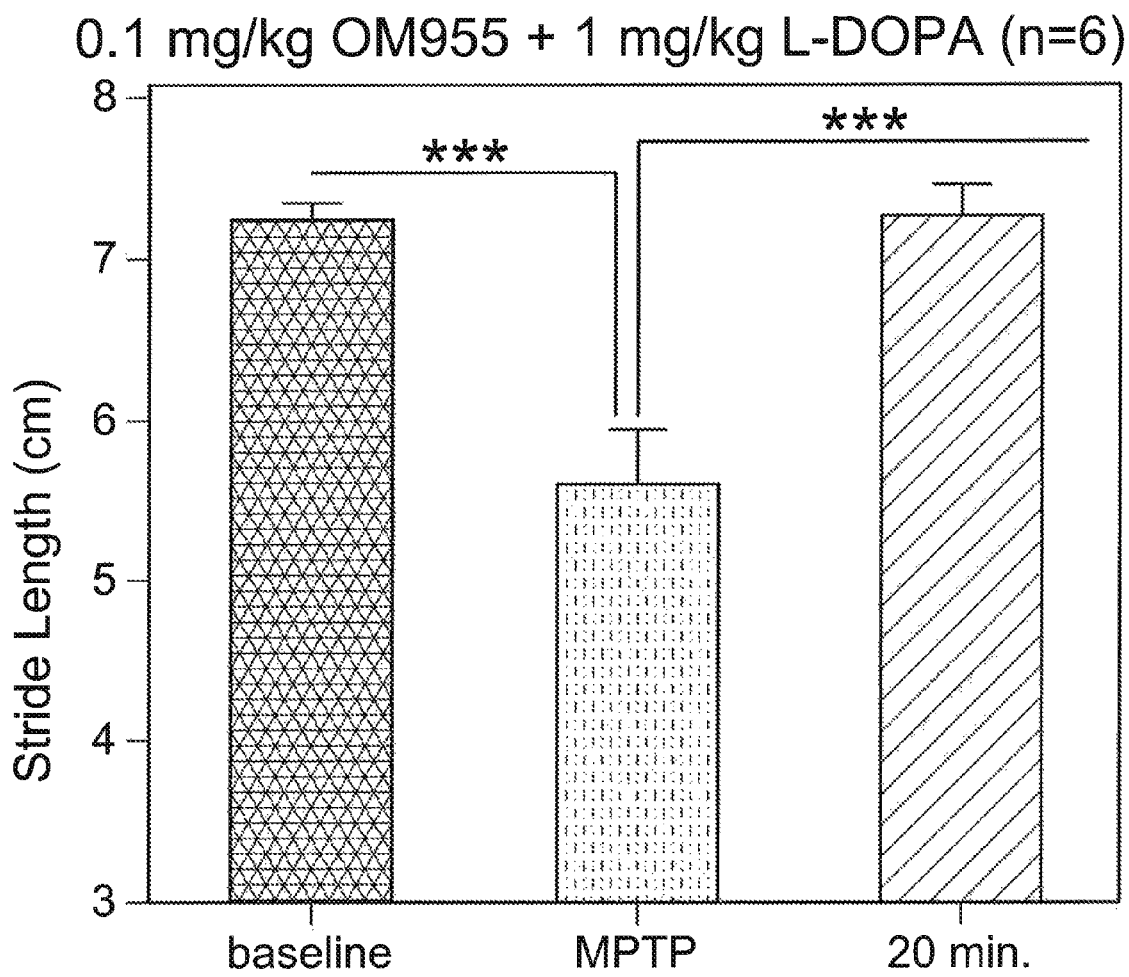
FIG. 15C is a bar graph illustrating the testing of inked paw stride length in the MPTP mouse model, demonstrating that mice administered the combination of 0.1 mg/kg of OM955 (compound 2) and 1 mg/kg L-dopa showed full recovery of stride length in MPTP-treated mice to a significant level at 20 minutes after administration, thus demonstrating synergistic results of the combination, as described in Example 7.

Results:

The results of this study are shown in FIGS. 14-17. FIG. 14 shows that OM955 at a dose of 0.5 mg/kg causes a statistically significant improvement in the stride length of MPTP-treated mice (p<0.005 compared to MPTP group). At both 20 minutes and one hour after injection, the stride length is fully restored to that of unlesioned animals. FIGS. 15A-C demonstrate that the combination of OM955 and L-dopa exerts greater-than-additive effects to restore stride length. FIGS. 15A and 15B show, respectively, that low doses of L-dopa (1 mg/kg) or OM955 (0.1 mg/kg) do not increase stride length when administered alone. However, FIG. 15C shows that when these low doses are given together, stride length is completely restored to that of unlesioned animals (p<0.005 compared to MPTP group).

Figure 16:
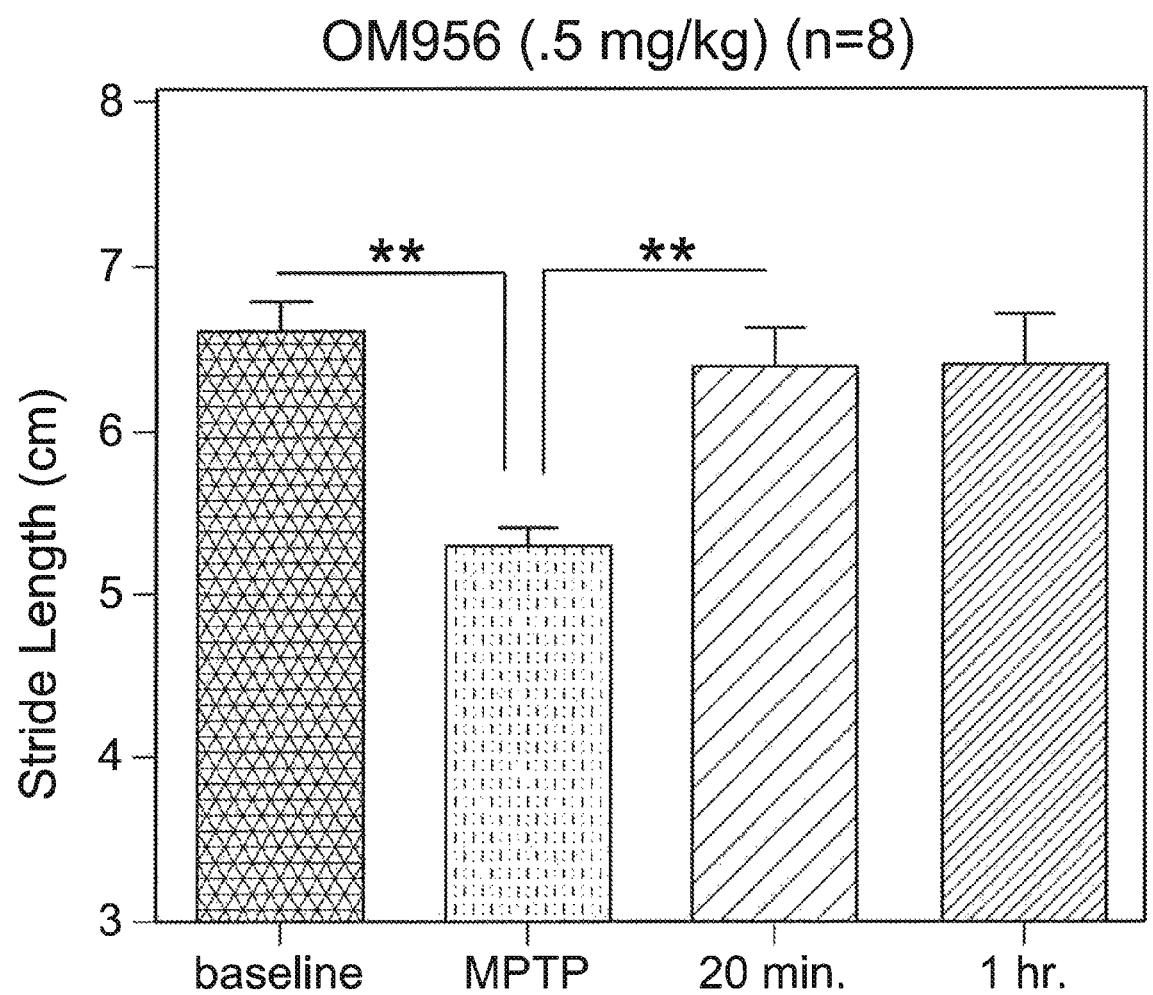
FIG. 16 is a bar graph illustrating the testing of inked paw stride length in the MPTP mouse model, demonstrating that the representative PDE7 inhibitory agent OM956 (compound 3) increases stride length in MPTP-treated mice, with full recovery of baseline stride length at 20 minutes after a dose of 0.5 mg/kg, as described in Example 7.
Figure 17:
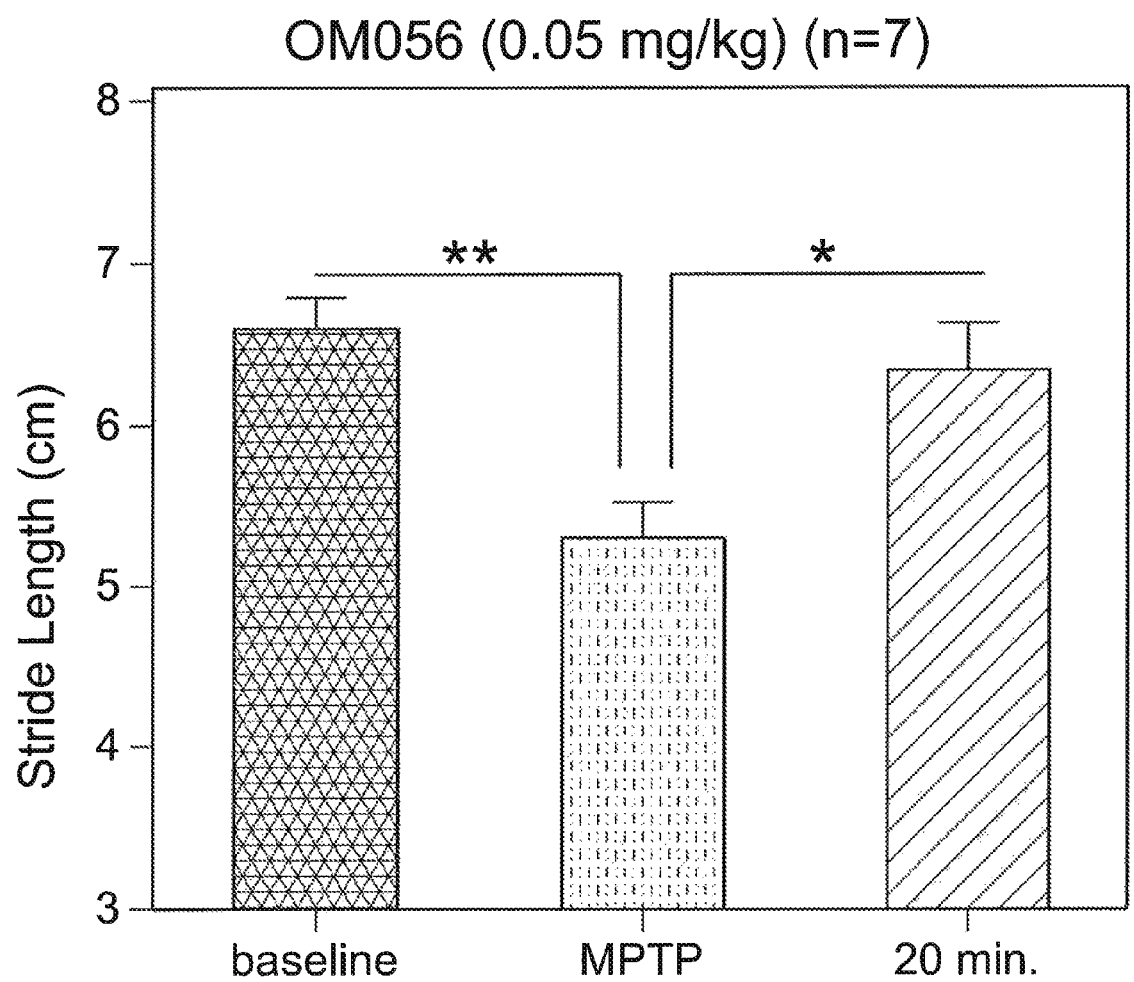
FIG. 17 is a bar graph illustrating the testing of inked paw stride length in the MPTP mouse model, demonstrating that the representative PDE7 inhibitory agent OM056 (compound 4) increases stride length in MPTP-treated mice, with full recovery of baseline stride length at 20 minutes after a dose of 0.05 mg/kg, as described in Example 7.

FIG. 16 shows that OM956, also at a dose of 0.5 mg/kg, causes a statistically significant increase (p<0.01 compared to MPTP group) in the stride length of MPTP-treated animals. FIG. 17 shows that OM056 at the lower dose of 0.05 mg/kg also causes a statistically significant increase (p<0.05 compared to MPTP group) in the stride length of MPTP-treated animals.

The results in this Example show that three different PDE7 inhibitory compounds, which are structurally unrelated to each other and structurally unrelated to OM69, all cause the same complete recovery of stride length in MPTP-treated animals that was observed with OM69 (as described in Examples 5 and 6). Because the only known common property of these compounds is their ability to inhibit PDE7, and because one of these compounds (OM69) was tested for its interaction with other known Parkinson's disease targets and found not to interact significantly with them, it is concluded that PDE7 inhibitory activity is both necessary and sufficient for the improvement in stride length reported with these compounds.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of alleviating a movement abnormality associated with the pathology of a neurological movement disorder that is treatable with a dopamine receptor agonist or a precursor of a dopamine receptor agonist, wherein the neurological movement disorder is selected from the group consisting of Periodic Limb Movement Disorder (PLMD), Periodic Limb Movements in Sleep (PLMS), Tourette's Syndrome, and Restless Leg(s) Syndrome (RLS), comprising administering to a patient in need thereof an amount of a PDE7 inhibitory agent effective to inhibit the enzymatic activity of PDE7, wherein such inhibition of PDE7 enzymatic activity is the principal therapeutic mode of action of the PDE7 inhibitor in the treatment of the movement abnormality.

2. The method of claim 1, wherein the neurological movement disorder is Periodic Limb Movement Disorder (PLMD).

3. The method of claim 1, wherein the neurological movement disorder is Periodic Limb Movements in Sleep (PLMS).

4. The method of claim 1, wherein the neurological movement disorder is Tourette's Syndrome.

5. The method of claim 1, wherein the neurological movement disorder is Restless Leg(s) Syndrome (RLS).

6. The method of claim 1, wherein the PDE7 inhibitory agent has an IC50 for inhibiting PDE7A and/or PDE7B activity of less than about 1 μM.

7. The method of claim 1, wherein the PDE7 inhibitory agent has an IC50 for inhibiting PDE7A and/or PDE7B activity of less than about 100 nM.

8. The method of claim 1, wherein the PDE7 inhibitory agent has an IC50 for inhibiting PDE1B activity of greater than 5 times the lesser of the IC50 for inhibiting PDE7A activity and the IC50 for inhibiting PDE7B activity.

9. The method of claim 1, wherein the PDE7 inhibitory agent has an IC50 for inhibiting PDE10 activity of greater than 5 times the lesser of the IC50 for inhibiting PDE7A activity and the IC50 for inhibiting PDE7B activity.

10. The method of claim 1, wherein the PDE7 inhibitory agent has an IC50 for inhibiting PDE3 activity of greater than 10 times the lesser of the IC50 for inhibiting PDE7A activity and the IC50 for inhibiting PDE7B activity.

11. The method of claim 1, wherein the PDE7 inhibitory agent has an IC50 for inhibiting PDE3 and PDE4 activity of greater than 10 times the lesser of the IC50 for inhibiting PDE7A activity and the IC50 for inhibiting PDE7B activity.

12. The method of claim 1, wherein the PDE7 inhibitory agent has an IC50 for inhibiting PDE 4 and PDE 8 activity of greater than 10 times the lesser of the IC50 for inhibiting PDE7A activity and the IC50 for inhibiting PDE7B activity.

13. The method of claim 1, wherein the PDE7 agent has an IC50 for inhibiting PDE1, PDE2, PDE3, PDE 4, PDE 8, PDE10, and PDE11 activity of greater than 10 times the lesser of the IC50 for inhibiting PDE7A activity and the IC50 for inhibiting PDE7B activity.

14. The method of claim 1, wherein the PDE7 inhibitory agent is a selective PDE7 inhibitor for which the lesser of the IC50 for inhibiting PDE7A activity and the IC50 for inhibiting PDE7B activity is less than one tenth the IC50 that the agent has for inhibiting the activity of any other PDE enzyme from the PDE1 6 and PDE8 11 enzyme families.

15. The method of claim 1, wherein the PDE7 inhibitory agent is a highly selective PDE7 inhibitor for which the lesser of the IC50 for inhibiting PDE7A activity and the IC50 for inhibiting PDE7B activity is less than one fiftieth the IC50 that the agent has for inhibiting the activity of any other PDE enzyme from the PDE1 6 and PDE8 11 enzyme families.

16. The method of claim 1, wherein the PDE7 inhibitory agent is a PDE7 inhibitory agent for which the lesser of the IC50 for inhibiting PDE7A activity and the IC50 for inhibiting PDE7B activity is less than one half of the IC50 that the agent has for inhibiting the activity at other molecular targets (i) known to be involved with the pathology of the selected neurological movement disorder or (ii) at which other drugs(s) that are therapeutically effective to treat the disorder act.

17. The method of claim 1, wherein the PDE7 inhibitory agent is a PDE7 inhibitory agent for which the lesser of the IC50 for inhibiting PDE7A activity and the IC50 for inhibiting PDE7B activity is less than is less than one half of the IC50 that the agent has for inhibiting activity at other molecular targets known to be associated with the dopamine signaling pathway.

18. The method of claim 1, wherein the PDE7 inhibitory agent has a molecular weight of less than about 450 g/mole.

19. The method of claim 1, wherein the PDE7 inhibitory agent is administered in conjunction with a dopaminergic agent or a precursor of a dopaminergic agent.

20. The method of claim 1, wherein the PDE7 inhibitory agent is administered in conjunction with a therapeutic agent or precursor of a therapeutic agent that activates the dopamine D1 receptor and/or increases the concentration of dopamine in the nigrostriatal nerve terminals and/or the nigrostriatal synaptic cleft.

21. The method of claim 1, wherein the PDE7 inhibitory agent is able to cross the blood/brain barrier.

22. A method of alleviating a movement abnormality associated with the pathology of a neurological movement disorder that is treatable with a dopamine receptor agonist or a precursor of a dopamine receptor agonist, wherein the neurological movement disorder is selected from the group consisting of Periodic Limb Movement Disorder (PLMD), Periodic Limb Movements in Sleep (PLMS), Tourette's Syndrome, and Restless Leg(s) Syndrome (RLS), comprising administering to a patient in need thereof a therapeutically effective amount of a chemical compound that is a PDE7 inhibitor, the chemical compound characterized in that:
  (i) the chemical compound has an IC50 for inhibiting PDE7A and/or PDE7B activity of less than about 1 μM; and
  (ii) the chemical compound has an IC50 for inhibiting PDE 3 greater than 10 times the lesser of the IC50 for inhibiting PDE7A activity and the IC50 for inhibiting PDE7B activity.

23. The method of claim 22, wherein the chemical compound has an IC50 for inhibiting PDE7A and/or PDE7B activity of less than about 100 nM.

24. The method of claim 22, wherein the chemical compound has an IC50 for inhibiting PDE1B activity of greater than 5 times the lesser of the IC50 for inhibiting PDE7A activity and the IC50 for inhibiting PDE7B activity.

25. The method of claim 22, wherein the chemical compound has an IC50 for inhibiting PDE10 activity of greater than 5 times the lesser of the IC50 for inhibiting PDE7A activity and the IC50 for inhibiting PDE7B activity.

26. The method of claim 22, wherein the chemical compound has an IC50 for inhibiting PDE4 activity of greater than 10 times the lesser of the IC50 for inhibiting PDE7A activity and the IC50 for inhibiting PDE7B activity.

27. The method of claim 22, wherein the chemical compound has an IC50 for inhibiting PDE8 activity of greater than 10 times the lesser of the IC50 for inhibiting PDE7A activity and the IC50 for inhibiting PDE7B activity.

28. The method of claim 22, wherein the chemical compound has an IC50 for inhibiting PDE1, PDE2, PDE3, PDE4, PDE8, and PDE11 activity of greater than 10 times the lesser of the IC50 for inhibiting PDE7A activity and the IC50 for inhibiting PDE7B activity.

29. The method of claim 22, wherein the chemical compound is a chemical compound for which the lesser of the IC50 for inhibiting PDE7A activity and the IC50 for inhibiting PDE7B activity is less than one tenth the IC50 that the compound has for inhibiting the activity of any other PDE enzyme from the PDE1 6 and PDE8 11 enzyme families.

30. The method of claim 22, wherein the chemical compound is a chemical compound for which the lesser of the IC50 for inhibiting PDE7A activity and the IC50 for inhibiting PDE7B activity is less than one fiftieth the IC50 that the compound has for inhibiting activity of any other PDE enzyme from the PDE1 6 and PDE8 11 enzyme families.

31. The method of claim 22, wherein the chemical compound is a chemical compound for which the lesser of the IC50 for inhibiting PDE7A activity and the IC50 for inhibiting PDE7B activity is less than one half of the IC50 that the agent has for inhibiting activity at other molecular target(s) known to be involved with the pathology of the selected neurological movement disorder or at which other drug(s) that are therapeutically effective to treat the disorder act.

32. The method of claim 22, wherein the chemical compound is a chemical compound for which the lesser of the IC50 for inhibiting PDE7A and the IC50 for inhibiting PDE7B is less than one half of the IC50 that the agent has for inhibiting activity at other molecular target(s) known to be associated with the dopamine signaling pathway.

33. The method of claim 22, wherein the chemical compound is administered in conjunction with a dopaminergic agent or a precursor of a dopaminergic agent.

34. The method of claim 22, wherein the chemical compound is administered in conjunction with a therapeutic agent or precursor of a therapeutic agent that activates the dopamine D1 receptor and/or increases the concentration of dopamine in the nigrostriatal nerve terminals and/or the nigrostriatal synaptic cleft.

35. The method of claim 22, wherein the chemical compound has a molecular weight of less than about 450 g/mole.

36. The method of claim 22, wherein the chemical compound is able to cross the blood/brain barrier.

37. A method of alleviating a movement abnormality associated with the pathology of a neurological disorder selected from the group consisting of Periodic Limb Movement Disorder (PLMD), Periodic Limb Movements in Sleep (PLMS), Tourette's Syndrome, and Restless Leg(s) Syndrome (RLS), comprising administering to a patient in need thereof a therapeutically effective amount of a chemical compound that is a PDE7 inhibitor, the chemical compound selected from the group consisting of the following formulas: 1A, 1B, 2A, 2B, 2C, 3, 4A, 4B, 5, 6, 7A, 7B, 8, 9, 10, 11, 12, 13, 14, 15A, 15B, 16, 16A, 17A, 171B, 18, 19, 20, 21, 22, 23, 24, 25, 26, 27A, 27B, 27C, 27D, 28, 29, 30, 31, 32, 33, 34, 35, 36, 37, 38, 39, 40, 41, 42, 43A, 43B, 44, 45, 46, 47, 48, 49, 50, 51, 52, and 53.

* * * * *

SEQUENCE LISTING

```
<160> NUMBER OF SEQ ID NOS: 6

<210> SEQ ID NO 1
<211> LENGTH: 1739
<212> TYPE: DNA
<213> ORGANISM: Homo sapiens
<220> FEATURE:
<221> NAME/KEY: CDS
<222> LOCATION: (157)..(1527)

<400> SEQUENCE: 1 gggatcact gttggaaggc agctgcttga ggtccaaggc agtcagtgtc ccctctcttt      60
tgcctcggga cagctggtat ttatcagact cctaagaagt tttccttgct ccctagtaga     120
agagagagat tatgcagcgg gcttttgatt gatcca atg gga att aca ttg atc      174
                                        Met Gly Ile Thr Leu Ile
                                        1               5 tgg tgt ctg gcc ttg gtt ctt atc aag tgg atc acc tct aag agg cgt      222
Trp Cys Leu Ala Leu Val Leu Ile Lys Trp Ile Thr Ser Lys Arg Arg
             10                  15                  20 gga gct att tcc tat gac agt tct gat cag act gca tta tac att cgt      270
Gly Ala Ile Ser Tyr Asp Ser Ser Asp Gln Thr Ala Leu Tyr Ile Arg
         25                  30                  35 atg cta gga gat gta cgt gta agg agc cga gca gga ttt gaa tca gaa      318
Met Leu Gly Asp Val Arg Val Arg Ser Arg Ala Gly Phe Glu Ser Glu
     40                  45                  50 aga aga ggt tct cac cca tat att gat ttt cgt att ttc cac tct caa      366
Arg Arg Gly Ser His Pro Tyr Ile Asp Phe Arg Ile Phe His Ser Gln
55                  60                  65                  70
```

| | | |
|---|---|---|
| tct gaa att gaa gtg tct gtc tct gca agg aat atc aga agg cta cta<br>Ser Glu Ile Glu Val Ser Val Ser Ala Arg Asn Ile Arg Arg Leu Leu<br>                    75                        80                    85 | 414 |
| agt ttc cag cga tat ctt aga tct tca cgc ttt ttt cgt ggt act gcg<br>Ser Phe Gln Arg Tyr Leu Arg Ser Ser Arg Phe Phe Arg Gly Thr Ala<br>          90                          95                          100 | 462 |
| gtt tca aat tcc cta aac att tta gat gat gat tat aat gga caa gcc<br>Val Ser Asn Ser Leu Asn Ile Leu Asp Asp Asp Tyr Asn Gly Gln Ala<br>        105                     110                    115 | 510 |
| aag tgt atg ctg gaa aaa gtt gga aat tgg aat ttt gat atc ttt cta<br>Lys Cys Met Leu Glu Lys Val Gly Asn Trp Asn Phe Asp Ile Phe Leu<br>120                      125                    130 | 558 |
| ttt gat aga cta aca aat gga aat agt cta gta agc tta acc ttt cat<br>Phe Asp Arg Leu Thr Asn Gly Asn Ser Leu Val Ser Leu Thr Phe His<br>135                      140                    145                    150 | 606 |
| tta ttt agt ctt cat gga tta att gag tac ttc cat tta gat atg atg<br>Leu Phe Ser Leu His Gly Leu Ile Glu Tyr Phe His Leu Asp Met Met<br>                  155                     160                    165 | 654 |
| aaa ctt cgt aga ttt tta gtt atg att caa gaa gat tac cac agt caa<br>Lys Leu Arg Arg Phe Leu Val Met Ile Gln Glu Asp Tyr His Ser Gln<br>                170                    175                    180 | 702 |
| aat cct tac cat aac gca gtc cac gct gcg gat gtt act cag gcc atg<br>Asn Pro Tyr His Asn Ala Val His Ala Ala Asp Val Thr Gln Ala Met<br>        185                     190                    195 | 750 |
| cac tgt tac tta aag gaa cct aag ctt gcc aat tct gta act cct tgg<br>His Cys Tyr Leu Lys Glu Pro Lys Leu Ala Asn Ser Val Thr Pro Trp<br>200                      205                    210 | 798 |
| gat atc ttg ctg agc tta att gca gct gcc act cat gat ctg gat cat<br>Asp Ile Leu Leu Ser Leu Ile Ala Ala Ala Thr His Asp Leu Asp His<br>215                      220                    225                    230 | 846 |
| cca ggt gtt aat caa cct ttc ctt att aaa act aac cat tac ttg gca<br>Pro Gly Val Asn Gln Pro Phe Leu Ile Lys Thr Asn His Tyr Leu Ala<br>                235                    240                    245 | 894 |
| act tta tac aag aat acc tca gta ctg gaa aat cac cac tgg aga tct<br>Thr Leu Tyr Lys Asn Thr Ser Val Leu Glu Asn His His Trp Arg Ser<br>        250                     255                    260 | 942 |
| gca gtg ggc tta ttg aga gaa tca ggc tta ttc tca cat ctg cca tta<br>Ala Val Gly Leu Leu Arg Glu Ser Gly Leu Phe Ser His Leu Pro Leu<br>                265                    270                    275 | 990 |
| gaa agc agg caa caa atg gag aca cag ata ggt gct ctg ata cta gcc<br>Glu Ser Arg Gln Gln Met Glu Thr Gln Ile Gly Ala Leu Ile Leu Ala<br>280                      285                    290 | 1038 |
| aca gac atc agt cgc cag aat gag tat ctg tct ttg ttt agg tcc cat<br>Thr Asp Ile Ser Arg Gln Asn Glu Tyr Leu Ser Leu Phe Arg Ser His<br>295                      300                    305                    310 | 1086 |
| ttg gat aga ggt gat tta tgc cta gaa gac acc aga cac aga cat ttg<br>Leu Asp Arg Gly Asp Leu Cys Leu Glu Asp Thr Arg His Arg His Leu<br>                315                    320                    325 | 1134 |
| gtt tta cag atg gct ttg aaa tgt gct gat att tgt aac cca tgt cgg<br>Val Leu Gln Met Ala Leu Lys Cys Ala Asp Ile Cys Asn Pro Cys Arg<br>                330                    335                    340 | 1182 |
| acg tgg gaa tta agc aag cag tgg agt gaa aaa gta acg gag gaa ttc<br>Thr Trp Glu Leu Ser Lys Gln Trp Ser Glu Lys Val Thr Glu Glu Phe<br>        345                     350                    355 | 1230 |
| ttc cat caa gga gat ata gaa aaa aaa tat cat ttg ggt gtg agt cca<br>Phe His Gln Gly Asp Ile Glu Lys Lys Tyr His Leu Gly Val Ser Pro<br>360                      365                    370 | 1278 |
| ctt tgc gat cgt cac act gaa tct att gcc aac atc cag att ggt ttt<br>Leu Cys Asp Arg His Thr Glu Ser Ile Ala Asn Ile Gln Ile Gly Phe | 1326 |

```
               375                 380                 385                 390
atg act tac cta gtg gag cct tta ttt aca gaa tgg gcc agg ttt tcc            1374
Met Thr Tyr Leu Val Glu Pro Leu Phe Thr Glu Trp Ala Arg Phe Ser
                    395                 400                 405 aat aca agg cta tcc cag aca atg ctt gga cac gtg ggg ctg aat aaa            1422
Asn Thr Arg Leu Ser Gln Thr Met Leu Gly His Val Gly Leu Asn Lys
            410                 415                 420 gcc agc tgg aag gga ctg cag aga gaa cag tcg agc agt gag gac act            1470
Ala Ser Trp Lys Gly Leu Gln Arg Glu Gln Ser Ser Ser Glu Asp Thr
        425                 430                 435 gat gct gca ttt gag ttg aac tca cag tta tta cct cag gaa aat cgg            1518
Asp Ala Ala Phe Glu Leu Asn Ser Gln Leu Leu Pro Gln Glu Asn Arg
    440                 445                 450 tta tca taa cccccagaac cagtgggaca aactgcctcc tggaggtttt                    1567
Leu Ser
455 tagaaatgtg aaatggggtc ttgaggtgag agaacttaac tcttgactgc caaggtttcc          1627 aagtgagtga tgccagccag cattatttat ttccaagatt tcctctgttg gatcatttga          1687 acccacttgt taattgcaag acccgaacat acagcaatat gaatttggct tt                  1739

<210> SEQ ID NO 2
<211> LENGTH: 456
<212> TYPE: PRT
<213> ORGANISM: Homo sapiens

<400> SEQUENCE: 2

Met Gly Ile Thr Leu Ile Trp Cys Leu Ala Leu Val Leu Ile Lys Trp
1               5                   10                  15

Ile Thr Ser Lys Arg Gly Ala Ile Ser Tyr Asp Ser Ser Asp Gln
            20                  25                  30

Thr Ala Leu Tyr Ile Arg Met Leu Gly Asp Val Arg Val Arg Ser Arg
                35                  40                  45

Ala Gly Phe Glu Ser Glu Arg Arg Gly Ser His Pro Tyr Ile Asp Phe
        50                  55                  60

Arg Ile Phe His Ser Gln Ser Glu Ile Glu Val Ser Val Ser Ala Arg
65                  70                  75                  80

Asn Ile Arg Arg Leu Leu Ser Phe Gln Arg Tyr Leu Arg Ser Arg
                85                  90                  95

Phe Phe Arg Gly Thr Ala Val Ser Asn Ser Leu Asn Ile Leu Asp Asp
                100                 105                 110

Asp Tyr Asn Gly Gln Ala Lys Cys Met Leu Glu Lys Val Gly Asn Trp
            115                 120                 125

Asn Phe Asp Ile Phe Leu Phe Asp Arg Leu Thr Asn Gly Asn Ser Leu
        130                 135                 140

Val Ser Leu Thr Phe His Leu Phe Ser Leu His Gly Leu Ile Glu Tyr
145                 150                 155                 160

Phe His Leu Asp Met Met Lys Leu Arg Arg Phe Leu Val Met Ile Gln
                165                 170                 175

Glu Asp Tyr His Ser Gln Asn Pro Tyr His Asn Ala Val His Ala Ala
            180                 185                 190

Asp Val Thr Gln Ala Met His Cys Tyr Leu Lys Glu Pro Lys Leu Ala
        195                 200                 205

Asn Ser Val Thr Pro Trp Asp Ile Leu Leu Ser Leu Ile Ala Ala Ala
    210                 215                 220

Thr His Asp Leu Asp His Pro Gly Val Asn Gln Pro Phe Leu Ile Lys
```

```
              225                 230                 235                 240

Thr Asn His Tyr Leu Ala Thr Leu Tyr Lys Asn Thr Ser Val Leu Glu
                        245                 250                 255

Asn His His Trp Arg Ser Ala Val Gly Leu Leu Arg Glu Ser Gly Leu
                        260                 265                 270

Phe Ser His Leu Pro Leu Glu Ser Arg Gln Met Glu Thr Gln Ile
                        275                 280                 285

Gly Ala Leu Ile Leu Ala Thr Asp Ile Ser Arg Gln Asn Glu Tyr Leu
                        290                 295                 300

Ser Leu Phe Arg Ser His Leu Asp Arg Gly Asp Leu Cys Leu Glu Asp
        305                 310                 315                 320

Thr Arg His Arg His Leu Val Leu Gln Met Ala Leu Lys Cys Ala Asp
                        325                 330                 335

Ile Cys Asn Pro Cys Arg Thr Trp Glu Leu Ser Lys Gln Trp Ser Glu
                        340                 345                 350

Lys Val Thr Glu Glu Phe Phe His Gln Gly Asp Ile Glu Lys Lys Tyr
                        355                 360                 365

His Leu Gly Val Ser Pro Leu Cys Asp Arg His Thr Glu Ser Ile Ala
                        370                 375                 380

Asn Ile Gln Ile Gly Phe Met Thr Tyr Leu Val Glu Pro Leu Phe Thr
        385                 390                 395                 400

Glu Trp Ala Arg Phe Ser Asn Thr Arg Leu Ser Gln Thr Met Leu Gly
                        405                 410                 415

His Val Gly Leu Asn Lys Ala Ser Trp Lys Gly Leu Gln Arg Glu Gln
                        420                 425                 430

Ser Ser Ser Glu Asp Thr Asp Ala Ala Phe Glu Leu Asn Ser Gln Leu
                        435                 440                 445

Leu Pro Gln Glu Asn Arg Leu Ser
                        450                 455

<210> SEQ ID NO 3
<211> LENGTH: 2990
<212> TYPE: DNA
<213> ORGANISM: Homo sapiens
<220> FEATURE:
<221> NAME/KEY: CDS
<222> LOCATION: (1)..(1275)

<400> SEQUENCE: 3 atg gaa gtg tgt tac cag ctg ccg gta ctg ccc ctg gac agg ccg gtc      48
Met Glu Val Cys Tyr Gln Leu Pro Val Leu Pro Leu Asp Arg Pro Val
1               5                   10                  15 ccc cag cac gtc ctc agc cgc cga gga gcc atc agc ttc agc tcc agc      96
Pro Gln His Val Leu Ser Arg Arg Gly Ala Ile Ser Phe Ser Ser Ser
                20                  25                  30 tcc gct ctc ttc ggc tgc ccc aat ccc cgg cag ctc tct cag agg cgt     144
Ser Ala Leu Phe Gly Cys Pro Asn Pro Arg Gln Leu Ser Gln Arg Arg
            35                  40                  45 gga gct att tcc tat gac agt tct gat cag act gca tta tac att cgt     192
Gly Ala Ile Ser Tyr Asp Ser Ser Asp Gln Thr Ala Leu Tyr Ile Arg
        50                  55                  60 atg cta gga gat gta cgt gta agg agc cga gca gga ttt gaa tca gaa     240
Met Leu Gly Asp Val Arg Val Arg Ser Arg Ala Gly Phe Glu Ser Glu
65                  70                  75                  80 aga aga ggt tct cac cca tat att gat ttt cgt att ttc cac tct caa     288
Arg Arg Gly Ser His Pro Tyr Ile Asp Phe Arg Ile Phe His Ser Gln
                85                  90                  95
```

|  |  |
|---|---|
| tct gaa att gaa gtg tct gtc tct gca agg aat atc aga agg cta cta<br>Ser Glu Ile Glu Val Ser Val Ser Ala Arg Asn Ile Arg Arg Leu Leu<br>100                    105                    110 | 336 |
| agt ttc cag cga tat ctt aga tct tca cgc ttt ttt cgt ggt act gcg<br>Ser Phe Gln Arg Tyr Leu Arg Ser Ser Arg Phe Phe Arg Gly Thr Ala<br>115                    120                    125 | 384 |
| gtt tca aat tcc cta aac att tta gat gat gat tat aat gga caa gcc<br>Val Ser Asn Ser Leu Asn Ile Leu Asp Asp Asp Tyr Asn Gly Gln Ala<br>130                    135                    140 | 432 |
| aag tgt atg ctg gaa aaa gtt gga aat tgg aat ttt gat atc ttt cta<br>Lys Cys Met Leu Glu Lys Val Gly Asn Trp Asn Phe Asp Ile Phe Leu<br>145                    150                    155                    160 | 480 |
| ttt gat aga cta aca aat gga aat agt cta gta agc tta acc ttt cat<br>Phe Asp Arg Leu Thr Asn Gly Asn Ser Leu Val Ser Leu Thr Phe His<br>165                    170                    175 | 528 |
| tta ttt agt ctt cat gga tta att gag tac ttc cat tta gat atg atg<br>Leu Phe Ser Leu His Gly Leu Ile Glu Tyr Phe His Leu Asp Met Met<br>180                    185                    190 | 576 |
| aaa ctt cgt aga ttt tta gtt atg att caa gaa gat tac cac agt caa<br>Lys Leu Arg Arg Phe Leu Val Met Ile Gln Glu Asp Tyr His Ser Gln<br>195                    200                    205 | 624 |
| aat cct tac cat aac gca gtc cac gct gcg gat gtt act cag gcc atg<br>Asn Pro Tyr His Asn Ala Val His Ala Ala Asp Val Thr Gln Ala Met<br>210                    215                    220 | 672 |
| cac tgt tac tta aag gaa cct aag ctt gcc aat tct gta act cct tgg<br>His Cys Tyr Leu Lys Glu Pro Lys Leu Ala Asn Ser Val Thr Pro Trp<br>225                    230                    235                    240 | 720 |
| gat atc ttg ctg agc tta att gca gct gcc act cat gat ctg gat cat<br>Asp Ile Leu Leu Ser Leu Ile Ala Ala Ala Thr His Asp Leu Asp His<br>245                    250                    255 | 768 |
| cca ggt gtt aat caa cct ttc ctt att aaa act aac cat tac ttg gca<br>Pro Gly Val Asn Gln Pro Phe Leu Ile Lys Thr Asn His Tyr Leu Ala<br>260                    265                    270 | 816 |
| act tta tac aag aat acc tca gta ctg gaa aat cac cac tgg aga tct<br>Thr Leu Tyr Lys Asn Thr Ser Val Leu Glu Asn His His Trp Arg Ser<br>275                    280                    285 | 864 |
| gca gtg ggc tta ttg aga gaa tca ggc tta ttc tca cat ctg cca tta<br>Ala Val Gly Leu Leu Arg Glu Ser Gly Leu Phe Ser His Leu Pro Leu<br>290                    295                    300 | 912 |
| gaa agc agg caa caa atg gag aca cag ata ggt gct ctg ata cta gcc<br>Glu Ser Arg Gln Gln Met Glu Thr Gln Ile Gly Ala Leu Ile Leu Ala<br>305                    310                    315                    320 | 960 |
| aca gac atc agt cgc cag aat gag tat ctg tct ttg ttt agg tcc cat<br>Thr Asp Ile Ser Arg Gln Asn Glu Tyr Leu Ser Leu Phe Arg Ser His<br>325                    330                    335 | 1008 |
| ttg gat aga ggt gat tta tgc cta gaa gac acc aga cac aga cat ttg<br>Leu Asp Arg Gly Asp Leu Cys Leu Glu Asp Thr Arg His Arg His Leu<br>340                    345                    350 | 1056 |
| gtt tta cag atg gct ttg aaa tgt gct gat att tgt aac cca tgt cgg<br>Val Leu Gln Met Ala Leu Lys Cys Ala Asp Ile Cys Asn Pro Cys Arg<br>355                    360                    365 | 1104 |
| acg tgg gaa tta agc aag cag tgg agt gaa aaa gta acg gag gaa ttc<br>Thr Trp Glu Leu Ser Lys Gln Trp Ser Glu Lys Val Thr Glu Glu Phe<br>370                    375                    380 | 1152 |
| ttc cat caa gga gat ata gaa aaa aaa tat cat ttg ggt gtg agt cca<br>Phe His Gln Gly Asp Ile Glu Lys Lys Tyr His Leu Gly Val Ser Pro<br>385                    390                    395                    400 | 1200 |
| ctt tgc gat cgt cac act gaa tct att gcc aac atc cag att ggt aac<br>Leu Cys Asp Arg His Thr Glu Ser Ile Ala Asn Ile Gln Ile Gly Asn<br>405                    410                    415 | 1248 |

```
tat aca tat tta gat ata gct ggt tag aaaaatgcca ctgttttat      1295
Tyr Thr Tyr Leu Asp Ile Ala Gly
                420 caagaaggga aatatatttg aaatataaaa tattaaaatt atgctcattt ctattttaa   1355
aaataattta agaaatttta cccttgtttt cccttgttat ggctcttcta attctcattt   1415
aattttagga tgtaaaaagt atattttgc agaacaggca gcagcaataa cttgtttctg   1475
ttcttatgta aataagaatc cattattcgc tcatgtggaa gcttcttttg catcatttgg   1535
gactgccatt taaaaaagga taggtaaaca agaaatgac aaaaataaaa taaataaaat   1595
aaaaatggat aggtggtgac ccactgagcc tgatcataat acgaagacca gcttctgcca   1655
ctgcctttcc agactcttac cactgcctgt tgattaaatc taactcttca acatcctaga   1715
caggccctta taatcttgct tcaaatgctg tgcagccatc ttgcctcaac ttccctctca   1775
tttgcctaca gcatctcggg acgcttctgt gtttcccaag tatacgctgt tctttcgctc   1835
tttgtgcttc gccagtgctt tccatgtgcc tcgtagagtt atttttcttg aagaggcagc   1895
tcaaatgtca ccttctccag aagctgctct ccacttgctt taggcagagt cagtcacttt   1955
tcttctagat tccaaagtgc ctgatccact tggttgtgga ttcctggagc ctagcaccac   2015
accagaagca cgaggcccct tgagaactgtg tgttgagtga actaataact gtattataga   2075
aagcataatg aaaatgtcct gtgactgaag tatgtgtagc ttgttgcagg agtcacagga   2135
aagttgacta ggattgagtg tgttgggctt tgggtataaa ggaggggat tctacggggg   2195
cagtagctca acaaggaata gagggaggag tgtaattttg gtagctggtg ttgaatagggg   2255
cctttgagaa tcagactgaa cacagtgaaa tatgtgccca aagttcagaa agatgaagtt   2315
tccagaaact aagaaggtag cacaatatgt ggcatcatac tcagaaagga agaccatgcc   2375
atggggccag aaattcagaa acgtaattct tacattgtga ttgcaatgga tactcatgaa   2435
agaaagtggg tagtggccga tttgccttca gagtgacagg tagagaaggg aagagcgtgt   2495
agaactgtgg ccatacttta ggagtgtgag ggatgctgaa tctcccagag agctcacact   2555
ggccaggaat gctgagagta gcagatgctt ttcttttggg aggatagtaa acaatttag   2615
aaccagatat gctttgtctt gattctcaag tagaataatc ttcaaatgca aaagaataca   2675
ttagaaatgg acaaaagtgg ccaggagcgg tagctcatac ttgtaaccca gcactttggg   2735
aagccgaggc gggctgatcg cttgaggtca ggagttcgag accagcctgg ccaaaatagt   2795
gaaactcacg tttctactaa aaatacaaaa attagctggg tgtgatggcc acttgggagg   2855
ctgagatagg agaatcgctt gaacctggga ggcagaggtt gcagtgagcc aatatcgtgc   2915
cactgcattc cagcctgggt gacagaatga aactccatca ctccatctca aaaaaaaaaa   2975
aaaaaaaaaa aaaaa                                                  2990

<210> SEQ ID NO 4
<211> LENGTH: 424
<212> TYPE: PRT
<213> ORGANISM: Homo sapiens

<400> SEQUENCE: 4

Met Glu Val Cys Tyr Gln Leu Pro Val Leu Pro Leu Asp Arg Pro Val
1               5                   10                  15

Pro Gln His Val Leu Ser Arg Arg Gly Ala Ile Ser Phe Ser Ser
            20                  25                  30

Ser Ala Leu Phe Gly Cys Pro Asn Pro Arg Gln Leu Ser Gln Arg Arg
        35                  40                  45
```

```
Gly Ala Ile Ser Tyr Asp Ser Asp Gln Thr Ala Leu Tyr Ile Arg
    50                  55                  60

Met Leu Gly Asp Val Arg Val Arg Ser Arg Ala Gly Phe Glu Ser Glu
65                  70                  75                  80

Arg Arg Gly Ser His Pro Tyr Ile Asp Phe Arg Ile Phe His Ser Gln
                85                  90                  95

Ser Glu Ile Glu Val Ser Val Ser Ala Arg Asn Ile Arg Arg Leu Leu
            100                 105                 110

Ser Phe Gln Arg Tyr Leu Arg Ser Ser Arg Phe Phe Arg Gly Thr Ala
        115                 120                 125

Val Ser Asn Ser Leu Asn Ile Leu Asp Asp Tyr Asn Gly Gln Ala
    130                 135                 140

Lys Cys Met Leu Glu Lys Val Gly Asn Trp Asn Phe Asp Ile Phe Leu
145                 150                 155                 160

Phe Asp Arg Leu Thr Asn Gly Asn Ser Leu Val Ser Leu Thr Phe His
                165                 170                 175

Leu Phe Ser Leu His Gly Leu Ile Glu Tyr Phe His Leu Asp Met Met
            180                 185                 190

Lys Leu Arg Arg Phe Leu Val Met Ile Gln Glu Asp Tyr His Ser Gln
        195                 200                 205

Asn Pro Tyr His Asn Ala Val His Ala Ala Asp Val Thr Gln Ala Met
210                 215                 220

His Cys Tyr Leu Lys Glu Pro Lys Leu Ala Asn Ser Val Thr Pro Trp
225                 230                 235                 240

Asp Ile Leu Leu Ser Leu Ile Ala Ala Thr His Asp Leu Asp His
                245                 250                 255

Pro Gly Val Asn Gln Pro Phe Leu Ile Lys Thr Asn His Tyr Leu Ala
            260                 265                 270

Thr Leu Tyr Lys Asn Thr Ser Val Leu Glu Asn His His Trp Arg Ser
        275                 280                 285

Ala Val Gly Leu Leu Arg Glu Ser Gly Leu Phe Ser His Leu Pro Leu
    290                 295                 300

Glu Ser Arg Gln Gln Met Glu Thr Gln Ile Gly Ala Leu Ile Leu Ala
305                 310                 315                 320

Thr Asp Ile Ser Arg Gln Asn Glu Tyr Leu Ser Leu Phe Arg Ser His
                325                 330                 335

Leu Asp Arg Gly Asp Leu Cys Leu Glu Asp Thr Arg His Arg His Leu
            340                 345                 350

Val Leu Gln Met Ala Leu Lys Cys Ala Asp Ile Cys Asn Pro Cys Arg
        355                 360                 365

Thr Trp Glu Leu Ser Lys Gln Trp Ser Glu Lys Val Thr Glu Glu Phe
    370                 375                 380

Phe His Gln Gly Asp Ile Glu Lys Lys Tyr His Leu Gly Val Ser Pro
385                 390                 395                 400

Leu Cys Asp Arg His Thr Glu Ser Ile Ala Asn Ile Gln Ile Gly Asn
                405                 410                 415

Tyr Thr Tyr Leu Asp Ile Ala Gly
            420

<210> SEQ ID NO 5
<211> LENGTH: 2100
<212> TYPE: DNA
<213> ORGANISM: Homo sapiens
<220> FEATURE:
```

<221> NAME/KEY: CDS
<222> LOCATION: (304)..(1656)

<400> SEQUENCE: 5

```
cagtcagttg gtctgggcac tgcagcaggc tcggctctgt cccagcactt gtctgggaga      60
aaagtggtgt tactcaccca gggagagtct ctctttctac cttccttctt tctcgatctc     120
cttgtgtgct tttgtgtttc tttattctt ttcctttttt ttcttttttt ttttttgtta     180
cttaattata ttcctaatcc tggatgaagt tgctggattc tgcagcacaa gtcttcatga     240
acaagcagca ccgctcagag atttcacggc attcaaaggt cacagaactg ccactatggt     300
```

| taa atg tct tgt tta atg gtt gag agg tgt ggc gaa atc ttg ttt gag | 348 |
|---|---|
| Met Ser Cys Leu Met Val Glu Arg Cys Gly Glu Ile Leu Phe Glu | |
| 1               5             10           15 | |

| aac ccc gat cag aat gcc aaa tgt gtt tgc atg ctg gga gat ata cga | 396 |
|---|---|
| Asn Pro Asp Gln Asn Ala Lys Cys Val Cys Met Leu Gly Asp Ile Arg | |
|          20             25            30 | |

| cta agg ggt cag acg ggg gtt cgt gct gaa cgc cgt ggc tcc tac cca | 444 |
|---|---|
| Leu Arg Gly Gln Thr Gly Val Arg Ala Glu Arg Arg Gly Ser Tyr Pro | |
|     35              40            45 | |

| ttc att gac ttc cgc cta ctt aac agt aca aca tac tca ggg gag att | 492 |
|---|---|
| Phe Ile Asp Phe Arg Leu Leu Asn Ser Thr Thr Tyr Ser Gly Glu Ile | |
| 50              55            60 | |

| ggc acc aag aaa aag gtg aaa aga cta tta agc ttt caa aga tac ttc | 540 |
|---|---|
| Gly Thr Lys Lys Lys Val Lys Arg Leu Leu Ser Phe Gln Arg Tyr Phe | |
| 65              70            75 | |

| cat gca tca agg ctg ctt cgt gga att ata cca caa gcc cct ctg cac | 588 |
|---|---|
| His Ala Ser Arg Leu Leu Arg Gly Ile Ile Pro Gln Ala Pro Leu His | |
| 80              85            90            95 | |

| ctg ctg gat gaa gac tac ctt gga caa gca agg cat atg ctc tcc aaa | 636 |
|---|---|
| Leu Leu Asp Glu Asp Tyr Leu Gly Gln Ala Arg His Met Leu Ser Lys | |
|          100           105           110 | |

| gtg gga atg tgg gat ttt gac att ttc ttg ttt gat cgc ttg aca aat | 684 |
|---|---|
| Val Gly Met Trp Asp Phe Asp Ile Phe Leu Phe Asp Arg Leu Thr Asn | |
|          115           120           125 | |

| gga aac agc ctg gta aca ctg ttg tgc cac ctc ttc aat acc cat gga | 732 |
|---|---|
| Gly Asn Ser Leu Val Thr Leu Leu Cys His Leu Phe Asn Thr His Gly | |
| 130             135           140 | |

| ctc att cac cat ttc aag tta gat atg gtg acc tta cac cga ttt tta | 780 |
|---|---|
| Leu Ile His His Phe Lys Leu Asp Met Val Thr Leu His Arg Phe Leu | |
| 145             150           155 | |

| gtc atg gtt caa gaa gat tac cac agc caa aac ccg tat cac aat gct | 828 |
|---|---|
| Val Met Val Gln Glu Asp Tyr His Ser Gln Asn Pro Tyr His Asn Ala | |
| 160             165           170           175 | |

| gtt cac gca gcc gac gtc acc cag gcc atg cac tgc tac ctg aaa gag | 876 |
|---|---|
| Val His Ala Ala Asp Val Thr Gln Ala Met His Cys Tyr Leu Lys Glu | |
|          180           185           190 | |

| cca aag ctt gcc agc ttc ctc acg cct ctg gac atc atg ctt gga ctg | 924 |
|---|---|
| Pro Lys Leu Ala Ser Phe Leu Thr Pro Leu Asp Ile Met Leu Gly Leu | |
|          195           200           205 | |

| ctg gct gca gca gca cac gat gtg gac cac cca ggg gtg aac cag cca | 972 |
|---|---|
| Leu Ala Ala Ala Ala His Asp Val Asp His Pro Gly Val Asn Gln Pro | |
| 210             215           220 | |

| ttt ttg ata aaa act aac cac cat ctt gca aac cta tat cag aat atg | 1020 |
|---|---|
| Phe Leu Ile Lys Thr Asn His His Leu Ala Asn Leu Tyr Gln Asn Met | |
| 225             230           235 | |

| tct gtg ctg gag aat cat cac tgg cga tct aca att ggc atg ctt cga | 1068 |
|---|---|
| Ser Val Leu Glu Asn His His Trp Arg Ser Thr Ile Gly Met Leu Arg | |
| 240             245           250           255 | |

```
gaa tca agg ctt ctt gct cat ttg cca aag gaa atg aca cag gat att   1116
Glu Ser Arg Leu Leu Ala His Leu Pro Lys Glu Met Thr Gln Asp Ile
            260                 265                 270 gaa cag cag ctg ggc tcc ttg atc ttg gca aca gac atc aac agg cag   1164
Glu Gln Gln Leu Gly Ser Leu Ile Leu Ala Thr Asp Ile Asn Arg Gln
        275                 280                 285 aat gaa ttt ttg acc aga ttg aaa gct cac ctc cac aat aaa gac tta   1212
Asn Glu Phe Leu Thr Arg Leu Lys Ala His Leu His Asn Lys Asp Leu
    290                 295                 300 aga ctg gag gat gca cag gac agg cac ttt atg ctt cag atc gcc ttg   1260
Arg Leu Glu Asp Ala Gln Asp Arg His Phe Met Leu Gln Ile Ala Leu
305                 310                 315 aag tgt gct gac att tgc aat cct tgt aga atc tgg gag atg agc aag   1308
Lys Cys Ala Asp Ile Cys Asn Pro Cys Arg Ile Trp Glu Met Ser Lys
320                 325                 330                 335 cag tgg agt gaa agg gtc tgt gaa gaa ttc tac agg caa ggt gaa ctt   1356
Gln Trp Ser Glu Arg Val Cys Glu Glu Phe Tyr Arg Gln Gly Glu Leu
            340                 345                 350 gaa cag aaa ttt gaa ctg gaa atc agt cct ctt tgt aat caa cag aaa   1404
Glu Gln Lys Phe Glu Leu Glu Ile Ser Pro Leu Cys Asn Gln Gln Lys
        355                 360                 365 gat tcc atc cct agt ata caa att ggt ttc atg agc tac atc gtg gag   1452
Asp Ser Ile Pro Ser Ile Gln Ile Gly Phe Met Ser Tyr Ile Val Glu
    370                 375                 380 ccg ctc ttc cgg gaa tgg gcc cat ttc acg ggt aac agc acc ctg tcg   1500
Pro Leu Phe Arg Glu Trp Ala His Phe Thr Gly Asn Ser Thr Leu Ser
385                 390                 395 gag aac atg ctg ggc cac ctc gca cac aac aag gcc cag tgg aag agc   1548
Glu Asn Met Leu Gly His Leu Ala His Asn Lys Ala Gln Trp Lys Ser
400                 405                 410                 415 ctg ttg ccc agg cag cac aga agc agg ggc agc agt ggc agc ggg cct   1596
Leu Leu Pro Arg Gln His Arg Ser Arg Gly Ser Ser Gly Ser Gly Pro
            420                 425                 430 gac cac gac cac gca ggc caa ggg act gag agc gag gag cag gaa ggc   1644
Asp His Asp His Ala Gly Gln Gly Thr Glu Ser Glu Glu Gln Glu Gly
        435                 440                 445 gac agc ccc tag gggccggccc aacttagacg cggctctcct ccggcagggc       1696
Asp Ser Pro
    450 ccccagaggg cagaagcagc gtggagggc cctcacgcag cagcccagcc actttctgag   1756 tgttgtcctg gggctctttg aacgccatc ttcctccac ttacctgcct cccctccttt   1816 tcgcaaatgt acagaagcca tttgtcacct cagcattcgc tgccgaaatg agcaactcca   1876 ttcagtaacg tgggagctga tcccacgggc aggctctccc tgctccagga gaagactagg   1936 aggaagaatg aggtgctcct gccgtgtccg ccttgttccg ggtcgcactg gaacaggcag   1996 caattcctaa gtccggagcg tttgagcgtt tgctatctga ctgctgatct gcgtgacaga   2056 aacaccagca tatttgcaac gccaaggata ttggtcttaa gtgc                  2100

<210> SEQ ID NO 6
<211> LENGTH: 450
<212> TYPE: PRT
<213> ORGANISM: Homo sapiens

<400> SEQUENCE: 6

Met Ser Cys Leu Met Val Glu Arg Cys Gly Glu Ile Leu Phe Glu Asn
1               5                   10                  15

Pro Asp Gln Asn Ala Lys Cys Val Cys Met Leu Gly Asp Ile Arg Leu
            20                  25                  30
```

```
Arg Gly Gln Thr Gly Val Arg Ala Glu Arg Gly Ser Tyr Pro Phe
         35                  40                  45

Ile Asp Phe Arg Leu Leu Asn Ser Thr Thr Tyr Ser Gly Glu Ile Gly
 50                  55                  60

Thr Lys Lys Lys Val Lys Arg Leu Leu Ser Phe Gln Arg Tyr Phe His
 65                  70                  75                  80

Ala Ser Arg Leu Leu Arg Gly Ile Ile Pro Gln Ala Pro Leu His Leu
                 85                  90                  95

Leu Asp Glu Asp Tyr Leu Gly Gln Ala Arg His Met Leu Ser Lys Val
                100                 105                 110

Gly Met Trp Asp Phe Asp Ile Phe Leu Phe Asp Arg Leu Thr Asn Gly
                115                 120                 125

Asn Ser Leu Val Thr Leu Leu Cys His Leu Phe Asn Thr His Gly Leu
130                 135                 140

Ile His His Phe Lys Leu Asp Met Val Thr Leu His Arg Phe Leu Val
145                 150                 155                 160

Met Val Gln Glu Asp Tyr His Ser Gln Asn Pro Tyr His Asn Ala Val
                165                 170                 175

His Ala Ala Asp Val Thr Gln Ala Met His Cys Tyr Leu Lys Glu Pro
                180                 185                 190

Lys Leu Ala Ser Phe Leu Thr Pro Leu Asp Ile Met Leu Gly Leu Leu
                195                 200                 205

Ala Ala Ala Ala His Asp Val Asp His Pro Gly Val Asn Gln Pro Phe
                210                 215                 220

Leu Ile Lys Thr Asn His Leu Ala Asn Leu Tyr Gln Asn Met Ser
225                 230                 235                 240

Val Leu Glu Asn His His Trp Arg Ser Thr Ile Gly Met Leu Arg Glu
                245                 250                 255

Ser Arg Leu Leu Ala His Leu Pro Lys Glu Met Thr Gln Asp Ile Glu
                260                 265                 270

Gln Gln Leu Gly Ser Leu Ile Leu Ala Thr Asp Ile Asn Arg Gln Asn
                275                 280                 285

Glu Phe Leu Thr Arg Leu Lys Ala His Leu His Asn Lys Asp Leu Arg
                290                 295                 300

Leu Glu Asp Ala Gln Asp Arg His Phe Met Leu Gln Ile Ala Leu Lys
305                 310                 315                 320

Cys Ala Asp Ile Cys Asn Pro Cys Arg Ile Trp Glu Met Ser Lys Gln
                325                 330                 335

Trp Ser Glu Arg Val Cys Glu Glu Phe Tyr Arg Gln Gly Glu Leu Glu
                340                 345                 350

Gln Lys Phe Glu Leu Glu Ile Ser Pro Leu Cys Asn Gln Gln Lys Asp
                355                 360                 365

Ser Ile Pro Ser Ile Gln Ile Gly Phe Met Ser Tyr Ile Val Glu Pro
370                 375                 380

Leu Phe Arg Glu Trp Ala His Phe Thr Gly Asn Ser Thr Leu Ser Glu
385                 390                 395                 400

Asn Met Leu Gly His Leu Ala His Asn Lys Ala Gln Trp Lys Ser Leu
                405                 410                 415

Leu Pro Arg Gln His Arg Ser Arg Gly Ser Ser Gly Ser Gly Pro Asp
                420                 425                 430

His Asp His Ala Gly Gln Gly Thr Glu Ser Glu Glu Gln Glu Gly Asp
                435                 440                 445
```

```
Ser Pro
   450
```